United States Patent [19]

Belyaev et al.

[11] Patent Number: 5,766,916
[45] Date of Patent: Jun. 16, 1998

[54] HEPATITIS G VIRUS PROTEASE

[75] Inventors: Alexander S. Belyaev, Foster City; Susan M. Chong, San Carlos, both of Calif.

[73] Assignee: Genelabs Technologies, Inc., Redwood City, Calif.

[21] Appl. No.: 638,911

[22] Filed: Apr. 24, 1996

[51] Int. Cl.⁶ .............................. C12N 9/50; C12P 21/06; C12P 21/04; C07H 21/04

[52] U.S. Cl. .................. 435/219; 435/69.1; 435/69.7; 530/324; 530/826; 536/23.2; 536/23.72

[58] Field of Search ........................ 435/188, 212, 435/69.7, 69.1, 219; 530/402, 826, 324; 536/23.2, 23.72

[56] References Cited

FOREIGN PATENT DOCUMENTS 0 747 482 A2  12/1996  European Pat. Off. .
WO 91 15575  10/1991  WIPO .
WO 95/32291  11/1995  WIPO .

OTHER PUBLICATIONS

Leary, T.P., et al., "Sequence and Genomic Organization of GBV–C: A Novel Member of the Flaviviridae Associated with Human Non–A–E Hepatitis," *Journal of Medical Virology* 48(1):60–67 (1996).

*Primary Examiner*—Robert A. Wax
*Assistant Examiner*—Elizabeth H. Slobodyansky
*Attorney, Agent, or Firm*—Allan A. Brookes; Susan T. Evans

[57] ABSTRACT

The protease necessary for polyprotein processing in Hepatitis G virus (HGV) is identified, cloned, and expressed. Proteases, truncated protease, and altered proteases are disclosed which are useful for cleavage of specific polypeptides, and for assay and design of antiviral agents specific for HGV.

10 Claims, 5 Drawing Sheets

SEQUENCE LISTING ( 1 ) GENERAL INFORMATION:

( i i i ) NUMBER OF SEQUENCES: 56

( 2 ) INFORMATION FOR SEQ ID NO:1:

( i ) SEQUENCE CHARACTERISTICS:
        ( A ) LENGTH: 9391 base pairs
        ( B ) TYPE: nucleic acid
        ( C ) STRANDEDNESS: double
        ( D ) TOPOLOGY: linear ( i i ) MOLECULE TYPE: cDNA ( v i ) ORIGINAL SOURCE:
        ( C ) INDIVIDUAL ISOLATE: PNF-2161 genome ( i x ) FEATURE:
        ( A ) NAME/KEY: CDS
        ( B ) LOCATION: 459..9077

( x i ) SEQUENCE DESCRIPTION: SEQ ID NO:1:

```
ACGTGGGGA  GTTGATCCCC  CCCCCCCGGC  ACTGGGTGCA  AGCCCCAGAA  ACCGACGCCT      60

ATCTAAGTAG  ACGCAATGAC  TCGGCGCCGA  CTCGGCGACC  GGCCAAAAGG  TGGTGGATGG     120

GTGATGACAG  GGTTGGTAGG  TCGTAAATCC  CGGTCACCTT  GGTAGCCACT  ATAGGTGGGT     180

CTTAAGAGAA  GGTTAAGATT  CCTCTTGTGC  CTGCGGCGAG  ACCGCGCACG  GTCCACAGGT     240

GTTGGCCCTA  CCGGTGGGAA  TAAGGGCCCG  ACGTCAGGCT  CGTCGTTAAA  CCGAGCCCGT     300

TACCCACCTG  GGCAAACGAC  GCCCACGTAC  GGTCCACGTC  GCCCTTCAAT  GTCTCTCTTG     360

ACCAATAGGC  GTAGCCGGCG  AGTTGACAAG  GACCAGTGGG  GGCCGGGGGC  TTGGAGAGGG     420

ACTCCAAGTC  CCGCCCTTCC  CGGTGGGCCG  GGAAATGC  ATG  GGG  CCA  CCC  AGC       473
                                            Met  Gly  Pro  Pro  Ser
                                             1                    5

TCC  GCG  GCG  GCC  TGC  AGC  CGG  GGT  AGC  CCA  AGA  ATC  CTT  CGG  GTG  AGG   521
Ser  Ala  Ala  Ala  Cys  Ser  Arg  Gly  Ser  Pro  Arg  Ile  Leu  Arg  Val  Arg
               10                     15                         20

GCG  GGT  GGC  ATT  TCC  TTT  TTC  TAT  ACC  ATC  ATG  GCA  GTC  CTT  CTG  CTC   569
Ala  Gly  Gly  Ile  Ser  Phe  Phe  Tyr  Thr  Ile  Met  Ala  Val  Leu  Leu  Leu
                    25                      30                    35

CTT  CTC  GTG  GTT  GAG  GCC  GGG  GCC  ATT  CTG  GCC  CCG  GCC  ACC  CAC  GCT   617
Leu  Leu  Val  Val  Glu  Ala  Gly  Ala  Ile  Leu  Ala  Pro  Ala  Thr  His  Ala
              40                      45                    50

TGT  CGA  GCG  AAT  GGG  CAA  TAT  TTC  CTC  ACA  AAT  TGT  TGT  GCC  CCG  GAG   665
Cys  Arg  Ala  Asn  Gly  Gln  Tyr  Phe  Leu  Thr  Asn  Cys  Cys  Ala  Pro  Glu
          55                      60                    65

GAC  ATC  GGG  TTC  TGC  CTG  GAG  GGT  GGA  TGC  CTG  GTG  GCC  CTG  GGG  TGC   713
Asp  Ile  Gly  Phe  Cys  Leu  Glu  Gly  Gly  Cys  Leu  Val  Ala  Leu  Gly  Cys
70                      75                       80                      85

ACG  ATT  TGC  ACT  GAC  CAA  TGC  TGG  CCA  CTG  TAT  CAG  GCG  GGT  TTG  GCT   761
Thr  Ile  Cys  Thr  Asp  Gln  Cys  Trp  Pro  Leu  Tyr  Gln  Ala  Gly  Leu  Ala
                    90                      95                        100

GTG  CGG  CCT  GGC  AAG  TCC  GCG  GCC  CAA  CTG  GTG  GGG  GAG  CTG  GGT  AGC   809
Val  Arg  Pro  Gly  Lys  Ser  Ala  Ala  Gln  Leu  Val  Gly  Glu  Leu  Gly  Ser
              105                      110                     115

CTA  TAC  GGG  CCC  CTG  TCG  GTC  TCG  GCC  TAT  GTG  GCT  GGG  ATC  CTG  GGC   857
Leu  Tyr  Gly  Pro  Leu  Ser  Val  Ser  Ala  Tyr  Val  Ala  Gly  Ile  Leu  Gly
```

```
                    120                         125                           130
CTG GGT GAG GTG TAC TCG GGT GTC CTA ACG GTG GGA GTC GCG TTG ACG                      905
Leu Gly Glu Val Tyr Ser Gly Val Leu Thr Val Gly Val Ala Leu Thr
    135             140             145

CGC CGG GTC TAC CCG GTG CCT AAC CTG ACG TGT GCA GTC GCG TGT GAG                      953
Arg Arg Val Tyr Pro Val Pro Asn Leu Thr Cys Ala Val Ala Cys Glu
150             155             160             165

CTA AAG TGG GAA AGT GAG TTT TGG AGA TGG ACT GAA CAG CTG GCC TCC                     1001
Leu Lys Trp Glu Ser Glu Phe Trp Arg Trp Thr Glu Gln Leu Ala Ser
            170             175             180

AAC TAC TGG ATT CTG GAA TAC CTC TGG AAG GTC CCA TTT GAT TTC TGG                     1049
Asn Tyr Trp Ile Leu Glu Tyr Leu Trp Lys Val Pro Phe Asp Phe Trp
        185             190             195

AGA GGC GTG ATA AGC CTG ACC CCC TTG TTG GTT TGC GTG GCC GCA TTG                     1097
Arg Gly Val Ile Ser Leu Thr Pro Leu Leu Val Cys Val Ala Ala Leu
    200             205             210

CTG CTG CTT GAG CAA CGG ATT GTC ATG GTC TTC CTG TTG GTG ACG ATG                     1145
Leu Leu Leu Glu Gln Arg Ile Val Met Val Phe Leu Leu Val Thr Met
215             220             225

GCC GGG ATG TCG CAA GGC GCC CCT GCC TCC GTT TTG GGG TCA CGC CCC                     1193
Ala Gly Met Ser Gln Gly Ala Pro Ala Ser Val Leu Gly Ser Arg Pro
230             235             240             245

TTT GAC TAC GGG TTG ACT TGG CAG ACC TGC TCT TGC AGG GCC AAC GGT                     1241
Phe Asp Tyr Gly Leu Thr Trp Gln Thr Cys Ser Cys Arg Ala Asn Gly
            250             255             260

TCG CGT TTT TCG ACT GGG GAG AAG GTG TGG GAC CGT GGG AAC GTT ACG                     1289
Ser Arg Phe Ser Thr Gly Glu Lys Val Trp Asp Arg Gly Asn Val Thr
        265             270             275

CTT CAG TGT GAC TGC CCT AAC GGC CCC TGG GTG TGG TTG CCA GCC TTT                     1337
Leu Gln Cys Asp Cys Pro Asn Gly Pro Trp Val Trp Leu Pro Ala Phe
    280             285             290

TGC CAA GCA ATC GGC TGG GGT GAC CCC ATC ACT TAT TGG AGC CAC GGG                     1385
Cys Gln Ala Ile Gly Trp Gly Asp Pro Ile Thr Tyr Trp Ser His Gly
295             300             305

CAA AAT CAG TGG CCC CTT TCA TGC CCC CAG TAT GTC TAT GGG TCT GCT                     1433
Gln Asn Gln Trp Pro Leu Ser Cys Pro Gln Tyr Val Tyr Gly Ser Ala
310             315             320             325

ACA GTC ACT TGC GTG TGG GGT TCC GCT TCT TGG TTT GCC TCC ACC AGT                     1481
Thr Val Thr Cys Val Trp Gly Ser Ala Ser Trp Phe Ala Ser Thr Ser
            330             335             340

GGT CGC GAC TCG AAG ATA GAT GTG TGG AGT TTA GTG CCA GTT GGC TCT                     1529
Gly Arg Asp Ser Lys Ile Asp Val Trp Ser Leu Val Pro Val Gly Ser
        345             350             355

GCC ACC TGC ACC ATA GCC GCA CTT GGA TCA TCG GAT CGC GAC ACG GTG                     1577
Ala Thr Cys Thr Ile Ala Ala Leu Gly Ser Ser Asp Arg Asp Thr Val
    360             365             370

CCT GGG CTC TCC GAG TGG GGA ATC CCG TGC GTG ACG TGT GTT CTG GAC                     1625
Pro Gly Leu Ser Glu Trp Gly Ile Pro Cys Val Thr Cys Val Leu Asp
375             380             385

CGT CGG CCT GCC TCC TGC GGC ACC TGT GTG AGG GAC TGC TGG CCC GAG                     1673
Arg Arg Pro Ala Ser Cys Gly Thr Cys Val Arg Asp Cys Trp Pro Glu
390             395             400             405

ACC GGG TCG GTT AGG TTC CCA TTC CAT CGG TGC GGC GTG GGG CCT CGG                     1721
Thr Gly Ser Val Arg Phe Pro Phe His Arg Cys Gly Val Gly Pro Arg
            410             415             420

CTG ACA AAG GAC TTG GAA GCT GTG CCC TTC GTC AAC AGG ACA ACT CCC                     1769
Leu Thr Lys Asp Leu Glu Ala Val Pro Phe Val Asn Arg Thr Thr Pro
        425             430             435

TTC ACC ATT AGG GGG CCC CTG GGC AAC CAG GGC CGA GGC AAC CCG GTG                     1817
Phe Thr Ile Arg Gly Pro Leu Gly Asn Gln Gly Arg Gly Asn Pro Val
```

|     |     |     |     |     |     |     |     |     |     |     |     |     |     |     |     |      |
|-----|-----|-----|-----|-----|-----|-----|-----|-----|-----|-----|-----|-----|-----|-----|-----|------|
|     |     |     | 440 |     |     |     |     |     | 445 |     |     |     |     |     | 450 |      |
| CGG | TCG | CCC | TTG | GGT | TTT | GGG | TCC | TAC | GCC | ATG | ACC | AGG | ATC | CGA | GAT | 1865 |
| Arg | Ser | Pro | Leu | Gly | Phe | Gly | Ser | Tyr | Ala | Met | Thr | Arg | Ile | Arg | Asp |      |
|     | 455 |     |     |     | 460 |     |     |     |     | 465 |     |     |     |     |     |      |
| ACC | CTA | CAT | CTG | GTG | GAG | TGT | CCC | ACA | CCA | GCC | ATT | GAG | CCT | CCC | ACC | 1913 |
| Thr | Leu | His | Leu | Val | Glu | Cys | Pro | Thr | Pro | Ala | Ile | Glu | Pro | Pro | Thr |      |
| 470 |     |     |     |     | 475 |     |     |     |     | 480 |     |     |     |     | 485 |      |
| GGG | ACG | TTT | GGG | TTC | TTC | CCC | GGG | ACG | CCG | CCT | CTC | AAC | AAC | TGC | ATG | 1961 |
| Gly | Thr | Phe | Gly | Phe | Phe | Pro | Gly | Thr | Pro | Pro | Leu | Asn | Asn | Cys | Met |      |
|     |     |     |     | 490 |     |     |     |     | 495 |     |     |     |     |     | 500 |      |
| CTC | TTG | GGC | ACG | GAA | GTG | TCC | GAG | GCA | CTT | GGG | GGG | GCT | GGC | CTC | ACG | 2009 |
| Leu | Leu | Gly | Thr | Glu | Val | Ser | Glu | Ala | Leu | Gly | Gly | Ala | Gly | Leu | Thr |      |
|     |     |     | 505 |     |     |     |     | 510 |     |     |     |     | 515 |     |     |      |
| GGG | GGG | TTC | TAT | GAA | CCC | CTG | GTG | CGC | AGG | TGT | TCG | AAG | CTG | ATG | GGA | 2057 |
| Gly | Gly | Phe | Tyr | Glu | Pro | Leu | Val | Arg | Arg | Cys | Ser | Lys | Leu | Met | Gly |      |
|     |     | 520 |     |     |     |     | 525 |     |     |     |     | 530 |     |     |     |      |
| AGC | CGA | AAT | CCG | GTT | TGT | CCG | GGG | TTT | GCA | TGG | CTC | TCT | TCG | GGC | AGG | 2105 |
| Ser | Arg | Asn | Pro | Val | Cys | Pro | Gly | Phe | Ala | Trp | Leu | Ser | Ser | Gly | Arg |      |
|     | 535 |     |     |     | 540 |     |     |     |     | 545 |     |     |     |     |     |      |
| CCT | GAT | GGG | TTT | ATA | CAT | GTC | CAG | GGT | CAC | TTG | CAG | GAG | GTG | GAT | GCA | 2153 |
| Pro | Asp | Gly | Phe | Ile | His | Val | Gln | Gly | His | Leu | Gln | Glu | Val | Asp | Ala |      |
| 550 |     |     |     |     | 555 |     |     |     |     | 560 |     |     |     |     | 565 |      |
| GGC | AAC | TTC | ATC | CCG | CCC | CCG | CGC | TGG | TTG | CTC | TTG | GAC | TTT | GTA | TTT | 2201 |
| Gly | Asn | Phe | Ile | Pro | Pro | Pro | Arg | Trp | Leu | Leu | Leu | Asp | Phe | Val | Phe |      |
|     |     |     |     | 570 |     |     |     |     | 575 |     |     |     |     | 580 |     |      |
| GTC | CTG | TTA | TAC | CTG | ATG | AAG | CTG | GCT | GAG | GCA | CGG | TTG | GTC | CCG | CTG | 2249 |
| Val | Leu | Leu | Tyr | Leu | Met | Lys | Leu | Ala | Glu | Ala | Arg | Leu | Val | Pro | Leu |      |
|     |     |     | 585 |     |     |     |     | 590 |     |     |     |     | 595 |     |     |      |
| ATC | TTG | CTG | CTG | CTA | TGG | TGG | TGG | GTG | AAC | CAG | CTG | GCA | GTC | CTA | GGG | 2297 |
| Ile | Leu | Leu | Leu | Leu | Trp | Trp | Trp | Val | Asn | Gln | Leu | Ala | Val | Leu | Gly |      |
|     |     | 600 |     |     |     |     | 605 |     |     |     |     | 610 |     |     |     |      |
| CTG | CCG | GCT | GTG | GAA | GCC | GCC | GTG | GCA | GGT | GAG | GTC | TTC | GCG | GGC | CCT | 2345 |
| Leu | Pro | Ala | Val | Glu | Ala | Ala | Val | Ala | Gly | Glu | Val | Phe | Ala | Gly | Pro |      |
|     | 615 |     |     |     | 620 |     |     |     |     | 625 |     |     |     |     |     |      |
| GCC | CTG | TCC | TGG | TGT | CTG | GGA | CTC | CCG | GTC | GTC | AGT | ATG | ATA | TTG | GGT | 2393 |
| Ala | Leu | Ser | Trp | Cys | Leu | Gly | Leu | Pro | Val | Val | Ser | Met | Ile | Leu | Gly |      |
| 630 |     |     |     | 635 |     |     |     |     | 640 |     |     |     |     |     | 645 |      |
| TTG | GCA | AAC | CTG | GTG | CTG | TAC | TTT | AGA | TGG | TTG | GGA | CCC | CAA | CGC | CTG | 2441 |
| Leu | Ala | Asn | Leu | Val | Leu | Tyr | Phe | Arg | Trp | Leu | Gly | Pro | Gln | Arg | Leu |      |
|     |     |     |     | 650 |     |     |     |     | 655 |     |     |     |     | 660 |     |      |
| ATG | TTC | CTC | GTG | TTG | TGG | AAG | CTT | GCT | CGG | GGA | GCT | TTC | CCG | CTG | GCC | 2489 |
| Met | Phe | Leu | Val | Leu | Trp | Lys | Leu | Ala | Arg | Gly | Ala | Phe | Pro | Leu | Ala |      |
|     |     |     |     | 665 |     |     |     |     | 670 |     |     |     |     | 675 |     |      |
| CTC | TTG | ATG | GGG | ATT | TCG | GCG | ACC | CGC | GGG | CGC | ACC | TCA | GTG | CTC | GGG | 2537 |
| Leu | Leu | Met | Gly | Ile | Ser | Ala | Thr | Arg | Gly | Arg | Thr | Ser | Val | Leu | Gly |      |
|     |     | 680 |     |     |     |     | 685 |     |     |     |     | 690 |     |     |     |      |
| GCC | GAG | TTC | TGC | TTC | GAT | GCT | ACA | TTC | GAG | GTG | GAC | ACT | TCG | GTG | TTG | 2585 |
| Ala | Glu | Phe | Cys | Phe | Asp | Ala | Thr | Phe | Glu | Val | Asp | Thr | Ser | Val | Leu |      |
|     | 695 |     |     |     | 700 |     |     |     |     | 705 |     |     |     |     |     |      |
| GGC | TGG | GTG | GTG | GCC | AGT | GTG | GTA | GCT | TGG | GCC | ATT | GCG | CTC | CTG | AGC | 2633 |
| Gly | Trp | Val | Val | Ala | Ser | Val | Val | Ala | Trp | Ala | Ile | Ala | Leu | Leu | Ser |      |
| 710 |     |     |     |     | 715 |     |     |     |     | 720 |     |     |     |     | 725 |      |
| TCG | ATG | AGC | GCA | GGG | GGG | TGG | AGG | CAC | AAA | GCC | GTG | ATC | TAT | AGG | ACG | 2681 |
| Ser | Met | Ser | Ala | Gly | Gly | Trp | Arg | His | Lys | Ala | Val | Ile | Tyr | Arg | Thr |      |
|     |     |     |     | 730 |     |     |     |     | 735 |     |     |     |     | 740 |     |      |
| TGG | TGT | AAG | GGG | TAC | CAG | GCA | ATC | CGT | CAA | AGG | GTG | GTG | AGG | AGC | CCC | 2729 |
| Trp | Cys | Lys | Gly | Tyr | Gln | Ala | Ile | Arg | Gln | Arg | Val | Val | Arg | Ser | Pro |      |
|     |     |     | 745 |     |     |     |     | 750 |     |     |     |     | 755 |     |     |      |
| CTC | GGG | GAG | GGG | CGG | CCT | GCC | AAA | CCC | CTG | ACC | TTT | GCC | TGG | TGC | TTG | 2777 |
| Leu | Gly | Glu | Gly | Arg | Pro | Ala | Lys | Pro | Leu | Thr | Phe | Ala | Trp | Cys | Leu |      |

-continued

| | | | | | 760 | | | | | 765 | | | | | 770 | | | | |
|---|---|---|---|---|---|---|---|---|---|---|---|---|---|---|---|---|---|---|---|
| GCC | TCG | TAC | ATC | TGG | CCA | GAT | GCT | GTG | ATG | ATG | GTG | GTG | GTT | GCC | TTG | | | | 2825 |
| Ala | Ser | Tyr | Ile | Trp | Pro | Asp | Ala | Val | Met | Met | Val | Val | Val | Ala | Leu | | | | |
| | 775 | | | | | 780 | | | | 785 | | | | | | | | | |
| GTC | CTT | CTC | TTT | GGC | CTG | TTC | GAC | GCG | TTG | GAT | TGG | GCC | TTG | GAG | GAG | | | | 2873 |
| Val | Leu | Leu | Phe | Gly | Leu | Phe | Asp | Ala | Leu | Asp | Trp | Ala | Leu | Glu | Glu | | | | |
| 790 | | | | | 795 | | | | 800 | | | | | | 805 | | | | |
| ATC | TTG | GTG | TCC | CGG | CCC | TCG | TTG | CGG | CGT | TTG | GCT | CGG | GTG | GTT | GAG | | | | 2921 |
| Ile | Leu | Val | Ser | Arg | Pro | Ser | Leu | Arg | Arg | Leu | Ala | Arg | Val | Val | Glu | | | | |
| | | | | 810 | | | | | 815 | | | | | 820 | | | | | |
| TGC | TGT | GTG | ATG | GCG | GGT | GAG | AAG | GCC | ACA | ACC | GTC | CGG | CTG | GTC | TCC | | | | 2969 |
| Cys | Cys | Val | Met | Ala | Gly | Glu | Lys | Ala | Thr | Thr | Val | Arg | Leu | Val | Ser | | | | |
| | | | 825 | | | | | 830 | | | | | 835 | | | | | | |
| AAG | ATG | TGT | GCG | AGA | GGA | GCT | TAT | TTG | TTC | GAT | CAT | ATG | GGC | TCT | TTT | | | | 3017 |
| Lys | Met | Cys | Ala | Arg | Gly | Ala | Tyr | Leu | Phe | Asp | His | Met | Gly | Ser | Phe | | | | |
| | | | 840 | | | | | 845 | | | | | 850 | | | | | | |
| TCG | CGT | GCT | GTC | AAG | GAG | CGC | CTG | TTG | GAA | TGG | GAC | GCA | GCT | CTT | GAA | | | | 3065 |
| Ser | Arg | Ala | Val | Lys | Glu | Arg | Leu | Leu | Glu | Trp | Asp | Ala | Ala | Leu | Glu | | | | |
| | 855 | | | | | 860 | | | | | 865 | | | | | | | | |
| CCT | CTG | TCA | TTC | ACT | AGG | ACG | GAC | TGT | CGC | ATC | ATA | CGG | GAT | GCC | GCG | | | | 3113 |
| Pro | Leu | Ser | Phe | Thr | Arg | Thr | Asp | Cys | Arg | Ile | Ile | Arg | Asp | Ala | Ala | | | | |
| 870 | | | | | 875 | | | | | 880 | | | | | 885 | | | | |
| AGG | ACT | TTG | TCC | TGC | GGG | CAG | TGC | GTC | ATG | GGT | TTA | CCC | GTG | GTT | GCG | | | | 3161 |
| Arg | Thr | Leu | Ser | Cys | Gly | Gln | Cys | Val | Met | Gly | Leu | Pro | Val | Val | Ala | | | | |
| | | | | 890 | | | | | 895 | | | | | 900 | | | | | |
| CGC | CGT | GGT | GAT | GAG | GTT | CTC | ATC | GGC | GTC | TTC | CAG | GAT | GTG | AAT | CAT | | | | 3209 |
| Arg | Arg | Gly | Asp | Glu | Val | Leu | Ile | Gly | Val | Phe | Gln | Asp | Val | Asn | His | | | | |
| | | | | 905 | | | | | 910 | | | | | 915 | | | | | |
| TTG | CCT | CCC | GGG | TTT | GTT | CCG | ACC | GCG | CCT | GTT | GTC | ATC | CGA | CGG | TGC | | | | 3257 |
| Leu | Pro | Pro | Gly | Phe | Val | Pro | Thr | Ala | Pro | Val | Val | Ile | Arg | Arg | Cys | | | | |
| | | 920 | | | | | 925 | | | | | 930 | | | | | | | |
| GGA | AAG | GGC | TTC | TTG | GGG | GTC | ACA | AAG | GCT | GCC | TTG | ACA | GGT | CGG | GAT | | | | 3305 |
| Gly | Lys | Gly | Phe | Leu | Gly | Val | Thr | Lys | Ala | Ala | Leu | Thr | Gly | Arg | Asp | | | | |
| | 935 | | | | | 940 | | | | | 945 | | | | | | | | |
| CCT | GAC | TTA | CAT | CCA | GGG | AAC | GTC | ATG | GTG | TTG | GGG | ACG | GCT | ACG | TCG | | | | 3353 |
| Pro | Asp | Leu | His | Pro | Gly | Asn | Val | Met | Val | Leu | Gly | Thr | Ala | Thr | Ser | | | | |
| 950 | | | | | 955 | | | | | 960 | | | | | 965 | | | | |
| CGA | AGC | ATG | GGA | ACA | TGC | TTG | AAC | GGC | CTG | CTG | TTC | ACG | ACC | TTC | CAT | | | | 3401 |
| Arg | Ser | Met | Gly | Thr | Cys | Leu | Asn | Gly | Leu | Leu | Phe | Thr | Thr | Phe | His | | | | |
| | | | 970 | | | | | 975 | | | | | 980 | | | | | | |
| GGG | GCT | TCA | TCC | CGA | ACC | ATC | GCC | ACA | CCC | GTG | GGG | GCC | CTT | AAT | CCC | | | | 3449 |
| Gly | Ala | Ser | Ser | Arg | Thr | Ile | Ala | Thr | Pro | Val | Gly | Ala | Leu | Asn | Pro | | | | |
| | | | 985 | | | | | 990 | | | | | 995 | | | | | | |
| AGA | TGG | TGG | TCA | GCC | AGT | GAT | GAT | GTC | ACG | GTG | TAT | CCA | CTC | CCG | GAT | | | | 3497 |
| Arg | Trp | Trp | Ser | Ala | Ser | Asp | Asp | Val | Thr | Val | Tyr | Pro | Leu | Pro | Asp | | | | |
| | | | 1000 | | | | | 1005 | | | | | 1010 | | | | | | |
| GGG | GCT | ACT | TCG | TTA | ACA | CCT | TGT | ACT | TGC | CAG | GCT | GAG | TCC | TGT | TGG | | | | 3545 |
| Gly | Ala | Thr | Ser | Leu | Thr | Pro | Cys | Thr | Cys | Gln | Ala | Glu | Ser | Cys | Trp | | | | |
| | | 1015 | | | | | 1020 | | | | | 1025 | | | | | | | |
| GTC | ATC | AGA | TCC | GAC | GGG | GCC | CTA | TGC | CAT | GGC | TTG | AGC | AAG | GGG | GAC | | | | 3593 |
| Val | Ile | Arg | Ser | Asp | Gly | Ala | Leu | Cys | His | Gly | Leu | Ser | Lys | Gly | Asp | | | | |
| 1030 | | | | | 1035 | | | | | 1040 | | | | | 1045 | | | | |
| AAG | GTG | GAG | CTG | GAT | GTG | GCC | ATG | GAG | GTC | TCT | GAC | TTC | CGT | GGC | TCG | | | | 3641 |
| Lys | Val | Glu | Leu | Asp | Val | Ala | Met | Glu | Val | Ser | Asp | Phe | Arg | Gly | Ser | | | | |
| | | | | 1050 | | | | | 1055 | | | | | | 1060 | | | | |
| TCT | GGC | TCA | CCG | GTC | CTA | TGT | GAC | GAA | GGG | CAC | GCA | GTA | GGA | ATG | CTC | | | | 3689 |
| Ser | Gly | Ser | Pro | Val | Leu | Cys | Asp | Glu | Gly | His | Ala | Val | Gly | Met | Leu | | | | |
| | | | 1065 | | | | | 1070 | | | | | 1075 | | | | | | |
| GTG | TCT | GTG | CTT | CAC | TCC | GGT | GGT | AGG | GTC | ACC | GCG | GCA | CGG | TTC | ACT | | | | 3737 |
| Val | Ser | Val | Leu | His | Ser | Gly | Gly | Arg | Val | Thr | Ala | Ala | Arg | Phe | Thr | | | | |

```
                   1080                          1085                         1090
AGG  CCG  TGG  ACC  CAA  GTG  CCA  ACA  GAT  GCC  AAA  ACC  ACT  ACT  GAA  CCC          3785
Arg  Pro  Trp  Thr  Gln  Val  Pro  Thr  Asp  Ala  Lys  Thr  Thr  Thr  Glu  Pro
     1095                          1100                         1105

CCT  CCG  GTG  CCG  GCC  AAA  GGA  GTT  TTC  AAA  GAG  GCC  CCG  TTG  TTT  ATG          3833
Pro  Pro  Val  Pro  Ala  Lys  Gly  Val  Phe  Lys  Glu  Ala  Pro  Leu  Phe  Met
1110                          1115                         1120                    1125

CCT  ACG  GGA  GCG  GGA  AAG  AGC  ACT  CGC  GTC  CCG  TTG  GAG  TAC  GAT  AAC          3881
Pro  Thr  Gly  Ala  Gly  Lys  Ser  Thr  Arg  Val  Pro  Leu  Glu  Tyr  Asp  Asn
                    1130                         1135                        1140

ATG  GGG  CAC  AAG  GTC  TTA  ATC  TTG  AAC  CCC  TCA  GTG  GCC  ACT  GTG  CGG          3929
Met  Gly  His  Lys  Val  Leu  Ile  Leu  Asn  Pro  Ser  Val  Ala  Thr  Val  Arg
               1145                         1150                        1155

GCC  ATG  GGC  CCG  TAC  ATG  GAG  CGG  CTG  GCG  GGT  AAA  CAT  CCA  AGT  ATA          3977
Ala  Met  Gly  Pro  Tyr  Met  Glu  Arg  Leu  Ala  Gly  Lys  His  Pro  Ser  Ile
          1160                         1165                        1170

TAC  TGT  GGG  CAT  GAT  ACA  ACT  GCT  TTC  ACA  AGG  ATC  ACT  GAC  TCC  CCC          4025
Tyr  Cys  Gly  His  Asp  Thr  Thr  Ala  Phe  Thr  Arg  Ile  Thr  Asp  Ser  Pro
     1175                         1180                        1185

CTG  ACG  TAT  TCA  ACC  TAT  GGG  AGG  TTT  TTG  GCC  AAC  CCT  AGG  CAG  ATG          4073
Leu  Thr  Tyr  Ser  Thr  Tyr  Gly  Arg  Phe  Leu  Ala  Asn  Pro  Arg  Gln  Met
1190                          1195                         1200                    1205

CTA  CGG  GGC  GTT  TCG  GTG  GTC  ATT  TGT  GAT  GAG  TGC  CAC  AGT  CAT  GAC          4121
Leu  Arg  Gly  Val  Ser  Val  Val  Ile  Cys  Asp  Glu  Cys  His  Ser  His  Asp
                    1210                         1215                        1220

TCA  ACC  GTG  CTG  TTA  GGC  ATT  GGG  AGA  GTC  CGG  GAG  CTG  GCG  CGT  GGG          4169
Ser  Thr  Val  Leu  Leu  Gly  Ile  Gly  Arg  Val  Arg  Glu  Leu  Ala  Arg  Gly
               1225                         1230                        1235

TGC  GGG  GTG  CAA  CTA  GTG  CTC  TAC  GCC  ACC  GCT  ACA  CCT  CCC  GGA  TCC          4217
Cys  Gly  Val  Gln  Leu  Val  Leu  Tyr  Ala  Thr  Ala  Thr  Pro  Pro  Gly  Ser
          1240                         1245                        1250

CCT  ATG  ACG  CAG  CAC  CCT  TCC  ATA  ATT  GAG  ACA  AAA  TTG  GAC  GTG  GGC          4265
Pro  Met  Thr  Gln  His  Pro  Ser  Ile  Ile  Glu  Thr  Lys  Leu  Asp  Val  Gly
     1255                         1260                        1265

GAG  ATT  CCC  TTT  TAT  GGG  CAT  GGA  ATA  CCC  CTC  GAG  CGG  ATG  CGA  ACC          4313
Glu  Ile  Pro  Phe  Tyr  Gly  His  Gly  Ile  Pro  Leu  Glu  Arg  Met  Arg  Thr
1270                          1275                         1280                    1285

GGA  AGG  CAC  CTC  GTG  TTC  TGC  CAT  TCT  AAG  GCT  GAG  TGC  GAG  CGC  CTT          4361
Gly  Arg  His  Leu  Val  Phe  Cys  His  Ser  Lys  Ala  Glu  Cys  Glu  Arg  Leu
                    1290                         1295                        1300

GCT  GGC  CAG  TTC  TCC  GCT  AGG  GGG  GTC  AAT  GCC  ATT  GCC  TAT  TAT  AGG          4409
Ala  Gly  Gln  Phe  Ser  Ala  Arg  Gly  Val  Asn  Ala  Ile  Ala  Tyr  Tyr  Arg
               1305                         1310                        1315

GGT  AAA  GAC  AGT  TCT  ATC  ATC  AAG  GAT  GGG  GAC  CTG  GTG  GTC  TGT  GCT          4457
Gly  Lys  Asp  Ser  Ser  Ile  Ile  Lys  Asp  Gly  Asp  Leu  Val  Val  Cys  Ala
          1320                         1325                        1330

ACA  GAC  GCG  CTT  TCC  ACT  GGG  TAC  ACT  GGA  AAT  TTC  GAC  TCC  GTC  ACC          4505
Thr  Asp  Ala  Leu  Ser  Thr  Gly  Tyr  Thr  Gly  Asn  Phe  Asp  Ser  Val  Thr
     1335                         1340                        1345

GAC  TGT  GGA  TTA  GTG  GTG  GAG  GAG  GTC  GTT  GAG  GTG  ACC  CTT  GAT  CCC          4553
Asp  Cys  Gly  Leu  Val  Val  Glu  Glu  Val  Val  Glu  Val  Thr  Leu  Asp  Pro
1350                          1355                         1360                    1365

ACC  ATT  ACC  ATC  TCC  CTG  CGG  ACA  GTG  CCT  GCG  TCG  GCT  GAA  CTG  TCG          4601
Thr  Ile  Thr  Ile  Ser  Leu  Arg  Thr  Val  Pro  Ala  Ser  Ala  Glu  Leu  Ser
                    1370                         1375                        1380

ATG  CAA  AGA  CGA  GGA  CGC  ACG  GGT  AGG  GGC  AGG  TCT  GGA  CGC  TAC  TAC          4649
Met  Gln  Arg  Arg  Gly  Arg  Thr  Gly  Arg  Gly  Arg  Ser  Gly  Arg  Tyr  Tyr
               1385                         1390                        1395

TAC  GCG  GGG  GTG  GGC  AAA  GCC  CCT  GCG  GGT  GTG  GTG  CGC  TCA  GGT  CCT          4697
Tyr  Ala  Gly  Val  Gly  Lys  Ala  Pro  Ala  Gly  Val  Val  Arg  Ser  Gly  Pro
```

-continued

```
          1400                    1405                    1410
GTC  TGG  TCG  GCG  GTG  GAA  GCT  GGA  GTG  ACC  TGG  TAC  GGA  ATG  GAA  CCT          4745
Val  Trp  Ser  Ala  Val  Glu  Ala  Gly  Val  Thr  Trp  Tyr  Gly  Met  Glu  Pro
     1415                    1420                    1425

GAC  TTG  ACA  GCT  AAC  CTA  CTG  AGA  CTT  TAC  GAC  GAC  TGC  CCT  TAC  ACC          4793
Asp  Leu  Thr  Ala  Asn  Leu  Leu  Arg  Leu  Tyr  Asp  Asp  Cys  Pro  Tyr  Thr
1430                    1435                    1440                    1445

GCA  GCC  GTC  GCG  GCT  GAT  ATC  GGA  GAA  GCC  GCG  GTG  TTC  TTC  TCT  GGG          4841
Ala  Ala  Val  Ala  Ala  Asp  Ile  Gly  Glu  Ala  Ala  Val  Phe  Phe  Ser  Gly
                    1450                    1455                    1460

CTC  GCC  CCA  TTG  AGG  ATG  CAC  CCT  GAT  GTC  AGC  TGG  GCA  AAA  GTT  CGC          4889
Leu  Ala  Pro  Leu  Arg  Met  His  Pro  Asp  Val  Ser  Trp  Ala  Lys  Val  Arg
               1465                    1470                    1475

GGC  GTC  AAC  TGG  CCC  CTC  TTG  GTG  GGT  GTT  CAG  CGG  ACC  ATG  TGT  CGG          4937
Gly  Val  Asn  Trp  Pro  Leu  Leu  Val  Gly  Val  Gln  Arg  Thr  Met  Cys  Arg
          1480                    1485                    1490

GAA  ACA  CTG  TCT  CCC  GGC  CCA  TCG  GAT  GAC  CCC  CAA  TGG  GCA  GGT  CTG          4985
Glu  Thr  Leu  Ser  Pro  Gly  Pro  Ser  Asp  Asp  Pro  Gln  Trp  Ala  Gly  Leu
     1495                    1500                    1505

AAG  GGC  CCA  AAT  CCT  GTC  CCA  CTC  CTG  CTG  AGG  TGG  GGC  AAT  GAT  TTA          5033
Lys  Gly  Pro  Asn  Pro  Val  Pro  Leu  Leu  Leu  Arg  Trp  Gly  Asn  Asp  Leu
1510                    1515                    1520                    1525

CCA  TCT  AAA  GTG  GCC  GGC  CAC  CAC  ATA  GTG  GAC  GAC  CTG  GTC  CGG  AGA          5081
Pro  Ser  Lys  Val  Ala  Gly  His  His  Ile  Val  Asp  Asp  Leu  Val  Arg  Arg
                    1530                    1535                    1540

CTC  GGT  GTG  GCG  GAG  GGT  TAC  GTC  CGC  TGC  GAC  GCT  GGG  CCG  ATC  TTG          5129
Leu  Gly  Val  Ala  Glu  Gly  Tyr  Val  Arg  Cys  Asp  Ala  Gly  Pro  Ile  Leu
               1545                    1550                    1555

ATG  ATC  GGT  CTA  GCT  ATC  GCG  GGG  GGA  ATG  ATC  TAC  GCG  TCA  TAC  ACC          5177
Met  Ile  Gly  Leu  Ala  Ile  Ala  Gly  Gly  Met  Ile  Tyr  Ala  Ser  Tyr  Thr
          1560                    1565                    1570

GGG  TCG  CTA  GTG  GTG  GTG  ACA  GAC  TGG  GAT  GTG  AAG  GGG  GGT  GGC  GCC          5225
Gly  Ser  Leu  Val  Val  Val  Thr  Asp  Trp  Asp  Val  Lys  Gly  Gly  Gly  Ala
     1575                    1580                    1585

CCC  CTT  TAT  CGG  CAT  GGA  GAC  CAG  GCC  ACG  CCT  CAG  CCG  GTG  GTG  CAG          5273
Pro  Leu  Tyr  Arg  His  Gly  Asp  Gln  Ala  Thr  Pro  Gln  Pro  Val  Val  Gln
1590                    1595                    1600                    1605

GTT  CCT  CCG  GTA  GAC  CAT  CGG  CCG  GGG  GGT  GAA  TCA  GCA  CCA  TCG  GAT          5321
Val  Pro  Pro  Val  Asp  His  Arg  Pro  Gly  Gly  Glu  Ser  Ala  Pro  Ser  Asp
                    1610                    1615                    1620

GCC  AAG  ACA  GTG  ACA  GAT  GCG  GTG  GCA  GCC  ATC  CAG  GTG  GAC  TGC  GAT          5369
Ala  Lys  Thr  Val  Thr  Asp  Ala  Val  Ala  Ala  Ile  Gln  Val  Asp  Cys  Asp
               1625                    1630                    1635

TGG  ACT  ATC  ATG  ACT  CTG  TCG  ATC  GGA  GAA  GTG  TTG  TCC  TTG  GCT  CAG          5417
Trp  Thr  Ile  Met  Thr  Leu  Ser  Ile  Gly  Glu  Val  Leu  Ser  Leu  Ala  Gln
          1640                    1645                    1650

GCT  AAG  ACG  GCC  GAG  GCC  TAC  ACA  GCA  ACC  GCC  AAG  TGG  CTC  GCT  GGC          5465
Ala  Lys  Thr  Ala  Glu  Ala  Tyr  Thr  Ala  Thr  Ala  Lys  Trp  Leu  Ala  Gly
     1655                    1660                    1665

TGC  TAT  ACG  GGG  ACG  CGG  GCC  GTT  CCC  ACT  GTA  TCC  ATT  GTT  GAC  AAG          5513
Cys  Tyr  Thr  Gly  Thr  Arg  Ala  Val  Pro  Thr  Val  Ser  Ile  Val  Asp  Lys
1670                    1675                    1680                    1685

CTC  TTC  GCC  GGA  GGG  TGG  GCG  GCT  GTG  GTG  GGC  CAT  TGC  CAC  AGC  GTG          5561
Leu  Phe  Ala  Gly  Gly  Trp  Ala  Ala  Val  Val  Gly  His  Cys  His  Ser  Val
                    1690                    1695                    1700

ATT  GCT  GCG  GCG  GTG  GCG  GCC  TAC  GGG  GCT  TCA  AGG  AGC  CCG  CCG  TTG          5609
Ile  Ala  Ala  Ala  Val  Ala  Ala  Tyr  Gly  Ala  Ser  Arg  Ser  Pro  Pro  Leu
               1705                    1710                    1715

GCA  GCC  GCG  GCT  TCC  TAC  CTG  ATG  GGG  TTG  GGC  GTT  GGA  GGC  AAC  GCT          5657
Ala  Ala  Ala  Ala  Ser  Tyr  Leu  Met  Gly  Leu  Gly  Val  Gly  Gly  Asn  Ala
```

-continued

```
                1720                        1725                        1730
   CAG  ACG  CGC  CTG  GCG  TCT  GCC  CTC  CTA  TTG  GGG  GCT  GCT  GGA  ACC  GCC      5705
   Gln  Thr  Arg  Leu  Ala  Ser  Ala  Leu  Leu  Leu  Gly  Ala  Ala  Gly  Thr  Ala
        1735                     1740                     1745

TTG  GGC  ACT  CCT  GTC  GTG  GGC  TTG  ACC  ATG  GCA  GGT  GCG  TTC  ATG  GGG      5753
   Leu  Gly  Thr  Pro  Val  Val  Gly  Leu  Thr  Met  Ala  Gly  Ala  Phe  Met  Gly
   1750                     1755                     1760                     1765

GGG  GCC  AGT  GTC  TCC  CCC  TCC  TTG  GTC  ACC  ATT  TTA  TTG  GGG  GCC  GTC      5801
   Gly  Ala  Ser  Val  Ser  Pro  Ser  Leu  Val  Thr  Ile  Leu  Leu  Gly  Ala  Val
                            1770                     1775                     1780

GGA  GGT  TGG  GAG  GGT  GTT  GTC  AAC  GCG  GCG  AGC  CTA  GTC  TTT  GAC  TTC      5849
   Gly  Gly  Trp  Glu  Gly  Val  Val  Asn  Ala  Ala  Ser  Leu  Val  Phe  Asp  Phe
                  1785                     1790                     1795

ATG  GCG  GGG  AAA  CTT  TCA  TCA  GAA  GAT  CTG  TGG  TAT  GCC  ATC  CCG  GTA      5897
   Met  Ala  Gly  Lys  Leu  Ser  Ser  Glu  Asp  Leu  Trp  Tyr  Ala  Ile  Pro  Val
        1800                     1805                     1810

CTG  ACC  AGC  CCG  GGG  GCG  GGC  CTT  GCG  GGG  ATC  GCT  CTC  GGG  TTG  GTT      5945
   Leu  Thr  Ser  Pro  Gly  Ala  Gly  Leu  Ala  Gly  Ile  Ala  Leu  Gly  Leu  Val
   1815                     1820                     1825

TTG  TAT  TCA  GCT  AAC  AAC  TCT  GGC  ACT  ACC  ACT  TGG  TTG  AAC  CGT  CTG      5993
   Leu  Tyr  Ser  Ala  Asn  Asn  Ser  Gly  Thr  Thr  Thr  Trp  Leu  Asn  Arg  Leu
   1830                     1835                     1840                     1845

CTG  ACT  ACG  TTA  CCA  AGG  TCT  TCA  TGT  ATC  CCG  GAC  AGT  TAC  TTT  CAG      6041
   Leu  Thr  Thr  Leu  Pro  Arg  Ser  Ser  Cys  Ile  Pro  Asp  Ser  Tyr  Phe  Gln
                            1850                     1855                     1860

CAA  GTT  GAC  TAT  TGC  GAC  AAG  GTC  TCA  GCC  GTG  CTC  CGG  CGC  CTG  AGC      6089
   Gln  Val  Asp  Tyr  Cys  Asp  Lys  Val  Ser  Ala  Val  Leu  Arg  Arg  Leu  Ser
                  1865                     1870                     1875

CTC  ACC  CGC  ACA  GTG  GTT  GCC  CTG  GTC  AAC  AGG  GAG  CCT  AAG  GTG  GAT      6137
   Leu  Thr  Arg  Thr  Val  Val  Ala  Leu  Val  Asn  Arg  Glu  Pro  Lys  Val  Asp
        1880                     1885                     1890

GAG  GTA  CAG  GTG  GGG  TAT  GTC  TGG  GAC  CTG  TGG  GAG  TGG  ATC  ATG  CGC      6185
   Glu  Val  Gln  Val  Gly  Tyr  Val  Trp  Asp  Leu  Trp  Glu  Trp  Ile  Met  Arg
   1895                     1900                     1905

CAA  GTG  CGC  GTG  GTC  ATG  GCC  AGA  CTC  AGG  GCC  CTC  TGC  CCC  GTG  GTG      6233
   Gln  Val  Arg  Val  Val  Met  Ala  Arg  Leu  Arg  Ala  Leu  Cys  Pro  Val  Val
   1910                     1915                     1920                     1925

TCA  CTA  CCC  TTG  TGG  CAT  TGC  GGG  GAG  GGG  TGG  TCC  GGG  GAA  TGG  TTG      6281
   Ser  Leu  Pro  Leu  Trp  His  Cys  Gly  Glu  Gly  Trp  Ser  Gly  Glu  Trp  Leu
                            1930                     1935                     1940

CTT  GAC  GGT  CAT  GTT  GAG  AGT  CGC  TGC  CTC  TGT  GGC  TGC  GTG  ATC  ACT      6329
   Leu  Asp  Gly  His  Val  Glu  Ser  Arg  Cys  Leu  Cys  Gly  Cys  Val  Ile  Thr
                  1945                     1950                     1955

GGT  GAC  GTT  CTG  AAT  GGG  CAA  CTC  AAA  GAA  CCA  GTT  TAC  TCT  ACC  AAG      6377
   Gly  Asp  Val  Leu  Asn  Gly  Gln  Leu  Lys  Glu  Pro  Val  Tyr  Ser  Thr  Lys
        1960                     1965                     1970

CTG  TGC  CGG  CAC  TAT  TGG  ATG  GGG  ACT  GTC  CCT  GTG  AAC  ATG  CTG  GGT      6425
   Leu  Cys  Arg  His  Tyr  Trp  Met  Gly  Thr  Val  Pro  Val  Asn  Met  Leu  Gly
   1975                     1980                     1985

TAC  GGT  GAA  ACG  TCG  CCT  CTC  CTG  GCC  TCC  GAC  ACC  CCG  AAG  GTT  GTG      6473
   Tyr  Gly  Glu  Thr  Ser  Pro  Leu  Leu  Ala  Ser  Asp  Thr  Pro  Lys  Val  Val
   1990                     1995                     2000                     2005

CCC  TTC  GGG  ACG  TCT  GGC  TGG  GCT  GAG  GTG  GTG  GTG  ACC  ACT  ACC  CAC      6521
   Pro  Phe  Gly  Thr  Ser  Gly  Trp  Ala  Glu  Val  Val  Val  Thr  Thr  Thr  His
                            2010                     2015                     2020

GTG  GTA  ATC  AGG  AGG  ACC  TCC  GCC  TAT  AAG  CTG  CTG  CGC  CAG  CAA  ATC      6569
   Val  Val  Ile  Arg  Arg  Thr  Ser  Ala  Tyr  Lys  Leu  Leu  Arg  Gln  Gln  Ile
                  2025                     2030                     2035

CTA  TCG  GCT  GCT  GTA  GCT  GAG  CCC  TAC  TAC  GTC  GAC  GGC  ATT  CCG  GTC      6617
   Leu  Ser  Ala  Ala  Val  Ala  Glu  Pro  Tyr  Tyr  Val  Asp  Gly  Ile  Pro  Val
```

-continued

```
              2040                        2045                        2050

TCA  TGG  GAC  GCG  GAC  GCT  CGT  GCG  CCC  GCC  ATG  GTC  TAT  GGC  CCT  GGG         6665
Ser  Trp  Asp  Ala  Asp  Ala  Arg  Ala  Pro  Ala  Met  Val  Tyr  Gly  Pro  Gly
     2055                     2060                     2065

CAA  AGT  GTT  ACC  ATT  GAC  GGG  GAG  CGC  TAC  ACC  TTG  CCT  CAT  CAA  CTG         6713
Gln  Ser  Val  Thr  Ile  Asp  Gly  Glu  Arg  Tyr  Thr  Leu  Pro  His  Gln  Leu
2070                     2075                     2080                     2085

AGG  CTC  AGG  AAT  GTG  GCA  CCC  TCT  GAG  GTT  TCA  TCC  GAG  GTG  TCC  ATT         6761
Arg  Leu  Arg  Asn  Val  Ala  Pro  Ser  Glu  Val  Ser  Ser  Glu  Val  Ser  Ile
                    2090                     2095                     2100

GAC  ATT  GGG  ACG  GAG  ACT  GAA  GAC  TCA  GAA  CTG  ACT  GAG  GCC  GAT  CTG         6809
Asp  Ile  Gly  Thr  Glu  Thr  Glu  Asp  Ser  Glu  Leu  Thr  Glu  Ala  Asp  Leu
               2105                     2110                     2115

CCG  CCG  GCG  GCT  GCT  GCT  CTC  CAA  GCG  ATC  GAG  AAT  GCT  GCG  AGG  ATT         6857
Pro  Pro  Ala  Ala  Ala  Ala  Leu  Gln  Ala  Ile  Glu  Asn  Ala  Ala  Arg  Ile
          2120                     2125                     2130

CTT  GAA  CCG  CAC  ATT  GAT  GTC  ATC  ATG  GAG  GAC  TGC  AGT  ACA  CCC  TCT         6905
Leu  Glu  Pro  His  Ile  Asp  Val  Ile  Met  Glu  Asp  Cys  Ser  Thr  Pro  Ser
     2135                     2140                     2145

CTT  TGT  GGT  AGT  AGC  CGA  GAG  ATG  CCT  GTA  TGG  GGA  GAA  GAC  ATC  CCC         6953
Leu  Cys  Gly  Ser  Ser  Arg  Glu  Met  Pro  Val  Trp  Gly  Glu  Asp  Ile  Pro
2150                     2155                     2160                     2165

CGT  ACT  CCA  TCG  CCA  GCA  CTT  ATC  TCG  GTT  ACT  GAG  AGC  AGC  TCA  GAT         7001
Arg  Thr  Pro  Ser  Pro  Ala  Leu  Ile  Ser  Val  Thr  Glu  Ser  Ser  Ser  Asp
                    2170                     2175                     2180

GAG  AAG  ACC  CCG  TCG  GTG  TCC  TCC  TCG  CAG  GAG  GAT  ACC  CCG  TCC  TCT         7049
Glu  Lys  Thr  Pro  Ser  Val  Ser  Ser  Ser  Gln  Glu  Asp  Thr  Pro  Ser  Ser
               2185                     2190                     2195

GAC  TCA  TTC  GAG  GTC  ATC  CAA  GAG  TCC  GAG  ACA  GCC  GAA  GGG  GAG  GAA         7097
Asp  Ser  Phe  Glu  Val  Ile  Gln  Glu  Ser  Glu  Thr  Ala  Glu  Gly  Glu  Glu
          2200                     2205                     2210

AGT  GTC  TTC  AAC  GTG  GCT  CTT  TCC  GTA  TTA  AAA  GCC  TTA  TTT  CCA  CAG         7145
Ser  Val  Phe  Asn  Val  Ala  Leu  Ser  Val  Leu  Lys  Ala  Leu  Phe  Pro  Gln
     2215                     2220                     2225

AGC  GAC  GCG  ACC  AGG  AAG  CTT  ACC  GTC  AAG  ATG  TCG  TGC  TGC  GTT  GAA         7193
Ser  Asp  Ala  Thr  Arg  Lys  Leu  Thr  Val  Lys  Met  Ser  Cys  Cys  Val  Glu
2230                     2235                     2240                     2245

AAG  AGC  GTC  ACG  CGC  TTT  TTC  TCA  TTG  GGG  TTG  ACG  GTG  GCT  GAT  GTT         7241
Lys  Ser  Val  Thr  Arg  Phe  Phe  Ser  Leu  Gly  Leu  Thr  Val  Ala  Asp  Val
                    2250                     2255                     2260

GCT  AGC  CTG  TGT  GAG  ATG  GAA  ATC  CAG  AAC  CAT  ACA  GCC  TAT  TGT  GAC         7289
Ala  Ser  Leu  Cys  Glu  Met  Glu  Ile  Gln  Asn  His  Thr  Ala  Tyr  Cys  Asp
               2265                     2270                     2275

CAG  GTG  CGC  ACT  CCG  CTT  GAA  TTG  CAG  GTT  GGG  TGC  TTG  GTG  GGC  AAT         7337
Gln  Val  Arg  Thr  Pro  Leu  Glu  Leu  Gln  Val  Gly  Cys  Leu  Val  Gly  Asn
          2280                     2285                     2290

GAA  CTT  ACC  TTT  GAA  TGT  GAC  AAG  TGT  GAG  GCT  AGG  CAA  GAA  ACC  TTG         7385
Glu  Leu  Thr  Phe  Glu  Cys  Asp  Lys  Cys  Glu  Ala  Arg  Gln  Glu  Thr  Leu
     2295                     2300                     2305

GCC  TCC  TTC  TCT  TAC  ATT  TGG  TCT  GGA  GTG  CCG  CTG  ACT  AGG  GCC  ACG         7433
Ala  Ser  Phe  Ser  Tyr  Ile  Trp  Ser  Gly  Val  Pro  Leu  Thr  Arg  Ala  Thr
2310                     2315                     2320                     2325

CCG  GCC  AAG  CCT  CCC  GTG  GTG  AGG  CCG  GTT  GGC  TCT  TTG  TTA  GTG  GCC         7481
Pro  Ala  Lys  Pro  Pro  Val  Val  Arg  Pro  Val  Gly  Ser  Leu  Leu  Val  Ala
                    2330                     2335                     2340

GAC  ACT  ACT  AAG  GTG  TAT  GTT  ACC  AAT  CCA  GAC  AAT  GTG  GGA  CGG  AGG         7529
Asp  Thr  Thr  Lys  Val  Tyr  Val  Thr  Asn  Pro  Asp  Asn  Val  Gly  Arg  Arg
               2345                     2350                     2355

GTG  GAC  AAG  GTG  ACC  TTC  TGG  CGT  GCT  CCT  AGG  GTT  CAT  GAT  AAG  TAC         7577
Val  Asp  Lys  Val  Thr  Phe  Trp  Arg  Ala  Pro  Arg  Val  His  Asp  Lys  Tyr
```

-continued

|  |  |  | 2360 |  |  |  |  | 2365 |  |  |  |  | 2370 |  |  |  |  |
|---|---|---|---|---|---|---|---|---|---|---|---|---|---|---|---|---|---|---|
| CTC | GTG | GAC | TCT | ATT | GAG | CGC | GCT | AAG | AGG | GCC | GCT | CAA | GCC | TGC | CTA |  |  | 7625 |
| Leu | Val | Asp | Ser | Ile | Glu | Arg | Ala | Lys | Arg | Ala | Ala | Gln | Ala | Cys | Leu |  |  |  |
|  |  | 2375 |  |  |  |  | 2380 |  |  |  |  | 2385 |  |  |  |  |  |  |
| AGC | ATG | GGT | TAC | ACT | TAT | GAG | GAA | GCA | ATA | AGG | ACT | GTA | AGG | CCA | CAT |  |  | 7673 |
| Ser | Met | Gly | Tyr | Thr | Tyr | Glu | Glu | Ala | Ile | Arg | Thr | Val | Arg | Pro | His |  |  |  |
| 2390 |  |  |  |  | 2395 |  |  |  |  | 2400 |  |  |  |  | 2405 |  |  |  |
| GCT | GCC | ATG | GGC | TGG | GGA | TCT | AAG | GTG | TCG | GTT | AAG | GAC | TTA | GCC | ACC |  |  | 7721 |
| Ala | Ala | Met | Gly | Trp | Gly | Ser | Lys | Val | Ser | Val | Lys | Asp | Leu | Ala | Thr |  |  |  |
|  |  |  |  | 2410 |  |  |  |  | 2415 |  |  |  |  | 2420 |  |  |  |  |
| CCC | GCG | GGG | AAG | ATG | GCC | GTC | CAT | GAC | CGG | CTT | CAG | GAG | ATA | CTT | GAA |  |  | 7769 |
| Pro | Ala | Gly | Lys | Met | Ala | Val | His | Asp | Arg | Leu | Gln | Glu | Ile | Leu | Glu |  |  |  |
|  |  |  | 2425 |  |  |  |  | 2430 |  |  |  |  | 2435 |  |  |  |  |  |
| GGG | ACT | CCG | GTC | CCC | TTT | ACT | CTT | ACT | GTG | AAA | AAG | GAG | GTG | TTC | TTC |  |  | 7817 |
| Gly | Thr | Pro | Val | Pro | Phe | Thr | Leu | Thr | Val | Lys | Lys | Glu | Val | Phe | Phe |  |  |  |
|  |  | 2440 |  |  |  |  | 2445 |  |  |  |  | 2450 |  |  |  |  |  |  |
| AAA | GAC | CGG | AAG | GAG | GAG | AAG | GCC | CCC | CGC | CTC | ATT | GTG | TTC | CCC | CCC |  |  | 7865 |
| Lys | Asp | Arg | Lys | Glu | Glu | Lys | Ala | Pro | Arg | Leu | Ile | Val | Phe | Pro | Pro |  |  |  |
|  |  | 2455 |  |  |  |  | 2460 |  |  |  |  | 2465 |  |  |  |  |  |  |
| CTG | GAC | TTC | CGG | ATA | GCT | GAA | AAG | CTC | ATC | TTG | GGA | GAC | CCA | GGC | CGG |  |  | 7913 |
| Leu | Asp | Phe | Arg | Ile | Ala | Glu | Lys | Leu | Ile | Leu | Gly | Asp | Pro | Gly | Arg |  |  |  |
| 2470 |  |  |  |  | 2475 |  |  |  |  | 2480 |  |  |  |  | 2485 |  |  |  |
| GTA | GCC | AAG | GCG | GTG | TTG | GGG | GGG | GCC | TAC | GCC | TTC | CAG | TAC | ACC | CCA |  |  | 7961 |
| Val | Ala | Lys | Ala | Val | Leu | Gly | Gly | Ala | Tyr | Ala | Phe | Gln | Tyr | Thr | Pro |  |  |  |
|  |  |  |  | 2490 |  |  |  |  | 2495 |  |  |  |  | 2500 |  |  |  |  |
| AAT | CAG | CGA | GTT | AAG | GAG | ATG | CTC | AAG | CTA | TGG | GAG | TCT | AAG | AAG | ACC |  |  | 8009 |
| Asn | Gln | Arg | Val | Lys | Glu | Met | Leu | Lys | Leu | Trp | Glu | Ser | Lys | Lys | Thr |  |  |  |
|  |  |  |  | 2505 |  |  |  |  | 2510 |  |  |  |  | 2515 |  |  |  |  |
| CCT | TGC | GCC | ATC | TGT | GTG | GAC | GCC | ACC | TGC | TTC | GAC | AGT | AGC | ATA | ACT |  |  | 8057 |
| Pro | Cys | Ala | Ile | Cys | Val | Asp | Ala | Thr | Cys | Phe | Asp | Ser | Ser | Ile | Thr |  |  |  |
|  |  | 2520 |  |  |  |  | 2525 |  |  |  |  | 2530 |  |  |  |  |  |  |
| GAA | GAG | GAC | GTG | GCT | TTG | GAG | ACA | GAG | CTA | TAC | GCT | CTG | GCC | TCT | GAC |  |  | 8105 |
| Glu | Glu | Asp | Val | Ala | Leu | Glu | Thr | Glu | Leu | Tyr | Ala | Leu | Ala | Ser | Asp |  |  |  |
|  |  | 2535 |  |  |  |  | 2540 |  |  |  |  | 2545 |  |  |  |  |  |  |
| CAT | CCA | GAA | TGG | GTG | CGG | GCA | CTT | GGG | AAA | TAC | TAT | GCC | TCA | GGC | ACC |  |  | 8153 |
| His | Pro | Glu | Trp | Val | Arg | Ala | Leu | Gly | Lys | Tyr | Tyr | Ala | Ser | Gly | Thr |  |  |  |
| 2550 |  |  |  |  | 2555 |  |  |  |  | 2560 |  |  |  |  | 2565 |  |  |  |
| ATG | GTC | ACC | CCG | GAA | GGG | GTG | CCC | GTC | GGT | GAG | AGG | TAT | TGC | AGA | TCC |  |  | 8201 |
| Met | Val | Thr | Pro | Glu | Gly | Val | Pro | Val | Gly | Glu | Arg | Tyr | Cys | Arg | Ser |  |  |  |
|  |  |  |  | 2570 |  |  |  |  | 2575 |  |  |  |  | 2580 |  |  |  |  |
| TCG | GGT | GTC | CTA | ACA | ACT | AGC | GCG | AGC | AAC | TGC | TTG | ACC | TGC | TAC | ATC |  |  | 8249 |
| Ser | Gly | Val | Leu | Thr | Thr | Ser | Ala | Ser | Asn | Cys | Leu | Thr | Cys | Tyr | Ile |  |  |  |
|  |  |  |  | 2585 |  |  |  |  | 2590 |  |  |  |  | 2595 |  |  |  |  |
| AAG | GTG | AAA | GCT | GCC | TGT | GAG | AGA | GTG | GGG | CTG | AAA | AAT | GTC | TCT | CTT |  |  | 8297 |
| Lys | Val | Lys | Ala | Ala | Cys | Glu | Arg | Val | Gly | Leu | Lys | Asn | Val | Ser | Leu |  |  |  |
|  |  | 2600 |  |  |  |  | 2605 |  |  |  |  | 2610 |  |  |  |  |  |  |
| CTC | ATA | GCC | GGC | GAT | GAC | TGC | TTG | ATC | ATA | TGT | GAG | CGG | CCA | GTG | TGC |  |  | 8345 |
| Leu | Ile | Ala | Gly | Asp | Asp | Cys | Leu | Ile | Ile | Cys | Glu | Arg | Pro | Val | Cys |  |  |  |
| 2615 |  |  |  |  | 2620 |  |  |  |  | 2625 |  |  |  |  |  |  |  |  |
| GAC | CCA | AGC | GAC | GCT | TTG | GGC | AGA | GCC | CTA | GCG | AGC | TAT | GGG | TAC | GCG |  |  | 8393 |
| Asp | Pro | Ser | Asp | Ala | Leu | Gly | Arg | Ala | Leu | Ala | Ser | Tyr | Gly | Tyr | Ala |  |  |  |
| 2630 |  |  |  |  | 2635 |  |  |  |  | 2640 |  |  |  |  | 2645 |  |  |  |
| TGC | GAG | CCC | TCA | TAT | CAT | GCA | TCA | TTG | GAC | ACG | GCC | CCC | TTC | TGC | TCC |  |  | 8441 |
| Cys | Glu | Pro | Ser | Tyr | His | Ala | Ser | Leu | Asp | Thr | Ala | Pro | Phe | Cys | Ser |  |  |  |
|  |  |  |  | 2650 |  |  |  |  | 2655 |  |  |  |  | 2660 |  |  |  |  |
| ACT | TGG | CTT | GCT | GAG | TGC | AAT | GCA | GAT | GGG | AAG | CGC | CAT | TTC | TTC | CTG |  |  | 8489 |
| Thr | Trp | Leu | Ala | Glu | Cys | Asn | Ala | Asp | Gly | Lys | Arg | His | Phe | Phe | Leu |  |  |  |
|  |  |  |  | 2665 |  |  |  |  | 2670 |  |  |  |  | 2675 |  |  |  |  |
| ACC | ACG | GAC | TTC | CGG | AGG | CCG | CTC | GCT | CGC | ATG | TCG | AGT | GAG | TAT | AGT |  |  | 8537 |
| Thr | Thr | Asp | Phe | Arg | Arg | Pro | Leu | Ala | Arg | Met | Ser | Ser | Glu | Tyr | Ser |  |  |  |

-continued

```
             2680                    2685                    2690
GAC  CCG  ATG  GCT  TCG  GCG  ATC  GGT  TAC  ATC  CTC  CTT  TAT  CCT  TGG  CAC         8585
Asp  Pro  Met  Ala  Ser  Ala  Ile  Gly  Tyr  Ile  Leu  Leu  Tyr  Pro  Trp  His
          2695                    2700                    2705

CCC  ATC  ACA  CGG  TGG  GTC  ATC  ATC  CCT  CAT  GTG  CTA  ACG  TGC  GCA  TTC         8633
Pro  Ile  Thr  Arg  Trp  Val  Ile  Ile  Pro  His  Val  Leu  Thr  Cys  Ala  Phe
2710                    2715                    2720                    2725

AGG  GGT  GGA  GGC  ACA  CCG  TCT  GAT  CCG  GTT  TGG  TGC  CAG  GTG  CAT  GGT         8681
Arg  Gly  Gly  Gly  Thr  Pro  Ser  Asp  Pro  Val  Trp  Cys  Gln  Val  His  Gly
               2730                    2735                    2740

AAC  TAC  TAC  AAG  TTT  CCA  CTG  GAC  AAA  CTG  CCT  AAC  ATC  ATC  GTG  GCC         8729
Asn  Tyr  Tyr  Lys  Phe  Pro  Leu  Asp  Lys  Leu  Pro  Asn  Ile  Ile  Val  Ala
                    2745                    2750                    2755

CTC  CAC  GGA  CCA  GCA  GCG  TTG  AGG  GTT  ACC  GCA  GAC  ACA  ACT  AAA  ACA         8777
Leu  His  Gly  Pro  Ala  Ala  Leu  Arg  Val  Thr  Ala  Asp  Thr  Thr  Lys  Thr
               2760                    2765                    2770

AAG  ATG  GAG  GCT  GGT  AAG  GTT  CTG  AGC  GAC  CTC  AAG  CTC  CCT  GGC  TTA         8825
Lys  Met  Glu  Ala  Gly  Lys  Val  Leu  Ser  Asp  Leu  Lys  Leu  Pro  Gly  Leu
2775                    2780                    2785

GCA  GTC  CAC  CGA  AAG  AAG  GCC  GGG  GCG  TTG  CGA  ACA  CGC  ATG  CTC  CGC         8873
Ala  Val  His  Arg  Lys  Lys  Ala  Gly  Ala  Leu  Arg  Thr  Arg  Met  Leu  Arg
2790                    2795                    2800                    2805

TCG  CGC  GGT  TGG  GCT  GAG  TTG  GCT  AGG  GGC  TTG  TTG  TGG  CAT  CCA  GGC         8921
Ser  Arg  Gly  Trp  Ala  Glu  Leu  Ala  Arg  Gly  Leu  Leu  Trp  His  Pro  Gly
               2810                    2815                    2820

CTA  CGG  CTT  CCT  CCC  CCT  GAG  ATT  GCT  GGT  ATC  CCG  GGG  GGT  TTC  CCT         8969
Leu  Arg  Leu  Pro  Pro  Pro  Glu  Ile  Ala  Gly  Ile  Pro  Gly  Gly  Phe  Pro
                    2825                    2830                    2835

CTC  TCC  CCC  CCC  TAT  ATG  GGG  GTG  GTA  CAT  CAA  TTG  GAT  TTC  ACA  AGC         9017
Leu  Ser  Pro  Pro  Tyr  Met  Gly  Val  Val  His  Gln  Leu  Asp  Phe  Thr  Ser
               2840                    2845                    2850

CAG  AGG  AGT  CGC  TGG  CGG  TGG  TTG  GGG  TTC  TTA  GCC  CTG  CTC  ATC  GTA         9065
Gln  Arg  Ser  Arg  Trp  Arg  Trp  Leu  Gly  Phe  Leu  Ala  Leu  Leu  Ile  Val
          2855                    2860                    2865

GCC  CTC  TTC  GGG   TGAACTAAAT TCATCTGTTG CGGCAAGGTC TGGTGACTGA                      9117
Ala  Leu  Phe  Gly
2870

TCATCACCGG AGGAGGTTCC CGCCCTCCCC GCCCCAGGGG TCTCCCCGCT GGGTAAAAAG                      9177

GGCCCGGCCT TGGGAGGCAT GGTGGTTACT AACCCCCTGG CAGGGTCAAA GCCTGATGGT                      9237

GCTAATGCAC TGCCACTTCG GTGGCGGGTC GCTACCTTAT AGCGTAATCC GTGACTACGG                      9297

GCTGCTCGCA GAGCCCTCCC CGGATGGGGC ACAGTGCACT GTGATCTGAA GGGGTGCACC                      9357

CCGGGAAGAG CTCGGCCCGA AGGCCGGTTC TACT                                                  9391
```

( 2 ) INFORMATION FOR SEQ ID NO:2:

( i ) SEQUENCE CHARACTERISTICS:
        ( A ) LENGTH: 2873 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met  Gly  Pro  Pro  Ser  Ser  Ala  Ala  Ala  Cys  Ser  Arg  Gly  Ser  Pro  Arg
 1               5                        10                       15

Ile  Leu  Arg  Val  Arg  Ala  Gly  Gly  Ile  Ser  Phe  Phe  Tyr  Thr  Ile  Met
               20                       25                       30

Ala  Val  Leu  Leu  Leu  Leu  Leu  Val  Val  Glu  Ala  Gly  Ala  Ile  Leu  Ala
               35                       40                       45
```

-continued

| | | | | | | | | | | | | | | |
|---|---|---|---|---|---|---|---|---|---|---|---|---|---|---|
| Pro | Ala | Thr | His | Ala | Cys | Arg | Ala | Asn | Gly | Gln | Tyr | Phe | Leu | Thr | Asn |
| | 50 | | | | 55 | | | | 60 | | | | | |
| Cys | Cys | Ala | Pro | Glu | Asp | Ile | Gly | Phe | Cys | Leu | Glu | Gly | Gly | Cys | Leu |
| 65 | | | | 70 | | | | 75 | | | | | | 80 |
| Val | Ala | Leu | Gly | Cys | Thr | Ile | Cys | Thr | Asp | Gln | Cys | Trp | Pro | Leu | Tyr |
| | | | | 85 | | | | | 90 | | | | | 95 | |
| Gln | Ala | Gly | Leu | Ala | Val | Arg | Pro | Gly | Lys | Ser | Ala | Ala | Gln | Leu | Val |
| | | | 100 | | | | | 105 | | | | | 110 | | |
| Gly | Glu | Leu | Gly | Ser | Leu | Tyr | Gly | Pro | Leu | Ser | Val | Ser | Ala | Tyr | Val |
| | | 115 | | | | | 120 | | | | | 125 | | | |
| Ala | Gly | Ile | Leu | Gly | Leu | Gly | Glu | Val | Tyr | Ser | Gly | Val | Leu | Thr | Val |
| | 130 | | | | | 135 | | | | | 140 | | | | |
| Gly | Val | Ala | Leu | Thr | Arg | Arg | Val | Tyr | Pro | Val | Pro | Asn | Leu | Thr | Cys |
| 145 | | | | | 150 | | | | | 155 | | | | | 160 |
| Ala | Val | Ala | Cys | Glu | Leu | Lys | Trp | Glu | Ser | Glu | Phe | Trp | Arg | Trp | Thr |
| | | | | 165 | | | | | 170 | | | | | 175 | |
| Glu | Gln | Leu | Ala | Ser | Asn | Tyr | Trp | Ile | Leu | Glu | Tyr | Leu | Trp | Lys | Val |
| | | | 180 | | | | | 185 | | | | | 190 | | |
| Pro | Phe | Asp | Phe | Trp | Arg | Gly | Val | Ile | Ser | Leu | Thr | Pro | Leu | Leu | Val |
| | | 195 | | | | | 200 | | | | | 205 | | | |
| Cys | Val | Ala | Ala | Leu | Leu | Leu | Leu | Glu | Gln | Arg | Ile | Val | Met | Val | Phe |
| | 210 | | | | | 215 | | | | | 220 | | | | |
| Leu | Leu | Val | Thr | Met | Ala | Gly | Met | Ser | Gln | Gly | Ala | Pro | Ala | Ser | Val |
| 225 | | | | | 230 | | | | | 235 | | | | | 240 |
| Leu | Gly | Ser | Arg | Pro | Phe | Asp | Tyr | Gly | Leu | Thr | Trp | Gln | Thr | Cys | Ser |
| | | | | 245 | | | | | 250 | | | | | 255 | |
| Cys | Arg | Ala | Asn | Gly | Ser | Arg | Phe | Ser | Thr | Gly | Glu | Lys | Val | Trp | Asp |
| | | | 260 | | | | | 265 | | | | | 270 | | |
| Arg | Gly | Asn | Val | Thr | Leu | Gln | Cys | Asp | Cys | Pro | Asn | Gly | Pro | Trp | Val |
| | | 275 | | | | | 280 | | | | | 285 | | | |
| Trp | Leu | Pro | Ala | Phe | Cys | Gln | Ala | Ile | Gly | Trp | Gly | Asp | Pro | Ile | Thr |
| | 290 | | | | | 295 | | | | | 300 | | | | |
| Tyr | Trp | Ser | His | Gly | Gln | Asn | Gln | Trp | Pro | Leu | Ser | Cys | Pro | Gln | Tyr |
| 305 | | | | | 310 | | | | | 315 | | | | | 320 |
| Val | Tyr | Gly | Ser | Ala | Thr | Val | Thr | Cys | Val | Trp | Gly | Ser | Ala | Ser | Trp |
| | | | | 325 | | | | | 330 | | | | | 335 | |
| Phe | Ala | Ser | Thr | Ser | Gly | Arg | Asp | Ser | Lys | Ile | Asp | Val | Trp | Ser | Leu |
| | | | 340 | | | | | 345 | | | | | 350 | | |
| Val | Pro | Val | Gly | Ser | Ala | Thr | Cys | Thr | Ile | Ala | Ala | Leu | Gly | Ser | Ser |
| | | 355 | | | | | 360 | | | | | 365 | | | |
| Asp | Arg | Asp | Thr | Val | Pro | Gly | Leu | Ser | Glu | Trp | Gly | Ile | Pro | Cys | Val |
| | 370 | | | | | 375 | | | | | 380 | | | | |
| Thr | Cys | Val | Leu | Asp | Arg | Arg | Pro | Ala | Ser | Cys | Gly | Thr | Cys | Val | Arg |
| 385 | | | | | 390 | | | | | 395 | | | | | 400 |
| Asp | Cys | Trp | Pro | Glu | Thr | Gly | Ser | Val | Arg | Phe | Pro | Phe | His | Arg | Cys |
| | | | | 405 | | | | | 410 | | | | | 415 | |
| Gly | Val | Gly | Pro | Arg | Leu | Thr | Lys | Asp | Leu | Glu | Ala | Val | Pro | Phe | Val |
| | | | 420 | | | | | 425 | | | | | 430 | | |
| Asn | Arg | Thr | Thr | Pro | Phe | Thr | Ile | Arg | Gly | Pro | Leu | Gly | Asn | Gln | Gly |
| | | 435 | | | | | 440 | | | | | 445 | | | |
| Arg | Gly | Asn | Pro | Val | Arg | Ser | Pro | Leu | Gly | Phe | Gly | Ser | Tyr | Ala | Met |
| | 450 | | | | | 455 | | | | | 460 | | | | |
| Thr | Arg | Ile | Arg | Asp | Thr | Leu | His | Leu | Val | Glu | Cys | Pro | Thr | Pro | Ala |

-continued

| 465 | | | | | 470 | | | 475 | | | | | 480 |
|---|---|---|---|---|---|---|---|---|---|---|---|---|---|

Ile Glu Pro Pro Thr Gly Thr Phe Gly Phe Phe Pro Gly Thr Pro Pro
                            485                 490              495

Leu Asn Asn Cys Met Leu Leu Gly Thr Glu Val Ser Glu Ala Leu Gly
                500                 505                 510

Gly Ala Gly Leu Thr Gly Gly Phe Tyr Glu Pro Leu Val Arg Arg Cys
            515                 520                 525

Ser Lys Leu Met Gly Ser Arg Asn Pro Val Cys Pro Gly Phe Ala Trp
    530                 535                 540

Leu Ser Ser Gly Arg Pro Asp Gly Phe Ile His Val Gln Gly His Leu
545                 550                 555                 560

Gln Glu Val Asp Ala Gly Asn Phe Ile Pro Pro Arg Trp Leu Leu
                    565                 570                 575

Leu Asp Phe Val Phe Val Leu Leu Tyr Leu Met Lys Leu Ala Glu Ala
            580                 585                 590

Arg Leu Val Pro Leu Ile Leu Leu Leu Trp Trp Trp Val Asn Gln
            595             600                 605

Leu Ala Val Leu Gly Leu Pro Ala Val Glu Ala Ala Val Ala Gly Glu
    610                 615                 620

Val Phe Ala Gly Pro Ala Leu Ser Trp Cys Leu Gly Leu Pro Val Val
625                 630                 635                 640

Ser Met Ile Leu Gly Leu Ala Asn Leu Val Leu Tyr Phe Arg Trp Leu
                645                 650                 655

Gly Pro Gln Arg Leu Met Phe Leu Val Leu Trp Lys Leu Ala Arg Gly
            660                 665                 670

Ala Phe Pro Leu Ala Leu Leu Met Gly Ile Ser Ala Thr Arg Gly Arg
        675                 680                 685

Thr Ser Val Leu Gly Ala Glu Phe Cys Phe Asp Ala Thr Phe Glu Val
    690                 695                 700

Asp Thr Ser Val Leu Gly Trp Val Val Ala Ser Val Val Ala Trp Ala
705                 710                 715                 720

Ile Ala Leu Leu Ser Ser Met Ser Ala Gly Gly Trp Arg His Lys Ala
                725                 730                 735

Val Ile Tyr Arg Thr Trp Cys Lys Gly Tyr Gln Ala Ile Arg Gln Arg
            740                 745                 750

Val Val Arg Ser Pro Leu Gly Glu Gly Arg Pro Ala Lys Pro Leu Thr
        755                 760                 765

Phe Ala Trp Cys Leu Ala Ser Tyr Ile Trp Pro Asp Ala Val Met Met
    770                 775                 780

Val Val Val Ala Leu Val Leu Leu Phe Gly Leu Phe Asp Ala Leu Asp
785                 790                 795                 800

Trp Ala Leu Glu Glu Ile Leu Val Ser Arg Pro Ser Leu Arg Arg Leu
                805                 810                 815

Ala Arg Val Val Glu Cys Cys Val Met Ala Gly Glu Lys Ala Thr Thr
            820                 825                 830

Val Arg Leu Val Ser Lys Met Cys Ala Arg Gly Ala Tyr Leu Phe Asp
        835                 840                 845

His Met Gly Ser Phe Ser Arg Ala Val Lys Glu Arg Leu Leu Glu Trp
    850                 855                 860

Asp Ala Ala Leu Glu Pro Leu Ser Phe Thr Arg Thr Asp Cys Arg Ile
865                 870                 875                 880

Ile Arg Asp Ala Ala Arg Thr Leu Ser Cys Gly Gln Cys Val Met Gly
                885                 890                 895

-continued

```
Leu Pro Val Val Ala Arg Arg Gly Asp Glu Val Leu Ile Gly Val Phe
            900                 905                 910
Gln Asp Val Asn His Leu Pro Pro Gly Phe Val Pro Thr Ala Pro Val
        915                 920                 925
Val Ile Arg Arg Cys Gly Lys Gly Phe Leu Gly Val Thr Lys Ala Ala
    930                 935                 940
Leu Thr Gly Arg Asp Pro Asp Leu His Pro Gly Asn Val Met Val Leu
945                 950                 955                 960
Gly Thr Ala Thr Ser Arg Ser Met Gly Thr Cys Leu Asn Gly Leu Leu
                965                 970                 975
Phe Thr Thr Phe His Gly Ala Ser Ser Arg Thr Ile Ala Thr Pro Val
            980                 985                 990
Gly Ala Leu Asn Pro Arg Trp Trp Ser Ala Ser Asp Asp Val Thr Val
        995                 1000                1005
Tyr Pro Leu Pro Asp Gly Ala Thr Ser Leu Thr Pro Cys Thr Cys Gln
    1010                1015                1020
Ala Glu Ser Cys Trp Val Ile Arg Ser Asp Gly Ala Leu Cys His Gly
1025                1030                1035                1040
Leu Ser Lys Gly Asp Lys Val Glu Leu Asp Val Ala Met Glu Val Ser
                1045                1050                1055
Asp Phe Arg Gly Ser Ser Gly Ser Pro Val Leu Cys Asp Glu Gly His
            1060                1065                1070
Ala Val Gly Met Leu Val Ser Val Leu His Ser Gly Gly Arg Val Thr
        1075                1080                1085
Ala Ala Arg Phe Thr Arg Pro Trp Thr Gln Val Pro Thr Asp Ala Lys
    1090                1095                1100
Thr Thr Thr Glu Pro Pro Pro Val Pro Ala Lys Gly Val Phe Lys Glu
1105                1110                1115                1120
Ala Pro Leu Phe Met Pro Thr Gly Ala Gly Lys Ser Thr Arg Val Pro
                1125                1130                1135
Leu Glu Tyr Asp Asn Met Gly His Lys Val Leu Ile Leu Asn Pro Ser
            1140                1145                1150
Val Ala Thr Val Arg Ala Met Gly Pro Tyr Met Glu Arg Leu Ala Gly
        1155                1160                1165
Lys His Pro Ser Ile Tyr Cys Gly His Asp Thr Thr Ala Phe Thr Arg
    1170                1175                1180
Ile Thr Asp Ser Pro Leu Thr Tyr Ser Thr Tyr Gly Arg Phe Leu Ala
1185                1190                1195                1200
Asn Pro Arg Gln Met Leu Arg Gly Val Ser Val Val Ile Cys Asp Glu
                1205                1210                1215
Cys His Ser His Asp Ser Thr Val Leu Leu Gly Ile Gly Arg Val Arg
            1220                1225                1230
Glu Leu Ala Arg Gly Cys Gly Val Gln Leu Val Leu Tyr Ala Thr Ala
        1235                1240                1245
Thr Pro Pro Gly Ser Pro Met Thr Gln His Pro Ser Ile Ile Glu Thr
    1250                1255                1260
Lys Leu Asp Val Gly Glu Ile Pro Phe Tyr Gly His Gly Ile Pro Leu
1265                1270                1275                1280
Glu Arg Met Arg Thr Gly Arg His Leu Val Phe Cys His Ser Lys Ala
                1285                1290                1295
Glu Cys Glu Arg Leu Ala Gly Gln Phe Ser Ala Arg Gly Val Asn Ala
            1300                1305                1310
Ile Ala Tyr Tyr Arg Gly Lys Asp Ser Ser Ile Ile Lys Asp Gly Asp
        1315                1320                1325
```

-continued

```
Leu Val Val Cys Ala Thr Asp Ala Leu Ser Thr Gly Tyr Thr Gly Asn
    1330                1335                1340
Phe Asp Ser Val Thr Asp Cys Gly Leu Val Val Glu Glu Val Val Glu
1345                1350                1355                1360
Val Thr Leu Asp Pro Thr Ile Thr Ile Ser Leu Arg Thr Val Pro Ala
                1365                1370                1375
Ser Ala Glu Leu Ser Met Gln Arg Arg Gly Arg Thr Gly Arg Gly Arg
                1380                1385                1390
Ser Gly Arg Tyr Tyr Tyr Ala Gly Val Gly Lys Ala Pro Ala Gly Val
            1395                1400                1405
Val Arg Ser Gly Pro Val Trp Ser Ala Val Glu Ala Gly Val Thr Trp
    1410                1415                1420
Tyr Gly Met Glu Pro Asp Leu Thr Ala Asn Leu Leu Arg Leu Tyr Asp
1425                1430                1435                1440
Asp Cys Pro Tyr Thr Ala Ala Val Ala Ala Asp Ile Gly Glu Ala Ala
                1445                1450                1455
Val Phe Phe Ser Gly Leu Ala Pro Leu Arg Met His Pro Asp Val Ser
            1460                1465                1470
Trp Ala Lys Val Arg Gly Val Asn Trp Pro Leu Leu Val Gly Val Gln
        1475                1480                1485
Arg Thr Met Cys Arg Glu Thr Leu Ser Pro Gly Pro Ser Asp Asp Pro
    1490                1495                1500
Gln Trp Ala Gly Leu Lys Gly Pro Asn Pro Val Pro Leu Leu Leu Arg
1505                1510                1515                1520
Trp Gly Asn Asp Leu Pro Ser Lys Val Ala Gly His His Ile Val Asp
                1525                1530                1535
Asp Leu Val Arg Arg Leu Gly Val Ala Glu Gly Tyr Val Arg Cys Asp
            1540                1545                1550
Ala Gly Pro Ile Leu Met Ile Gly Leu Ala Ile Ala Gly Gly Met Ile
        1555                1560                1565
Tyr Ala Ser Tyr Thr Gly Ser Leu Val Val Val Thr Asp Trp Asp Val
    1570                1575                1580
Lys Gly Gly Gly Ala Pro Leu Tyr Arg His Gly Asp Gln Ala Thr Pro
1585                1590                1595                1600
Gln Pro Val Val Gln Val Pro Pro Val Asp His Arg Pro Gly Gly Glu
                1605                1610                1615
Ser Ala Pro Ser Asp Ala Lys Thr Val Thr Asp Ala Val Ala Ala Ile
            1620                1625                1630
Gln Val Asp Cys Asp Trp Thr Ile Met Thr Leu Ser Ile Gly Glu Val
        1635                1640                1645
Leu Ser Leu Ala Gln Ala Lys Thr Ala Glu Ala Tyr Thr Ala Thr Ala
    1650                1655                1660
Lys Trp Leu Ala Gly Cys Tyr Thr Gly Thr Arg Ala Val Pro Thr Val
1665                1670                1675                1680
Ser Ile Val Asp Lys Leu Phe Ala Gly Gly Trp Ala Ala Val Val Gly
                1685                1690                1695
His Cys His Ser Val Ile Ala Ala Ala Val Ala Ala Tyr Gly Ala Ser
            1700                1705                1710
Arg Ser Pro Pro Leu Ala Ala Ala Ala Ser Tyr Leu Met Gly Leu Gly
        1715                1720                1725
Val Gly Gly Asn Ala Gln Thr Arg Leu Ala Ser Ala Leu Leu Leu Gly
    1730                1735                1740
Ala Ala Gly Thr Ala Leu Gly Thr Pro Val Val Gly Leu Thr Met Ala
```

-continued

```
1745                      1750                      1755                      1760
Gly Ala Phe Met Gly Gly Ala Ser Val Ser Pro Ser Leu Val Thr Ile
                1765                    1770                    1775
Leu Leu Gly Ala Val Gly Gly Trp Glu Gly Val Val Asn Ala Ala Ser
                1780                    1785                    1790
Leu Val Phe Asp Phe Met Ala Gly Lys Leu Ser Ser Glu Asp Leu Trp
                1795                    1800                    1805
Tyr Ala Ile Pro Val Leu Thr Ser Pro Gly Ala Gly Leu Ala Gly Ile
                1810                    1815                    1820
Ala Leu Gly Leu Val Leu Tyr Ser Ala Asn Asn Ser Gly Thr Thr Thr
1825                    1830                    1835                    1840
Trp Leu Asn Arg Leu Leu Thr Thr Leu Pro Arg Ser Ser Cys Ile Pro
                1845                    1850                    1855
Asp Ser Tyr Phe Gln Gln Val Asp Tyr Cys Asp Lys Val Ser Ala Val
                1860                    1865                    1870
Leu Arg Arg Leu Ser Leu Thr Arg Thr Val Val Ala Leu Val Asn Arg
                1875                    1880                    1885
Glu Pro Lys Val Asp Glu Val Gln Val Gly Tyr Val Trp Asp Leu Trp
                1890                    1895                    1900
Glu Trp Ile Met Arg Gln Val Arg Val Val Met Ala Arg Leu Arg Ala
1905                    1910                    1915                    1920
Leu Cys Pro Val Val Ser Leu Pro Leu Trp His Cys Gly Glu Gly Trp
                1925                    1930                    1935
Ser Gly Glu Trp Leu Leu Asp Gly His Val Glu Ser Arg Cys Leu Cys
                1940                    1945                    1950
Gly Cys Val Ile Thr Gly Asp Val Leu Asn Gly Gln Leu Lys Glu Pro
                1955                    1960                    1965
Val Tyr Ser Thr Lys Leu Cys Arg His Tyr Trp Met Gly Thr Val Pro
                1970                    1975                    1980
Val Asn Met Leu Gly Tyr Gly Glu Thr Ser Pro Leu Leu Ala Ser Asp
1985                    1990                    1995                    2000
Thr Pro Lys Val Val Pro Phe Gly Thr Ser Gly Trp Ala Glu Val Val
                2005                    2010                    2015
Val Thr Thr Thr His Val Val Ile Arg Arg Thr Ser Ala Tyr Lys Leu
                2020                    2025                    2030
Leu Arg Gln Gln Ile Leu Ser Ala Ala Val Ala Glu Pro Tyr Tyr Val
                2035                    2040                    2045
Asp Gly Ile Pro Val Ser Trp Asp Ala Asp Ala Arg Ala Pro Ala Met
                2050                    2055                    2060
Val Tyr Gly Pro Gly Gln Ser Val Thr Ile Asp Gly Glu Arg Tyr Thr
2065                    2070                    2075                    2080
Leu Pro His Gln Leu Arg Leu Arg Asn Val Ala Pro Ser Glu Val Ser
                2085                    2090                    2095
Ser Glu Val Ser Ile Asp Ile Gly Thr Glu Thr Glu Asp Ser Glu Leu
                2100                    2105                    2110
Thr Glu Ala Asp Leu Pro Pro Ala Ala Ala Leu Gln Ala Ile Glu
                2115                    2120                    2125
Asn Ala Ala Arg Ile Leu Glu Pro His Ile Asp Val Ile Met Glu Asp
                2130                    2135                    2140
Cys Ser Thr Pro Ser Leu Cys Gly Ser Ser Arg Glu Met Pro Val Trp
2145                    2150                    2155                    2160
Gly Glu Asp Ile Pro Arg Thr Pro Ser Pro Ala Leu Ile Ser Val Thr
                2165                    2170                    2175
```

-continued

```
Glu Ser Ser Ser Asp Glu Lys Thr Pro Ser Val Ser Ser Ser Gln Glu
            2180                2185                2190
Asp Thr Pro Ser Ser Asp Ser Phe Glu Val Ile Gln Glu Ser Glu Thr
        2195                2200                2205
Ala Glu Gly Glu Glu Ser Val Phe Asn Val Ala Leu Ser Val Leu Lys
    2210                2215                2220
Ala Leu Phe Pro Gln Ser Asp Ala Thr Arg Lys Leu Thr Val Lys Met
2225                2230                2235                2240
Ser Cys Cys Val Glu Lys Ser Val Thr Arg Phe Phe Ser Leu Gly Leu
                2245                2250                2255
Thr Val Ala Asp Val Ala Ser Leu Cys Glu Met Glu Ile Gln Asn His
            2260                2265                2270
Thr Ala Tyr Cys Asp Gln Val Arg Thr Pro Leu Glu Leu Gln Val Gly
        2275                2280                2285
Cys Leu Val Gly Asn Glu Leu Thr Phe Glu Cys Asp Lys Cys Glu Ala
    2290                2295                2300
Arg Gln Glu Thr Leu Ala Ser Phe Ser Tyr Ile Trp Ser Gly Val Pro
2305                2310                2315                2320
Leu Thr Arg Ala Thr Pro Ala Lys Pro Pro Val Arg Pro Val Gly
                2325                2330                2335
Ser Leu Leu Val Ala Asp Thr Thr Lys Val Tyr Val Thr Asn Pro Asp
            2340                2345                2350
Asn Val Gly Arg Arg Val Asp Lys Val Thr Phe Trp Arg Ala Pro Arg
        2355                2360                2365
Val His Asp Lys Tyr Leu Val Asp Ser Ile Glu Arg Ala Lys Arg Ala
    2370                2375                2380
Ala Gln Ala Cys Leu Ser Met Gly Tyr Thr Tyr Glu Glu Ala Ile Arg
2385                2390                2395                2400
Thr Val Arg Pro His Ala Ala Met Gly Trp Gly Ser Lys Val Ser Val
                2405                2410                2415
Lys Asp Leu Ala Thr Pro Ala Gly Lys Met Ala Val His Asp Arg Leu
            2420                2425                2430
Gln Glu Ile Leu Glu Gly Thr Pro Val Pro Phe Thr Leu Thr Val Lys
        2435                2440                2445
Lys Glu Val Phe Phe Lys Asp Arg Lys Glu Glu Lys Ala Pro Arg Leu
    2450                2455                2460
Ile Val Phe Pro Pro Leu Asp Phe Arg Ile Ala Glu Lys Leu Ile Leu
2465                2470                2475                2480
Gly Asp Pro Gly Arg Val Ala Lys Ala Val Leu Gly Gly Ala Tyr Ala
                2485                2490                2495
Phe Gln Tyr Thr Pro Asn Gln Arg Val Lys Glu Met Leu Lys Leu Trp
            2500                2505                2510
Glu Ser Lys Lys Thr Pro Cys Ala Ile Cys Val Asp Ala Thr Cys Phe
        2515                2520                2525
Asp Ser Ser Ile Thr Glu Glu Asp Val Ala Leu Glu Thr Glu Leu Tyr
    2530                2535                2540
Ala Leu Ala Ser Asp His Pro Glu Trp Val Arg Ala Leu Gly Lys Tyr
2545                2550                2555                2560
Tyr Ala Ser Gly Thr Met Val Thr Pro Glu Gly Val Pro Val Gly Glu
                2565                2570                2575
Arg Tyr Cys Arg Ser Ser Gly Val Leu Thr Thr Ser Ala Ser Asn Cys
            2580                2585                2590
Leu Thr Cys Tyr Ile Lys Val Lys Ala Ala Cys Glu Arg Val Gly Leu
        2595                2600                2605
```

| | | | | | | | | | | | | | | |
|---|---|---|---|---|---|---|---|---|---|---|---|---|---|---|
|Lys|Asn|Val|Ser|Leu|Leu|Ile|Ala|Gly|Asp|Asp|Cys|Leu|Ile|Ile|Cys|
| |2610| | | |2615| | | |2620| | | | | |

| | | | | | | | | | | | | | | |
|---|---|---|---|---|---|---|---|---|---|---|---|---|---|---|
|Glu|Arg|Pro|Val|Cys|Asp|Pro|Ser|Asp|Ala|Leu|Gly|Arg|Ala|Leu|Ala|
|2625| | | | |2630| | | |2635| | | | | |2640|

| | | | | | | | | | | | | | | |
|---|---|---|---|---|---|---|---|---|---|---|---|---|---|---|
|Ser|Tyr|Gly|Tyr|Ala|Cys|Glu|Pro|Ser|Tyr|His|Ala|Ser|Leu|Asp|Thr|
| | | | |2645| | | |2650| | | | |2655| | |

| | | | | | | | | | | | | | | |
|---|---|---|---|---|---|---|---|---|---|---|---|---|---|---|
|Ala|Pro|Phe|Cys|Ser|Thr|Trp|Leu|Ala|Glu|Cys|Asn|Ala|Asp|Gly|Lys|
| | | |2660| | | | |2665| | | | |2670| | |

| | | | | | | | | | | | | | |
|---|---|---|---|---|---|---|---|---|---|---|---|---|---|
|Arg|His|Phe|Phe|Leu|Thr|Thr|Asp|Phe|Arg|Arg|Pro|Leu|Ala|Arg|Met|
| | |2675| | | | |2680| | | | |2685| | | |

| | | | | | | | | | | | | | |
|---|---|---|---|---|---|---|---|---|---|---|---|---|---|
|Ser|Ser|Glu|Tyr|Ser|Asp|Pro|Met|Ala|Ser|Ala|Ile|Gly|Tyr|Ile|Leu|
| |2690| | | | |2695| | | | |2700| | | | |

| | | | | | | | | | | | | | |
|---|---|---|---|---|---|---|---|---|---|---|---|---|---|
|Leu|Tyr|Pro|Trp|His|Pro|Ile|Thr|Arg|Trp|Val|Ile|Ile|Pro|His|Val|
|2705| | | | |2710| | | | |2715| | | | |2720|

| | | | | | | | | | | | | | |
|---|---|---|---|---|---|---|---|---|---|---|---|---|---|
|Leu|Thr|Cys|Ala|Phe|Arg|Gly|Gly|Gly|Thr|Pro|Ser|Asp|Pro|Val|Trp|
| | | | |2725| | | | |2730| | | | |2735| |

| | | | | | | | | | | | | | |
|---|---|---|---|---|---|---|---|---|---|---|---|---|---|
|Cys|Gln|Val|His|Gly|Asn|Tyr|Tyr|Lys|Phe|Pro|Leu|Asp|Lys|Leu|Pro|
| | | |2740| | | | |2745| | | | |2750| | |

| | | | | | | | | | | | | | |
|---|---|---|---|---|---|---|---|---|---|---|---|---|---|
|Asn|Ile|Ile|Val|Ala|Leu|His|Gly|Pro|Ala|Ala|Leu|Arg|Val|Thr|Ala|
| | |2755| | | | |2760| | | | |2765| | | |

| | | | | | | | | | | | | | |
|---|---|---|---|---|---|---|---|---|---|---|---|---|---|
|Asp|Thr|Thr|Lys|Thr|Lys|Met|Glu|Ala|Gly|Lys|Val|Leu|Ser|Asp|Leu|
|2770| | | | |2775| | | | |2780| | | | | |

| | | | | | | | | | | | | | |
|---|---|---|---|---|---|---|---|---|---|---|---|---|---|
|Lys|Leu|Pro|Gly|Leu|Ala|Val|His|Arg|Lys|Lys|Ala|Gly|Ala|Leu|Arg|
|2785| | | | |2790| | | | |2795| | | | |2800|

| | | | | | | | | | | | | | |
|---|---|---|---|---|---|---|---|---|---|---|---|---|---|
|Thr|Arg|Met|Leu|Arg|Ser|Arg|Gly|Trp|Ala|Glu|Leu|Ala|Arg|Gly|Leu|
| | | |2805| | | | |2810| | | | |2815| | |

| | | | | | | | | | | | | | |
|---|---|---|---|---|---|---|---|---|---|---|---|---|---|
|Leu|Trp|His|Pro|Gly|Leu|Arg|Leu|Pro|Pro|Pro|Glu|Ile|Ala|Gly|Ile|
| | |2820| | | | |2825| | | | |2830| | | |

| | | | | | | | | | | | | | |
|---|---|---|---|---|---|---|---|---|---|---|---|---|---|
|Pro|Gly|Gly|Phe|Pro|Leu|Ser|Pro|Pro|Tyr|Met|Gly|Val|Val|His|Gln|
| |2835| | | | |2840| | | | |2845| | | | |

| | | | | | | | | | | | | | |
|---|---|---|---|---|---|---|---|---|---|---|---|---|---|
|Leu|Asp|Phe|Thr|Ser|Gln|Arg|Ser|Arg|Trp|Arg|Trp|Leu|Gly|Phe|Leu|
|2850| | | | |2855| | | | |2860| | | | | |

| | | | | | | | |
|---|---|---|---|---|---|---|---|
|Ala|Leu|Leu|Ile|Val|Ala|Leu|Phe|Gly|
|2865| | | | |2870| | | |

( 2 ) INFORMATION FOR SEQ ID NO:3:

( i ) SEQUENCE CHARACTERISTICS:
        ( A ) LENGTH: 360 base pairs
        ( B ) TYPE: nucleic acid
        ( C ) STRANDEDNESS: double
        ( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
        ( C ) INDIVIDUAL ISOLATE: NS2B Protease Region ( x i ) SEQUENCE DESCRIPTION: SEQ ID NO:3:

ATCTTGGTGT CCCGGCCCTC GTTGCGGCGT TTGGCTCGGG TGGTTGAGTG CTGTGTGATG 60

GCGGGTGAGA AGGCCACAAC CGTCCGGCTG GTCTCCAAGA TGTGTGCGAG AGGAGCTTAT 120

TTGTTCGATC ATATGGGCTC TTTTTCGCGT GCTGTCAAGG AGCGCCTGTT GGAATGGGAC 180

GCAGCTCTTG AACCTCTGTC ATTCACTAGG ACGGACTGTC GCATCATACG GGATGCCGCG 240

| AGGACTTTGT | CCTGCGGGCA | GTGCGTCATG | GGTTTACCCG | TGGTTGCGCG | CCGTGGTGAT | 300 |
| GAGGTTCTCA | TCGGCGTCTT | CCAGGATGTG | AATCATTTGC | CTCCCGGGTT | TGTTCCGACC | 360 |

( 2 ) INFORMATION FOR SEQ ID NO:4:

( i ) SEQUENCE CHARACTERISTICS:
        ( A ) LENGTH: 573 base pairs
        ( B ) TYPE: nucleic acid
        ( C ) STRANDEDNESS: double
        ( D ) TOPOLOGY: linear ( i i ) MOLECULE TYPE: cDNA ( v i ) ORIGINAL SOURCE:
        ( C ) INDIVIDUAL ISOLATE: NS3 protease region ( x i ) SEQUENCE DESCRIPTION: SEQ ID NO:4:

| GCGCCTGTTG | TCATCCGACG | GTGCGGAAAG | GGCTTCTTGG | GGGTCACAAA | GGCTGCCTTG | 60 |
| ACAGGTCGGG | ATCCTGACTT | ACATCCAGGG | AACGTCATGG | TGTTGGGGAC | GGCTACGTCG | 120 |
| CGAAGCATGG | GAACATGCTT | GAACGGCCTG | CTGTTCACGA | CCTTCCATGG | GGCTTCATCC | 180 |
| CGAACCATCG | CCACACCCGT | GGGGGCCCTT | AATCCAGAT | GGTGGTCAGC | CAGTGATGAT | 240 |
| GTCACGGTGT | ATCCACTCCC | GGATGGGGCT | ACTTCGTTAA | CACCTTGTAC | TTGCCAGGCT | 300 |
| GAGTCCTGTT | GGGTCATCAG | ATCCGACGGG | GCCCTATGCC | ATGGCTTGAG | CAAGGGGAC | 360 |
| AAGGTGGAGC | TGGATGTGGC | CATGGAGGTC | TCTGACTTCC | GTGGCTCGTC | TGGCTCACCG | 420 |
| GTCCTATGTG | ACGAAGGGCA | CGCAGTAGGA | ATGCTCGTGT | CTGTGCTTCA | CTCCGGTGGT | 480 |
| AGGGTCACCG | CGGCACGGTT | CACTAGGCCG | TGGACCCAAG | TGCCAACAGA | TGCCAAAACC | 540 |
| ACTACTGAAC | CCCCTCCGGT | GCCGGCCAAA | GGA | | | 573 |

( 2 ) INFORMATION FOR SEQ ID NO:5:

( i ) SEQUENCE CHARACTERISTICS:
        ( A ) LENGTH: 147 base pairs
        ( B ) TYPE: nucleic acid
        ( C ) STRANDEDNESS: double
        ( D ) TOPOLOGY: linear ( i i ) MOLECULE TYPE: cDNA ( v i ) ORIGINAL SOURCE:
        ( C ) INDIVIDUAL ISOLATE: NS4A-B protease region ( x i ) SEQUENCE DESCRIPTION: SEQ ID NO:5:

| CGCTGCGACG | CTGGGCCGAT | CTTGATGATC | GGTCTAGCTA | TCGCGGGGGG | AATGATCTAC | 60 |
| GCGTCATACA | CCGGGTCGCT | AGTGGTGGTG | ACAGACTGGG | ATGTGAAGGG | GGGTGGCGCC | 120 |
| CCCCTTTATC | GGCATGGAGA | CCAGGCC | | | | 147 |

( 2 ) INFORMATION FOR SEQ ID NO:6:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i i ) MOLECULE TYPE: peptide ( v i ) ORIGINAL SOURCE:
        ( C ) INDIVIDUAL ISOLATE: Catalytic His region of HGV NS3

( x i ) SEQUENCE DESCRIPTION: SEQ ID NO:6:

Leu Phe Thr Thr Phe His Gly Ala Ser
1                 5

( 2 ) INFORMATION FOR SEQ ID NO:7:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i i ) MOLECULE TYPE: peptide ( v i ) ORIGINAL SOURCE:
        ( C ) INDIVIDUAL ISOLATE: Catalytic Asp region of HGV NS3

( x i ) SEQUENCE DESCRIPTION: SEQ ID NO:7:

Ala Ser Asp Asp Val Thr Val Tyr Pro
1               5

( 2 ) INFORMATION FOR SEQ ID NO:8:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i i ) MOLECULE TYPE: peptide ( v i ) ORIGINAL SOURCE:
        ( C ) INDIVIDUAL ISOLATE: Catalytic Ser region of HGV NS3

( x i ) SEQUENCE DESCRIPTION: SEQ ID NO:8:

Phe Arg Gly Ser Ser Gly Ser Pro Val
1               5

( 2 ) INFORMATION FOR SEQ ID NO:9:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i i ) MOLECULE TYPE: peptide ( v i ) ORIGINAL SOURCE:
        ( C ) INDIVIDUAL ISOLATE: catalytic His region of HCV NS3

( x i ) SEQUENCE DESCRIPTION: SEQ ID NO:9:

Cys Trp Thr Val Tyr His Gly Ala Gly
1               5

( 2 ) INFORMATION FOR SEQ ID NO:10:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear ( i i ) MOLECULE TYPE: peptide ( v i ) ORIGINAL SOURCE:
        ( C ) INDIVIDUAL ISOLATE: Catalytic Asp region of HCV NS3

( x i ) SEQUENCE DESCRIPTION: SEQ ID NO:10:

Asp Asp Leu Gly Trp Pro Ala Pro
1               5

( 2 ) INFORMATION FOR SEQ ID NO:11:

( i ) SEQUENCE CHARACTERISTICS:
  ( A ) LENGTH: 9 amino acids
  ( B ) TYPE: amino acid
  ( C ) STRANDEDNESS: single
  ( D ) TOPOLOGY: linear ( i i ) MOLECULE TYPE: peptide ( v i ) ORIGINAL SOURCE:
  ( C ) INDIVIDUAL ISOLATE: Catalytic Ser region of HCV NS3

( x i ) SEQUENCE DESCRIPTION: SEQ ID NO:11:

Leu Lys Gly Ser Ser Gly Gly Pro Leu
1               5

( 2 ) INFORMATION FOR SEQ ID NO:12:

( i ) SEQUENCE CHARACTERISTICS:
    ( A ) LENGTH: 9 amino acids
    ( B ) TYPE: amino acid
    ( C ) STRANDEDNESS: single
    ( D ) TOPOLOGY: linear ( i i ) MOLECULE TYPE: peptide ( v i ) ORIGINAL SOURCE:
    ( C ) INDIVIDUAL ISOLATE: Catalytic His region of Yellow Fever
        Virus NS3

( x i ) SEQUENCE DESCRIPTION: SEQ ID NO:12:

Phe His Thr Met Trp His Val Thr Arg
1               5

( 2 ) INFORMATION FOR SEQ ID NO:13:

( i ) SEQUENCE CHARACTERISTICS:
    ( A ) LENGTH: 9 amino acids
    ( B ) TYPE: amino acid
    ( C ) STRANDEDNESS: single
    ( D ) TOPOLOGY: linear ( i i ) MOLECULE TYPE: peptide ( v i ) ORIGINAL SOURCE:
    ( C ) INDIVIDUAL ISOLATE: catalytic Asp region of Yellow Fever
        Virus NS3

( x i ) SEQUENCE DESCRIPTION: SEQ ID NO:13:

Lys Glu Asp Leu Val Ala Thr Gly Gly
1               5

( 2 ) INFORMATION FOR SEQ ID NO:14:

( i ) SEQUENCE CHARACTERISTICS:
    ( A ) LENGTH: 9 amino acids
    ( B ) TYPE: amino acid
    ( C ) STRANDEDNESS: single
    ( D ) TOPOLOGY: linear ( i i ) MOLECULE TYPE: peptide ( v i ) ORIGINAL SOURCE:
    ( C ) INDIVIDUAL ISOLATE: catalytic Ser region of Yellow Fever
        Virus NS3

( x i ) SEQUENCE DESCRIPTION: SEQ ID NO:14:

Pro Ser Gly Thr Ser Gly Ser Pro Ile
1               5

( 2 ) INFORMATION FOR SEQ ID NO:15:

( i ) SEQUENCE CHARACTERISTICS:

(A) LENGTH: 9 amino acids
(B) TYPE: amino acid
(C) STRANDEDNESS: single
(D) TOPOLOGY: linear (i i) MOLECULE TYPE: peptide (v i) ORIGINAL SOURCE:
(C) INDIVIDUAL ISOLATE: catalytic His region of West Nile Fever Virus NS3

(x i) SEQUENCE DESCRIPTION: SEQ ID NO:15:

Phe His Thr Leu Trp His Thr Thr Lys
1               5

(2) INFORMATION FOR SEQ ID NO:16:

(i) SEQUENCE CHARACTERISTICS:
(A) LENGTH: 9 amino acids
(B) TYPE: amino acid
(C) STRANDEDNESS: single
(D) TOPOLOGY: linear (i i) MOLECULE TYPE: peptide (v i) ORIGINAL SOURCE:
(C) INDIVIDUAL ISOLATE: catalytic Asp region of West Nile Fever Virus NS3

(x i) SEQUENCE DESCRIPTION: SEQ ID NO:16:

Lys Glu Asp Arg Leu Cys Tyr Gly Gly
1               5

(2) INFORMATION FOR SEQ ID NO:17:

(i) SEQUENCE CHARACTERISTICS:
(A) LENGTH: 9 amino acids
(B) TYPE: amino acid
(C) STRANDEDNESS: single
(D) TOPOLOGY: linear (i i) MOLECULE TYPE: peptide (v i) ORIGINAL SOURCE:
(C) INDIVIDUAL ISOLATE: catalytic Ser region of West Nile Fever Virus NS2B (x i) SEQUENCE DESCRIPTION: SEQ ID NO:17:

Pro Thr Gly Thr Ser Gly Ser Pro Ile
1               5

(2) INFORMATION FOR SEQ ID NO:18:

(i) SEQUENCE CHARACTERISTICS:
(A) LENGTH: 9 amino acids
(B) TYPE: amino acid
(C) STRANDEDNESS: single
(D) TOPOLOGY: linear (i i) MOLECULE TYPE: peptide (v i) ORIGINAL SOURCE:
(C) INDIVIDUAL ISOLATE: catalytic His region of Murray Valley Virus NS3

(x i) SEQUENCE DESCRIPTION: SEQ ID NO:18:

Phe His Thr Leu Trp His Thr Thr Arg
1               5

(2) INFORMATION FOR SEQ ID NO:19:

(i) SEQUENCE CHARACTERISTICS:

(A) LENGTH: 9 amino acids
(B) TYPE: amino acid
(C) STRANDEDNESS: single
(D) TOPOLOGY: linear (i i) MOLECULE TYPE: peptide (v i) ORIGINAL SOURCE:
(C) INDIVIDUAL ISOLATE: catalytic Asp region of Murray Valley Virus NS3

(x i) SEQUENCE DESCRIPTION: SEQ ID NO:19:

Lys Glu Asp Arg Val Thr Tyr Gly Gly
1               5

(2) INFORMATION FOR SEQ ID NO:20:

(i) SEQUENCE CHARACTERISTICS:
(A) LENGTH: 9 amino acids
(B) TYPE: amino acid
(C) STRANDEDNESS: single
(D) TOPOLOGY: linear (i i) MOLECULE TYPE: peptide (v i) ORIGINAL SOURCE:
(C) INDIVIDUAL ISOLATE: catalytic Ser region of Murray Valley Virus NS3

(x i) SEQUENCE DESCRIPTION: SEQ ID NO:20:

Pro Thr Gly Thr Ser Gly Ser Pro Ile
1               5

(2) INFORMATION FOR SEQ ID NO:21:

(i) SEQUENCE CHARACTERISTICS:
(A) LENGTH: 9 amino acids
(B) TYPE: amino acid
(C) STRANDEDNESS: single
(D) TOPOLOGY: linear (i i) MOLECULE TYPE: peptide (v i) ORIGINAL SOURCE:
(C) INDIVIDUAL ISOLATE: catalytic His region of Kunjin Virus NS#

(x i) SEQUENCE DESCRIPTION: SEQ ID NO:21:

Phe His Thr Leu Trp His Thr Thr Lys
1               5

(2) INFORMATION FOR SEQ ID NO:22:

(i) SEQUENCE CHARACTERISTICS:
(A) LENGTH: 9 amino acids
(B) TYPE: amino acid
(C) STRANDEDNESS: single
(D) TOPOLOGY: linear (i i) MOLECULE TYPE: peptide (v i) ORIGINAL SOURCE:
(C) INDIVIDUAL ISOLATE: catalytic Asp region of Kunjin Virus NS3

(x i) SEQUENCE DESCRIPTION: SEQ ID NO:22:

Lys Glu Asp Arg Leu Cys Tyr Gly Gly
1               5

(2) INFORMATION FOR SEQ ID NO:23:

(i) SEQUENCE CHARACTERISTICS:

(A) LENGTH: 9 amino acids
(B) TYPE: amino acid
(C) STRANDEDNESS: single
(D) TOPOLOGY: linear (ii) MOLECULE TYPE: peptide (vi) ORIGINAL SOURCE:
(C) INDIVIDUAL ISOLATE: catalytic Ser region of Kunjin Virus NS3

(xi) SEQUENCE DESCRIPTION: SEQ ID NO:23:

```
Pro Thr Gly Thr Ser Gly Ser Pro Ile
1               5
```

(2) INFORMATION FOR SEQ ID NO:24:

(i) SEQUENCE CHARACTERISTICS:
(A) LENGTH: 2561 base pairs
(B) TYPE: nucleic acid
(C) STRANDEDNESS: single
(D) TOPOLOGY: linear (ii) MOLECULE TYPE: DNA (genomic)

(vi) ORIGINAL SOURCE:
(C) INDIVIDUAL ISOLATE: HGV DNA contained in vector "L"

(ix) FEATURE:
(A) NAME/KEY: CDS
(B) LOCATION: 2..2560

(xi) SEQUENCE DESCRIPTION: SEQ ID NO:24:

```
G ATC TTG GTG TCC CGG CCC TCG CTG CGG CGT TTG GCT CGG GTG GTT          46
  Ile Leu Val Ser Arg Pro Ser Leu Arg Arg Leu Ala Arg Val Val
  1               5                   10                  15

GAG TGC TGT GTG ATG GCG GGT GAG AAG GCC ACA ACC GTC CGG CTG GTC        94
Glu Cys Cys Val Met Ala Gly Glu Lys Ala Thr Thr Val Arg Leu Val
                20                  25                  30

TCC AAG ATG TGT GCG AGA GGA GCT TAT TTG TTC GAT CAT ATG GGC TCA       142
Ser Lys Met Cys Ala Arg Gly Ala Tyr Leu Phe Asp His Met Gly Ser
            35                  40                  45

TTT TCG CGT GCT GTC AAG GAG CGC CTG TTG GAA TGG GAC GCG GCT CTT       190
Phe Ser Arg Ala Val Lys Glu Arg Leu Leu Glu Trp Asp Ala Ala Leu
        50                  55                  60

GAA CCT CTG TCA TTC ACT AGG ACG GAC TGT CGC ATC ATA CGG GAT GCC       238
Glu Pro Leu Ser Phe Thr Arg Thr Asp Cys Arg Ile Ile Arg Asp Ala
    65                  70                  75

GCG AGG ACT TTG TCC TGC GGG CAA TGC GTC ATG GGT TTA CCC GTG GTT       286
Ala Arg Thr Leu Ser Cys Gly Gln Cys Val Met Gly Leu Pro Val Val
80                  85                  90                  95

GCG CGC CGT GGT GAT GAG GTT CTC ATC GGC GTC TTC CAG GAT GTG AAT       334
Ala Arg Arg Gly Asp Glu Val Leu Ile Gly Val Phe Gln Asp Val Asn
                100                 105                 110

CAT TTG CCT CCC GGG TTT GTT CCG ACC GCG CCT GTT GTC ATC CGA CGG       382
His Leu Pro Pro Gly Phe Val Pro Thr Ala Pro Val Val Ile Arg Arg
            115                 120                 125

TGC GGA AAG GGC TTC TTG GGG GTC ACA AAG GCT GCC TTG ACA GGT CGG       430
Cys Gly Lys Gly Phe Leu Gly Val Thr Lys Ala Ala Leu Thr Gly Arg
        130                 135                 140

GAT CCT GAC TTA CAT CCA GGG AAC GTC ATG GTG TTG GGG ACG GCT ACG       478
Asp Pro Asp Leu His Pro Gly Asn Val Met Val Leu Gly Thr Ala Thr
    145                 150                 155

TCG CGA AGC ATG GGA ACA TGC TTG AAC GGC CTG CTG TTC ACG ACC TTC       526
Ser Arg Ser Met Gly Thr Cys Leu Asn Gly Leu Leu Phe Thr Thr Phe
160                 165                 170                 175
```

-continued

| | | | | | | | | | | | | | | | | |
|---|---|---|---|---|---|---|---|---|---|---|---|---|---|---|---|---|
| CAT | GGG | GCT | TCA | TCC | CGA | ACC | ATC | GCC | ACA | CCC | GTG | GGG | GCC | CTT | AAT | 574 |
| His | Gly | Ala | Ser | Ser | Arg | Thr | Ile | Ala | Thr | Pro | Val | Gly | Ala | Leu | Asn | |
| | | | 180 | | | | | 185 | | | | | | 190 | | |
| CCC | AGA | TGG | TGG | TCA | GCC | AGT | GAT | GAT | GTC | ACG | GTG | TAT | CCA | CTC | CCG | 622 |
| Pro | Arg | Trp | Trp | Ser | Ala | Ser | Asp | Asp | Val | Thr | Val | Tyr | Pro | Leu | Pro | |
| | | | 195 | | | | | 200 | | | | | 205 | | | |
| GAT | GGG | GCT | ACT | TCG | TTA | ACG | CCT | TGT | ACT | TGC | CAG | GCT | GAG | TCC | TGT | 670 |
| Asp | Gly | Ala | Thr | Ser | Leu | Thr | Pro | Cys | Thr | Cys | Gln | Ala | Glu | Ser | Cys | |
| | | 210 | | | | | 215 | | | | | 220 | | | | |
| TGG | GTC | ATC | AGA | TCC | GAC | GGG | GCC | CTA | TGC | CAT | GGC | TTG | AGC | AAG | GGG | 718 |
| Trp | Val | Ile | Arg | Ser | Asp | Gly | Ala | Leu | Cys | His | Gly | Leu | Ser | Lys | Gly | |
| | 225 | | | | | 230 | | | | | 235 | | | | | |
| GAC | AAG | GTG | GAG | CTG | GAT | GTG | GCC | ATG | GAG | GTC | CCT | GAT | TTC | CGT | GGC | 766 |
| Asp | Lys | Val | Glu | Leu | Asp | Val | Ala | Met | Glu | Val | Pro | Asp | Phe | Arg | Gly | |
| 240 | | | | | 245 | | | | | 250 | | | | | 255 | |
| TCG | TCT | GGC | TCA | CCG | GTC | CTA | TGT | GAC | GAG | GGG | CAC | GCA | GTA | GGA | ATG | 814 |
| Ser | Ser | Gly | Ser | Pro | Val | Leu | Cys | Asp | Glu | Gly | His | Ala | Val | Gly | Met | |
| | | | | 260 | | | | | 265 | | | | | 270 | | |
| CTC | GTG | TCT | GTG | CTT | CAC | TCC | GGT | GGT | AGG | GTC | ACC | GCG | GCA | CGG | TTC | 862 |
| Leu | Val | Ser | Val | Leu | His | Ser | Gly | Gly | Arg | Val | Thr | Ala | Ala | Arg | Phe | |
| | | | 275 | | | | | 280 | | | | | 285 | | | |
| ACT | AGG | CCG | TGG | ACC | CAA | GTG | CCA | ACA | GAT | GCC | AAA | ACC | ACC | ACT | GAA | 910 |
| Thr | Arg | Pro | Trp | Thr | Gln | Val | Pro | Thr | Asp | Ala | Lys | Thr | Thr | Thr | Glu | |
| | | | 290 | | | | | 295 | | | | | 300 | | | |
| CCC | CCT | CCG | GTG | CCG | GCC | AAA | GGA | GTT | TTC | AAA | GAG | GCC | CCG | TTG | TTT | 958 |
| Pro | Pro | Pro | Val | Pro | Ala | Lys | Gly | Val | Phe | Lys | Glu | Ala | Pro | Leu | Phe | |
| | | 305 | | | | | 310 | | | | | 315 | | | | |
| ATG | CCT | ACG | GGA | GCG | GGA | AAG | AGC | ACT | CGC | GTC | CCG | TTG | GAG | TAC | GGC | 1006 |
| Met | Pro | Thr | Gly | Ala | Gly | Lys | Ser | Thr | Arg | Val | Pro | Leu | Glu | Tyr | Gly | |
| 320 | | | | | 325 | | | | | 330 | | | | | 335 | |
| AAC | ATG | GGG | CAC | AAG | GTC | TTA | GTC | TTG | AAC | CCC | TCA | GTG | GCC | ACT | GTG | 1054 |
| Asn | Met | Gly | His | Lys | Val | Leu | Val | Leu | Asn | Pro | Ser | Val | Ala | Thr | Val | |
| | | | | 340 | | | | | 345 | | | | | 350 | | |
| CGG | GCC | ATG | GGC | CCG | TAC | ATG | GAG | CGG | CTG | GCG | GGT | AAA | CAT | CCA | AGT | 1102 |
| Arg | Ala | Met | Gly | Pro | Tyr | Met | Glu | Arg | Leu | Ala | Gly | Lys | His | Pro | Ser | |
| | | | 355 | | | | | 360 | | | | | 365 | | | |
| ATA | TAC | TGT | GGG | CAT | GAT | ACA | ACT | GCT | TTC | ACA | AGG | ATC | ACT | GAC | TCC | 1150 |
| Ile | Tyr | Cys | Gly | His | Asp | Thr | Thr | Ala | Phe | Thr | Arg | Ile | Thr | Asp | Ser | |
| | | | 370 | | | | | 375 | | | | | 380 | | | |
| CCC | CTG | ACG | TAT | TCA | ACC | TAT | GGG | AGG | TTT | TTG | GCC | AAC | CCT | AGG | CAG | 1198 |
| Pro | Leu | Thr | Tyr | Ser | Thr | Tyr | Gly | Arg | Phe | Leu | Ala | Asn | Pro | Arg | Gln | |
| | | 385 | | | | | 390 | | | | | 395 | | | | |
| ATG | CTA | CGG | GGC | GTT | TCG | GTG | GTC | ATT | TGT | GAT | GAG | TGC | CAC | AGT | TAT | 1246 |
| Met | Leu | Arg | Gly | Val | Ser | Val | Val | Ile | Cys | Asp | Glu | Cys | His | Ser | Tyr | |
| 400 | | | | | 405 | | | | | 410 | | | | | 415 | |
| GAC | TCA | ACC | GTG | CTG | TTA | GGC | ATT | GGG | AGG | GTT | CGG | GAG | CTG | GCG | CGT | 1294 |
| Asp | Ser | Thr | Val | Leu | Leu | Gly | Ile | Gly | Arg | Val | Arg | Glu | Leu | Ala | Arg | |
| | | | | 420 | | | | | 425 | | | | | 430 | | |
| GGG | TGC | GGA | GTG | CAA | CTA | GTG | CTC | TAC | GCC | ACC | GCT | ACG | CCT | CCC | GGA | 1342 |
| Gly | Cys | Gly | Val | Gln | Leu | Val | Leu | Tyr | Ala | Thr | Ala | Thr | Pro | Pro | Gly | |
| | | | 435 | | | | | 440 | | | | | 445 | | | |
| TCC | CCT | ATG | ACG | CAG | CAC | CCT | TCC | ATA | ATT | GAG | ACA | AAA | TTG | GAC | GTG | 1390 |
| Ser | Pro | Met | Thr | Gln | His | Pro | Ser | Ile | Ile | Glu | Thr | Lys | Leu | Asp | Val | |
| | | 450 | | | | | 455 | | | | | 460 | | | | |
| GGC | GAG | ATT | CCC | TTT | TAT | GGG | CAC | GGA | ATA | CCC | CTC | GAG | CGG | ATG | CGA | 1438 |
| Gly | Glu | Ile | Pro | Phe | Tyr | Gly | His | Gly | Ile | Pro | Leu | Glu | Arg | Met | Arg | |
| | 465 | | | | | 470 | | | | | 475 | | | | | |
| ACC | GGA | AGG | CAC | CTC | GTG | TTC | TGC | CAT | TCT | AAG | GCT | GAG | TGC | GAG | CGC | 1486 |
| Thr | Gly | Arg | His | Leu | Val | Phe | Cys | His | Ser | Lys | Ala | Glu | Cys | Glu | Arg | |
| 480 | | | | 485 | | | | | 490 | | | | | 495 | | |

| | | | | | | | | | | | | | | | | |
|---|---|---|---|---|---|---|---|---|---|---|---|---|---|---|---|---|
| CTT | GCT | GGC | CAG | TTC | TCC | GCT | AGG | GGG | GTC | AAT | GCC | ATT | GCC | TAT | TAT | 1534 |
| Leu | Ala | Gly | Gln | Phe | Ser | Ala | Arg | Gly | Val | Asn | Ala | Ile | Ala | Tyr | Tyr | |
| | | | 500 | | | | | | 505 | | | | | 510 | | |
| AGG | GGT | AAA | GAC | AGT | TCT | ATC | ATC | AAG | GAT | GGG | GAC | CTG | GTG | GTC | TGT | 1582 |
| Arg | Gly | Lys | Asp | Ser | Ser | Ile | Ile | Lys | Asp | Gly | Asp | Leu | Val | Val | Cys | |
| | | | | 515 | | | | | 520 | | | | | 525 | | |
| GCC | ACA | GAC | GCG | CTT | TCC | ACT | GGG | TAC | ACT | GGA | AAT | TTC | GAC | TCC | GTC | 1630 |
| Ala | Thr | Asp | Ala | Leu | Ser | Thr | Gly | Tyr | Thr | Gly | Asn | Phe | Asp | Ser | Val | |
| | | 530 | | | | | 535 | | | | | 540 | | | | |
| ACC | GAC | TGT | GGA | TTA | GTG | GTG | GAG | GAG | GTC | GTT | GAG | GTG | ACC | CTT | GAT | 1678 |
| Thr | Asp | Cys | Gly | Leu | Val | Val | Glu | Glu | Val | Val | Glu | Val | Thr | Leu | Asp | |
| | | 545 | | | | 550 | | | | | 555 | | | | | |
| CCT | ACC | ATT | ACC | ATC | TCC | CTG | CGG | ACA | GTG | CCT | GCG | TCG | GCT | GAA | CTG | 1726 |
| Pro | Thr | Ile | Thr | Ile | Ser | Leu | Arg | Thr | Val | Pro | Ala | Ser | Ala | Glu | Leu | |
| 560 | | | | | 565 | | | | | 570 | | | | | 575 | |
| TCG | ATG | CAA | AGA | CGA | GGA | CGC | ACG | GGT | AGG | GGC | AGG | TCT | GGA | CGC | TAC | 1774 |
| Ser | Met | Gln | Arg | Arg | Gly | Arg | Thr | Gly | Arg | Gly | Arg | Ser | Gly | Arg | Tyr | |
| | | | | 580 | | | | | 585 | | | | | 590 | | |
| TAC | TAC | GCG | GGG | GTG | GGC | AAA | GCC | CCT | GCG | GGT | GTG | GTG | CGC | TCA | GGT | 1822 |
| Tyr | Tyr | Ala | Gly | Val | Gly | Lys | Ala | Pro | Ala | Gly | Val | Val | Arg | Ser | Gly | |
| | | | 595 | | | | | 600 | | | | | 605 | | | |
| CCT | GTC | TGG | TCG | GCG | GTG | GAA | GCT | GGA | GTG | ACC | TGG | TAC | GGA | ATG | GAA | 1870 |
| Pro | Val | Trp | Ser | Ala | Val | Glu | Ala | Gly | Val | Thr | Trp | Tyr | Gly | Met | Glu | |
| | | 610 | | | | | 615 | | | | | 620 | | | | |
| CCT | GAC | TTG | ACA | GCT | AAC | CTA | CTG | AGA | CTT | TAC | GAC | GAC | TGC | CCT | TAC | 1918 |
| Pro | Asp | Leu | Thr | Ala | Asn | Leu | Leu | Arg | Leu | Tyr | Asp | Asp | Cys | Pro | Tyr | |
| | 625 | | | | | 630 | | | | | 635 | | | | | |
| ACC | GCA | GCC | GTC | GCG | GCT | GAT | ATC | GGA | GAA | GCC | GCG | GTG | TTC | TTC | TCT | 1966 |
| Thr | Ala | Ala | Val | Ala | Ala | Asp | Ile | Gly | Glu | Ala | Ala | Val | Phe | Phe | Ser | |
| 640 | | | | | 645 | | | | | 650 | | | | | 655 | |
| GGG | CTC | GCC | CCA | TTG | AGG | ATG | CAC | CCT | GAT | GTC | AGC | TGG | GCA | AAA | GTT | 2014 |
| Gly | Leu | Ala | Pro | Leu | Arg | Met | His | Pro | Asp | Val | Ser | Trp | Ala | Lys | Val | |
| | | | | 660 | | | | | 665 | | | | | 670 | | |
| CGC | GGC | GTC | AAC | TGG | CCC | CTC | TTG | GTG | GGT | GTT | CAG | CGG | ACC | ATG | TGT | 2062 |
| Arg | Gly | Val | Asn | Trp | Pro | Leu | Leu | Val | Gly | Val | Gln | Arg | Thr | Met | Cys | |
| | | | 675 | | | | | 680 | | | | | 685 | | | |
| CGG | GAA | ACA | CTG | TCT | CCC | GGC | CCA | TCG | GAT | GAC | CCC | CAA | TGG | GCA | GGT | 2110 |
| Arg | Glu | Thr | Leu | Ser | Pro | Gly | Pro | Ser | Asp | Asp | Pro | Gln | Trp | Ala | Gly | |
| | | 690 | | | | | 695 | | | | | 700 | | | | |
| CTG | AAG | GGC | CCA | AAT | CCT | GTC | CCA | CTC | CTG | CTG | AGG | TGG | GGC | AAT | GAT | 2158 |
| Leu | Lys | Gly | Pro | Asn | Pro | Val | Pro | Leu | Leu | Leu | Arg | Trp | Gly | Asn | Asp | |
| 705 | | | | | 710 | | | | | 715 | | | | | | |
| TTA | CCA | TCT | AAA | GTG | GCC | GGC | CAC | CAC | ATA | GTG | GAC | GAC | CTG | GTC | CGG | 2206 |
| Leu | Pro | Ser | Lys | Val | Ala | Gly | His | His | Ile | Val | Asp | Asp | Leu | Val | Arg | |
| 720 | | | | | 725 | | | | | 730 | | | | | 735 | |
| AGA | CTC | GGT | GTG | GCG | GAG | GGT | TAC | GCC | CGC | TGC | GAC | GCT | GGG | CCG | ATC | 2254 |
| Arg | Leu | Gly | Val | Ala | Glu | Gly | Tyr | Ala | Arg | Cys | Asp | Ala | Gly | Pro | Ile | |
| | | | | 740 | | | | | 745 | | | | | 750 | | |
| TTG | ATG | ATC | GGT | CTA | GCT | ATC | GCG | GGG | GGA | ATG | ATC | TAC | GCG | TCG | TAC | 2302 |
| Leu | Met | Ile | Gly | Leu | Ala | Ile | Ala | Gly | Gly | Met | Ile | Tyr | Ala | Ser | Tyr | |
| | | | 755 | | | | | 760 | | | | | 765 | | | |
| ACC | GGG | TCG | CTA | GTG | GTG | GTG | ACA | GAC | TGG | GAT | GTG | AAG | GGG | GGT | GGC | 2350 |
| Thr | Gly | Ser | Leu | Val | Val | Val | Thr | Asp | Trp | Asp | Val | Lys | Gly | Gly | Gly | |
| | | 770 | | | | | 775 | | | | | 780 | | | | |
| GCC | CCC | CTT | TAT | CGG | CAT | GGA | GAC | CAG | GCC | ACG | CCT | CAG | CCG | GTG | GTG | 2398 |
| Ala | Pro | Leu | Tyr | Arg | His | Gly | Asp | Gln | Ala | Thr | Pro | Gln | Pro | Val | Val | |
| | 785 | | | | | 790 | | | | | 795 | | | | | |
| CAG | GTT | CCT | CCG | GTA | GAC | CAT | CGG | CCG | GGG | GGT | GAA | TCA | GCA | CCA | TCG | 2446 |
| Gln | Val | Pro | Pro | Val | Asp | His | Arg | Pro | Gly | Gly | Glu | Ser | Ala | Pro | Ser | |
| 800 | | | | | 805 | | | | | 810 | | | | | 815 | |

```
GAT  GCC  AAG  ACA  GTG  ACA  GAT  GCG  GTG  GCA  GCG  ATC  CAG  GTG  GAC  TGC        2494
Asp  Ala  Lys  Thr  Val  Thr  Asp  Ala  Val  Ala  Ala  Ile  Gln  Val  Asp  Cys
               820            825                      830

GAT  TGG  ACT  ATC  ATG  ACT  CTG  TCG  ATC  GGA  GAA  GTG  TTG  TCC  TTG  GCT        2542
Asp  Trp  Thr  Ile  Met  Thr  Leu  Ser  Ile  Gly  Glu  Val  Leu  Ser  Leu  Ala
               835                      840                      845

CAG  GCT  AAG  ACG  GCC  GAG  G                                                        2561
Gln  Ala  Lys  Thr  Ala  Glu
               850
```

( 2 ) INFORMATION FOR SEQ ID NO:25:

( i ) SEQUENCE CHARACTERISTICS:
        ( A ) LENGTH: 853 amino acids
        ( B ) TYPE: amino acid
        ( D ) TOPOLOGY: linear ( i i ) MOLECULE TYPE: protein ( x i ) SEQUENCE DESCRIPTION: SEQ ID NO:25:

```
Ile  Leu  Val  Ser  Arg  Pro  Ser  Leu  Arg  Arg  Leu  Ala  Arg  Val  Val  Glu
 1              5                        10                       15

Cys  Cys  Val  Met  Ala  Gly  Glu  Lys  Ala  Thr  Thr  Val  Arg  Leu  Val  Ser
               20                  25                       30

Lys  Met  Cys  Ala  Arg  Gly  Ala  Tyr  Leu  Phe  Asp  His  Met  Gly  Ser  Phe
               35                  40                       45

Ser  Arg  Ala  Val  Lys  Glu  Arg  Leu  Leu  Glu  Trp  Asp  Ala  Ala  Leu  Glu
     50                       55                       60

Pro  Leu  Ser  Phe  Thr  Arg  Thr  Asp  Cys  Arg  Ile  Ile  Arg  Asp  Ala  Ala
 65                      70                       75                       80

Arg  Thr  Leu  Ser  Cys  Gly  Gln  Cys  Val  Met  Gly  Leu  Pro  Val  Val  Ala
               85                       90                       95

Arg  Arg  Gly  Asp  Glu  Val  Leu  Ile  Gly  Val  Phe  Gln  Asp  Val  Asn  His
               100                      105                      110

Leu  Pro  Pro  Gly  Phe  Val  Pro  Thr  Ala  Pro  Val  Val  Ile  Arg  Arg  Cys
          115                      120                      125

Gly  Lys  Gly  Phe  Leu  Gly  Val  Thr  Lys  Ala  Ala  Leu  Thr  Gly  Arg  Asp
     130                      135                      140

Pro  Asp  Leu  His  Pro  Gly  Asn  Val  Met  Val  Leu  Gly  Thr  Ala  Thr  Ser
145                      150                      155                      160

Arg  Ser  Met  Gly  Thr  Cys  Leu  Asn  Gly  Leu  Leu  Phe  Thr  Thr  Phe  His
               165                      170                      175

Gly  Ala  Ser  Ser  Arg  Thr  Ile  Ala  Thr  Pro  Val  Gly  Ala  Leu  Asn  Pro
               180                      185                      190

Arg  Trp  Trp  Ser  Ala  Ser  Asp  Asp  Val  Thr  Val  Tyr  Pro  Leu  Pro  Asp
          195                      200                      205

Gly  Ala  Thr  Ser  Leu  Thr  Pro  Cys  Thr  Cys  Gln  Ala  Glu  Ser  Cys  Trp
     210                      215                      220

Val  Ile  Arg  Ser  Asp  Gly  Ala  Leu  Cys  His  Gly  Leu  Ser  Lys  Gly  Asp
225                      230                      235                      240

Lys  Val  Glu  Leu  Asp  Val  Ala  Met  Glu  Val  Pro  Asp  Phe  Arg  Gly  Ser
               245                      250                      255

Ser  Gly  Ser  Pro  Val  Leu  Cys  Asp  Glu  Gly  His  Ala  Val  Gly  Met  Leu
               260                      265                      270

Val  Ser  Val  Leu  His  Ser  Gly  Gly  Arg  Val  Thr  Ala  Ala  Arg  Phe  Thr
          275                      280                      285

Arg  Pro  Trp  Thr  Gln  Val  Pro  Thr  Asp  Ala  Lys  Thr  Thr  Thr  Glu  Pro
     290                      295                      300
```

```
Pro  Pro  Val  Pro  Ala  Lys  Gly  Val  Phe  Lys  Glu  Ala  Pro  Leu  Phe  Met
305            310                 315                      320

Pro  Thr  Gly  Ala  Gly  Lys  Ser  Thr  Arg  Val  Pro  Leu  Glu  Tyr  Gly  Asn
                    325                 330                      335

Met  Gly  His  Lys  Val  Leu  Val  Leu  Asn  Pro  Ser  Val  Ala  Thr  Val  Arg
               340                 345                      350

Ala  Met  Gly  Pro  Tyr  Met  Glu  Arg  Leu  Ala  Gly  Lys  His  Pro  Ser  Ile
          355                 360                      365

Tyr  Cys  Gly  His  Asp  Thr  Thr  Ala  Phe  Thr  Arg  Ile  Thr  Asp  Ser  Pro
     370                 375                 380

Leu  Thr  Tyr  Ser  Thr  Tyr  Gly  Arg  Phe  Leu  Ala  Asn  Pro  Arg  Gln  Met
385                 390                 395                          400

Leu  Arg  Gly  Val  Ser  Val  Val  Ile  Cys  Asp  Glu  Cys  His  Ser  Tyr  Asp
               405                 410                      415

Ser  Thr  Val  Leu  Leu  Gly  Ile  Gly  Arg  Val  Arg  Glu  Leu  Ala  Arg  Gly
               420                 425                      430

Cys  Gly  Val  Gln  Leu  Val  Leu  Tyr  Ala  Thr  Ala  Thr  Pro  Pro  Gly  Ser
          435                 440                      445

Pro  Met  Thr  Gln  His  Pro  Ser  Ile  Ile  Glu  Thr  Lys  Leu  Asp  Val  Gly
450                      455                 460

Glu  Ile  Pro  Phe  Tyr  Gly  His  Gly  Ile  Pro  Leu  Glu  Arg  Met  Arg  Thr
465                      470                 475                      480

Gly  Arg  His  Leu  Val  Phe  Cys  His  Ser  Lys  Ala  Glu  Cys  Glu  Arg  Leu
               485                 490                      495

Ala  Gly  Gln  Phe  Ser  Ala  Arg  Gly  Val  Asn  Ala  Ile  Ala  Tyr  Tyr  Arg
          500                 505                      510

Gly  Lys  Asp  Ser  Ser  Ile  Ile  Lys  Asp  Gly  Asp  Leu  Val  Val  Cys  Ala
     515                 520                      525

Thr  Asp  Ala  Leu  Ser  Thr  Gly  Tyr  Thr  Gly  Asn  Phe  Asp  Ser  Val  Thr
530                 535                      540

Asp  Cys  Gly  Leu  Val  Val  Glu  Glu  Val  Val  Glu  Val  Thr  Leu  Asp  Pro
545                      550                 555                      560

Thr  Ile  Thr  Ile  Ser  Leu  Arg  Thr  Val  Pro  Ala  Ser  Ala  Glu  Leu  Ser
                    565                 570                      575

Met  Gln  Arg  Arg  Gly  Arg  Thr  Gly  Arg  Gly  Arg  Ser  Gly  Arg  Tyr  Tyr
          580                 585                      590

Tyr  Ala  Gly  Val  Gly  Lys  Ala  Pro  Ala  Gly  Val  Val  Arg  Ser  Gly  Pro
          595                 600                      605

Val  Trp  Ser  Ala  Val  Glu  Ala  Gly  Val  Thr  Trp  Tyr  Gly  Met  Glu  Pro
610                      615                 620

Asp  Leu  Thr  Ala  Asn  Leu  Leu  Arg  Leu  Tyr  Asp  Asp  Cys  Pro  Tyr  Thr
625                 630                 635                          640

Ala  Ala  Val  Ala  Ala  Asp  Ile  Gly  Glu  Ala  Ala  Val  Phe  Phe  Ser  Gly
               645                 650                      655

Leu  Ala  Pro  Leu  Arg  Met  His  Pro  Asp  Val  Ser  Trp  Ala  Lys  Val  Arg
               660                 665                      670

Gly  Val  Asn  Trp  Pro  Leu  Leu  Val  Gly  Val  Gln  Arg  Thr  Met  Cys  Arg
          675                 680                      685

Glu  Thr  Leu  Ser  Pro  Gly  Pro  Ser  Asp  Asp  Pro  Gln  Trp  Ala  Gly  Leu
     690                 695                      700

Lys  Gly  Pro  Asn  Pro  Val  Pro  Leu  Leu  Leu  Arg  Trp  Gly  Asn  Asp  Leu
705                 710                 715                          720

Pro  Ser  Lys  Val  Ala  Gly  His  His  Ile  Val  Asp  Asp  Leu  Val  Arg  Arg
```

```
                              725                          730                          735
Leu  Gly  Val  Ala  Glu  Gly  Tyr  Ala  Arg  Cys  Asp  Ala  Gly  Pro  Ile  Leu
                    740                      745                     750

Met  Ile  Gly  Leu  Ala  Ile  Ala  Gly  Met  Ile  Tyr  Ala  Ser  Tyr  Thr
               755                      760                765

Gly  Ser  Leu  Val  Val  Val  Thr  Asp  Trp  Asp  Val  Lys  Gly  Gly  Gly  Ala
          770                      775                     780

Pro  Leu  Tyr  Arg  His  Gly  Asp  Gln  Ala  Thr  Pro  Gln  Pro  Val  Val  Gln
785                      790                     795                          800

Val  Pro  Pro  Val  Asp  His  Arg  Pro  Gly  Gly  Glu  Ser  Ala  Pro  Ser  Asp
                    805                      810                     815

Ala  Lys  Thr  Val  Thr  Asp  Ala  Val  Ala  Ala  Ile  Gln  Val  Asp  Cys  Asp
               820                      825                     830

Trp  Thr  Ile  Met  Thr  Leu  Ser  Ile  Gly  Glu  Val  Leu  Ser  Leu  Ala  Gln
               835                      840                     845

Ala  Lys  Thr  Ala  Glu
               850

( 2 ) INFORMATION FOR SEQ ID NO:26:

( i ) SEQUENCE CHARACTERISTICS:
        ( A ) LENGTH: 2561 base pairs
        ( B ) TYPE: nucleic acid
        ( C ) STRANDEDNESS: double
        ( D ) TOPOLOGY: linear ( i i ) MOLECULE TYPE: DNA (genomic)

( v i ) ORIGINAL SOURCE:
        ( C ) INDIVIDUAL ISOLATE: HGV DNA contained in vector "LH"

( i x ) FEATURE:
        ( A ) NAME/KEY: CDS
        ( B ) LOCATION: 2..2560

( x i ) SEQUENCE DESCRIPTION: SEQ ID NO:26:

G  ATC  TTG  GTG  TCC  CGG  CCC  TCG  CTG  CGG  CGT  TTG  GCT  CGG  GTG  GTT        46
   Ile  Leu  Val  Ser  Arg  Pro  Ser  Leu  Arg  Arg  Leu  Ala  Arg  Val  Val
   1              5                        10                       15

GAG  TGC  TGT  GTG  ATG  GCG  GGT  GAG  AAG  GCC  ACA  ACC  GTC  CGG  CTG  GTC      94
Glu  Cys  Cys  Val  Met  Ala  Gly  Glu  Lys  Ala  Thr  Thr  Val  Arg  Leu  Val
                    20                        25                       30

TCC  AAG  ATG  TGT  GCG  AGA  GGA  GCT  TAT  TTG  TTC  GAT  TAT  ATG  GGC  TCA     142
Ser  Lys  Met  Cys  Ala  Arg  Gly  Ala  Tyr  Leu  Phe  Asp  Tyr  Met  Gly  Ser
                    35                        40                       45

TTT  TCG  CGT  GCT  GTC  AAG  GAG  CGC  CTG  TTG  GAA  TGG  GAC  GCG  GCT  CTT     190
Phe  Ser  Arg  Ala  Val  Lys  Glu  Arg  Leu  Leu  Glu  Trp  Asp  Ala  Ala  Leu
          50                        55                       60

GAA  CCT  CTG  TCA  TTC  ACT  AGG  ACG  GAC  TGT  CGC  ATC  ATA  CGG  GAT  GCC     238
Glu  Pro  Leu  Ser  Phe  Thr  Arg  Thr  Asp  Cys  Arg  Ile  Ile  Arg  Asp  Ala
     65                        70                       75

GCG  AGG  ACT  TTG  TCC  TGC  GGG  CAA  TGC  GTC  ATG  GGT  TTA  CCC  GTG  GTT     286
Ala  Arg  Thr  Leu  Ser  Cys  Gly  Gln  Cys  Val  Met  Gly  Leu  Pro  Val  Val
80                        85                       90                        95

GCG  CGC  CGT  GGT  GAT  GAG  GTT  CTC  ATC  GGC  GTC  TTC  CAG  GAT  GTG  AAT     334
Ala  Arg  Arg  Gly  Asp  Glu  Val  Leu  Ile  Gly  Val  Phe  Gln  Asp  Val  Asn
                    100                       105                      110

CAT  TTG  CCT  CCC  GGG  TTT  GTT  CCG  ACC  GCG  CCT  GTT  GTC  ATC  CGA  CGG     382
His  Leu  Pro  Pro  Gly  Phe  Val  Pro  Thr  Ala  Pro  Val  Val  Ile  Arg  Arg
               115                       120                      125

TGC  GGA  AAG  GGC  TTC  TTG  GGG  GTC  ACA  AAG  GCT  GCC  TTG  ACA  GGT  CGG     430
Cys  Gly  Lys  Gly  Phe  Leu  Gly  Val  Thr  Lys  Ala  Ala  Leu  Thr  Gly  Arg
```

-continued

|     |     |     |     |     |     |     |     |     |     |     |     |     |     |     |     |      |
|-----|-----|-----|-----|-----|-----|-----|-----|-----|-----|-----|-----|-----|-----|-----|-----|------|
|     |     | 130 |     |     |     |     | 135 |     |     |     |     | 140 |     |     |     |      |
| GAT | CCT | GAC | TTA | CAT | CCA | GGG | AAC | GTC | ATG | GTG | TTG | GGG | ACG | GCT | ACG | 478  |
| Asp | Pro | Asp | Leu | His | Pro | Gly | Asn | Val | Met | Val | Leu | Gly | Thr | Ala | Thr |      |
|     | 145 |     |     |     | 150 |     |     |     |     | 155 |     |     |     |     |     |      |
| TCG | CGA | AGC | ATG | GGA | ACA | TGC | TTG | AAC | GGC | CTG | CTG | TTC | ACG | ACC | TTC | 526  |
| Ser | Arg | Ser | Met | Gly | Thr | Cys | Leu | Asn | Gly | Leu | Leu | Phe | Thr | Thr | Phe |      |
| 160 |     |     |     |     | 165 |     |     |     |     | 170 |     |     |     |     | 175 |      |
| CAT | GGG | GCT | TCA | TCC | CGA | ACC | ATC | GCC | ACA | CCC | GTG | GGG | GCC | CTT | AAT | 574  |
| His | Gly | Ala | Ser | Ser | Arg | Thr | Ile | Ala | Thr | Pro | Val | Gly | Ala | Leu | Asn |      |
|     |     |     |     | 180 |     |     |     |     | 185 |     |     |     |     | 190 |     |      |
| CCC | AGA | TGG | TGG | TCA | GCC | AGT | GAT | GAT | GTC | ACG | GTG | TAT | CCA | CTC | CCG | 622  |
| Pro | Arg | Trp | Trp | Ser | Ala | Ser | Asp | Asp | Val | Thr | Val | Tyr | Pro | Leu | Pro |      |
|     |     |     | 195 |     |     |     |     | 200 |     |     |     |     | 205 |     |     |      |
| GAT | GGG | GCT | ACT | TCG | TTA | ACG | CCT | TGT | ACT | TGC | CAG | GCT | GAG | TCC | TGT | 670  |
| Asp | Gly | Ala | Thr | Ser | Leu | Thr | Pro | Cys | Thr | Cys | Gln | Ala | Glu | Ser | Cys |      |
|     |     | 210 |     |     |     |     | 215 |     |     |     |     | 220 |     |     |     |      |
| TGG | GTC | ATC | AGA | TCC | GAC | GGG | GCC | CTA | TGC | CAT | GGC | TTG | AGC | AAG | GGG | 718  |
| Trp | Val | Ile | Arg | Ser | Asp | Gly | Ala | Leu | Cys | His | Gly | Leu | Ser | Lys | Gly |      |
|     |     | 225 |     |     |     |     | 230 |     |     |     |     | 235 |     |     |     |      |
| GAC | AAG | GTG | GAG | CTG | GAT | GTG | GCC | ATG | GAG | GTC | CCT | GAT | TTC | CGT | GGC | 766  |
| Asp | Lys | Val | Glu | Leu | Asp | Val | Ala | Met | Glu | Val | Pro | Asp | Phe | Arg | Gly |      |
| 240 |     |     |     |     | 245 |     |     |     |     | 250 |     |     |     |     | 255 |      |
| TCG | TCT | GGC | TCA | CCG | GTC | CTA | TGT | GAC | GAG | GGG | CAC | GCA | GTA | GGA | ATG | 814  |
| Ser | Ser | Gly | Ser | Pro | Val | Leu | Cys | Asp | Glu | Gly | His | Ala | Val | Gly | Met |      |
|     |     |     |     | 260 |     |     |     |     | 265 |     |     |     |     | 270 |     |      |
| CTC | GTG | TCT | GTG | CTT | CAC | TCC | GGT | GGT | AGG | GTC | ACC | GCG | GCA | CGG | TTC | 862  |
| Leu | Val | Ser | Val | Leu | His | Ser | Gly | Gly | Arg | Val | Thr | Ala | Ala | Arg | Phe |      |
|     |     |     | 275 |     |     |     |     | 280 |     |     |     |     | 285 |     |     |      |
| ACT | AGG | CCG | TGG | ACC | CAA | GTG | CCA | ACA | GAT | GCC | AAA | ACC | ACC | ACT | GAA | 910  |
| Thr | Arg | Pro | Trp | Thr | Gln | Val | Pro | Thr | Asp | Ala | Lys | Thr | Thr | Thr | Glu |      |
|     |     | 290 |     |     |     |     | 295 |     |     |     |     | 300 |     |     |     |      |
| CCC | CCT | CCG | GTG | CCG | GCC | AAA | GGA | GTT | TTC | AAA | GAG | GCC | CCG | TTG | TTT | 958  |
| Pro | Pro | Pro | Val | Pro | Ala | Lys | Gly | Val | Phe | Lys | Glu | Ala | Pro | Leu | Phe |      |
|     | 305 |     |     |     |     | 310 |     |     |     |     | 315 |     |     |     |     |      |
| ATG | CCT | ACG | GGA | GCG | GGA | AAG | AGC | ACT | CGC | GTC | CCG | TTG | GAG | TAC | GGC | 1006 |
| Met | Pro | Thr | Gly | Ala | Gly | Lys | Ser | Thr | Arg | Val | Pro | Leu | Glu | Tyr | Gly |      |
| 320 |     |     |     |     | 325 |     |     |     |     | 330 |     |     |     |     | 335 |      |
| AAC | ATG | GGG | CAC | AAG | GTC | TTA | GTC | TTG | AAC | CCC | TCA | GTG | GCC | ACT | GTG | 1054 |
| Asn | Met | Gly | His | Lys | Val | Leu | Val | Leu | Asn | Pro | Ser | Val | Ala | Thr | Val |      |
|     |     |     |     | 340 |     |     |     |     | 345 |     |     |     |     | 350 |     |      |
| CGG | GCC | ATG | GGC | CCG | TAC | ATG | GAG | CGG | CTG | GCG | GGT | AAA | CAT | CCA | AGT | 1102 |
| Arg | Ala | Met | Gly | Pro | Tyr | Met | Glu | Arg | Leu | Ala | Gly | Lys | His | Pro | Ser |      |
|     |     |     | 355 |     |     |     |     | 360 |     |     |     |     | 365 |     |     |      |
| ATA | TAC | TGT | GGG | CAT | GAT | ACA | ACT | GCT | TTC | ACA | AGG | ATC | ACT | GAC | TCC | 1150 |
| Ile | Tyr | Cys | Gly | His | Asp | Thr | Thr | Ala | Phe | Thr | Arg | Ile | Thr | Asp | Ser |      |
|     |     | 370 |     |     |     |     | 375 |     |     |     |     | 380 |     |     |     |      |
| CCC | CTG | ACG | TAT | TCA | ACC | TAT | GGG | AGG | TTT | TTG | GCC | AAC | CCT | AGG | CAG | 1198 |
| Pro | Leu | Thr | Tyr | Ser | Thr | Tyr | Gly | Arg | Phe | Leu | Ala | Asn | Pro | Arg | Gln |      |
|     | 385 |     |     |     |     | 390 |     |     |     |     | 395 |     |     |     |     |      |
| ATG | CTA | CGG | GGC | GTT | TCG | GTG | GTC | ATT | TGT | GAT | GAG | TGC | CAC | AGT | TAT | 1246 |
| Met | Leu | Arg | Gly | Val | Ser | Val | Val | Ile | Cys | Asp | Glu | Cys | His | Ser | Tyr |      |
| 400 |     |     |     |     | 405 |     |     |     |     | 410 |     |     |     |     | 415 |      |
| GAC | TCA | ACC | GTG | CTG | TTA | GGC | ATT | GGG | AGG | GTT | CGG | GAG | CTG | GCG | CGT | 1294 |
| Asp | Ser | Thr | Val | Leu | Leu | Gly | Ile | Gly | Arg | Val | Arg | Glu | Leu | Ala | Arg |      |
|     |     |     |     | 420 |     |     |     |     | 425 |     |     |     |     | 430 |     |      |
| GGG | TGC | GGA | GTG | CAA | CTA | GTG | CTC | TAC | GCC | ACC | GCT | ACG | CCT | CCC | GGA | 1342 |
| Gly | Cys | Gly | Val | Gln | Leu | Val | Leu | Tyr | Ala | Thr | Ala | Thr | Pro | Pro | Gly |      |
|     |     |     | 435 |     |     |     |     | 440 |     |     |     |     | 445 |     |     |      |
| TCC | CCT | ATG | ACG | CAG | CAC | CCT | TCC | ATA | ATT | GAG | ACA | AAA | TTG | GAC | GTG | 1390 |
| Ser | Pro | Met | Thr | Gln | His | Pro | Ser | Ile | Ile | Glu | Thr | Lys | Leu | Asp | Val |      |

-continued

|     | 450 |     |     |     |     | 455 |     |     |     |     | 460 |     |     |     |     |      |
|-----|-----|-----|-----|-----|-----|-----|-----|-----|-----|-----|-----|-----|-----|-----|-----|------|
| GGC | GAG | ATT | CCC | TTT | TAT | GGG | CAC | GGA | ATA | CCC | CTC | GAG | CGG | ATG | CGA | 1438 |
| Gly | Glu | Ile | Pro | Phe | Tyr | Gly | His | Gly | Ile | Pro | Leu | Glu | Arg | Met | Arg |      |
|     | 465 |     |     |     |     | 470 |     |     |     |     | 475 |     |     |     |     |      |
| ACC | GGA | AGG | CAC | CTC | GTG | TTC | TGC | CAT | TCT | AAG | GCT | GAG | TGC | GAG | CGC | 1486 |
| Thr | Gly | Arg | His | Leu | Val | Phe | Cys | His | Ser | Lys | Ala | Glu | Cys | Glu | Arg |      |
| 480 |     |     |     |     | 485 |     |     |     |     | 490 |     |     |     |     | 495 |      |
| CTT | GCT | GGC | CAG | TTC | TCC | GCT | AGG | GGG | GTC | AAT | GCC | ATT | GCC | TAT | TAT | 1534 |
| Leu | Ala | Gly | Gln | Phe | Ser | Ala | Arg | Gly | Val | Asn | Ala | Ile | Ala | Tyr | Tyr |      |
|     |     |     |     | 500 |     |     |     |     | 505 |     |     |     |     | 510 |     |      |
| AGG | GGT | AAA | GAC | AGT | TCT | ATC | ATC | AAG | GAT | GGG | GAC | CTG | GTG | GTC | TGT | 1582 |
| Arg | Gly | Lys | Asp | Ser | Ser | Ile | Ile | Lys | Asp | Gly | Asp | Leu | Val | Val | Cys |      |
|     |     |     | 515 |     |     |     |     | 520 |     |     |     |     | 525 |     |     |      |
| GCC | ACA | GAC | GCG | CTT | TCC | ACT | GGG | TAC | ACT | GGA | AAT | TTC | GAC | TCC | GTC | 1630 |
| Ala | Thr | Asp | Ala | Leu | Ser | Thr | Gly | Tyr | Thr | Gly | Asn | Phe | Asp | Ser | Val |      |
|     | 530 |     |     |     |     | 535 |     |     |     |     | 540 |     |     |     |     |      |
| ACC | GAC | TGT | GGA | TTA | GTG | GTG | GAG | GAG | GTC | GTT | GAG | GTG | ACC | CTT | GAT | 1678 |
| Thr | Asp | Cys | Gly | Leu | Val | Val | Glu | Glu | Val | Val | Glu | Val | Thr | Leu | Asp |      |
|     | 545 |     |     |     |     | 550 |     |     |     |     | 555 |     |     |     |     |      |
| CCT | ACC | ATT | ACC | ATC | TCC | CTG | CGG | ACA | GTG | CCT | GCG | TCG | GCT | GAA | CTG | 1726 |
| Pro | Thr | Ile | Thr | Ile | Ser | Leu | Arg | Thr | Val | Pro | Ala | Ser | Ala | Glu | Leu |      |
| 560 |     |     |     |     | 565 |     |     |     |     | 570 |     |     |     |     | 575 |      |
| TCG | ATG | CAA | AGA | CGA | GGA | CGC | ACG | GGT | AGG | GGC | AGG | TCT | GGA | CGC | TAC | 1774 |
| Ser | Met | Gln | Arg | Arg | Gly | Arg | Thr | Gly | Arg | Gly | Arg | Ser | Gly | Arg | Tyr |      |
|     |     |     |     | 580 |     |     |     |     | 585 |     |     |     |     | 590 |     |      |
| TAC | TAC | GCG | GGG | GTG | GGC | AAA | GCC | CCT | GCG | GGT | GTG | GTG | CGC | TCA | GGT | 1822 |
| Tyr | Tyr | Ala | Gly | Val | Gly | Lys | Ala | Pro | Ala | Gly | Val | Val | Arg | Ser | Gly |      |
|     |     |     | 595 |     |     |     |     | 600 |     |     |     |     | 605 |     |     |      |
| CCT | GTC | TGG | TCG | GCG | GTG | GAA | GCT | GGA | GTG | ACC | TGG | TAC | GGA | ATG | GAA | 1870 |
| Pro | Val | Trp | Ser | Ala | Val | Glu | Ala | Gly | Val | Thr | Trp | Tyr | Gly | Met | Glu |      |
|     |     | 610 |     |     |     |     | 615 |     |     |     |     | 620 |     |     |     |      |
| CCT | GAC | TTG | ACA | GCT | AAC | CTA | CTG | AGA | CTT | TAC | GAC | GAC | TGC | CCT | TAC | 1918 |
| Pro | Asp | Leu | Thr | Ala | Asn | Leu | Leu | Arg | Leu | Tyr | Asp | Asp | Cys | Pro | Tyr |      |
|     | 625 |     |     |     |     | 630 |     |     |     |     | 635 |     |     |     |     |      |
| ACC | GCA | GCC | GTC | GCG | GCT | GAT | ATC | GGA | GAA | GCC | GCG | GTG | TTC | TTC | TCT | 1966 |
| Thr | Ala | Ala | Val | Ala | Ala | Asp | Ile | Gly | Glu | Ala | Ala | Val | Phe | Phe | Ser |      |
| 640 |     |     |     |     | 645 |     |     |     |     | 650 |     |     |     |     | 655 |      |
| GGG | CTC | GCC | CCA | TTG | AGG | ATG | CAC | CCT | GAT | GTC | AGC | TGG | GCA | AAA | GTT | 2014 |
| Gly | Leu | Ala | Pro | Leu | Arg | Met | His | Pro | Asp | Val | Ser | Trp | Ala | Lys | Val |      |
|     |     |     |     | 660 |     |     |     |     | 665 |     |     |     |     | 670 |     |      |
| CGC | GGC | GTC | AAC | TGG | CCC | CTC | TTG | GTG | GGT | GTT | CAG | CGG | ACC | ATG | TGT | 2062 |
| Arg | Gly | Val | Asn | Trp | Pro | Leu | Leu | Val | Gly | Val | Gln | Arg | Thr | Met | Cys |      |
|     |     |     | 675 |     |     |     |     | 680 |     |     |     |     | 685 |     |     |      |
| CGG | GAA | ACA | CTG | TCT | CCC | GGC | CCA | TCG | GAT | GAC | CCC | CAA | TGG | GCA | GGT | 2110 |
| Arg | Glu | Thr | Leu | Ser | Pro | Gly | Pro | Ser | Asp | Asp | Pro | Gln | Trp | Ala | Gly |      |
|     |     | 690 |     |     |     |     | 695 |     |     |     |     | 700 |     |     |     |      |
| CTG | AAG | GGC | CCA | AAT | CCT | GTC | CCA | CTC | CTG | CTG | AGG | TGG | GGC | AAT | GAT | 2158 |
| Leu | Lys | Gly | Pro | Asn | Pro | Val | Pro | Leu | Leu | Leu | Arg | Trp | Gly | Asn | Asp |      |
|     | 705 |     |     |     |     | 710 |     |     |     |     | 715 |     |     |     |     |      |
| TTA | CCA | TCT | AAA | GTG | GCC | GGC | CAC | CAC | ATA | GTG | GAC | GAC | CTG | GTC | CGG | 2206 |
| Leu | Pro | Ser | Lys | Val | Ala | Gly | His | His | Ile | Val | Asp | Asp | Leu | Val | Arg |      |
| 720 |     |     |     |     | 725 |     |     |     |     | 730 |     |     |     |     | 735 |      |
| AGA | CTC | GGT | GTG | GCG | GAG | GGT | TAC | GCC | CGC | TGC | GAC | GCT | GGG | CCG | ATC | 2254 |
| Arg | Leu | Gly | Val | Ala | Glu | Gly | Tyr | Ala | Arg | Cys | Asp | Ala | Gly | Pro | Ile |      |
|     |     |     |     | 740 |     |     |     |     | 745 |     |     |     |     | 750 |     |      |
| TTG | ATG | ATC | GGT | CTA | GCT | ATC | GCG | GGA | ATG | ATC | TAC | GCG | TCG | TAC | ACC | 2302 |
| Leu | Met | Ile | Gly | Leu | Ala | Ile | Ala | Gly | Met | Ile | Tyr | Ala | Ser | Tyr |     |      |
|     |     |     | 755 |     |     |     |     | 760 |     |     |     |     | 765 |     |     |      |
| ACC | GGG | TCG | CTA | GTG | GTG | GTG | ACA | GAC | TGG | GAT | GTG | AAG | GGG | GGT | GGC | 2350 |
| Thr | Gly | Ser | Leu | Val | Val | Val | Thr | Asp | Trp | Asp | Val | Lys | Gly | Gly | Gly |      |

|  |  |  |  |  |  |  |  |  |  |  |  |  |  |  |  |
|---|---|---|---|---|---|---|---|---|---|---|---|---|---|---|---|
|  | 770 |  |  |  |  | 775 |  |  |  |  | 780 |  |  |  |  |
| GCC | CCC | CTT | TAT | CGG | CAT | GGA | GAC | CAG | GCC | ACG | CCT | CAG | CCG | GTG | GTG |
| Ala | Pro | Leu | Tyr | Arg | His | Gly | Asp | Gln | Ala | Thr | Pro | Gln | Pro | Val | Val |
|  | 785 |  |  |  |  | 790 |  |  |  |  | 795 |  |  |  |  |

2398

| CAG | GTT | CCT | CCG | GTA | GAC | CAT | CGG | CCG | GGG | GGT | GAA | TCA | GCA | CCA | TCG |
|---|---|---|---|---|---|---|---|---|---|---|---|---|---|---|---|
| Gln | Val | Pro | Pro | Val | Asp | His | Arg | Pro | Gly | Gly | Glu | Ser | Ala | Pro | Ser |
| 800 |  |  |  |  | 805 |  |  |  |  | 810 |  |  |  |  | 815 |

2446

| GAT | GCC | AAG | ACA | GTG | ACA | GAT | GCG | GTG | GCA | GCG | ATC | CAG | GTG | GAC | TGC |
|---|---|---|---|---|---|---|---|---|---|---|---|---|---|---|---|
| Asp | Ala | Lys | Thr | Val | Thr | Asp | Ala | Val | Ala | Ala | Ile | Gln | Val | Asp | Cys |
|  |  |  |  | 820 |  |  |  |  | 825 |  |  |  |  | 830 |  |

2494

| GAT | TGG | ACT | ATC | ATG | ACT | CTG | TCG | ATC | GGA | GAA | GTG | TTG | TCC | TTG | GCT |
|---|---|---|---|---|---|---|---|---|---|---|---|---|---|---|---|
| Asp | Trp | Thr | Ile | Met | Thr | Leu | Ser | Ile | Gly | Glu | Val | Leu | Ser | Leu | Ala |
|  |  |  | 835 |  |  |  |  | 840 |  |  |  |  | 845 |  |  |

2542

| CAG | GCT | AAG | ACG | GCC | GAG | G |
|---|---|---|---|---|---|---|
| Gln | Ala | Lys | Thr | Ala | Glu |  |
|  |  | 850 |  |  |  |  |

2561

( 2 ) INFORMATION FOR SEQ ID NO:27:

( i ) SEQUENCE CHARACTERISTICS:
        ( A ) LENGTH: 853 amino acids
        ( B ) TYPE: amino acid
        ( D ) TOPOLOGY: linear ( i i ) MOLECULE TYPE: protein ( x i ) SEQUENCE DESCRIPTION: SEQ ID NO:27:

| Ile | Leu | Val | Ser | Arg | Pro | Ser | Leu | Arg | Arg | Leu | Ala | Arg | Val | Val | Glu |
|---|---|---|---|---|---|---|---|---|---|---|---|---|---|---|---|
| 1 |  |  |  | 5 |  |  |  |  | 10 |  |  |  |  | 15 |  |
| Cys | Cys | Val | Met | Ala | Gly | Glu | Lys | Ala | Thr | Thr | Val | Arg | Leu | Val | Ser |
|  |  |  | 20 |  |  |  |  | 25 |  |  |  |  | 30 |  |  |
| Lys | Met | Cys | Ala | Arg | Gly | Ala | Tyr | Leu | Phe | Asp | Tyr | Met | Gly | Ser | Phe |
|  |  | 35 |  |  |  |  | 40 |  |  |  |  | 45 |  |  |  |
| Ser | Arg | Ala | Val | Lys | Glu | Arg | Leu | Leu | Glu | Trp | Asp | Ala | Ala | Leu | Glu |
|  | 50 |  |  |  |  | 55 |  |  |  |  | 60 |  |  |  |  |
| Pro | Leu | Ser | Phe | Thr | Arg | Thr | Asp | Cys | Arg | Ile | Ile | Arg | Asp | Ala | Ala |
| 65 |  |  |  |  | 70 |  |  |  |  | 75 |  |  |  |  | 80 |
| Arg | Thr | Leu | Ser | Cys | Gly | Gln | Cys | Val | Met | Gly | Leu | Pro | Val | Val | Ala |
|  |  |  |  | 85 |  |  |  |  | 90 |  |  |  |  | 95 |  |
| Arg | Arg | Gly | Asp | Glu | Val | Leu | Ile | Gly | Val | Phe | Gln | Asp | Val | Asn | His |
|  |  |  | 100 |  |  |  |  | 105 |  |  |  |  | 110 |  |  |
| Leu | Pro | Pro | Gly | Phe | Val | Pro | Thr | Ala | Pro | Val | Val | Ile | Arg | Arg | Cys |
|  |  | 115 |  |  |  |  | 120 |  |  |  |  | 125 |  |  |  |
| Gly | Lys | Gly | Phe | Leu | Gly | Val | Thr | Lys | Ala | Ala | Leu | Thr | Gly | Arg | Asp |
|  | 130 |  |  |  |  | 135 |  |  |  |  | 140 |  |  |  |  |
| Pro | Asp | Leu | His | Pro | Gly | Asn | Val | Met | Val | Leu | Gly | Thr | Ala | Thr | Ser |
| 145 |  |  |  |  | 150 |  |  |  |  | 155 |  |  |  |  | 160 |
| Arg | Ser | Met | Gly | Thr | Cys | Leu | Asn | Gly | Leu | Leu | Phe | Thr | Thr | Phe | His |
|  |  |  |  | 165 |  |  |  |  | 170 |  |  |  |  | 175 |  |
| Gly | Ala | Ser | Ser | Arg | Thr | Ile | Ala | Thr | Pro | Val | Gly | Ala | Leu | Asn | Pro |
|  |  |  | 180 |  |  |  |  | 185 |  |  |  |  | 190 |  |  |
| Arg | Trp | Trp | Ser | Ala | Ser | Asp | Asp | Val | Thr | Val | Tyr | Pro | Leu | Pro | Asp |
|  |  | 195 |  |  |  |  | 200 |  |  |  |  | 205 |  |  |  |
| Gly | Ala | Thr | Ser | Leu | Thr | Pro | Cys | Thr | Cys | Gln | Ala | Glu | Ser | Cys | Trp |
|  | 210 |  |  |  |  | 215 |  |  |  |  | 220 |  |  |  |  |
| Val | Ile | Arg | Ser | Asp | Gly | Ala | Leu | Cys | His | Gly | Leu | Ser | Lys | Gly | Asp |
| 225 |  |  |  |  | 230 |  |  |  |  | 235 |  |  |  |  | 240 |
| Lys | Val | Glu | Leu | Asp | Val | Ala | Met | Glu | Val | Pro | Asp | Phe | Arg | Gly | Ser |

-continued

```
                         245                         250                         255
Ser  Gly  Ser  Pro  Val  Leu  Cys  Asp  Glu  Gly  His  Ala  Val  Gly  Met  Leu
               260                 265                 270

Val  Ser  Val  Leu  His  Ser  Gly  Gly  Arg  Val  Thr  Ala  Ala  Arg  Phe  Thr
               275                 280                 285

Arg  Pro  Trp  Thr  Gln  Val  Pro  Thr  Asp  Ala  Lys  Thr  Thr  Glu  Pro
     290                 295                 300

Pro  Pro  Val  Pro  Ala  Lys  Gly  Val  Phe  Lys  Glu  Ala  Pro  Leu  Phe  Met
305                      310                 315                           320

Pro  Thr  Gly  Ala  Gly  Lys  Ser  Thr  Arg  Val  Pro  Leu  Glu  Tyr  Gly  Asn
                    325                 330                      335

Met  Gly  His  Lys  Val  Leu  Val  Leu  Asn  Pro  Ser  Val  Ala  Thr  Val  Arg
               340                 345                 350

Ala  Met  Gly  Pro  Tyr  Met  Glu  Arg  Leu  Ala  Gly  Lys  His  Pro  Ser  Ile
               355            360                 365

Tyr  Cys  Gly  His  Asp  Thr  Thr  Ala  Phe  Thr  Arg  Ile  Thr  Asp  Ser  Pro
     370                      375                 380

Leu  Thr  Tyr  Ser  Thr  Tyr  Gly  Arg  Phe  Leu  Ala  Asn  Pro  Arg  Gln  Met
385                           390                 395                      400

Leu  Arg  Gly  Val  Ser  Val  Val  Ile  Cys  Asp  Glu  Cys  His  Ser  Tyr  Asp
               405                 410                           415

Ser  Thr  Val  Leu  Leu  Gly  Ile  Gly  Arg  Val  Arg  Glu  Leu  Ala  Arg  Gly
               420                 425                      430

Cys  Gly  Val  Gln  Leu  Val  Leu  Tyr  Ala  Thr  Ala  Thr  Pro  Pro  Gly  Ser
               435                 440                      445

Pro  Met  Thr  Gln  His  Pro  Ser  Ile  Ile  Glu  Thr  Lys  Leu  Asp  Val  Gly
     450                      455                 460

Glu  Ile  Pro  Phe  Tyr  Gly  His  Gly  Ile  Pro  Leu  Glu  Arg  Met  Arg  Thr
465                      470                      475                      480

Gly  Arg  His  Leu  Val  Phe  Cys  His  Ser  Lys  Ala  Glu  Cys  Glu  Arg  Leu
               485                 490                      495

Ala  Gly  Gln  Phe  Ser  Ala  Arg  Gly  Val  Asn  Ala  Ile  Ala  Tyr  Tyr  Arg
          500                      505                      510

Gly  Lys  Asp  Ser  Ser  Ile  Ile  Lys  Asp  Gly  Asp  Leu  Val  Val  Cys  Ala
          515                 520                      525

Thr  Asp  Ala  Leu  Ser  Thr  Gly  Tyr  Thr  Gly  Asn  Phe  Asp  Ser  Val  Thr
     530                      535                 540

Asp  Cys  Gly  Leu  Val  Val  Glu  Glu  Val  Val  Glu  Val  Thr  Leu  Asp  Pro
545                      550                 555                           560

Thr  Ile  Thr  Ile  Ser  Leu  Arg  Thr  Val  Pro  Ala  Ser  Ala  Glu  Leu  Ser
               565                      570                      575

Met  Gln  Arg  Arg  Gly  Arg  Thr  Gly  Arg  Gly  Arg  Ser  Gly  Arg  Tyr  Tyr
               580                 585                 590

Tyr  Ala  Gly  Val  Gly  Lys  Ala  Pro  Ala  Gly  Val  Val  Arg  Ser  Gly  Pro
          595            600                      605

Val  Trp  Ser  Ala  Val  Glu  Ala  Gly  Val  Thr  Trp  Tyr  Gly  Met  Glu  Pro
     610                 615                 620

Asp  Leu  Thr  Ala  Asn  Leu  Leu  Arg  Leu  Tyr  Asp  Asp  Cys  Pro  Tyr  Thr
625                      630                 635                           640

Ala  Ala  Val  Ala  Ala  Asp  Ile  Gly  Glu  Ala  Ala  Val  Phe  Phe  Ser  Gly
               645                 650                      655

Leu  Ala  Pro  Leu  Arg  Met  His  Pro  Asp  Val  Ser  Trp  Ala  Lys  Val  Arg
               660            665                      670
```

```
Gly Val Asn Trp Pro Leu Leu Val Gly Val Gln Arg Thr Met Cys Arg
        675                 680                 685
Glu Thr Leu Ser Pro Gly Pro Ser Asp Asp Pro Gln Trp Ala Gly Leu
        690                 695                 700
Lys Gly Pro Asn Pro Val Pro Leu Leu Leu Arg Trp Gly Asn Asp Leu
705                 710                 715                 720
Pro Ser Lys Val Ala Gly His His Ile Val Asp Asp Leu Val Arg Arg
                725                 730                 735
Leu Gly Val Ala Glu Gly Tyr Ala Arg Cys Asp Ala Gly Pro Ile Leu
                740                 745                 750
Met Ile Gly Leu Ala Ile Ala Gly Gly Met Ile Tyr Ala Ser Tyr Thr
        755                 760                 765
Gly Ser Leu Val Val Val Thr Asp Trp Asp Val Lys Gly Gly Gly Ala
        770                 775                 780
Pro Leu Tyr Arg His Gly Asp Gln Ala Thr Pro Gln Pro Val Val Gln
785                 790                 795                 800
Val Pro Pro Val Asp His Arg Pro Gly Gly Glu Ser Ala Pro Ser Asp
                805                 810                 815
Ala Lys Thr Val Thr Asp Ala Val Ala Ala Ile Gln Val Asp Cys Asp
                820                 825                 830
Trp Thr Ile Met Thr Leu Ser Ile Gly Glu Val Leu Ser Leu Ala Gln
        835                 840                 845
Ala Lys Thr Ala Glu
        850
```

( 2 ) INFORMATION FOR SEQ ID NO:28:

( i ) SEQUENCE CHARACTERISTICS:
        ( A ) LENGTH: 2561 base pairs
        ( B ) TYPE: nucleic acid
        ( C ) STRANDEDNESS: double
        ( D ) TOPOLOGY: linear ( i i ) MOLECULE TYPE: DNA (genomic)

( v i ) ORIGINAL SOURCE:
        ( C ) INDIVIDUAL ISOLATE: HGV DNA contained in vector "LC"

( i x ) FEATURE:
        ( A ) NAME/KEY: CDS
        ( B ) LOCATION: 2..2560

( x i ) SEQUENCE DESCRIPTION: SEQ ID NO:28:

```
G ATC TTG GTG TCC CGG CCC TCG CTG CGG CGT TTG GCT CGG GTG GTT            46
  Ile Leu Val Ser Arg Pro Ser Leu Arg Arg Leu Ala Arg Val Val
    1               5                   10                  15

GAG TGC TGT GTG ATG GCG GGT GAG AAG GCC ACA ACC GTC CGG CTG GTC          94
Glu Cys Cys Val Met Ala Gly Glu Lys Ala Thr Thr Val Arg Leu Val
                20                  25                  30

TCC AAG ATG TGT GCG AGA GGA GCT TAT TTG TTC GAT CAT ATG GGC TCA         142
Ser Lys Met Cys Ala Arg Gly Ala Tyr Leu Phe Asp His Met Gly Ser
                35                  40                  45

TTT TCG CGT GCT GTC AAG GAG CGC CTG TTG GAA TGG GAC GCG GCT CTT         190
Phe Ser Arg Ala Val Lys Glu Arg Leu Leu Glu Trp Asp Ala Ala Leu
            50                  55                  60

GAA CCT CTG TCA TTC ACT AGG ACG GAC TGT CGC ATC ATA CGG GAT GCC         238
Glu Pro Leu Ser Phe Thr Arg Thr Asp Cys Arg Ile Ile Arg Asp Ala
        65                  70                  75

GCG AGG ACT TTG TCC TTA GGG CAA TGC GTC ATG GGT TTA CCC GTG GTT         286
Ala Arg Thr Leu Ser Leu Gly Gln Cys Val Met Gly Leu Pro Val Val
80                  85                  90                  95
```

| | | | | | | | | | | | | | | | | |
|---|---|---|---|---|---|---|---|---|---|---|---|---|---|---|---|---|
| GCG | CGC | CGT | GGT | GAT | GAG | GTT | CTC | ATC | GGC | GTC | TTC | CAG | GAT | GTG | AAT | 334 |
| Ala | Arg | Arg | Gly | Asp 100 | Glu | Val | Leu | Ile 105 | Gly | Val | Phe | Gln | Asp | Val 110 | Asn | |
| CAT | TTG | CCT | CCC | GGG | TTT | GTT | CCG | ACC | GCG | CCT | GTT | GTC | ATC | CGA | CGG | 382 |
| His | Leu | Pro | Pro 115 | Gly | Phe | Val | Pro | Thr 120 | Ala | Pro | Val | Val | Ile 125 | Arg | Arg | |
| TGC | GGA | AAG | GGC | TTC | TTG | GGG | GTC | ACA | AAG | GCT | GCC | TTG | ACA | GGT | CGG | 430 |
| Cys | Gly | Lys 130 | Gly | Phe | Leu | Gly | Val | Thr 135 | Lys | Ala | Ala | Leu | Thr 140 | Gly | Arg | |
| GAT | CCT | GAC | TTA | CAT | CCA | GGG | AAC | GTC | ATG | GTG | TTG | GGG | ACG | GCT | ACG | 478 |
| Asp | Pro | Asp 145 | Leu | His | Pro | Gly | Asn 150 | Val | Met | Val | Leu | Gly 155 | Thr | Ala | Thr | |
| TCG | CGA | AGC | ATG | GGA | ACA | TGC | TTG | AAC | GGC | CTG | CTG | TTC | ACG | ACC | TTC | 526 |
| Ser 160 | Arg | Ser | Met | Gly | Thr 165 | Cys | Leu | Asn | Gly | Leu 170 | Leu | Phe | Thr | Thr | Phe 175 | |
| CAT | GGG | GCT | TCA | TCC | CGA | ACC | ATC | GCC | ACA | CCC | GTG | GGG | GCC | CTT | AAT | 574 |
| His | Gly | Ala | Ser | Ser 180 | Arg | Thr | Ile | Ala | Thr 185 | Pro | Val | Gly | Ala | Leu 190 | Asn | |
| CCC | AGA | TGG | TGG | TCA | GCC | AGT | GAT | GAT | GTC | ACG | GTG | TAT | CCA | CTC | CCG | 622 |
| Pro | Arg | Trp | Trp 195 | Ser | Ala | Ser | Asp | Asp 200 | Val | Thr | Val | Tyr | Pro 205 | Leu | Pro | |
| GAT | GGG | GCT | ACT | TCG | TTA | ACG | CCT | TGT | ACT | TGC | CAG | GCT | GAG | TCC | TGT | 670 |
| Asp | Gly | Ala | Thr 210 | Ser | Leu | Thr | Pro | Cys 215 | Thr | Cys | Gln | Ala | Glu 220 | Ser | Cys | |
| TGG | GTC | ATC | AGA | TCC | GAC | GGG | GCC | CTA | TGC | CAT | GGC | TTG | AGC | AAG | GGG | 718 |
| Trp | Val | Ile 225 | Arg | Ser | Asp | Gly | Ala 230 | Leu | Cys | His | Gly | Leu 235 | Ser | Lys | Gly | |
| GAC | AAG | GTG | GAG | CTG | GAT | GTG | GCC | ATG | GAG | GTC | CCT | GAT | TTC | CGT | GGC | 766 |
| Asp | Lys 240 | Val | Glu | Leu | Asp | Val 245 | Ala | Met | Glu | Val | Pro 250 | Asp | Phe | Arg | Gly 255 | |
| TCG | TCT | GGC | TCA | CCG | GTC | CTA | TGT | GAC | GAG | GGG | CAC | GCA | GTA | GGA | ATG | 814 |
| Ser | Ser | Gly | Ser | Pro 260 | Val | Leu | Cys | Asp | Glu 265 | Gly | His | Ala | Val | Gly 270 | Met | |
| CTC | GTG | TCT | GTG | CTT | CAC | TCC | GGT | GGT | AGG | GTC | ACC | GCG | GCA | CGG | TTC | 862 |
| Leu | Val | Ser | Val 275 | Leu | His | Ser | Gly | Gly 280 | Arg | Val | Thr | Ala | Ala 285 | Arg | Phe | |
| ACT | AGG | CCG | TGG | ACC | CAA | GTG | CCA | ACA | GAT | GCC | AAA | ACC | ACC | ACT | GAA | 910 |
| Thr | Arg | Pro | Trp 290 | Thr | Gln | Val | Pro | Thr 295 | Asp | Ala | Lys | Thr | Thr 300 | Thr | Glu | |
| CCC | CCT | CCG | GTG | CCG | GCC | AAA | GGA | GTT | TTC | AAA | GAG | GCC | CCG | TTG | TTT | 958 |
| Pro | Pro | Pro 305 | Val | Pro | Ala | Lys | Gly 310 | Val | Phe | Lys | Glu | Ala 315 | Pro | Leu | Phe | |
| ATG | CCT | ACG | GGA | GCG | GGA | AAG | AGC | ACT | CGC | GTC | CCG | TTG | GAG | TAC | GGC | 1006 |
| Met | Pro 320 | Thr | Gly | Ala | Gly | Lys 325 | Ser | Thr | Arg | Val | Pro 330 | Leu | Glu | Tyr | Gly 335 | |
| AAC | ATG | GGG | CAC | AAG | GTC | TTA | GTC | TTG | AAC | CCC | TCA | GTG | GCC | ACT | GTG | 1054 |
| Asn | Met | Gly | His | Lys 340 | Val | Leu | Val | Leu | Asn 345 | Pro | Ser | Val | Ala | Thr 350 | Val | |
| CGG | GCC | ATG | GGC | CCG | TAC | ATG | GAG | CGG | CTG | GCG | GGT | AAA | CAT | CCA | AGT | 1102 |
| Arg | Ala | Met | Gly | Pro 355 | Tyr | Met | Glu | Arg | Leu 360 | Ala | Gly | Lys | His | Pro 365 | Ser | |
| ATA | TAC | TGT | GGG | CAT | GAT | ACA | ACT | GCT | TTC | ACA | AGG | ATC | ACT | GAC | TCC | 1150 |
| Ile | Tyr | Cys | Gly 370 | His | Asp | Thr | Thr | Ala 375 | Phe | Thr | Arg | Ile | Thr 380 | Asp | Ser | |
| CCC | CTG | ACG | TAT | TCA | ACC | TAT | GGG | AGG | TTT | TTG | GCC | AAC | CCT | AGG | CAG | 1198 |
| Pro | Leu | Thr 385 | Tyr | Ser | Thr | Tyr | Gly 390 | Arg | Phe | Leu | Ala | Asn 395 | Pro | Arg | Gln | |
| ATG | CTA | CGG | GGC | GTT | TCG | GTG | GTC | ATT | TGT | GAT | GAG | TGC | CAC | AGT | TAT | 1246 |
| Met | Leu | Arg | Gly 400 | Val | Ser | Val | Val | Ile 405 | Cys | Asp | Glu | Cys | His 410 | Ser | Tyr 415 | |

| | | | | | | | | | | | | | | | | |
|---|---|---|---|---|---|---|---|---|---|---|---|---|---|---|---|---|
| GAC | TCA | ACC | GTG | CTG | TTA | GGC | ATT | GGG | AGG | GTT | CGG | GAG | CTG | GCG | CGT | 1294 |
| Asp | Ser | Thr | Val | Leu 420 | Leu | Gly | Ile | Gly | Arg 425 | Val | Arg | Glu | Leu | Ala 430 | Arg | |
| GGG | TGC | GGA | GTG | CAA | CTA | GTG | CTC | TAC | GCC | ACC | GCT | ACG | CCT | CCC | GGA | 1342 |
| Gly | Cys | Gly | Val 435 | Gln | Leu | Val | Leu | Tyr 440 | Ala | Thr | Ala | Thr | Pro 445 | Pro | Gly | |
| TCC | CCT | ATG | ACG | CAG | CAC | CCT | TCC | ATA | ATT | GAG | ACA | AAA | TTG | GAC | GTG | 1390 |
| Ser | Pro | Met 450 | Thr | Gln | His | Pro | Ser 455 | Ile | Ile | Glu | Thr | Lys 460 | Leu | Asp | Val | |
| GGC | GAG | ATT | CCC | TTT | TAT | GGG | CAC | GGA | ATA | CCC | CTC | GAG | CGG | ATG | CGA | 1438 |
| Gly | Glu | Ile 465 | Pro | Phe | Tyr | Gly | His 470 | Gly | Ile | Pro | Leu | Glu 475 | Arg | Met | Arg | |
| ACC | GGA | AGG | CAC | CTC | GTG | TTC | TGC | CAT | TCT | AAG | GCT | GAG | TGC | GAG | CGC | 1486 |
| Thr 480 | Gly | Arg | His | Leu | Val 485 | Phe | Cys | His | Ser | Lys 490 | Ala | Glu | Cys | Glu | Arg 495 | |
| CTT | GCT | GGC | CAG | TTC | TCC | GCT | AGG | GGG | GTC | AAT | GCC | ATT | GCC | TAT | TAT | 1534 |
| Leu | Ala | Gly | Gln | Phe 500 | Ser | Ala | Arg | Gly | Val 505 | Asn | Ala | Ile | Ala | Tyr 510 | Tyr | |
| AGG | GGT | AAA | GAC | AGT | TCT | ATC | ATC | AAG | GAT | GGG | GAC | CTG | GTG | GTC | TGT | 1582 |
| Arg | Gly | Lys | Asp 515 | Ser | Ser | Ile | Ile | Lys 520 | Asp | Gly | Asp | Leu | Val 525 | Val | Cys | |
| GCC | ACA | GAC | GCG | CTT | TCC | ACT | GGG | TAC | ACT | GGA | AAT | TTC | GAC | TCC | GTC | 1630 |
| Ala | Thr | Asp 530 | Ala | Leu | Ser | Thr | Gly 535 | Tyr | Thr | Gly | Asn | Phe 540 | Asp | Ser | Val | |
| ACC | GAC | TGT | GGA | TTA | GTG | GTG | GAG | GAG | GTC | GTT | GAG | GTG | ACC | CTT | GAT | 1678 |
| Thr | Asp | Cys 545 | Gly | Leu | Val | Val 550 | Glu | Glu | Val | Val | Glu 555 | Val | Thr | Leu | Asp | |
| CCT | ACC | ATT | ACC | ATC | TCC | CTG | CGG | ACA | GTG | CCT | GCG | TCG | GCT | GAA | CTG | 1726 |
| Pro 560 | Thr | Ile | Thr | Ile | Ser 565 | Leu | Arg | Thr | Val | Pro 570 | Ala | Ser | Ala | Glu | Leu 575 | |
| TCG | ATG | CAA | AGA | CGA | GGA | CGC | ACG | GGT | AGG | GGC | AGG | TCT | GGA | CGC | TAC | 1774 |
| Ser | Met | Gln | Arg | Arg 580 | Gly | Arg | Thr | Gly | Arg 585 | Gly | Arg | Ser | Gly | Arg 590 | Tyr | |
| TAC | TAC | GCG | GGG | GTG | GGC | AAA | GCC | CCT | GCG | GGT | GTG | GTG | CGC | TCA | GGT | 1822 |
| Tyr | Tyr | Ala | Gly 595 | Val | Gly | Lys | Ala | Pro 600 | Ala | Gly | Val | Val | Arg 605 | Ser | Gly | |
| CCT | GTC | TGG | TCG | GCG | GTG | GAA | GCT | GGA | GTG | ACC | TGG | TAC | GGA | ATG | GAA | 1870 |
| Pro | Val | Trp 610 | Ser | Ala | Val | Glu | Ala 615 | Gly | Val | Thr | Trp | Tyr 620 | Gly | Met | Glu | |
| CCT | GAC | TTG | ACA | GCT | AAC | CTA | CTG | AGA | CTT | TAC | GAC | GAC | TGC | CCT | TAC | 1918 |
| Pro | Asp | Leu 625 | Thr | Ala | Asn | Leu | Leu 630 | Arg | Leu | Tyr | Asp | Asp 635 | Cys | Pro | Tyr | |
| ACC | GCA | GCC | GTC | GCG | GCT | GAT | ATC | GGA | GAA | GCC | GCG | GTG | TTC | TTC | TCT | 1966 |
| Thr 640 | Ala | Ala | Val | Ala | Ala 645 | Asp | Ile | Gly | Glu | Ala 650 | Ala | Val | Phe | Phe | Ser 655 | |
| GGG | CTC | GCC | CCA | TTG | AGG | ATG | CAC | CCT | GAT | GTC | AGC | TGG | GCA | AAA | GTT | 2014 |
| Gly | Leu | Ala | Pro | Leu 660 | Arg | Met | His | Pro | Asp 665 | Val | Ser | Trp | Ala | Lys 670 | Val | |
| CGC | GGC | GTC | AAC | TGG | CCC | CTC | TTG | GTG | GGT | GTT | CAG | CGG | ACC | ATG | TGT | 2062 |
| Arg | Gly | Val | Asn 675 | Trp | Pro | Leu | Leu | Val 680 | Gly | Val | Gln | Arg | Thr 685 | Met | Cys | |
| CGG | GAA | ACA | CTG | TCT | CCC | GGC | CCA | TCG | GAT | GAC | CCC | CAA | TGG | GCA | GGT | 2110 |
| Arg | Glu | Thr 690 | Leu | Ser | Pro | Gly | Pro 695 | Ser | Asp | Asp | Pro | Gln 700 | Trp | Ala | Gly | |
| CTG | AAG | GGC | CCA | AAT | CCT | GTC | CCA | CTC | CTG | AGG | TGG | GGC | AAT | GAT | | 2158 |
| Leu | Lys | Gly | Pro | Asn 710 | Pro | Val | Pro | Leu | Leu 715 | Arg | Trp | Gly | Asn | Asp | | |
| Leu | Lys 705 | Gly | Pro | Asn | Pro | Val 710 | Pro | Leu | Leu | Arg 715 | Trp | Gly | Asn | Asp | | |
| TTA | CCA | TCT | AAA | GTG | GCC | GGC | CAC | CAC | ATA | GTG | GAC | GAC | CTG | GTC | CGG | 2206 |
| Leu 720 | Pro | Ser | Lys | Val 725 | Ala | Gly | His | His | Ile 730 | Val | Asp | Asp | Leu | Val 735 | Arg | |

```
AGA  CTC  GGT  GTG  GCG  GAG  GGT  TAC  GCC  CGC  TGC  GAC  GCT  GGG  CCG  ATC    2254
Arg  Leu  Gly  Val  Ala  Glu  Gly  Tyr  Ala  Arg  Cys  Asp  Ala  Gly  Pro  Ile
               740                     745                     750

TTG  ATG  ATC  GGT  CTA  GCT  ATC  GCG  GGG  GGA  ATG  ATC  TAC  GCG  TCG  TAC    2302
Leu  Met  Ile  Gly  Leu  Ala  Ile  Ala  Gly  Gly  Met  Ile  Tyr  Ala  Ser  Tyr
               755                     760                     765

ACC  GGG  TCG  CTA  GTG  GTG  GTG  ACA  GAC  TGG  GAT  GTG  AAG  GGG  GGT  GGC    2350
Thr  Gly  Ser  Leu  Val  Val  Val  Thr  Asp  Trp  Asp  Val  Lys  Gly  Gly  Gly
               770                     775                     780

GCC  CCC  CTT  TAT  CGG  CAT  GGA  GAC  CAG  GCC  ACG  CCT  CAG  CCG  GTG  GTG    2398
Ala  Pro  Leu  Tyr  Arg  His  Gly  Asp  Gln  Ala  Thr  Pro  Gln  Pro  Val  Val
               785                     790                     795

CAG  GTT  CCT  CCG  GTA  GAC  CAT  CGG  CCG  GGG  GGT  GAA  TCA  GCA  CCA  TCG    2446
Gln  Val  Pro  Pro  Val  Asp  His  Arg  Pro  Gly  Gly  Glu  Ser  Ala  Pro  Ser
800                      805                     810                     815

GAT  GCC  AAG  ACA  GTG  ACA  GAT  GCG  GTG  GCA  GCG  ATC  CAG  GTG  GAC  TGC    2494
Asp  Ala  Lys  Thr  Val  Thr  Asp  Ala  Val  Ala  Ala  Ile  Gln  Val  Asp  Cys
               820                     825                     830

GAT  TGG  ACT  ATC  ATG  ACT  CTG  TCG  ATC  GGA  GAA  GTG  TTG  TCC  TTG  GCT    2542
Asp  Trp  Thr  Ile  Met  Thr  Leu  Ser  Ile  Gly  Glu  Val  Leu  Ser  Leu  Ala
               835                     840                     845

CAG  GCT  AAG  ACG  GCC  GAG  G                                                    2561
Gln  Ala  Lys  Thr  Ala  Glu
               850
```

( 2 ) INFORMATION FOR SEQ ID NO:29:

( i ) SEQUENCE CHARACTERISTICS:
        ( A ) LENGTH: 853 amino acids
        ( B ) TYPE: amino acid
        ( D ) TOPOLOGY: linear ( i i ) MOLECULE TYPE: protein ( x i ) SEQUENCE DESCRIPTION: SEQ ID NO:29:

```
Ile  Leu  Val  Ser  Arg  Pro  Ser  Leu  Arg  Arg  Leu  Ala  Arg  Val  Val  Glu
 1                    5                        10                       15

Cys  Cys  Val  Met  Ala  Gly  Glu  Lys  Ala  Thr  Thr  Val  Arg  Leu  Val  Ser
                20                       25                       30

Lys  Met  Cys  Ala  Arg  Gly  Ala  Tyr  Leu  Phe  Asp  His  Met  Gly  Ser  Phe
           35                       40                       45

Ser  Arg  Ala  Val  Lys  Glu  Arg  Leu  Leu  Glu  Trp  Asp  Ala  Ala  Leu  Glu
      50                       55                       60

Pro  Leu  Ser  Phe  Thr  Arg  Thr  Asp  Cys  Arg  Ile  Ile  Arg  Asp  Ala  Ala
 65                       70                       75                       80

Arg  Thr  Leu  Ser  Leu  Gly  Gln  Cys  Val  Met  Gly  Leu  Pro  Val  Val  Ala
                     85                       90                       95

Arg  Arg  Gly  Asp  Glu  Val  Leu  Ile  Gly  Val  Phe  Gln  Asp  Val  Asn  His
                100                      105                      110

Leu  Pro  Pro  Gly  Phe  Val  Pro  Thr  Ala  Pro  Val  Val  Ile  Arg  Arg  Cys
           115                      120                      125

Gly  Lys  Gly  Phe  Leu  Gly  Val  Thr  Lys  Ala  Ala  Leu  Thr  Gly  Arg  Asp
      130                      135                      140

Pro  Asp  Leu  His  Pro  Gly  Asn  Val  Met  Val  Leu  Gly  Thr  Ala  Thr  Ser
145                      150                      155                      160

Arg  Ser  Met  Gly  Thr  Cys  Leu  Asn  Gly  Leu  Leu  Phe  Thr  Thr  Phe  His
                165                      170                      175

Gly  Ala  Ser  Ser  Arg  Thr  Ile  Ala  Thr  Pro  Val  Gly  Ala  Leu  Asn  Pro
                180                      185                      190
```

```
Arg  Trp  Trp  Ser  Ala  Ser  Asp  Asp  Val  Thr  Val  Tyr  Pro  Leu  Pro  Asp
          195                200                     205

Gly  Ala  Thr  Ser  Leu  Thr  Pro  Cys  Thr  Cys  Gln  Ala  Glu  Ser  Cys  Trp
     210                215                     220

Val  Ile  Arg  Ser  Asp  Gly  Ala  Leu  Cys  His  Gly  Leu  Ser  Lys  Gly  Asp
225                230                     235                          240

Lys  Val  Glu  Leu  Asp  Val  Ala  Met  Glu  Val  Pro  Asp  Phe  Arg  Gly  Ser
               245                250                          255

Ser  Gly  Ser  Pro  Val  Leu  Cys  Asp  Glu  Gly  His  Ala  Val  Gly  Met  Leu
               260                265                          270

Val  Ser  Val  Leu  His  Ser  Gly  Gly  Arg  Val  Thr  Ala  Ala  Arg  Phe  Thr
          275                280                          285

Arg  Pro  Trp  Thr  Gln  Val  Pro  Thr  Asp  Ala  Lys  Thr  Thr  Thr  Glu  Pro
     290                     295                     300

Pro  Pro  Val  Pro  Ala  Lys  Gly  Val  Phe  Lys  Glu  Ala  Pro  Leu  Phe  Met
305                     310                     315                          320

Pro  Thr  Gly  Ala  Gly  Lys  Ser  Thr  Arg  Val  Pro  Leu  Glu  Tyr  Gly  Asn
                    325                     330                          335

Met  Gly  His  Lys  Val  Leu  Val  Leu  Asn  Pro  Ser  Val  Ala  Thr  Val  Arg
               340                     345                     350

Ala  Met  Gly  Pro  Tyr  Met  Glu  Arg  Leu  Ala  Gly  Lys  His  Pro  Ser  Ile
          355                     360                     365

Tyr  Cys  Gly  His  Asp  Thr  Thr  Ala  Phe  Thr  Arg  Ile  Thr  Asp  Ser  Pro
370                          375                     380

Leu  Thr  Tyr  Ser  Thr  Tyr  Gly  Arg  Phe  Leu  Ala  Asn  Pro  Arg  Gln  Met
385                     390                     395                          400

Leu  Arg  Gly  Val  Ser  Val  Val  Ile  Cys  Asp  Glu  Cys  His  Ser  Tyr  Asp
                    405                     410                     415

Ser  Thr  Val  Leu  Leu  Gly  Ile  Gly  Arg  Val  Arg  Glu  Leu  Ala  Arg  Gly
               420                     425                     430

Cys  Gly  Val  Gln  Leu  Val  Leu  Tyr  Ala  Thr  Ala  Thr  Pro  Pro  Gly  Ser
          435                     440                     445

Pro  Met  Thr  Gln  His  Pro  Ser  Ile  Ile  Glu  Thr  Lys  Leu  Asp  Val  Gly
     450                     455                     460

Glu  Ile  Pro  Phe  Tyr  Gly  His  Gly  Ile  Pro  Leu  Glu  Arg  Met  Arg  Thr
465                     470                     475                          480

Gly  Arg  His  Leu  Val  Phe  Cys  His  Ser  Lys  Ala  Glu  Cys  Glu  Arg  Leu
                    485                     490                     495

Ala  Gly  Gln  Phe  Ser  Ala  Arg  Gly  Val  Asn  Ala  Ile  Ala  Tyr  Tyr  Arg
               500                     505                     510

Gly  Lys  Asp  Ser  Ser  Ile  Ile  Lys  Asp  Gly  Asp  Leu  Val  Val  Cys  Ala
               515                     520                     525

Thr  Asp  Ala  Leu  Ser  Thr  Gly  Tyr  Thr  Gly  Asn  Phe  Asp  Ser  Val  Thr
     530                     535                     540

Asp  Cys  Gly  Leu  Val  Val  Glu  Glu  Val  Val  Glu  Val  Thr  Leu  Asp  Pro
545                     550                     555                          560

Thr  Ile  Thr  Ile  Ser  Leu  Arg  Thr  Val  Pro  Ala  Ser  Ala  Glu  Leu  Ser
                    565                     570                          575

Met  Gln  Arg  Arg  Gly  Arg  Thr  Gly  Arg  Gly  Arg  Ser  Gly  Arg  Tyr  Tyr
               580                     585                          590

Tyr  Ala  Gly  Val  Gly  Lys  Ala  Pro  Ala  Gly  Val  Val  Arg  Ser  Gly  Pro
          595                     600                     605

Val  Trp  Ser  Ala  Val  Glu  Ala  Gly  Val  Thr  Trp  Tyr  Gly  Met  Glu  Pro
610                          615                     620
```

```
Asp Leu Thr Ala Asn Leu Leu Arg Leu Tyr Asp Asp Cys Pro Tyr Thr
625                 630                 635                 640

Ala Ala Val Ala Ala Asp Ile Gly Glu Ala Ala Val Phe Phe Ser Gly
                645                 650                 655

Leu Ala Pro Leu Arg Met His Pro Asp Val Ser Trp Ala Lys Val Arg
            660                 665                 670

Gly Val Asn Trp Pro Leu Leu Val Gly Val Gln Arg Thr Met Cys Arg
        675                 680                 685

Glu Thr Leu Ser Pro Gly Pro Ser Asp Asp Pro Gln Trp Ala Gly Leu
    690                 695                 700

Lys Gly Pro Asn Pro Val Pro Leu Leu Leu Arg Trp Gly Asn Asp Leu
705                 710                 715                 720

Pro Ser Lys Val Ala Gly His His Ile Val Asp Asp Leu Val Arg Arg
                725                 730                 735

Leu Gly Val Ala Glu Gly Tyr Ala Arg Cys Asp Ala Gly Pro Ile Leu
            740                 745                 750

Met Ile Gly Leu Ala Ile Ala Gly Gly Met Ile Tyr Ala Ser Tyr Thr
        755                 760                 765

Gly Ser Leu Val Val Val Thr Asp Trp Asp Val Lys Gly Gly Gly Ala
    770                 775                 780

Pro Leu Tyr Arg His Gly Asp Gln Ala Thr Pro Gln Pro Val Val Gln
785                 790                 795                 800

Val Pro Pro Val Asp His Arg Pro Gly Gly Glu Ser Ala Pro Ser Asp
                805                 810                 815

Ala Lys Thr Val Thr Asp Ala Val Ala Ala Ile Gln Val Asp Cys Asp
            820                 825                 830

Trp Thr Ile Met Thr Leu Ser Ile Gly Glu Val Leu Ser Leu Ala Gln
        835                 840                 845

Ala Lys Thr Ala Glu
    850
```

( 2 ) INFORMATION FOR SEQ ID NO:30:

( i ) SEQUENCE CHARACTERISTICS:
        ( A ) LENGTH: 2561 base pairs
        ( B ) TYPE: nucleic acid
        ( C ) STRANDEDNESS: double
        ( D ) TOPOLOGY: linear ( i i ) MOLECULE TYPE: DNA (genomic)

( v i ) ORIGINAL SOURCE:
        ( C ) INDIVIDUAL ISOLATE: HGV DNA contained in vector "LS"

( i x ) FEATURE:
        ( A ) NAME/KEY: CDS
        ( B ) LOCATION: 2..2560

( x i ) SEQUENCE DESCRIPTION: SEQ ID NO:30:

```
G ATC TTG GTG TCC CGG CCC TCG CTG CGG CGT TTG GCT CGG GTG GTT        46
  Ile Leu Val Ser Arg Pro Ser Leu Arg Arg Leu Ala Arg Val Val
  1               5                   10                  15

GAG TGC TGT GTG ATG GCG GGT GAG AAG GCC ACA ACC GTC CGG CTG GTC      94
Glu Cys Cys Val Met Ala Gly Glu Lys Ala Thr Thr Val Arg Leu Val
                20                  25                  30

TCC AAG ATG TGT GCG AGA GGA GCT TAT TTG TTC GAT CAT ATG GGC TCA      142
Ser Lys Met Cys Ala Arg Gly Ala Tyr Leu Phe Asp His Met Gly Ser
                35                  40                  45

TTT TCG CGT GCT GTC AAG GAG CGC CTG TTG GAA TGG GAC GCG GCT CTT      190
Phe Ser Arg Ala Val Lys Glu Arg Leu Leu Glu Trp Asp Ala Ala Leu
```

-continued

|   |   |   |   |   |   |   |   |   |   |   |   |   |   |   |   |     |
|---|---|---|---|---|---|---|---|---|---|---|---|---|---|---|---|-----|
|   |   | 50 |   |   |   |   | 55 |   |   |   |   |   | 60 |   |   |     |
| GAA | CCT | CTG | TCA | TTC | ACT | AGG | ACG | GAC | TGT | CGC | ATC | ATA | CGG | GAT | GCC | 238 |
| Glu | Pro | Leu | Ser | Phe | Thr | Arg | Thr | Asp | Cys | Arg | Ile | Ile | Arg | Asp | Ala |     |
|     | 65  |     |     |     | 70  |     |     |     |     |     | 75  |     |     |     |     |     |
| GCG | AGG | ACT | TTG | TCC | TGC | GGG | CAA | TGC | GTC | ATG | GGT | TTA | CCC | GTG | GTT | 286 |
| Ala | Arg | Thr | Leu | Ser | Cys | Gly | Gln | Cys | Val | Met | Gly | Leu | Pro | Val | Val |     |
| 80  |     |     |     |     | 85  |     |     |     |     | 90  |     |     |     |     | 95  |     |
| GCG | CGC | CGT | GGT | GAT | GAG | GTT | CTC | ATC | GGC | GTC | TTC | CAG | GAT | GTG | AAT | 334 |
| Ala | Arg | Arg | Gly | Asp | Glu | Val | Leu | Ile | Gly | Val | Phe | Gln | Asp | Val | Asn |     |
|     |     |     |     | 100 |     |     |     |     | 105 |     |     |     |     | 110 |     |     |
| CAT | TTG | CCT | CCC | GGG | TTT | GTT | CCG | ACC | GCG | CCT | GTT | GTC | ATC | CGA | CGG | 382 |
| His | Leu | Pro | Pro | Gly | Phe | Val | Pro | Thr | Ala | Pro | Val | Val | Ile | Arg | Arg |     |
|     |     |     | 115 |     |     |     |     | 120 |     |     |     |     | 125 |     |     |     |
| TGC | GGA | AAG | GGC | TTC | TTG | GGG | GTC | ACA | AAG | GCT | GCC | TTG | ACA | GGT | CGG | 430 |
| Cys | Gly | Lys | Gly | Phe | Leu | Gly | Val | Thr | Lys | Ala | Ala | Leu | Thr | Gly | Arg |     |
|     |     | 130 |     |     |     |     | 135 |     |     |     |     | 140 |     |     |     |     |
| GAT | CCT | GAC | TTA | CAT | CCA | GGG | AAC | GTC | ATG | GTG | TTG | GGG | ACG | GCT | ACG | 478 |
| Asp | Pro | Asp | Leu | His | Pro | Gly | Asn | Val | Met | Val | Leu | Gly | Thr | Ala | Thr |     |
|     | 145 |     |     |     |     | 150 |     |     |     |     | 155 |     |     |     |     |     |
| TCG | CGA | AGC | ATG | GGA | ACA | TGC | TTG | AAC | GGC | CTG | CTG | TTC | ACG | ACC | TTC | 526 |
| Ser | Arg | Ser | Met | Gly | Thr | Cys | Leu | Asn | Gly | Leu | Leu | Phe | Thr | Thr | Phe |     |
| 160 |     |     |     |     | 165 |     |     |     |     | 170 |     |     |     |     | 175 |     |
| CAT | GGG | GCT | TCA | TCC | CGA | ACC | ATC | GCC | ACA | CCC | GTG | GGG | GCC | CTT | AAT | 574 |
| His | Gly | Ala | Ser | Ser | Arg | Thr | Ile | Ala | Thr | Pro | Val | Gly | Ala | Leu | Asn |     |
|     |     |     |     | 180 |     |     |     |     | 185 |     |     |     |     | 190 |     |     |
| CCC | AGA | TGG | TGG | TCA | GCC | AGT | GAT | GAT | GTC | ACG | GTG | TAT | CCA | CTC | CCG | 622 |
| Pro | Arg | Trp | Trp | Ser | Ala | Ser | Asp | Asp | Val | Thr | Val | Tyr | Pro | Leu | Pro |     |
|     |     |     | 195 |     |     |     |     | 200 |     |     |     |     | 205 |     |     |     |
| GAT | GGG | GCT | ACT | TCG | TTA | ACG | CCT | TGT | ACT | TGC | CAG | GCT | GAG | TCC | TGT | 670 |
| Asp | Gly | Ala | Thr | Ser | Leu | Thr | Pro | Cys | Thr | Cys | Gln | Ala | Glu | Ser | Cys |     |
|     |     | 210 |     |     |     |     | 215 |     |     |     |     | 220 |     |     |     |     |
| TGG | GTC | ATC | AGA | TCC | GAC | GGG | GCC | CTA | TGC | CAT | GGC | TTG | AGC | AAG | GGG | 718 |
| Trp | Val | Ile | Arg | Ser | Asp | Gly | Ala | Leu | Cys | His | Gly | Leu | Ser | Lys | Gly |     |
|     | 225 |     |     |     |     | 230 |     |     |     |     | 235 |     |     |     |     |     |
| GAC | AAG | GTG | GAG | CTG | GAT | GTG | GCC | ATG | GAG | GTC | CCT | GAT | TTC | CGT | GGC | 766 |
| Asp | Lys | Val | Glu | Leu | Asp | Val | Ala | Met | Glu | Val | Pro | Asp | Phe | Arg | Gly |     |
| 240 |     |     |     |     | 245 |     |     |     |     | 250 |     |     |     |     | 255 |     |
| TCG | GCT | GGC | TCA | CCG | GTC | CTA | TGT | GAC | GAG | GGG | CAC | GCA | GTA | GGA | ATG | 814 |
| Ser | Ala | Gly | Ser | Pro | Val | Leu | Cys | Asp | Glu | Gly | His | Ala | Val | Gly | Met |     |
|     |     |     |     | 260 |     |     |     |     | 265 |     |     |     |     | 270 |     |     |
| CTC | GTG | TCT | GTG | CTT | CAC | TCC | GGT | GGT | AGG | GTC | ACC | GCG | GCA | CGG | TTC | 862 |
| Leu | Val | Ser | Val | Leu | His | Ser | Gly | Gly | Arg | Val | Thr | Ala | Ala | Arg | Phe |     |
|     |     |     | 275 |     |     |     |     | 280 |     |     |     |     | 285 |     |     |     |
| ACT | AGG | CCG | TGG | ACC | CAA | GTG | CCA | ACA | GAT | GCC | AAA | ACC | ACC | ACT | GAA | 910 |
| Thr | Arg | Pro | Trp | Thr | Gln | Val | Pro | Thr | Asp | Ala | Lys | Thr | Thr | Thr | Glu |     |
|     |     | 290 |     |     |     |     | 295 |     |     |     |     | 300 |     |     |     |     |
| CCC | CCT | CCG | GTG | CCG | GCC | AAA | GGA | GTT | TTC | AAA | GAG | GCC | CCG | TTG | TTT | 958 |
| Pro | Pro | Pro | Val | Pro | Ala | Lys | Gly | Val | Phe | Lys | Glu | Ala | Pro | Leu | Phe |     |
|     | 305 |     |     |     |     | 310 |     |     |     |     | 315 |     |     |     |     |     |
| ATG | CCT | ACG | GGA | GCG | GGA | AAG | AGC | ACT | CGC | GTC | CCG | TTG | GAG | TAC | GGC | 1006 |
| Met | Pro | Thr | Gly | Ala | Gly | Lys | Ser | Thr | Arg | Val | Pro | Leu | Glu | Tyr | Gly |     |
| 320 |     |     |     |     | 325 |     |     |     |     | 330 |     |     |     |     | 335 |     |
| AAC | ATG | GGG | CAC | AAG | GTC | TTA | GTC | TTG | AAC | CCC | TCA | GTG | GCC | ACT | GTG | 1054 |
| Asn | Met | Gly | His | Lys | Val | Leu | Val | Leu | Asn | Pro | Ser | Val | Ala | Thr | Val |     |
|     |     |     |     | 340 |     |     |     |     | 345 |     |     |     |     | 350 |     |     |
| CGG | GCC | ATG | GGC | CCG | TAC | ATG | GAG | CGG | CTG | GCG | GGT | AAA | CAT | CCA | AGT | 1102 |
| Arg | Ala | Met | Gly | Pro | Tyr | Met | Glu | Arg | Leu | Ala | Gly | Lys | His | Pro | Ser |     |
|     |     |     | 355 |     |     |     |     | 360 |     |     |     |     | 365 |     |     |     |
| ATA | TAC | TGT | GGG | CAT | GAT | ACA | ACT | GCT | TTC | ACA | AGG | ATC | ACT | GAC | TCC | 1150 |
| Ile | Tyr | Cys | Gly | His | Asp | Thr | Thr | Ala | Phe | Thr | Arg | Ile | Thr | Asp | Ser |     |

-continued

| | | | 370 | | | | 375 | | | | 380 | | | | |
|---|---|---|---|---|---|---|---|---|---|---|---|---|---|---|---|
| CCC | CTG | ACG | TAT | TCA | ACC | TAT | GGG | AGG | TTT | TTG | GCC | AAC | CCT | AGG | CAG |
| Pro | Leu | Thr | Tyr | Ser | Thr | Tyr | Gly | Arg | Phe | Leu | Ala | Asn | Pro | Arg | Gln |
| 385 | | | | | 390 | | | | | 395 | | | | | | 1198 |

| ATG | CTA | CGG | GGC | GTT | TCG | GTG | GTC | ATT | TGT | GAT | GAG | TGC | CAC | AGT | TAT |
|---|---|---|---|---|---|---|---|---|---|---|---|---|---|---|---|
| Met | Leu | Arg | Gly | Val | Ser | Val | Val | Ile | Cys | Asp | Glu | Cys | His | Ser | Tyr |
| 400 | | | | | 405 | | | | | 410 | | | | | 415 | 1246 |

| GAC | TCA | ACC | GTG | CTG | TTA | GGC | ATT | GGG | AGG | GTT | CGG | GAG | CTG | GCG | CGT |
|---|---|---|---|---|---|---|---|---|---|---|---|---|---|---|---|
| Asp | Ser | Thr | Val | Leu | Leu | Gly | Ile | Gly | Arg | Val | Arg | Glu | Leu | Ala | Arg |
| | | | | 420 | | | | | 425 | | | | | 430 | | 1294 |

| GGG | TGC | GGA | GTG | CAA | CTA | GTG | CTC | TAC | GCC | ACC | GCT | ACG | CCT | CCC | GGA |
|---|---|---|---|---|---|---|---|---|---|---|---|---|---|---|---|
| Gly | Cys | Gly | Val | Gln | Leu | Val | Leu | Tyr | Ala | Thr | Ala | Thr | Pro | Pro | Gly |
| | | | 435 | | | | | 440 | | | | | 445 | | | 1342 |

| TCC | CCT | ATG | ACG | CAG | CAC | CCT | TCC | ATA | ATT | GAG | ACA | AAA | TTG | GAC | GTG |
|---|---|---|---|---|---|---|---|---|---|---|---|---|---|---|---|
| Ser | Pro | Met | Thr | Gln | His | Pro | Ser | Ile | Ile | Glu | Thr | Lys | Leu | Asp | Val |
| | | 450 | | | | | 455 | | | | | 460 | | | | 1390 |

| GGC | GAG | ATT | CCC | TTT | TAT | GGG | CAC | GGA | ATA | CCC | CTC | GAG | CGG | ATG | CGA |
|---|---|---|---|---|---|---|---|---|---|---|---|---|---|---|---|
| Gly | Glu | Ile | Pro | Phe | Tyr | Gly | His | Gly | Ile | Pro | Leu | Glu | Arg | Met | Arg |
| | 465 | | | | | 470 | | | | | 475 | | | | | 1438 |

| ACC | GGA | AGG | CAC | CTC | GTG | TTC | TGC | CAT | TCT | AAG | GCT | GAG | TGC | GAG | CGC |
|---|---|---|---|---|---|---|---|---|---|---|---|---|---|---|---|
| Thr | Gly | Arg | His | Leu | Val | Phe | Cys | His | Ser | Lys | Ala | Glu | Cys | Glu | Arg |
| 480 | | | | | 485 | | | | | 490 | | | | | 495 | 1486 |

| CTT | GCT | GGC | CAG | TTC | TCC | GCT | AGG | GGG | GTC | AAT | GCC | ATT | GCC | TAT | TAT |
|---|---|---|---|---|---|---|---|---|---|---|---|---|---|---|---|
| Leu | Ala | Gly | Gln | Phe | Ser | Ala | Arg | Gly | Val | Asn | Ala | Ile | Ala | Tyr | Tyr |
| | | | | 500 | | | | | 505 | | | | | 510 | | 1534 |

| AGG | GGT | AAA | GAC | AGT | TCT | ATC | ATC | AAG | GAT | GGG | GAC | CTG | GTG | GTC | TGT |
|---|---|---|---|---|---|---|---|---|---|---|---|---|---|---|---|
| Arg | Gly | Lys | Asp | Ser | Ser | Ile | Ile | Lys | Asp | Gly | Asp | Leu | Val | Val | Cys |
| | | | | 515 | | | | | 520 | | | | | 525 | | 1582 |

| GCC | ACA | GAC | GCG | CTT | TCC | ACT | GGG | TAC | ACT | GGA | AAT | TTC | GAC | TCC | GTC |
|---|---|---|---|---|---|---|---|---|---|---|---|---|---|---|---|
| Ala | Thr | Asp | Ala | Leu | Ser | Thr | Gly | Tyr | Thr | Gly | Asn | Phe | Asp | Ser | Val |
| | | 530 | | | | | 535 | | | | | 540 | | | | 1630 |

| ACC | GAC | TGT | GGA | TTA | GTG | GTG | GAG | GAG | GTC | GTT | GAG | GTG | ACC | CTT | GAT |
|---|---|---|---|---|---|---|---|---|---|---|---|---|---|---|---|
| Thr | Asp | Cys | Gly | Leu | Val | Val | Glu | Glu | Val | Val | Glu | Val | Thr | Leu | Asp |
| | | 545 | | | | | 550 | | | | | 555 | | | | 1678 |

| CCT | ACC | ATT | ACC | ATC | TCC | CTG | CGG | ACA | GTG | CCT | GCG | TCG | GCT | GAA | CTG |
|---|---|---|---|---|---|---|---|---|---|---|---|---|---|---|---|
| Pro | Thr | Ile | Thr | Ile | Ser | Leu | Arg | Thr | Val | Pro | Ala | Ser | Ala | Glu | Leu |
| 560 | | | | | 565 | | | | | 570 | | | | | 575 | 1726 |

| TCG | ATG | CAA | AGA | CGA | GGA | CGC | ACG | GGT | AGG | GGC | AGG | TCT | GGA | CGC | TAC |
|---|---|---|---|---|---|---|---|---|---|---|---|---|---|---|---|
| Ser | Met | Gln | Arg | Arg | Gly | Arg | Thr | Gly | Arg | Gly | Arg | Ser | Gly | Arg | Tyr |
| | | | | 580 | | | | | 585 | | | | | 590 | | 1774 |

| TAC | TAC | GCG | GGG | GTG | GGC | AAA | GCC | CCT | GCG | GGT | GTG | GTG | CGC | TCA | GGT |
|---|---|---|---|---|---|---|---|---|---|---|---|---|---|---|---|
| Tyr | Tyr | Ala | Gly | Val | Gly | Lys | Ala | Pro | Ala | Gly | Val | Val | Arg | Ser | Gly |
| | | | 595 | | | | | 600 | | | | | 605 | | | 1822 |

| CCT | GTC | TGG | TCG | GCG | GTG | GAA | GCT | GGA | GTG | ACC | TGG | TAC | GGA | ATG | GAA |
|---|---|---|---|---|---|---|---|---|---|---|---|---|---|---|---|
| Pro | Val | Trp | Ser | Ala | Val | Glu | Ala | Gly | Val | Thr | Trp | Tyr | Gly | Met | Glu |
| | | 610 | | | | | 615 | | | | | 620 | | | | 1870 |

| CCT | GAC | TTG | ACA | GCT | AAC | CTA | CTG | AGA | CTT | TAC | GAC | GAC | TGC | CCT | TAC |
|---|---|---|---|---|---|---|---|---|---|---|---|---|---|---|---|
| Pro | Asp | Leu | Thr | Ala | Asn | Leu | Leu | Arg | Leu | Tyr | Asp | Asp | Cys | Pro | Tyr |
| 625 | | | | | 630 | | | | | 635 | | | | | | 1918 |

| ACC | GCA | GCC | GTC | GCG | GCT | GAT | ATC | GGA | GAA | GCC | GCG | GTG | TTC | TTC | TCT |
|---|---|---|---|---|---|---|---|---|---|---|---|---|---|---|---|
| Thr | Ala | Ala | Val | Ala | Ala | Asp | Ile | Gly | Glu | Ala | Ala | Val | Phe | Phe | Ser |
| 640 | | | | | 645 | | | | | 650 | | | | | 655 | 1966 |

| GGG | CTC | GCC | CCA | TTG | AGG | ATG | CAC | CCT | GAT | GTC | AGC | TGG | GCA | AAA | GTT |
|---|---|---|---|---|---|---|---|---|---|---|---|---|---|---|---|
| Gly | Leu | Ala | Pro | Leu | Arg | Met | His | Pro | Asp | Val | Ser | Trp | Ala | Lys | Val |
| | | | | 660 | | | | | 665 | | | | | 670 | | 2014 |

| CGC | GGC | GTC | AAC | TGG | CCC | CTC | TTG | GTG | GGT | GTT | CAG | CGG | ACC | ATG | TGT |
|---|---|---|---|---|---|---|---|---|---|---|---|---|---|---|---|
| Arg | Gly | Val | Asn | Trp | Pro | Leu | Leu | Val | Gly | Val | Gln | Arg | Thr | Met | Cys |
| | | | 675 | | | | | 680 | | | | | 685 | | | 2062 |

| CGG | GAA | ACA | CTG | TCT | CCC | GGC | CCA | TCG | GAT | GAC | CCC | CAA | TGG | GCA | GGT |
|---|---|---|---|---|---|---|---|---|---|---|---|---|---|---|---|
| Arg | Glu | Thr | Leu | Ser | Pro | Gly | Pro | Ser | Asp | Asp | Pro | Gln | Trp | Ala | Gly |
| | | | | | | | | | | | | | | | | 2110 |

```
                        690                            695                           700
    CTG  AAG  GGC  CCA  AAT  CCT  GTC  CCA  CTC  CTG  CTG  AGG  TGG  GGC  AAT  GAT      2158
    Leu  Lys  Gly  Pro  Asn  Pro  Val  Pro  Leu  Leu  Leu  Arg  Trp  Gly  Asn  Asp
         705                     710                          715

TTA  CCA  TCT  AAA  GTG  GCC  GGC  CAC  CAC  ATA  GTG  GAC  GAC  CTG  GTC  CGG      2206
    Leu  Pro  Ser  Lys  Val  Ala  Gly  His  His  Ile  Val  Asp  Asp  Leu  Val  Arg
    720                      725                     730                          735

AGA  CTC  GGT  GTG  GCG  GAG  GGT  TAC  GCC  CGC  TGC  GAC  GCT  GGG  CCG  ATC      2254
    Arg  Leu  Gly  Val  Ala  Glu  Gly  Tyr  Ala  Arg  Cys  Asp  Ala  Gly  Pro  Ile
                        740                     745                     750

TTG  ATG  ATC  GGT  CTA  GCT  ATC  GCG  GGG  GGA  ATG  ATC  TAC  GCG  TCG  TAC      2302
    Leu  Met  Ile  Gly  Leu  Ala  Ile  Ala  Gly  Gly  Met  Ile  Tyr  Ala  Ser  Tyr
                   755                          760                     765

ACC  GGG  TCG  CTA  GTG  GTG  GTG  ACA  GAC  TGG  GAT  GTG  AAG  GGG  GGT  GGC      2350
    Thr  Gly  Ser  Leu  Val  Val  Val  Thr  Asp  Trp  Asp  Val  Lys  Gly  Gly  Gly
              770                          775                     780

GCC  CCC  CTT  TAT  CGG  CAT  GGA  GAC  CAG  GCC  ACG  CCT  CAG  CCG  GTG  GTG      2398
    Ala  Pro  Leu  Tyr  Arg  His  Gly  Asp  Gln  Ala  Thr  Pro  Gln  Pro  Val  Val
         785                          790                     795

CAG  GTT  CCT  CCG  GTA  GAC  CAT  CGG  CCG  GGG  GGT  GAA  TCA  GCA  CCA  TCG      2446
    Gln  Val  Pro  Pro  Val  Asp  His  Arg  Pro  Gly  Gly  Glu  Ser  Ala  Pro  Ser
    800                          805                     810                     815

GAT  GCC  AAG  ACA  GTG  ACA  GAT  GCG  GTG  GCA  GCG  ATC  CAG  GTG  GAC  TGC      2494
    Asp  Ala  Lys  Thr  Val  Thr  Asp  Ala  Val  Ala  Ala  Ile  Gln  Val  Asp  Cys
                        820                          825                     830

GAT  TGG  ACT  ATC  ATG  ACT  CTG  TCG  ATC  GGA  GAA  GTG  TTG  TCC  TTG  GCT      2542
    Asp  Trp  Thr  Ile  Met  Thr  Leu  Ser  Ile  Gly  Glu  Val  Leu  Ser  Leu  Ala
                   835                          840                     845

CAG  GCT  AAG  ACG  GCC  GAG  G                                                     2561
    Gln  Ala  Lys  Thr  Ala  Glu
              850
```

( 2 ) INFORMATION FOR SEQ ID NO:31:

( i ) SEQUENCE CHARACTERISTICS:
        ( A ) LENGTH: 853 amino acids
        ( B ) TYPE: amino acid
        ( D ) TOPOLOGY: linear ( i i ) MOLECULE TYPE: protein ( x i ) SEQUENCE DESCRIPTION: SEQ ID NO:31:

```
Ile  Leu  Val  Ser  Arg  Pro  Ser  Leu  Arg  Arg  Leu  Ala  Arg  Val  Val  Glu
  1              5                       10                          15

Cys  Cys  Val  Met  Ala  Gly  Glu  Lys  Ala  Thr  Thr  Val  Arg  Leu  Val  Ser
               20                      25                      30

Lys  Met  Cys  Ala  Arg  Gly  Ala  Tyr  Leu  Phe  Asp  His  Met  Gly  Ser  Phe
               35                      40                      45

Ser  Arg  Ala  Val  Lys  Glu  Arg  Leu  Leu  Glu  Trp  Asp  Ala  Ala  Leu  Glu
          50                      55                      60

Pro  Leu  Ser  Phe  Thr  Arg  Thr  Asp  Cys  Arg  Ile  Ile  Arg  Asp  Ala  Ala
 65                      70                      75                      80

Arg  Thr  Leu  Ser  Cys  Gly  Gln  Cys  Val  Met  Gly  Leu  Pro  Val  Val  Ala
                    85                      90                      95

Arg  Arg  Gly  Asp  Glu  Val  Leu  Ile  Gly  Val  Phe  Gln  Asp  Val  Asn  His
               100                     105                     110

Leu  Pro  Pro  Gly  Phe  Val  Pro  Thr  Ala  Pro  Val  Val  Ile  Arg  Arg  Cys
          115                     120                     125

Gly  Lys  Gly  Phe  Leu  Gly  Val  Thr  Lys  Ala  Ala  Leu  Thr  Gly  Arg  Asp
130                     135                     140
```

| Pro | Asp | Leu | His | Pro | Gly | Asn | Val | Met | Val | Leu | Gly | Thr | Ala | Thr | Ser |
| 145 | | | | 150 | | | | | 155 | | | | | | 160 |

| Arg | Ser | Met | Gly | Thr | Cys | Leu | Asn | Gly | Leu | Leu | Phe | Thr | Thr | Phe | His |
| | | | | 165 | | | | | 170 | | | | | 175 | |

| Gly | Ala | Ser | Ser | Arg | Thr | Ile | Ala | Thr | Pro | Val | Gly | Ala | Leu | Asn | Pro |
| | | | 180 | | | | | 185 | | | | | 190 | | |

| Arg | Trp | Trp | Ser | Ala | Ser | Asp | Asp | Val | Thr | Val | Tyr | Pro | Leu | Pro | Asp |
| | | 195 | | | | | 200 | | | | | 205 | | | |

| Gly | Ala | Thr | Ser | Leu | Thr | Pro | Cys | Thr | Cys | Gln | Ala | Glu | Ser | Cys | Trp |
| | 210 | | | | | 215 | | | | | 220 | | | | |

| Val | Ile | Arg | Ser | Asp | Gly | Ala | Leu | Cys | His | Gly | Leu | Ser | Lys | Gly | Asp |
| 225 | | | | | 230 | | | | | 235 | | | | | 240 |

| Lys | Val | Glu | Leu | Asp | Val | Ala | Met | Glu | Val | Pro | Asp | Phe | Arg | Gly | Ser |
| | | | | 245 | | | | | 250 | | | | | 255 | |

| Ala | Gly | Ser | Pro | Val | Leu | Cys | Asp | Glu | Gly | His | Ala | Val | Gly | Met | Leu |
| | | | | 260 | | | | | 265 | | | | 270 | | |

| Val | Ser | Val | Leu | His | Ser | Gly | Gly | Arg | Val | Thr | Ala | Ala | Arg | Phe | Thr |
| | | 275 | | | | | 280 | | | | | 285 | | | |

| Arg | Pro | Trp | Thr | Gln | Val | Pro | Thr | Asp | Ala | Lys | Thr | Thr | Thr | Glu | Pro |
| | 290 | | | | | 295 | | | | | 300 | | | | |

| Pro | Pro | Val | Pro | Ala | Lys | Gly | Val | Phe | Lys | Glu | Ala | Pro | Leu | Phe | Met |
| 305 | | | | | 310 | | | | | 315 | | | | | 320 |

| Pro | Thr | Gly | Ala | Gly | Lys | Ser | Thr | Arg | Val | Pro | Leu | Glu | Tyr | Gly | Asn |
| | | | | 325 | | | | | 330 | | | | | 335 | |

| Met | Gly | His | Lys | Val | Leu | Val | Leu | Asn | Pro | Ser | Val | Ala | Thr | Val | Arg |
| | | | 340 | | | | | 345 | | | | | 350 | | |

| Ala | Met | Gly | Pro | Tyr | Met | Glu | Arg | Leu | Ala | Gly | Lys | His | Pro | Ser | Ile |
| | | 355 | | | | | 360 | | | | | 365 | | | |

| Tyr | Cys | Gly | His | Asp | Thr | Thr | Ala | Phe | Thr | Arg | Ile | Thr | Asp | Ser | Pro |
| | 370 | | | | | 375 | | | | | 380 | | | | |

| Leu | Thr | Tyr | Ser | Thr | Tyr | Gly | Arg | Phe | Leu | Ala | Asn | Pro | Arg | Gln | Met |
| 385 | | | | | 390 | | | | | 395 | | | | | 400 |

| Leu | Arg | Gly | Val | Ser | Val | Val | Ile | Cys | Asp | Glu | Cys | His | Ser | Tyr | Asp |
| | | | | 405 | | | | | 410 | | | | | 415 | |

| Ser | Thr | Val | Leu | Leu | Gly | Ile | Gly | Arg | Val | Arg | Glu | Leu | Ala | Arg | Gly |
| | | | 420 | | | | | 425 | | | | | 430 | | |

| Cys | Gly | Val | Gln | Leu | Val | Leu | Tyr | Ala | Thr | Ala | Thr | Pro | Pro | Gly | Ser |
| | | 435 | | | | | 440 | | | | | 445 | | | |

| Pro | Met | Thr | Gln | His | Pro | Ser | Ile | Ile | Glu | Thr | Lys | Leu | Asp | Val | Gly |
| | 450 | | | | | 455 | | | | | 460 | | | | |

| Glu | Ile | Pro | Phe | Tyr | Gly | His | Gly | Ile | Pro | Leu | Glu | Arg | Met | Arg | Thr |
| 465 | | | | | 470 | | | | | 475 | | | | | 480 |

| Gly | Arg | His | Leu | Val | Phe | Cys | His | Ser | Lys | Ala | Glu | Cys | Glu | Arg | Leu |
| | | | | 485 | | | | | 490 | | | | | 495 | |

| Ala | Gly | Gln | Phe | Ser | Ala | Arg | Gly | Val | Asn | Ala | Ile | Ala | Tyr | Tyr | Arg |
| | | | 500 | | | | | 505 | | | | | 510 | | |

| Gly | Lys | Asp | Ser | Ser | Ile | Ile | Lys | Asp | Gly | Asp | Leu | Val | Val | Cys | Ala |
| | | 515 | | | | | 520 | | | | | 525 | | | |

| Thr | Asp | Ala | Leu | Ser | Thr | Gly | Tyr | Thr | Gly | Asn | Phe | Asp | Ser | Val | Thr |
| | 530 | | | | | 535 | | | | | 540 | | | | |

| Asp | Cys | Gly | Leu | Val | Val | Glu | Glu | Val | Val | Glu | Val | Thr | Leu | Asp | Pro |
| 545 | | | | | 550 | | | | | 555 | | | | | 560 |

| Thr | Ile | Thr | Ile | Ser | Leu | Arg | Thr | Val | Pro | Ala | Ser | Ala | Glu | Leu | Ser |

|     |     |     |     |     |     | 565 |     |     |     | 570 |     |     |     | 575 |     |
|---|---|---|---|---|---|---|---|---|---|---|---|---|---|---|---|

Met Gln Arg Arg Gly Arg Thr Gly Arg Gly Arg Ser Gly Arg Tyr Tyr
              580                585                590

Tyr Ala Gly Val Gly Lys Ala Pro Ala Gly Val Val Arg Ser Gly Pro
        595                600                605

Val Trp Ser Ala Val Glu Ala Gly Val Thr Trp Tyr Gly Met Glu Pro
    610                615                620

Asp Leu Thr Ala Asn Leu Leu Arg Leu Tyr Asp Asp Cys Pro Tyr Thr
625                630                635                640

Ala Ala Val Ala Ala Asp Ile Gly Glu Ala Ala Val Phe Phe Ser Gly
                645                650                655

Leu Ala Pro Leu Arg Met His Pro Asp Val Ser Trp Ala Lys Val Arg
            660                665                670

Gly Val Asn Trp Pro Leu Leu Val Gly Val Gln Arg Thr Met Cys Arg
        675                680                685

Glu Thr Leu Ser Pro Gly Pro Ser Asp Asp Pro Gln Trp Ala Gly Leu
    690                695                700

Lys Gly Pro Asn Pro Val Pro Leu Leu Leu Arg Trp Gly Asn Asp Leu
705                710                715                720

Pro Ser Lys Val Ala Gly His His Ile Val Asp Asp Leu Val Arg Arg
                725                730                735

Leu Gly Val Ala Glu Gly Tyr Ala Arg Cys Asp Ala Gly Pro Ile Leu
            740                745                750

Met Ile Gly Leu Ala Ile Ala Gly Gly Met Ile Tyr Ala Ser Tyr Thr
        755                760                765

Gly Ser Leu Val Val Val Thr Asp Trp Asp Val Lys Gly Gly Gly Ala
    770                775                780

Pro Leu Tyr Arg His Gly Asp Gln Ala Thr Pro Gln Pro Val Val Gln
785                790                795                800

Val Pro Pro Val Asp His Arg Pro Gly Gly Glu Ser Ala Pro Ser Asp
                805                810                815

Ala Lys Thr Val Thr Asp Ala Val Ala Ala Ile Gln Val Asp Cys Asp
            820                825                830

Trp Thr Ile Met Thr Leu Ser Ile Gly Glu Val Leu Ser Leu Ala Gln
        835                840                845

Ala Lys Thr Ala Glu
    850

( 2 ) INFORMATION FOR SEQ ID NO:32:

( i ) SEQUENCE CHARACTERISTICS:
    ( A ) LENGTH: 696 base pairs
    ( B ) TYPE: nucleic acid
    ( C ) STRANDEDNESS: double
    ( D ) TOPOLOGY: linear ( i i ) MOLECULE TYPE: DNA (genomic)

( v i ) ORIGINAL SOURCE:
    ( C ) INDIVIDUAL ISOLATE: HGV NS2B ( i x ) FEATURE:
    ( A ) NAME/KEY: CDS
    ( B ) LOCATION: 1..696

( x i ) SEQUENCE DESCRIPTION: SEQ ID NO:32:

GCC GAG TTC TGC TTC GAT GCT ACA TTC GAG GTG GAC ACT TCG GTG TTG  48
Ala Glu Phe Cys Phe Asp Ala Thr Phe Glu Val Asp Thr Ser Val Leu
1               5                   10                  15

| | | | | | | | | | | | | | | | | |
|---|---|---|---|---|---|---|---|---|---|---|---|---|---|---|---|---|
| GGC | TGG | GTG | GTG | GCC | AGT | GTG | GTA | GCT | TGG | GCC | ATT | GCG | CTC | CTG | AGC | 96 |
| Gly | Trp | Val | Val 20 | Ala | Ser | Val | Val | Ala 25 | Trp | Ala | Ile | Ala | Leu 30 | Leu | Ser | |
| TCG | ATG | AGC | GCA | GGG | GGG | TGG | AGG | CAC | AAA | GCC | GTG | ATC | TAT | AGG | ACG | 144 |
| Ser | Met | Ser 35 | Ala | Gly | Gly | Trp | Arg 40 | His | Lys | Ala | Val | Ile 45 | Tyr | Arg | Thr | |
| TGG | TGT | AAG | GGG | TAC | CAG | GCA | ATC | CGT | CAA | AGG | GTG | GTG | AGG | AGC | CCC | 192 |
| Trp | Cys 50 | Lys | Gly | Tyr | Gln | Ala 55 | Ile | Arg | Gln | Arg | Val 60 | Val | Arg | Ser | Pro | |
| CTC | GGG | GAG | GGG | CGG | CCT | GCC | AAA | CCC | CTG | ACC | TTT | GCC | TGG | TGC | TTG | 240 |
| Leu 65 | Gly | Glu | Gly | Arg | Pro 70 | Ala | Lys | Pro | Leu | Thr 75 | Phe | Ala | Trp | Cys | Leu 80 | |
| GCC | TCG | TAC | ATC | TGG | CCA | GAT | GCT | GTG | ATG | ATG | GTG | GTG | GTT | GCC | TTG | 288 |
| Ala | Ser | Tyr | Ile | Trp 85 | Pro | Asp | Ala | Val | Met 90 | Met | Val | Val | Val | Ala 95 | Leu | |
| GTC | CTT | CTC | TTT | GGC | CTG | TTC | GAC | GCG | TTG | GAT | TGG | GCC | TTG | GAG | GAG | 336 |
| Val | Leu | Leu | Phe 100 | Gly | Leu | Phe | Asp | Ala 105 | Leu | Asp | Trp | Ala | Leu 110 | Glu | Glu | |
| ATC | TTG | GTG | TCC | CGG | CCC | TCG | TTG | CGG | CGT | TTG | GCT | CGG | GTG | GTT | GAG | 384 |
| Ile | Leu | Val 115 | Ser | Arg | Pro | Ser | Leu 120 | Arg | Arg | Leu | Ala | Arg 125 | Val | Val | Glu | |
| TGC | TGT | GTG | ATG | GCG | GGT | GAG | AAG | GCC | ACA | ACC | GTC | CGG | CTG | GTC | TCC | 432 |
| Cys | Cys 130 | Val | Met | Ala | Gly | Glu 135 | Lys | Ala | Thr | Thr | Val 140 | Arg | Leu | Val | Ser | |
| AAG | ATG | TGT | GCG | AGA | GGA | GCT | TAT | TTG | TTC | GAT | CAT | ATG | GGC | TCT | TTT | 480 |
| Lys 145 | Met | Cys | Ala | Arg | Gly 150 | Ala | Tyr | Leu | Phe | Asp 155 | His | Met | Gly | Ser | Phe 160 | |
| TCG | CGT | GCT | GTC | AAG | GAG | CGC | CTG | TTG | GAA | TGG | GAC | GCA | GCT | CTT | GAA | 528 |
| Ser | Arg | Ala | Val | Lys 165 | Glu | Arg | Leu | Leu | Glu 170 | Trp | Asp | Ala | Ala | Leu 175 | Glu | |
| CCT | CTG | TCA | TTC | ACT | AGG | ACG | GAC | TGT | CGC | ATC | ATA | CGG | GAT | GCC | GCG | 576 |
| Pro | Leu | Ser | Phe 180 | Thr | Arg | Thr | Asp | Cys 185 | Arg | Ile | Ile | Arg | Asp 190 | Ala | Ala | |
| AGG | ACT | TTG | TCC | TGC | GGG | CAG | TGC | GTC | ATG | GGT | TTA | CCC | GTG | GTT | GCG | 624 |
| Arg | Thr | Leu | Ser 195 | Cys | Gly | Gln | Cys | Val 200 | Met | Gly | Leu | Pro | Val 205 | Val | Ala | |
| CGC | CGT | GGT | GAT | GAG | GTT | CTC | ATC | GGC | GTC | TTC | CAG | GAT | GTG | AAT | CAT | 672 |
| Arg | Arg 210 | Gly | Asp | Glu | Val | Leu 215 | Ile | Gly | Val | Phe | Gln 220 | Asp | Val | Asn | His | |
| TTG | CCT | CCC | GGG | TTT | GTT | CCG | ACC | | | | | | | | | 696 |
| Leu 225 | Pro | Pro | Gly | Phe | Val 230 | Pro | Thr | | | | | | | | | |

( 2 ) INFORMATION FOR SEQ ID NO:33:

( i ) SEQUENCE CHARACTERISTICS:
        ( A ) LENGTH: 232 amino acids
        ( B ) TYPE: amino acid
        ( D ) TOPOLOGY: linear ( i i ) MOLECULE TYPE: protein ( x i ) SEQUENCE DESCRIPTION: SEQ ID NO:33:

| | | | | | | | | | | | | | | |
|---|---|---|---|---|---|---|---|---|---|---|---|---|---|---|
| Ala 1 | Glu | Phe | Cys | Phe 5 | Asp | Ala | Thr | Phe | Glu 10 | Val | Asp | Thr | Ser | Val Leu 15 |
| Gly | Trp | Val | Val 20 | Ala | Ser | Val | Val | Ala 25 | Trp | Ala | Ile | Ala | Leu 30 | Leu Ser |
| Ser | Met | Ser 35 | Ala | Gly | Gly | Trp | Arg 40 | His | Lys | Ala | Val | Ile 45 | Tyr | Arg Thr |
| Trp | Cys 50 | Lys | Gly | Tyr | Gln | Ala 55 | Ile | Arg | Gln | Arg | Val 60 | Val | Arg | Ser Pro |

```
Leu  Gly  Glu  Gly  Arg  Pro  Ala  Lys  Pro  Leu  Thr  Phe  Ala  Trp  Cys  Leu
 65             70                  75                       80

Ala  Ser  Tyr  Ile  Trp  Pro  Asp  Ala  Val  Met  Met  Val  Val  Val  Ala  Leu
                85                  90                       95

Val  Leu  Leu  Phe  Gly  Leu  Phe  Asp  Ala  Leu  Asp  Trp  Ala  Leu  Glu  Glu
               100                 105                      110

Ile  Leu  Val  Ser  Arg  Pro  Ser  Leu  Arg  Arg  Leu  Ala  Arg  Val  Val  Glu
               115                 120                      125

Cys  Cys  Val  Met  Ala  Gly  Glu  Lys  Ala  Thr  Thr  Val  Arg  Leu  Val  Ser
     130                 135                      140

Lys  Met  Cys  Ala  Arg  Gly  Ala  Tyr  Leu  Phe  Asp  His  Met  Gly  Ser  Phe
145                      150                 155                           160

Ser  Arg  Ala  Val  Lys  Glu  Arg  Leu  Leu  Glu  Trp  Asp  Ala  Ala  Leu  Glu
                    165                 170                      175

Pro  Leu  Ser  Phe  Thr  Arg  Thr  Asp  Cys  Arg  Ile  Ile  Arg  Asp  Ala  Ala
               180                 185                      190

Arg  Thr  Leu  Ser  Cys  Gly  Gln  Cys  Val  Met  Gly  Leu  Pro  Val  Val  Ala
               195                 200                      205

Arg  Arg  Gly  Asp  Glu  Val  Leu  Ile  Gly  Val  Phe  Gln  Asp  Val  Asn  His
     210                 215                      220

Leu  Pro  Pro  Gly  Phe  Val  Pro  Thr
225                      230
```

( 2 ) INFORMATION FOR SEQ ID NO:34:

( i ) SEQUENCE CHARACTERISTICS:
        ( A ) LENGTH: 1848 base pairs
        ( B ) TYPE: nucleic acid
        ( C ) STRANDEDNESS: double
        ( D ) TOPOLOGY: linear ( i i ) MOLECULE TYPE: DNA (genomic)

( v i ) ORIGINAL SOURCE:
        ( C ) INDIVIDUAL ISOLATE: HGV NS3

( i x ) FEATURE:
        ( A ) NAME/KEY: CDS
        ( B ) LOCATION: 1..1848

( x i ) SEQUENCE DESCRIPTION: SEQ ID NO:34:

```
GCG  CCT  GTT  GTC  ATC  CGA  CGG  TGC  GGA  AAG  GGC  TTC  TTG  GGG  GTC  ACA      48
Ala  Pro  Val  Val  Ile  Arg  Arg  Cys  Gly  Lys  Gly  Phe  Leu  Gly  Val  Thr
  1                  5                  10                      15

AAG  GCT  GCC  TTG  ACA  GGT  CGG  GAT  CCT  GAC  TTA  CAT  CCA  GGG  AAC  GTC      96
Lys  Ala  Ala  Leu  Thr  Gly  Arg  Asp  Pro  Asp  Leu  His  Pro  Gly  Asn  Val
                20                       25                      30

ATG  GTG  TTG  GGG  ACG  GCT  ACG  TCG  CGA  AGC  ATG  GGA  ACA  TGC  TTG  AAC     144
Met  Val  Leu  Gly  Thr  Ala  Thr  Ser  Arg  Ser  Met  Gly  Thr  Cys  Leu  Asn
               35                       40                      45

GGC  CTG  CTG  TTC  ACG  ACC  TTC  CAT  GGG  GCT  TCA  TCC  CGA  ACC  ATC  GCC     192
Gly  Leu  Leu  Phe  Thr  Thr  Phe  His  Gly  Ala  Ser  Ser  Arg  Thr  Ile  Ala
          50                       55                      60

ACA  CCC  GTG  GGG  GCC  CTT  AAT  CCC  AGA  TGG  TGG  TCA  GCC  AGT  GAT  GAT     240
Thr  Pro  Val  Gly  Ala  Leu  Asn  Pro  Arg  Trp  Trp  Ser  Ala  Ser  Asp  Asp
 65                      70                       75                      80

GTC  ACG  GTG  TAT  CCA  CTC  CCG  GAT  GGG  GCT  ACT  TCG  TTA  ACA  CCT  TGT     288
Val  Thr  Val  Tyr  Pro  Leu  Pro  Asp  Gly  Ala  Thr  Ser  Leu  Thr  Pro  Cys
                    85                       90                      95

ACT  TGC  CAG  GCT  GAG  TCC  TGT  TGG  GTC  ATC  AGA  TCC  GAC  GGG  GCC  CTA     336
Thr  Cys  Gln  Ala  Glu  Ser  Cys  Trp  Val  Ile  Arg  Ser  Asp  Gly  Ala  Leu
               100                      105                     110
```

-continued

| | | | | | | | | | | | | | | | | |
|---|---|---|---|---|---|---|---|---|---|---|---|---|---|---|---|---|
| TGC | CAT | GGC | TTG | AGC | AAG | GGG | GAC | AAG | GTG | GAG | CTG | GAT | GTG | GCC | ATG | 384 |
| Cys | His | Gly | Leu | Ser | Lys | Gly | Asp | Lys | Val | Glu | Leu | Asp | Val | Ala | Met | |
| | | 115 | | | | | 120 | | | | | 125 | | | | |
| GAG | GTC | TCT | GAC | TTC | CGT | GGC | TCG | TCT | GGC | TCA | CCG | GTC | CTA | TGT | GAC | 432 |
| Glu | Val | Ser | Asp | Phe | Arg | Gly | Ser | Ser | Gly | Ser | Pro | Val | Leu | Cys | Asp | |
| | 130 | | | | | 135 | | | | | 140 | | | | | |
| GAA | GGG | CAC | GCA | GTA | GGA | ATG | CTC | GTG | TCT | GTG | CTT | CAC | TCC | GGT | GGT | 480 |
| Glu | Gly | His | Ala | Val | Gly | Met | Leu | Val | Ser | Val | Leu | His | Ser | Gly | Gly | |
| 145 | | | | | 150 | | | | | 155 | | | | | 160 | |
| AGG | GTC | ACC | GCG | GCA | CGG | TTC | ACT | AGG | CCG | TGG | ACC | CAA | GTG | CCA | ACA | 528 |
| Arg | Val | Thr | Ala | Ala | Arg | Phe | Thr | Arg | Pro | Trp | Thr | Gln | Val | Pro | Thr | |
| | | | | 165 | | | | | 170 | | | | | 175 | | |
| GAT | GCC | AAA | ACC | ACT | ACT | GAA | CCC | CCT | CCG | GTG | CCG | GCC | AAA | GGA | GTT | 576 |
| Asp | Ala | Lys | Thr | Thr | Thr | Glu | Pro | Pro | Pro | Val | Pro | Ala | Lys | Gly | Val | |
| | | | | 180 | | | | | 185 | | | | | 190 | | |
| TTC | AAA | GAG | GCC | CCG | TTG | TTT | ATG | CCT | ACG | GGA | GCG | GGA | AAG | AGC | ACT | 624 |
| Phe | Lys | Glu | Ala | Pro | Leu | Phe | Met | Pro | Thr | Gly | Ala | Gly | Lys | Ser | Thr | |
| | | | | 195 | | | | | 200 | | | | | 205 | | |
| CGC | GTC | CCG | TTG | GAG | TAC | GAT | AAC | ATG | GGG | CAC | AAG | GTC | TTA | ATC | TTG | 672 |
| Arg | Val | Pro | Leu | Glu | Tyr | Asp | Asn | Met | Gly | His | Lys | Val | Leu | Ile | Leu | |
| | 210 | | | | | 215 | | | | | 220 | | | | | |
| AAC | CCC | TCA | GTG | GCC | ACT | GTG | CGG | GCC | ATG | GGC | CCG | TAC | ATG | GAG | CGG | 720 |
| Asn | Pro | Ser | Val | Ala | Thr | Val | Arg | Ala | Met | Gly | Pro | Tyr | Met | Glu | Arg | |
| 225 | | | | | 230 | | | | | 235 | | | | | 240 | |
| CTG | GCG | GGT | AAA | CAT | CCA | AGT | ATA | TAC | TGT | GGG | CAT | GAT | ACA | ACT | GCT | 768 |
| Leu | Ala | Gly | Lys | His | Pro | Ser | Ile | Tyr | Cys | Gly | His | Asp | Thr | Thr | Ala | |
| | | | | 245 | | | | | 250 | | | | | 255 | | |
| TTC | ACA | AGG | ATC | ACT | GAC | TCC | CCC | CTG | ACG | TAT | TCA | ACC | TAT | GGG | AGG | 816 |
| Phe | Thr | Arg | Ile | Thr | Asp | Ser | Pro | Leu | Thr | Tyr | Ser | Thr | Tyr | Gly | Arg | |
| | | | | 260 | | | | | 265 | | | | | 270 | | |
| TTT | TTG | GCC | AAC | CCT | AGG | CAG | ATG | CTA | CGG | GGC | GTT | TCG | GTG | GTC | ATT | 864 |
| Phe | Leu | Ala | Asn | Pro | Arg | Gln | Met | Leu | Arg | Gly | Val | Ser | Val | Val | Ile | |
| | | | 275 | | | | | 280 | | | | | 285 | | | |
| TGT | GAT | GAG | TGC | CAC | AGT | CAT | GAC | TCA | ACC | GTG | CTG | TTA | GGC | ATT | GGG | 912 |
| Cys | Asp | Glu | Cys | His | Ser | His | Asp | Ser | Thr | Val | Leu | Leu | Gly | Ile | Gly | |
| | 290 | | | | | 295 | | | | | 300 | | | | | |
| AGA | GTC | CGG | GAG | CTG | GCG | CGT | GGG | TGC | GGG | GTG | CAA | CTA | GTG | CTC | TAC | 960 |
| Arg | Val | Arg | Glu | Leu | Ala | Arg | Gly | Cys | Gly | Val | Gln | Leu | Val | Leu | Tyr | |
| 305 | | | | | 310 | | | | | 315 | | | | | 320 | |
| GCC | ACC | GCT | ACA | CCT | CCC | GGA | TCC | CCT | ATG | ACG | CAG | CAC | CCT | TCC | ATA | 1008 |
| Ala | Thr | Ala | Thr | Pro | Pro | Gly | Ser | Pro | Met | Thr | Gln | His | Pro | Ser | Ile | |
| | | | | 325 | | | | | 330 | | | | | 335 | | |
| ATT | GAG | ACA | AAA | TTG | GAC | GTG | GGC | GAG | ATT | CCC | TTT | TAT | GGG | CAT | GGA | 1056 |
| Ile | Glu | Thr | Lys | Leu | Asp | Val | Gly | Glu | Ile | Pro | Phe | Tyr | Gly | His | Gly | |
| | | | 340 | | | | | 345 | | | | | 350 | | | |
| ATA | CCC | CTC | GAG | CGG | ATG | CGA | ACC | GGA | AGG | CAC | CTC | GTG | TTC | TGC | CAT | 1104 |
| Ile | Pro | Leu | Glu | Arg | Met | Arg | Thr | Gly | Arg | His | Leu | Val | Phe | Cys | His | |
| | | 355 | | | | | 360 | | | | | 365 | | | | |
| TCT | AAG | GCT | GAG | TGC | GAG | CGC | CTT | GCT | GGC | CAG | TTC | TCC | GCT | AGG | GGG | 1152 |
| Ser | Lys | Ala | Glu | Cys | Glu | Arg | Leu | Ala | Gly | Gln | Phe | Ser | Ala | Arg | Gly | |
| | 370 | | | | | 375 | | | | | 380 | | | | | |
| GTC | AAT | GCC | ATT | GCC | TAT | TAT | AGG | GGT | AAA | GAC | AGT | TCT | ATC | ATC | AAG | 1200 |
| Val | Asn | Ala | Ile | Ala | Tyr | Tyr | Arg | Gly | Lys | Asp | Ser | Ser | Ile | Ile | Lys | |
| 385 | | | | | 390 | | | | | 395 | | | | | 400 | |
| GAT | GGG | GAC | CTG | GTG | GTC | TGT | GCT | ACA | GAC | GCG | CTT | TCC | ACT | GGG | TAC | 1248 |
| Asp | Gly | Asp | Leu | Val | Val | Cys | Ala | Thr | Asp | Ala | Leu | Ser | Thr | Gly | Tyr | |
| | | | | 405 | | | | | 410 | | | | | 415 | | |
| ACT | GGA | AAT | TTC | GAC | TCC | GTC | ACC | GAC | TGT | GGA | TTA | GTG | GTG | GAG | GAG | 1296 |
| Thr | Gly | Asn | Phe | Asp | Ser | Val | Thr | Asp | Cys | Gly | Leu | Val | Val | Glu | Glu | |
| | | | 420 | | | | | 425 | | | | | 430 | | | |

```
GTC GTT GAG GTG ACC CTT GAT CCC ACC ATT ACC ATC TCC CTG CGG ACA        1344
Val Val Glu Val Thr Leu Asp Pro Thr Ile Thr Ile Ser Leu Arg Thr
        435                 440                 445

GTG CCT GCG TCG GCT GAA CTG TCG ATG CAA AGA CGA GGA CGC ACG GGT        1392
Val Pro Ala Ser Ala Glu Leu Ser Met Gln Arg Arg Gly Arg Thr Gly
    450                 455                 460

AGG GGC AGG TCT GGA CGC TAC TAC TAC GCG GGG GTG GGC AAA GCC CCT        1440
Arg Gly Arg Ser Gly Arg Tyr Tyr Tyr Ala Gly Val Gly Lys Ala Pro
465                 470                 475                 480

GCG GGT GTG GTG CGC TCA GGT CCT GTC TGG TCG GCG GTG GAA GCT GGA        1488
Ala Gly Val Val Arg Ser Gly Pro Val Trp Ser Ala Val Glu Ala Gly
                485                 490                 495

GTG ACC TGG TAC GGA ATG GAA CCT GAC TTG ACA GCT AAC CTA CTG AGA        1536
Val Thr Trp Tyr Gly Met Glu Pro Asp Leu Thr Ala Asn Leu Leu Arg
            500                 505                 510

CTT TAC GAC GAC TGC CCT TAC ACC GCA GCC GTC GCG GCT GAT ATC GGA        1584
Leu Tyr Asp Asp Cys Pro Tyr Thr Ala Ala Val Ala Ala Asp Ile Gly
            515                 520                 525

GAA GCC GCG GTG TTC TTC TCT GGG CTC GCC CCA TTG AGG ATG CAC CCT        1632
Glu Ala Ala Val Phe Phe Ser Gly Leu Ala Pro Leu Arg Met His Pro
    530                 535                 540

GAT GTC AGC TGG GCA AAA GTT CGC GGC GTC AAC TGG CCC CTC TTG GTG        1680
Asp Val Ser Trp Ala Lys Val Arg Gly Val Asn Trp Pro Leu Leu Val
545                 550                 555                 560

GGT GTT CAG CGG ACC ATG TGT CGG GAA ACA CTG TCT CCC GGC CCA TCG        1728
Gly Val Gln Arg Thr Met Cys Arg Glu Thr Leu Ser Pro Gly Pro Ser
                565                 570                 575

GAT GAC CCC CAA TGG GCA GGT CTG AAG GGC CCA AAT CCT GTC CCA CTC        1776
Asp Asp Pro Gln Trp Ala Gly Leu Lys Gly Pro Asn Pro Val Pro Leu
            580                 585                 590

CTG CTG AGG TGG GGC AAT GAT TTA CCA TCT AAA GTG GCC GGC CAC CAC        1824
Leu Leu Arg Trp Gly Asn Asp Leu Pro Ser Lys Val Ala Gly His His
        595                 600                 605

ATA GTG GAC GAC CTG GTC CGG AGA                                        1848
Ile Val Asp Asp Leu Val Arg Arg
        610                 615
```

( 2 ) INFORMATION FOR SEQ ID NO:35:

( i ) SEQUENCE CHARACTERISTICS:
        ( A ) LENGTH: 616 amino acids
        ( B ) TYPE: amino acid
        ( D ) TOPOLOGY: linear ( i i ) MOLECULE TYPE: protein ( x i ) SEQUENCE DESCRIPTION: SEQ ID NO:35:

```
Ala Pro Val Val Ile Arg Arg Cys Gly Lys Gly Phe Leu Gly Val Thr
1               5                   10                  15

Lys Ala Ala Leu Thr Gly Arg Asp Pro Asp Leu His Pro Gly Asn Val
            20                  25                  30

Met Val Leu Gly Thr Ala Thr Ser Arg Ser Met Gly Thr Cys Leu Asn
        35                  40                  45

Gly Leu Leu Phe Thr Thr Phe His Gly Ala Ser Ser Arg Thr Ile Ala
    50                  55                  60

Thr Pro Val Gly Ala Leu Asn Pro Arg Trp Trp Ser Ala Ser Asp Asp
65                  70                  75                  80

Val Thr Val Tyr Pro Leu Pro Asp Gly Ala Thr Ser Leu Thr Pro Cys
                85                  90                  95

Thr Cys Gln Ala Glu Ser Cys Trp Val Ile Arg Ser Asp Gly Ala Leu
```

|     |     |     |     |     | 100 |     |     |     |     | 105 |     |     |     |     | 110 |     |     |     |
|-----|-----|-----|-----|-----|-----|-----|-----|-----|-----|-----|-----|-----|-----|-----|-----|-----|-----|-----|

Cys His Gly Leu Ser Lys Gly Asp Lys Val Glu Leu Asp Val Ala Met
     115                            120                    125

Glu Val Ser Asp Phe Arg Gly Ser Ser Gly Ser Pro Val Leu Cys Asp
130                        135                            140

Glu Gly His Ala Val Gly Met Leu Val Ser Val Leu His Ser Gly Gly
145                    150                    155              160

Arg Val Thr Ala Ala Arg Phe Thr Arg Pro Trp Thr Gln Val Pro Thr
               165                 170                  175

Asp Ala Lys Thr Thr Thr Glu Pro Pro Val Pro Ala Lys Gly Val
          180                  185                190

Phe Lys Glu Ala Pro Leu Phe Met Pro Thr Gly Ala Gly Lys Ser Thr
     195                       200                205

Arg Val Pro Leu Glu Tyr Asp Asn Met Gly His Lys Val Leu Ile Leu
210                      215                220

Asn Pro Ser Val Ala Thr Val Arg Ala Met Gly Pro Tyr Met Glu Arg
225                    230                235              240

Leu Ala Gly Lys His Pro Ser Ile Tyr Cys Gly His Asp Thr Thr Ala
               245                 250                255

Phe Thr Arg Ile Thr Asp Ser Pro Leu Thr Tyr Ser Thr Tyr Gly Arg
               260                 265                270

Phe Leu Ala Asn Pro Arg Gln Met Leu Arg Gly Val Ser Val Val Ile
         275                  280                285

Cys Asp Glu Cys His Ser His Asp Ser Thr Val Leu Leu Gly Ile Gly
290                      295                300

Arg Val Arg Glu Leu Ala Arg Gly Cys Gly Val Gln Leu Val Leu Tyr
305                    310                315              320

Ala Thr Ala Thr Pro Pro Gly Ser Pro Met Thr Gln His Pro Ser Ile
                  325                  330              335

Ile Glu Thr Lys Leu Asp Val Gly Glu Ile Pro Phe Tyr Gly His Gly
               340                 345                350

Ile Pro Leu Glu Arg Met Arg Thr Gly Arg His Leu Val Phe Cys His
         355                  360                365

Ser Lys Ala Glu Cys Glu Arg Leu Ala Gly Gln Phe Ser Ala Arg Gly
     370                       375                380

Val Asn Ala Ile Ala Tyr Tyr Arg Gly Lys Asp Ser Ser Ile Ile Lys
385                    390                395              400

Asp Gly Asp Leu Val Val Cys Ala Thr Asp Ala Leu Ser Thr Gly Tyr
               405                 410              415

Thr Gly Asn Phe Asp Ser Val Thr Asp Cys Gly Leu Val Val Glu Glu
         420                  425                430

Val Val Glu Val Thr Leu Asp Pro Thr Ile Thr Ile Ser Leu Arg Thr
         435                  440              445

Val Pro Ala Ser Ala Glu Leu Ser Met Gln Arg Arg Gly Arg Thr Gly
450                    455                460

Arg Gly Arg Ser Gly Arg Tyr Tyr Tyr Ala Gly Val Gly Lys Ala Pro
465                    470                475              480

Ala Gly Val Val Arg Ser Gly Pro Val Trp Ser Ala Val Glu Ala Gly
               485                 490              495

Val Thr Trp Tyr Gly Met Glu Pro Asp Leu Thr Ala Asn Leu Leu Arg
         500                  505                510

Leu Tyr Asp Asp Cys Pro Tyr Thr Ala Ala Val Ala Ala Asp Ile Gly
         515                  520              525

Glu Ala Ala Val Phe Phe Ser Gly Leu Ala Pro Leu Arg Met His Pro
                        530                 535                 540

Asp Val Ser Trp Ala Lys Val Arg Gly Val Asn Trp Pro Leu Leu Val
                    545                 550                 555                 560

Gly Val Gln Arg Thr Met Cys Arg Glu Thr Leu Ser Pro Gly Pro Ser
                                    565                 570                 575

Asp Asp Pro Gln Trp Ala Gly Leu Lys Gly Pro Asn Pro Val Pro Leu
                                580                 585                 590

Leu Leu Arg Trp Gly Asn Asp Leu Pro Ser Lys Val Ala Gly His His
                            595                 600                 605

Ile Val Asp Asp Leu Val Arg Arg
                        610                 615

( 2 ) INFORMATION FOR SEQ ID NO:36:

( i ) SEQUENCE CHARACTERISTICS:
        ( A ) LENGTH: 1071 base pairs
        ( B ) TYPE: nucleic acid
        ( C ) STRANDEDNESS: double
        ( D ) TOPOLOGY: linear ( i i ) MOLECULE TYPE: DNA (genomic)

( v i ) ORIGINAL SOURCE:
        ( C ) INDIVIDUAL ISOLATE: HGV NS4A- B ( i x ) FEATURE:
        ( A ) NAME/KEY: CDS
        ( B ) LOCATION: 1..1071

( x i ) SEQUENCE DESCRIPTION: SEQ ID NO:36:

CTC GGT GTG GCG GAG GGT TAC GTC CGC TGC GAC GCT GGG CCG ATC TTG        48
Leu Gly Val Ala Glu Gly Tyr Val Arg Cys Asp Ala Gly Pro Ile Leu
 1               5                  10                  15

ATG ATC GGT CTA GCT ATC GCG GGG GGA ATG ATC TAC GCG TCA TAC ACC        96
Met Ile Gly Leu Ala Ile Ala Gly Gly Met Ile Tyr Ala Ser Tyr Thr
            20                  25                  30

GGG TCG CTA GTG GTG GTG ACA GAC TGG GAT GTG AAG GGG GGT GGC GCC       144
Gly Ser Leu Val Val Val Thr Asp Trp Asp Val Lys Gly Gly Gly Ala
        35                  40                  45

CCC CTT TAT CGG CAT GGA GAC CAG GCC ACG CCT CAG CCG GTG GTG CAG       192
Pro Leu Tyr Arg His Gly Asp Gln Ala Thr Pro Gln Pro Val Val Gln
    50                  55                  60

GTT CCT CCG GTA GAC CAT CGG CCG GGG GGT GAA TCA GCA CCA TCG GAT       240
Val Pro Pro Val Asp His Arg Pro Gly Gly Glu Ser Ala Pro Ser Asp
65                  70                  75                  80

GCC AAG ACA GTG ACA GAT GCG GTG GCA GCC ATC CAG GTG GAC TGC GAT       288
Ala Lys Thr Val Thr Asp Ala Val Ala Ala Ile Gln Val Asp Cys Asp
                85                  90                  95

TGG ACT ATC ATG ACT CTG TCG ATC GGA GAA GTG TTG TCC TTG GCT CAG       336
Trp Thr Ile Met Thr Leu Ser Ile Gly Glu Val Leu Ser Leu Ala Gln
            100                 105                 110

GCT AAG ACG GCC GAG GCC TAC ACA GCA ACC GCC AAG TGG CTC GCT GGC       384
Ala Lys Thr Ala Glu Ala Tyr Thr Ala Thr Ala Lys Trp Leu Ala Gly
        115                 120                 125

TGC TAT ACG GGG ACG CGG GCC GTT CCC ACT GTA TCC ATT GTT GAC AAG       432
Cys Tyr Thr Gly Thr Arg Ala Val Pro Thr Val Ser Ile Val Asp Lys
    130                 135                 140

CTC TTC GCC GGA GGG TGG GCG GCT GTG GTG GGC CAT TGC CAC AGC GTG       480
Leu Phe Ala Gly Gly Trp Ala Ala Val Val Gly His Cys His Ser Val
145                 150                 155                 160

ATT GCT GCG GCG GTG GCG GCC TAC GGG GCT TCA AGG AGC CCG CCG TTG       528
Ile Ala Ala Ala Val Ala Ala Tyr Gly Ala Ser Arg Ser Pro Pro Leu

-continued

|  |  |  |  |  |  |  |  |  |  |  |  |  |  |  |  |  |
|---|---|---|---|---|---|---|---|---|---|---|---|---|---|---|---|---|
|  |  |  |  |  | 165 |  |  |  | 170 |  |  |  | 175 |  |  |  |
| GCA | GCC | GCG | GCT | TCC | TAC | CTG | ATG | GGG | TTG | GGC | GTT | GGA | GGC | AAC | GCT | 576 |
| Ala | Ala | Ala | Ala 180 | Ser | Tyr | Leu | Met | Gly 185 | Leu | Gly | Val | Gly | Gly 190 | Asn | Ala |  |
| CAG | ACG | CGC | CTG | GCG | TCT | GCC | CTC | CTA | TTG | GGG | GCT | GCT | GGA | ACC | GCC | 624 |
| Gln | Thr | Arg 195 | Leu | Ala | Ser | Ala | Leu 200 | Leu | Gly | Ala | Ala | Gly 205 | Thr | Ala |  |  |
| TTG | GGC | ACT | CCT | GTC | GTG | GGC | TTG | ACC | ATG | GCA | GGT | GCG | TTC | ATG | GGG | 672 |
| Leu | Gly 210 | Thr | Pro | Val | Val | Gly 215 | Leu | Thr | Met | Ala | Gly 220 | Ala | Phe | Met | Gly |  |
| GGG | GCC | AGT | GTC | TCC | CCC | TCC | TTG | GTC | ACC | ATT | TTA | TTG | GGG | GCC | GTC | 720 |
| Gly 225 | Ala | Ser | Val | Ser | Pro 230 | Ser | Leu | Val | Thr | Ile 235 | Leu | Leu | Gly | Ala | Val 240 |  |
| GGA | GGT | TGG | GAG | GGT | GTT | GTC | AAC | GCG | GCG | AGC | CTA | GTC | TTT | GAC | TTC | 768 |
| Gly | Gly | Trp | Glu | Gly 245 | Val | Val | Asn | Ala | Ala 250 | Ser | Leu | Val | Phe | Asp 255 | Phe |  |
| ATG | GCG | GGG | AAA | CTT | TCA | TCA | GAA | GAT | CTG | TGG | TAT | GCC | ATC | CCG | GTA | 816 |
| Met | Ala | Gly | Lys 260 | Leu | Ser | Ser | Glu | Asp 265 | Leu | Trp | Tyr | Ala | Ile 270 | Pro | Val |  |
| CTG | ACC | AGC | CCG | GGG | GCG | GGC | CTT | GCG | GGG | ATC | GCT | CTC | GGG | TTG | GTT | 864 |
| Leu | Thr | Ser 275 | Pro | Gly | Ala | Gly | Leu 280 | Ala | Gly | Ile | Ala | Leu 285 | Gly | Leu | Val |  |
| TTG | TAT | TCA | GCT | AAC | AAC | TCT | GGC | ACT | ACC | ACT | TGG | TTG | AAC | CGT | CTG | 912 |
| Leu | Tyr 290 | Ser | Ala | Asn | Asn | Ser 295 | Gly | Thr | Thr | Thr | Trp 300 | Leu | Asn | Arg | Leu |  |
| CTG | ACT | ACG | TTA | CCA | AGG | TCT | TCA | TGT | ATC | CCG | GAC | AGT | TAC | TTT | CAG | 960 |
| Leu 305 | Thr | Thr | Leu | Pro | Arg 310 | Ser | Ser | Cys | Ile | Pro 315 | Asp | Ser | Tyr | Phe | Gln 320 |  |
| CAA | GTT | GAC | TAT | TGC | GAC | AAG | GTC | TCA | GCC | GTG | CTC | CGG | CGC | CTG | AGC | 1008 |
| Gln | Val | Asp | Tyr | Cys 325 | Asp | Lys | Val | Ser | Ala 330 | Val | Leu | Arg | Arg | Leu 335 | Ser |  |
| CTC | ACC | CGC | ACA | GTG | GTT | GCC | CTG | GTC | AAC | AGG | GAG | CCT | AAG | GTG | GAT | 1056 |
| Leu | Thr | Arg | Thr 340 | Val | Val | Ala | Leu | Val 345 | Asn | Arg | Glu | Pro | Lys 350 | Val | Asp |  |
| GAG | GTA | CAG | GTG | GGG |  |  |  |  |  |  |  |  |  |  |  | 1071 |
| Glu | Val | Gln 355 | Val | Gly |  |  |  |  |  |  |  |  |  |  |  |  |

( 2 ) INFORMATION FOR SEQ ID NO:37:

( i ) SEQUENCE CHARACTERISTICS:
        ( A ) LENGTH: 357 amino acids
        ( B ) TYPE: amino acid
        ( D ) TOPOLOGY: linear ( i i ) MOLECULE TYPE: protein ( x i ) SEQUENCE DESCRIPTION: SEQ ID NO:37:

| Leu | Gly | Val | Ala | Glu | Gly | Tyr | Val | Arg | Cys | Asp | Ala | Gly | Pro | Ile | Leu |
|---|---|---|---|---|---|---|---|---|---|---|---|---|---|---|---|
| 1 |  |  |  | 5 |  |  |  |  | 10 |  |  |  |  | 15 |  |
| Met | Ile | Gly | Leu | Ala | Ile | Ala | Gly | Gly | Met | Ile | Tyr | Ala | Ser | Tyr | Thr |
|  |  |  | 20 |  |  |  |  | 25 |  |  |  |  | 30 |  |  |
| Gly | Ser | Leu | Val | Val | Val | Thr | Asp | Trp | Asp | Val | Lys | Gly | Gly | Gly | Ala |
|  |  | 35 |  |  |  |  | 40 |  |  |  |  | 45 |  |  |  |
| Pro | Leu | Tyr | Arg | His | Gly | Asp | Gln | Ala | Thr | Pro | Gln | Pro | Val | Val | Gln |
|  | 50 |  |  |  |  | 55 |  |  |  |  | 60 |  |  |  |  |
| Val | Pro | Pro | Val | Asp | His | Arg | Pro | Gly | Gly | Glu | Ser | Ala | Pro | Ser | Asp |
| 65 |  |  |  |  | 70 |  |  |  |  | 75 |  |  |  |  | 80 |
| Ala | Lys | Thr | Val | Thr | Asp | Ala | Val | Ala | Ala | Ile | Gln | Val | Asp | Cys | Asp |
|  |  |  |  | 85 |  |  |  |  | 90 |  |  |  |  | 95 |  |

|   |   |   |   |   |   |   |   |   |   |   |   |   |   |   |
|---|---|---|---|---|---|---|---|---|---|---|---|---|---|---|
| Trp | Thr | Ile | Met<br>100 | Thr | Leu | Ser | Ile | Gly<br>105 | Glu | Val | Leu | Ser<br>110 | Leu | Ala | Gln |
| Ala | Lys | Thr<br>115 | Ala | Glu | Ala | Tyr | Thr<br>120 | Ala | Thr | Ala | Lys | Trp<br>125 | Leu | Ala | Gly |
| Cys | Tyr<br>130 | Thr | Gly | Thr | Arg<br>135 | Ala | Val | Pro | Thr | Val<br>140 | Ser | Ile | Val | Asp | Lys |
| Leu<br>145 | Phe | Ala | Gly | Gly | Trp<br>150 | Ala | Ala | Val | Val | Gly<br>155 | His | Cys | His | Ser | Val<br>160 |
| Ile | Ala | Ala | Ala | Val<br>165 | Ala | Ala | Tyr | Gly | Ala<br>170 | Ser | Arg | Ser | Pro | Pro<br>175 | Leu |
| Ala | Ala | Ala | Ala<br>180 | Ser | Tyr | Leu | Met | Gly<br>185 | Leu | Gly | Val | Gly | Gly<br>190 | Asn | Ala |
| Gln | Thr | Arg<br>195 | Leu | Ala | Ser | Ala | Leu<br>200 | Leu | Leu | Gly | Ala | Ala<br>205 | Gly | Thr | Ala |
| Leu | Gly<br>210 | Thr | Pro | Val | Val | Gly<br>215 | Leu | Thr | Met | Ala | Gly<br>220 | Ala | Phe | Met | Gly |
| Gly<br>225 | Ala | Ser | Val | Ser | Pro<br>230 | Ser | Leu | Val | Thr | Ile<br>235 | Leu | Leu | Gly | Ala | Val<br>240 |
| Gly | Gly | Trp | Glu | Gly<br>245 | Val | Val | Asn | Ala | Ala<br>250 | Ser | Leu | Val | Phe | Asp<br>255 | Phe |
| Met | Ala | Gly | Lys<br>260 | Leu | Ser | Ser | Glu | Asp<br>265 | Leu | Trp | Tyr | Ala | Ile<br>270 | Pro | Val |
| Leu | Thr | Ser<br>275 | Pro | Gly | Ala | Gly | Leu<br>280 | Ala | Gly | Ile | Ala | Leu<br>285 | Gly | Leu | Val |
| Leu | Tyr<br>290 | Ser | Ala | Asn | Asn | Ser<br>295 | Gly | Thr | Thr | Thr | Trp<br>300 | Leu | Asn | Arg | Leu |
| Leu<br>305 | Thr | Thr | Leu | Pro | Arg<br>310 | Ser | Ser | Cys | Ile | Pro<br>315 | Asp | Ser | Tyr | Phe | Gln<br>320 |
| Gln | Val | Asp | Tyr | Cys<br>325 | Asp | Lys | Val | Ser | Ala<br>330 | Val | Leu | Arg | Arg | Leu<br>335 | Ser |
| Leu | Thr | Arg | Thr<br>340 | Val | Val | Ala | Leu | Val<br>345 | Asn | Arg | Glu | Pro | Lys<br>350 | Val | Asp |
| Glu | Val | Gln | Val | Gly<br>355 |   |   |   |   |   |   |   |   |   |   |   |

( 2 ) INFORMATION FOR SEQ ID NO:38:

( i ) SEQUENCE CHARACTERISTICS:
        ( A ) LENGTH: 1377 base pairs
        ( B ) TYPE: nucleic acid
        ( C ) STRANDEDNESS: double
        ( D ) TOPOLOGY: linear ( i i ) MOLECULE TYPE: DNA (genomic)

( v i ) ORIGINAL SOURCE:
        ( C ) INDIVIDUAL ISOLATE: HGV NS5A ( i x ) FEATURE:
        ( A ) NAME/KEY: CDS
        ( B ) LOCATION: 1..1377

( x i ) SEQUENCE DESCRIPTION: SEQ ID NO:38:

| TAT | GTC | TGG | GAC | CTG | TGG | GAG | TGG | ATC | ATG | CGC | CAA | GTG | CGC | GTG | GTC | 48 |
|---|---|---|---|---|---|---|---|---|---|---|---|---|---|---|---|---|
| Tyr<br>1 | Val | Trp | Asp | Leu<br>5 | Trp | Glu | Trp | Ile | Met<br>10 | Arg | Gln | Val | Arg | Val<br>15 | Val | |

| ATG | GCC | AGA | CTC | AGG | GCC | CTC | TGC | CCC | GTG | GTG | TCA | CTA | CCC | TTG | TGG | 96 |
|---|---|---|---|---|---|---|---|---|---|---|---|---|---|---|---|---|
| Met | Ala | Arg | Leu<br>20 | Arg | Ala | Leu | Cys | Pro<br>25 | Val | Val | Ser | Leu | Pro<br>30 | Leu | Trp | |

| CAT | TGC | GGG | GAG | GGG | TGG | TCC | GGG | GAA | TGG | TTG | CTT | GAC | GGT | CAT | GTT | 144 |

|     |     |     |     |     |     |     |     |     |     |     |     |     |     |     |     |     |
|-----|-----|-----|-----|-----|-----|-----|-----|-----|-----|-----|-----|-----|-----|-----|-----|-----|
| His | Cys | Gly 35 | Glu | Gly | Trp | Ser | Gly 40 | Glu | Trp | Leu | Leu | Asp 45 | Gly | His | Val |     |
| GAG | AGT | CGC | TGC | CTC | TGT | GGC | TGC | GTG | ATC | ACT | GGT | GAC | GTT | CTG | AAT | 192 |
| Glu | Ser 50 | Arg | Cys | Leu | Cys | Gly 55 | Cys | Val | Ile | Thr | Gly 60 | Asp | Val | Leu | Asn |     |
| GGG | CAA | CTC | AAA | GAA | CCA | GTT | TAC | TCT | ACC | AAG | CTG | TGC | CGG | CAC | TAT | 240 |
| Gly 65 | Gln | Leu | Lys | Glu | Pro 70 | Val | Tyr | Ser | Thr | Lys 75 | Leu | Cys | Arg | His | Tyr 80 |     |
| TGG | ATG | GGG | ACT | GTC | CCT | GTG | AAC | ATG | CTG | GGT | TAC | GGT | GAA | ACG | TCG | 288 |
| Trp | Met | Gly | Thr | Val 85 | Pro | Val | Asn | Met | Leu 90 | Gly | Tyr | Gly | Glu | Thr 95 | Ser |     |
| CCT | CTC | CTG | GCC | TCC | GAC | ACC | CCG | AAG | GTT | GTG | CCC | TTC | GGG | ACG | TCT | 336 |
| Pro | Leu | Leu | Ala 100 | Ser | Asp | Thr | Pro | Lys 105 | Val | Val | Pro | Phe | Gly 110 | Thr | Ser |     |
| GGC | TGG | GCT | GAG | GTG | GTG | GTG | ACC | ACT | ACC | CAC | GTG | GTA | ATC | AGG | AGG | 384 |
| Gly | Trp | Ala 115 | Glu | Val | Val | Val | Thr 120 | Thr | Thr | His | Val | Val 125 | Ile | Arg | Arg |     |
| ACC | TCC | GCC | TAT | AAG | CTG | CTG | CGC | CAG | CAA | ATC | CTA | TCG | GCT | GCT | GTA | 432 |
| Thr | Ser 130 | Ala | Tyr | Lys | Leu | Leu 135 | Arg | Gln | Gln | Ile | Leu 140 | Ser | Ala | Ala | Val |     |
| GCT | GAG | CCC | TAC | TAC | GTC | GAC | GGC | ATT | CCG | GTC | TCA | TGG | GAC | GCG | GAC | 480 |
| Ala 145 | Glu | Pro | Tyr | Tyr | Val 150 | Asp | Gly | Ile | Pro | Val 155 | Ser | Trp | Asp | Ala | Asp 160 |     |
| GCT | CGT | GCG | CCC | GCC | ATG | GTC | TAT | GGC | CCT | GGG | CAA | AGT | GTT | ACC | ATT | 528 |
| Ala | Arg | Ala | Pro | Ala 165 | Met | Val | Tyr | Gly | Pro 170 | Gly | Gln | Ser | Val | Thr 175 | Ile |     |
| GAC | GGG | GAG | CGC | TAC | ACC | TTG | CCT | CAT | CAA | CTG | AGG | CTC | AGG | AAT | GTG | 576 |
| Asp | Gly | Glu | Arg 180 | Tyr | Thr | Leu | Pro | His 185 | Gln | Leu | Arg | Leu | Arg 190 | Asn | Val |     |
| GCA | CCC | TCT | GAG | GTT | TCA | TCC | GAG | GTG | TCC | ATT | GAC | ATT | GGG | ACG | GAG | 624 |
| Ala | Pro | Ser 195 | Glu | Val | Ser | Ser | Glu 200 | Val | Ser | Ile | Asp | Ile 205 | Gly | Thr | Glu |     |
| ACT | GAA | GAC | TCA | GAA | CTG | ACT | GAG | GCC | GAT | CTG | CCG | CCG | GCG | GCT | GCT | 672 |
| Thr | Glu 210 | Asp | Ser | Glu | Leu | Thr 215 | Glu | Ala | Asp | Leu | Pro 220 | Pro | Ala | Ala | Ala |     |
| GCT | CTC | CAA | GCG | ATC | GAG | AAT | GCT | GCG | AGG | ATT | CTT | GAA | CCG | CAC | ATT | 720 |
| Ala 225 | Leu | Gln | Ala | Ile | Glu 230 | Asn | Ala | Ala | Arg | Ile 235 | Leu | Glu | Pro | His | Ile 240 |     |
| GAT | GTC | ATC | ATG | GAG | GAC | TGC | AGT | ACA | CCC | TCT | CTT | TGT | GGT | AGT | AGC | 768 |
| Asp | Val | Ile | Met | Glu 245 | Asp | Cys | Ser | Thr | Pro 250 | Ser | Leu | Cys | Gly | Ser 255 | Ser |     |
| CGA | GAG | ATG | CCT | GTA | TGG | GGA | GAA | GAC | ATC | CCC | CGT | ACT | CCA | TCG | CCA | 816 |
| Arg | Glu | Met | Pro 260 | Val | Trp | Gly | Glu | Asp 265 | Ile | Pro | Arg | Thr | Pro 270 | Ser | Pro |     |
| GCA | CTT | ATC | TCG | GTT | ACT | GAG | AGC | AGC | TCA | GAT | GAG | AAG | ACC | CCG | TCG | 864 |
| Ala | Leu | Ile | Ser 275 | Val | Thr | Glu | Ser | Ser 280 | Ser | Asp | Glu | Lys | Thr 285 | Pro | Ser |     |
| GTG | TCC | TCC | TCG | CAG | GAG | GAT | ACC | CCG | TCC | TCT | GAC | TCA | TTC | GAG | GTC | 912 |
| Val | Ser 290 | Ser | Ser | Gln | Glu | Asp 295 | Thr | Pro | Ser | Ser | Asp 300 | Ser | Phe | Glu | Val |     |
| ATC | CAA | GAG | TCC | GAG | ACA | GCC | GAA | GGG | GAG | GAA | AGT | GTC | TTC | AAC | GTG | 960 |
| Ile | Gln | Glu 305 | Ser | Glu | Thr | Ala 310 | Glu | Gly | Glu | Glu | Ser 315 | Val | Phe | Asn | Val 320 |     |
| GCT | CTT | TCC | GTA | TTA | AAA | GCC | TTA | TTT | CCA | CAG | AGC | GAC | GCG | ACC | AGG | 1008 |
| Ala | Leu | Ser | Val | Leu 325 | Lys | Ala | Leu | Phe | Pro 330 | Gln | Ser | Asp | Ala | Thr 335 | Arg |     |
| AAG | CTT | ACC | GTC | AAG | ATG | TCG | TGC | TGC | GTT | GAA | AAG | AGC | GTC | ACG | CGC | 1056 |
| Lys | Leu | Thr | Val 340 | Lys | Met | Ser | Cys | Cys 345 | Val | Glu | Lys | Ser | Val 350 | Thr | Arg |     |
| TTT | TTC | TCA | TTG | GGG | TTG | ACG | GTG | GCT | GAT | GTT | GCT | AGC | CTG | TGT | GAG | 1104 |

|     |     |     |     |     |     |     |     |     |     |     |     |     |     |     |      |
|-----|-----|-----|-----|-----|-----|-----|-----|-----|-----|-----|-----|-----|-----|-----|------|
| Phe | Phe | Ser | Leu | Gly | Leu | Thr | Val | Ala | Asp | Val | Ala | Ser | Leu | Cys | Glu  |
|     |     | 355 |     |     |     | 360 |     |     |     | 365 |     |     |     |     |      |

| ATG | GAA | ATC | CAG | AAC | CAT | ACA | GCC | TAT | TGT | GAC | CAG | GTG | CGC | ACT | CCG | 1152 |
|-----|-----|-----|-----|-----|-----|-----|-----|-----|-----|-----|-----|-----|-----|-----|-----|------|
| Met | Glu | Ile | Gln | Asn | His | Thr | Ala | Tyr | Cys | Asp | Gln | Val | Arg | Thr | Pro |      |
|     | 370 |     |     |     |     | 375 |     |     |     | 380 |     |     |     |     |     |      |

| CTT | GAA | TTG | CAG | GTT | GGG | TGC | TTG | GTG | GGC | AAT | GAA | CTT | ACC | TTT | GAA | 1200 |
|-----|-----|-----|-----|-----|-----|-----|-----|-----|-----|-----|-----|-----|-----|-----|-----|------|
| Leu | Glu | Leu | Gln | Val | Gly | Cys | Leu | Val | Gly | Asn | Glu | Leu | Thr | Phe | Glu |      |
| 385 |     |     |     |     | 390 |     |     |     |     | 395 |     |     |     |     | 400 |      |

| TGT | GAC | AAG | TGT | GAG | GCT | AGG | CAA | GAA | ACC | TTG | GCC | TCC | TTC | TCT | TAC | 1248 |
|-----|-----|-----|-----|-----|-----|-----|-----|-----|-----|-----|-----|-----|-----|-----|-----|------|
| Cys | Asp | Lys | Cys | Glu | Ala | Arg | Gln | Glu | Thr | Leu | Ala | Ser | Phe | Ser | Tyr |      |
|     |     |     |     | 405 |     |     |     |     | 410 |     |     |     |     | 415 |     |      |

| ATT | TGG | TCT | GGA | GTG | CCG | CTG | ACT | AGG | GCC | ACG | CCG | GCC | AAG | CCT | CCC | 1296 |
|-----|-----|-----|-----|-----|-----|-----|-----|-----|-----|-----|-----|-----|-----|-----|-----|------|
| Ile | Trp | Ser | Gly | Val | Pro | Leu | Thr | Arg | Ala | Thr | Pro | Ala | Lys | Pro | Pro |      |
|     |     |     | 420 |     |     |     | 425 |     |     |     |     | 430 |     |     |     |      |

| GTG | GTG | AGG | CCG | GTT | GGC | TCT | TTG | TTA | GTG | GCC | GAC | ACT | ACT | AAG | GTG | 1344 |
|-----|-----|-----|-----|-----|-----|-----|-----|-----|-----|-----|-----|-----|-----|-----|-----|------|
| Val | Val | Arg | Pro | Val | Gly | Ser | Leu | Leu | Val | Ala | Asp | Thr | Thr | Lys | Val |      |
|     |     | 435 |     |     |     | 440 |     |     |     | 445 |     |     |     |     |     |      |

| TAT | GTT | ACC | AAT | CCA | GAC | AAT | GTG | GGA | CGG | AGG | 1377 |
|-----|-----|-----|-----|-----|-----|-----|-----|-----|-----|-----|------|
| Tyr | Val | Thr | Asn | Pro | Asp | Asn | Val | Gly | Arg | Arg |      |
| 450 |     |     |     |     | 455 |     |     |     |     |     |      |

( 2 ) INFORMATION FOR SEQ ID NO:39:

( i ) SEQUENCE CHARACTERISTICS:
( A ) LENGTH: 459 amino acids
( B ) TYPE: amino acid
( D ) TOPOLOGY: linear ( i i ) MOLECULE TYPE: protein ( x i ) SEQUENCE DESCRIPTION: SEQ ID NO:39:

|     |     |     |     |     |     |     |     |     |     |     |     |     |     |     |
|-----|-----|-----|-----|-----|-----|-----|-----|-----|-----|-----|-----|-----|-----|-----|
| Tyr | Val | Trp | Asp | Leu | Trp | Glu | Trp | Ile | Met | Arg | Gln | Val | Arg | Val |
| 1   |     |     |     | 5   |     |     |     |     | 10  |     |     |     |     | 15  |

| Met | Ala | Arg | Leu | Arg | Ala | Leu | Cys | Pro | Val | Val | Ser | Leu | Pro | Leu | Trp |
|-----|-----|-----|-----|-----|-----|-----|-----|-----|-----|-----|-----|-----|-----|-----|-----|
|     |     |     | 20  |     |     |     |     | 25  |     |     |     | 30  |     |     |     |

| His | Cys | Gly | Glu | Gly | Trp | Ser | Gly | Glu | Trp | Leu | Leu | Asp | Gly | His | Val |
|-----|-----|-----|-----|-----|-----|-----|-----|-----|-----|-----|-----|-----|-----|-----|-----|
|     |     |     | 35  |     |     |     | 40  |     |     |     |     | 45  |     |     |     |

| Glu | Ser | Arg | Cys | Leu | Cys | Gly | Cys | Val | Ile | Thr | Gly | Asp | Val | Leu | Asn |
|-----|-----|-----|-----|-----|-----|-----|-----|-----|-----|-----|-----|-----|-----|-----|-----|
|     | 50  |     |     |     |     | 55  |     |     |     |     | 60  |     |     |     |     |

| Gly | Gln | Leu | Lys | Glu | Pro | Val | Tyr | Ser | Thr | Lys | Leu | Cys | Arg | His | Tyr |
|-----|-----|-----|-----|-----|-----|-----|-----|-----|-----|-----|-----|-----|-----|-----|-----|
| 65  |     |     |     |     | 70  |     |     |     |     | 75  |     |     |     |     | 80  |

| Trp | Met | Gly | Thr | Val | Pro | Val | Asn | Met | Leu | Gly | Tyr | Gly | Glu | Thr | Ser |
|-----|-----|-----|-----|-----|-----|-----|-----|-----|-----|-----|-----|-----|-----|-----|-----|
|     |     |     |     | 85  |     |     |     |     | 90  |     |     |     |     | 95  |     |

| Pro | Leu | Leu | Ala | Ser | Asp | Thr | Pro | Lys | Val | Val | Pro | Phe | Gly | Thr | Ser |
|-----|-----|-----|-----|-----|-----|-----|-----|-----|-----|-----|-----|-----|-----|-----|-----|
|     |     |     |     | 100 |     |     |     |     | 105 |     |     |     |     | 110 |     |

| Gly | Trp | Ala | Glu | Val | Val | Val | Thr | Thr | Thr | His | Val | Val | Ile | Arg | Arg |
|-----|-----|-----|-----|-----|-----|-----|-----|-----|-----|-----|-----|-----|-----|-----|-----|
|     |     |     | 115 |     |     |     |     | 120 |     |     |     |     | 125 |     |     |

| Thr | Ser | Ala | Tyr | Lys | Leu | Leu | Arg | Gln | Gln | Ile | Leu | Ser | Ala | Ala | Val |
|-----|-----|-----|-----|-----|-----|-----|-----|-----|-----|-----|-----|-----|-----|-----|-----|
|     |     | 130 |     |     |     |     | 135 |     |     |     |     | 140 |     |     |     |

| Ala | Glu | Pro | Tyr | Tyr | Val | Asp | Gly | Ile | Pro | Val | Ser | Trp | Asp | Ala | Asp |
|-----|-----|-----|-----|-----|-----|-----|-----|-----|-----|-----|-----|-----|-----|-----|-----|
| 145 |     |     |     |     | 150 |     |     |     |     | 155 |     |     |     |     | 160 |

| Ala | Arg | Ala | Pro | Ala | Met | Val | Tyr | Gly | Pro | Gly | Gln | Ser | Val | Thr | Ile |
|-----|-----|-----|-----|-----|-----|-----|-----|-----|-----|-----|-----|-----|-----|-----|-----|
|     |     |     |     | 165 |     |     |     |     | 170 |     |     |     |     | 175 |     |

| Asp | Gly | Glu | Arg | Tyr | Thr | Leu | Pro | His | Gln | Leu | Arg | Leu | Arg | Asn | Val |
|-----|-----|-----|-----|-----|-----|-----|-----|-----|-----|-----|-----|-----|-----|-----|-----|
|     |     |     | 180 |     |     |     |     | 185 |     |     |     |     | 190 |     |     |

| Ala | Pro | Ser | Glu | Val | Ser | Ser | Glu | Val | Ser | Ile | Asp | Ile | Gly | Thr | Glu |
|-----|-----|-----|-----|-----|-----|-----|-----|-----|-----|-----|-----|-----|-----|-----|-----|
|     |     |     | 195 |     |     |     |     | 200 |     |     |     |     | 205 |     |     |

| Thr | Glu | Asp | Ser | Glu | Leu | Thr | Glu | Ala | Asp | Leu | Pro | Pro | Ala | Ala | Ala |
|-----|-----|-----|-----|-----|-----|-----|-----|-----|-----|-----|-----|-----|-----|-----|-----|
|     | 210 |     |     |     |     | 215 |     |     |     |     | 220 |     |     |     |     |

| Ala | Leu | Gln | Ala | Ile | Glu | Asn | Ala | Ala | Arg | Ile | Leu | Glu | Pro | His | Ile |
| --- | --- | --- | --- | --- | --- | --- | --- | --- | --- | --- | --- | --- | --- | --- | --- |
| 225 | | | | 230 | | | | | 235 | | | | | | 240 |
| Asp | Val | Ile | Met | Glu | Asp | Cys | Ser | Thr | Pro | Ser | Leu | Cys | Gly | Ser | Ser |
| | | | | 245 | | | | | 250 | | | | | 255 | |
| Arg | Glu | Met | Pro | Val | Trp | Gly | Glu | Asp | Ile | Pro | Arg | Thr | Pro | Ser | Pro |
| | | | 260 | | | | | 265 | | | | | 270 | | |
| Ala | Leu | Ile | Ser | Val | Thr | Glu | Ser | Ser | Ser | Asp | Glu | Lys | Thr | Pro | Ser |
| | | | 275 | | | | 280 | | | | | 285 | | | |
| Val | Ser | Ser | Ser | Gln | Glu | Asp | Thr | Pro | Ser | Ser | Asp | Ser | Phe | Glu | Val |
| | | 290 | | | | 295 | | | | | 300 | | | | |
| Ile | Gln | Glu | Ser | Glu | Thr | Ala | Glu | Gly | Glu | Glu | Ser | Val | Phe | Asn | Val |
| 305 | | | | | 310 | | | | | 315 | | | | | 320 |
| Ala | Leu | Ser | Val | Leu | Lys | Ala | Leu | Phe | Pro | Gln | Ser | Asp | Ala | Thr | Arg |
| | | | | 325 | | | | | 330 | | | | | 335 | |
| Lys | Leu | Thr | Val | Lys | Met | Ser | Cys | Cys | Val | Glu | Lys | Ser | Val | Thr | Arg |
| | | | 340 | | | | | 345 | | | | | 350 | | |
| Phe | Phe | Ser | Leu | Gly | Leu | Thr | Val | Ala | Asp | Val | Ala | Ser | Leu | Cys | Glu |
| | | 355 | | | | 360 | | | | | 365 | | | | |
| Met | Glu | Ile | Gln | Asn | His | Thr | Ala | Tyr | Cys | Asp | Gln | Val | Arg | Thr | Pro |
| 370 | | | | | 375 | | | | | 380 | | | | | |
| Leu | Glu | Leu | Gln | Val | Gly | Cys | Leu | Val | Gly | Asn | Glu | Leu | Thr | Phe | Glu |
| 385 | | | | 390 | | | | | 395 | | | | | | 400 |
| Cys | Asp | Lys | Cys | Glu | Ala | Arg | Gln | Glu | Thr | Leu | Ala | Ser | Phe | Ser | Tyr |
| | | | 405 | | | | | 410 | | | | | 415 | | |
| Ile | Trp | Ser | Gly | Val | Pro | Leu | Thr | Arg | Ala | Thr | Pro | Ala | Lys | Pro | Pro |
| | | | 420 | | | | | 425 | | | | | 430 | | |
| Val | Val | Arg | Pro | Val | Gly | Ser | Leu | Leu | Val | Ala | Asp | Thr | Thr | Lys | Val |
| | | 435 | | | | | 440 | | | | | 445 | | | |
| Tyr | Val | Thr | Asn | Pro | Asp | Asn | Val | Gly | Arg | Arg | | | | | |
| 450 | | | | | 455 | | | | | | | | | | |

(2) INFORMATION FOR SEQ ID NO:40:

(i) SEQUENCE CHARACTERISTICS:
        (A) LENGTH: 1548 base pairs
        (B) TYPE: nucleic acid
        (C) STRANDEDNESS: double
        (D) TOPOLOGY: linear (ii) MOLECULE TYPE: DNA (genomic)

(vi) ORIGINAL SOURCE:
        (C) INDIVIDUAL ISOLATE: HGV NS5B (ix) FEATURE:
        (A) NAME/KEY: CDS
  -continued

|  |  |  |  | 50 |  |  |  |  | 55 |  |  |  |  | 60 |  |  |
|---|---|---|---|---|---|---|---|---|---|---|---|---|---|---|---|---|
| CCC | GCG | GGG | AAG | ATG | GCC | GTC | CAT | GAC | CGG | CTT | CAG | GAG | ATA | CTT | GAA | 240 |
| Pro | Ala | Gly | Lys | Met | Ala | Val | His | Asp | Arg | Leu | Gln | Glu | Ile | Leu | Glu |  |
| 65 |  |  |  | 70 |  |  |  |  | 75 |  |  |  |  |  | 80 |  |
| GGG | ACT | CCG | GTC | CCC | TTT | ACT | CTT | ACT | GTG | AAA | AAG | GAG | GTG | TTC | TTC | 288 |
| Gly | Thr | Pro | Val | Pro | Phe | Thr | Leu | Thr | Val | Lys | Lys | Glu | Val | Phe | Phe |  |
|  |  |  |  |  | 85 |  |  |  | 90 |  |  |  |  | 95 |  |  |
| AAA | GAC | CGG | AAG | GAG | GAG | AAG | GCC | CCC | CGC | CTC | ATT | GTG | TTC | CCC | CCC | 336 |
| Lys | Asp | Arg | Lys | Glu | Glu | Lys | Ala | Pro | Arg | Leu | Ile | Val | Phe | Pro | Pro |  |
|  |  |  | 100 |  |  |  |  | 105 |  |  |  |  | 110 |  |  |  |
| CTG | GAC | TTC | CGG | ATA | GCT | GAA | AAG | CTC | ATC | TTG | GGA | GAC | CCA | GGC | CGG | 384 |
| Leu | Asp | Phe | Arg | Ile | Ala | Glu | Lys | Leu | Ile | Leu | Gly | Asp | Pro | Gly | Arg |  |
|  |  | 115 |  |  |  |  | 120 |  |  |  |  | 125 |  |  |  |  |
| GTA | GCC | AAG | GCG | GTG | TTG | GGG | GGG | GCC | TAC | GCC | TTC | CAG | TAC | ACC | CCA | 432 |
| Val | Ala | Lys | Ala | Val | Leu | Gly | Gly | Ala | Tyr | Ala | Phe | Gln | Tyr | Thr | Pro |  |
|  | 130 |  |  |  |  | 135 |  |  |  |  | 140 |  |  |  |  |  |
| AAT | CAG | CGA | GTT | AAG | GAG | ATG | CTC | AAG | CTA | TGG | GAG | TCT | AAG | AAG | ACC | 480 |
| Asn | Gln | Arg | Val | Lys | Glu | Met | Leu | Lys | Leu | Trp | Glu | Ser | Lys | Lys | Thr |  |
| 145 |  |  |  |  | 150 |  |  |  |  | 155 |  |  |  |  | 160 |  |
| CCT | TGC | GCC | ATC | TGT | GTG | GAC | GCC | ACC | TGC | TTC | GAC | AGT | AGC | ATA | ACT | 528 |
| Pro | Cys | Ala | Ile | Cys | Val | Asp | Ala | Thr | Cys | Phe | Asp | Ser | Ser | Ile | Thr |  |
|  |  |  |  | 165 |  |  |  |  | 170 |  |  |  |  | 175 |  |  |
| GAA | GAG | GAC | GTG | GCT | TTG | GAG | ACA | GAG | CTA | TAC | GCT | CTG | GCC | TCT | GAC | 576 |
| Glu | Glu | Asp | Val | Ala | Leu | Glu | Thr | Glu | Leu | Tyr | Ala | Leu | Ala | Ser | Asp |  |
|  |  |  | 180 |  |  |  |  | 185 |  |  |  |  | 190 |  |  |  |
| CAT | CCA | GAA | TGG | GTG | CGG | GCA | CTT | GGG | AAA | TAC | TAT | GCC | TCA | GGC | ACC | 624 |
| His | Pro | Glu | Trp | Val | Arg | Ala | Leu | Gly | Lys | Tyr | Tyr | Ala | Ser | Gly | Thr |  |
|  |  | 195 |  |  |  |  | 200 |  |  |  |  | 205 |  |  |  |  |
| ATG | GTC | ACC | CCG | GAA | GGG | GTG | CCC | GTC | GGT | GAG | AGG | TAT | TGC | AGA | TCC | 672 |
| Met | Val | Thr | Pro | Glu | Gly | Val | Pro | Val | Gly | Glu | Arg | Tyr | Cys | Arg | Ser |  |
| 210 |  |  |  |  | 215 |  |  |  |  | 220 |  |  |  |  |  |  |
| TCG | GGT | GTC | CTA | ACA | ACT | AGC | GCG | AGC | AAC | TGC | TTG | ACC | TGC | TAC | ATC | 720 |
| Ser | Gly | Val | Leu | Thr | Thr | Ser | Ala | Ser | Asn | Cys | Leu | Thr | Cys | Tyr | Ile |  |
| 225 |  |  |  |  | 230 |  |  |  |  | 235 |  |  |  |  | 240 |  |
| AAG | GTG | AAA | GCT | GCC | TGT | GAG | AGA | GTG | GGG | CTG | AAA | AAT | GTC | TCT | CTT | 768 |
| Lys | Val | Lys | Ala | Ala | Cys | Glu | Arg | Val | Gly | Leu | Lys | Asn | Val | Ser | Leu |  |
|  |  |  |  | 245 |  |  |  |  | 250 |  |  |  |  | 255 |  |  |
| CTC | ATA | GCC | GGC | GAT | GAC | TGC | TTG | ATA | ATA | TGT | GAG | CGG | CCA | GTG | TGC | 816 |
| Leu | Ile | Ala | Gly | Asp | Asp | Cys | Leu | Ile | Ile | Cys | Glu | Arg | Pro | Val | Cys |  |
|  |  |  | 260 |  |  |  |  | 265 |  |  |  |  | 270 |  |  |  |
| GAC | CCA | AGC | GAC | GCT | TTG | GGC | AGA | GCC | CTA | GCG | AGC | TAT | GGG | TAC | GCG | 864 |
| Asp | Pro | Ser | Asp | Ala | Leu | Gly | Arg | Ala | Leu | Ala | Ser | Tyr | Gly | Tyr | Ala |  |
|  |  | 275 |  |  |  |  | 280 |  |  |  |  | 285 |  |  |  |  |
| TGC | GAG | CCC | TCA | TAT | CAT | GCA | TCA | TTG | GAC | ACG | GCC | CCC | TTC | TGC | TCC | 912 |
| Cys | Glu | Pro | Ser | Tyr | His | Ala | Ser | Leu | Asp | Thr | Ala | Pro | Phe | Cys | Ser |  |
|  | 290 |  |  |  |  | 295 |  |  |  |  | 300 |  |  |  |  |  |
| ACT | TGG | CTT | GCT | GAG | TGC | AAT | GCA | GAT | GGG | AAG | CGC | CAT | TTC | TTC | CTG | 960 |
| Thr | Trp | Leu | Ala | Glu | Cys | Asn | Ala | Asp | Gly | Lys | Arg | His | Phe | Phe | Leu |  |
| 305 |  |  |  |  | 310 |  |  |  |  | 315 |  |  |  |  | 320 |  |
| ACC | ACG | GAC | TTC | CGG | AGG | CCG | CTC | GCT | CGC | ATG | TCG | AGT | GAG | TAT | AGT | 1008 |
| Thr | Thr | Asp | Phe | Arg | Arg | Pro | Leu | Ala | Arg | Met | Ser | Ser | Glu | Tyr | Ser |  |
|  |  |  |  | 325 |  |  |  |  | 330 |  |  |  |  | 335 |  |  |
| GAC | CCG | ATG | GCT | TCG | GCG | ATC | GGT | TAC | ATC | CTC | CTT | TAT | CCT | TGG | CAC | 1056 |
| Asp | Pro | Met | Ala | Ser | Ala | Ile | Gly | Tyr | Ile | Leu | Leu | Tyr | Pro | Trp | His |  |
|  |  |  | 340 |  |  |  |  | 345 |  |  |  |  | 350 |  |  |  |
| CCC | ATC | ACA | CGG | TGG | GTC | ATC | ATC | CCT | CAT | GTG | CTA | ACG | TGC | GCA | TTC | 1104 |
| Pro | Ile | Thr | Arg | Trp | Val | Ile | Ile | Pro | His | Val | Leu | Thr | Cys | Ala | Phe |  |
|  |  | 355 |  |  |  |  | 360 |  |  |  |  | 365 |  |  |  |  |
| AGG | GGT | GGA | GGC | ACA | CCG | TCT | GAT | CCG | GTT | TGG | TGC | CAG | GTG | CAT | GGT | 1152 |
| Arg | Gly | Gly | Gly | Thr | Pro | Ser | Asp | Pro | Val | Trp | Cys | Gln | Val | His | Gly |  |

-continued

```
        370                       375                       380
AAC TAC TAC AAG TTT CCA CTG GAC AAA CTG CCT AAC ATC ATC GTG GCC    1200
Asn Tyr Tyr Lys Phe Pro Leu Asp Lys Leu Pro Asn Ile Ile Val Ala
385                 390                 395                 400

CTC CAC GGA CCA GCA GCG TTG AGG GTT ACC GCA GAC ACA ACT AAA ACA    1248
Leu His Gly Pro Ala Ala Leu Arg Val Thr Ala Asp Thr Thr Lys Thr
                405                 410                 415

AAG ATG GAG GCT GGT AAG GTT CTG AGC GAC CTC AAG CTC CCT GGC TTA    1296
Lys Met Glu Ala Gly Lys Val Leu Ser Asp Leu Lys Leu Pro Gly Leu
            420                 425                 430

GCA GTC CAC CGA AAG AAG GCC GGG GCG TTG CGA ACA CGC ATG CTC CGC    1344
Ala Val His Arg Lys Lys Ala Gly Ala Leu Arg Thr Arg Met Leu Arg
        435                 440                 445

TCG CGC GGT TGG GCT GAG TTG GCT AGG GGC TTG TTG TGG CAT CCA GGC    1392
Ser Arg Gly Trp Ala Glu Leu Ala Arg Gly Leu Leu Trp His Pro Gly
    450                 455                 460

CTA CGG CTT CCT CCC CCT GAG ATT GCT GGT ATC CCG GGG GGT TTC CCT    1440
Leu Arg Leu Pro Pro Pro Glu Ile Ala Gly Ile Pro Gly Gly Phe Pro
465                 470                 475                 480

CTC TCC CCC CCC TAT ATG GGG GTG GTA CAT CAA TTG GAT TTC ACA AGC    1488
Leu Ser Pro Pro Tyr Met Gly Val Val His Gln Leu Asp Phe Thr Ser
                485                 490                 495

CAG AGG AGT CGC TGG CGG TGG TTG GGG TTC TTA GCC CTG CTC ATC GTA    1536
Gln Arg Ser Arg Trp Arg Trp Leu Gly Phe Leu Ala Leu Leu Ile Val
            500                 505                 510

GCC CTC TTC GGG                                                    1548
Ala Leu Phe Gly
        515
```

( 2 ) INFORMATION FOR SEQ ID NO:41:

( i ) SEQUENCE CHARACTERISTICS:
        ( A ) LENGTH: 516 amino acids
        ( B ) TYPE: amino acid
        ( D ) TOPOLOGY: linear ( i i ) MOLECULE TYPE: protein ( x i ) SEQUENCE DESCRIPTION: SEQ ID NO:41:

```
Val Asp Lys Val Thr Phe Trp Arg Ala Pro Arg Val His Asp Lys Tyr
1               5                   10                  15

Leu Val Asp Ser Ile Glu Arg Ala Lys Arg Ala Ala Gln Ala Cys Leu
                20                  25                  30

Ser Met Gly Tyr Thr Tyr Glu Glu Ala Ile Arg Thr Val Arg Pro His
            35                  40                  45

Ala Ala Met Gly Trp Gly Ser Lys Val Ser Val Lys Asp Leu Ala Thr
        50                  55                  60

Pro Ala Gly Lys Met Ala Val His Asp Arg Leu Gln Glu Ile Leu Glu
65                  70                  75                  80

Gly Thr Pro Val Pro Phe Thr Leu Thr Val Lys Lys Glu Val Phe Phe
                85                  90                  95

Lys Asp Arg Lys Glu Glu Lys Ala Pro Arg Leu Ile Val Phe Pro Pro
                100                 105                 110

Leu Asp Phe Arg Ile Ala Glu Lys Leu Ile Leu Gly Asp Pro Gly Arg
            115                 120                 125

Val Ala Lys Ala Val Leu Gly Gly Ala Tyr Ala Phe Gln Tyr Thr Pro
        130                 135                 140

Asn Gln Arg Val Lys Glu Met Leu Lys Leu Trp Glu Ser Lys Lys Thr
145                 150                 155                 160
```

| Pro | Cys | Ala | Ile | Cys | Val | Asp | Ala | Thr | Cys | Phe | Asp | Ser | Ser | Ile | Thr |
|---|---|---|---|---|---|---|---|---|---|---|---|---|---|---|---|
| | | | | 165 | | | | 170 | | | | | | 175 | |

Glu Glu Asp Val Ala Leu Glu Thr Leu Tyr Ala Leu Ala Ser Asp
            180              185                  190

His Pro Glu Trp Val Arg Ala Leu Gly Lys Tyr Tyr Ala Ser Gly Thr
        195                 200                 205

Met Val Thr Pro Glu Gly Val Pro Val Gly Glu Arg Tyr Cys Arg Ser
    210             215                 220

Ser Gly Val Leu Thr Thr Ser Ala Ser Asn Cys Leu Thr Cys Tyr Ile
225             230                 235                     240

Lys Val Lys Ala Ala Cys Glu Arg Val Gly Leu Lys Asn Val Ser Leu
            245                 250                     255

Leu Ile Ala Gly Asp Asp Cys Leu Ile Ile Cys Glu Arg Pro Val Cys
            260                 265                 270

Asp Pro Ser Asp Ala Leu Gly Arg Ala Leu Ala Ser Tyr Gly Tyr Ala
        275                 280                 285

Cys Glu Pro Ser Tyr His Ala Ser Leu Asp Thr Ala Pro Phe Cys Ser
    290                 295                 300

Thr Trp Leu Ala Glu Cys Asn Ala Asp Gly Lys Arg His Phe Phe Leu
305                 310                 315                     320

Thr Thr Asp Phe Arg Arg Pro Leu Ala Arg Met Ser Ser Glu Tyr Ser
                325                 330                 335

Asp Pro Met Ala Ser Ala Ile Gly Tyr Ile Leu Leu Tyr Pro Trp His
            340                 345                 350

Pro Ile Thr Arg Trp Val Ile Ile Pro His Val Leu Thr Cys Ala Phe
        355                 360                 365

Arg Gly Gly Gly Thr Pro Ser Asp Pro Val Trp Cys Gln Val His Gly
    370                 375                 380

Asn Tyr Tyr Lys Phe Pro Leu Asp Lys Leu Pro Asn Ile Ile Val Ala
385                 390                 395                     400

Leu His Gly Pro Ala Ala Leu Arg Val Thr Ala Asp Thr Thr Lys Thr
            405                 410                 415

Lys Met Glu Ala Gly Lys Val Leu Ser Asp Leu Lys Leu Pro Gly Leu
            420                 425                 430

Ala Val His Arg Lys Lys Ala Gly Ala Leu Arg Thr Arg Met Leu Arg
        435                 440                 445

Ser Arg Gly Trp Ala Glu Leu Ala Arg Gly Leu Leu Trp His Pro Gly
    450                 455                 460

Leu Arg Leu Pro Pro Pro Glu Ile Ala Gly Ile Pro Gly Gly Phe Pro
465                 470                 475                     480

Leu Ser Pro Pro Tyr Met Gly Val Val His Gln Leu Asp Phe Thr Ser
            485                 490                 495

Gln Arg Ser Arg Trp Arg Trp Leu Gly Phe Leu Ala Leu Leu Ile Val
        500                 505                 510

Ala Leu Phe Gly
        515

( 2 ) INFORMATION FOR SEQ ID NO:42:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: DNA (genomic)

( v i ) ORIGINAL SOURCE:
( C ) INDIVIDUAL ISOLATE: Oligonucleotide "H"

( x i ) SEQUENCE DESCRIPTION: SEQ ID NO:42:

CGAATAAACA AGCTAATATA CCCGAG 26

( 2 ) INFORMATION FOR SEQ ID NO:43:

( i ) SEQUENCE CHARACTERISTICS:
( A ) LENGTH: 26 base pairs
( B ) TYPE: nucleic acid
( C ) STRANDEDNESS: single
( D ) TOPOLOGY: linear ( i i ) MOLECULE TYPE: DNA (genomic)

( v i ) ORIGINAL SOURCE:
( C ) INDIVIDUAL ISOLATE: Oligonucleotide "C"

( x i ) SEQUENCE DESCRIPTION: SEQ ID NO:43:

CCTGAAACAG GAATCCCGTC ACGCAG 26

( 2 ) INFORMATION FOR SEQ ID NO:44:

( i ) SEQUENCE CHARACTERISTICS:
( A ) LENGTH: 20 base pairs
( B ) TYPE: nucleic acid
( C ) STRANDEDNESS: single
( D ) TOPOLOGY: linear ( i i ) MOLECULE TYPE: DNA (genomic)

( v i ) ORIGINAL SOURCE:
( C ) INDIVIDUAL ISOLATE: Oligonucleotide "S"

( x i ) SEQUENCE DESCRIPTION: SEQ ID NO:44:

GCACCGAGCC GACCGAGTGG 20

( 2 ) INFORMATION FOR SEQ ID NO:45:

( i ) SEQUENCE CHARACTERISTICS:
( A ) LENGTH: 26 base pairs
( B ) TYPE: nucleic acid
( C ) STRANDEDNESS: single
( D ) TOPOLOGY: linear ( i i ) MOLECULE TYPE: DNA (genomic)

( v i ) ORIGINAL SOURCE:
( C ) INDIVIDUAL ISOLATE: Primer GF ( x i ) SEQUENCE DESCRIPTION: SEQ ID NO:45:

CGCGAGATCT CATGGGTTTA CCCGTG 26

( 2 ) INFORMATION FOR SEQ ID NO:46:

( i ) SEQUENCE CHARACTERISTICS:
( A ) LENGTH: 30 base pairs
( B ) TYPE: nucleic acid
( C ) STRANDEDNESS: single
( D ) TOPOLOGY: linear ( i i ) MOLECULE TYPE: DNA (genomic)

( v i ) ORIGINAL SOURCE:
( C ) INDIVIDUAL ISOLATE: Primer GR ( x i ) SEQUENCE DESCRIPTION: SEQ ID NO:46:

GCGCGAATTC TAGAGACGTA ACCCTCCGCC 30

(2) INFORMATION FOR SEQ ID NO:47:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (C) INDIVIDUAL ISOLATE: Primer 42F (xi) SEQUENCE DESCRIPTION: SEQ ID NO:47:

CTGCTGTTAG GCATTGG        17

(2) INFORMATION FOR SEQ ID NO:48:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (C) INDIVIDUAL ISOLATE: Primer 42R (xi) SEQUENCE DESCRIPTION: SEQ ID NO:48:

CGCGAATTCA GGCCTGGTCT CCATGC        26

(2) INFORMATION FOR SEQ ID NO:49:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (C) INDIVIDUAL ISOLATE: Primer 4F (xi) SEQUENCE DESCRIPTION: SEQ ID NO:49:

GCGCAGATCT CCGCTGCGAC GCTG        24

(2) INFORMATION FOR SEQ ID NO:50:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (C) INDIVIDUAL ISOLATE: Primer 4R (xi) SEQUENCE DESCRIPTION: SEQ ID NO:50:

GCGCGAATTC TTAGCCTGAG CCAAG        25

(2) INFORMATION FOR SEQ ID NO:51:

(i) SEQUENCE CHARACTERISTICS:
        (A) LENGTH: 1967 base pairs
        (B) TYPE: nucleic acid
        (C) STRANDEDNESS: double
        (D) TOPOLOGY: linear ( i i ) MOLECULE TYPE: DNA (genomic)

( v i ) ORIGINAL SOURCE:
    ( C ) INDIVIDUAL ISOLATE: Heterologous HGV DNA in Vector G ( x i ) SEQUENCE DESCRIPTION: SEQ ID NO:51:

```
TCATGGGTTT  ACCCGTGGTT  GCGCGCCGTG  GTGATGAGGT  TCTCATCGGC  GTCTTCCAGG     60
ATGTGAATCA  TTTGCCTCCC  GGGTTTGTTC  CGACCGCGCC  TGTTGTCATC  CGACGGTGCG    120
GAAAGGGCTT  CTTGGGGGTC  ACAAAGGCTG  CCTTGACAGG  TCGGGATCCT  GACTTACATC    180
CAGGGAACGT  CATGGTGTTG  GGGACGGCTA  CGTCGCGAAG  CATGGGAACA  TGCTTGAACG    240
GCCTGCTGTT  CACGACCTTC  CATGGGGCTT  CATCCCGAAC  CATCGCCACA  CCCGTGGGGG    300
CCCTTAATCC  CAGATGGTGG  TCAGCCAGTG  ATGATGTCAC  GGTGTATCCA  CTCCCGGATG    360
GGGCTACTTC  GTTAACACCT  TGTACTTGCC  AGGCTGAGTC  CTGTTGGGTC  ATCAGATCCG    420
ACGGGGCCCT  ATGCCATGGC  TTGAGCAAGG  GGGACAAGGT  GGAGCTGGAT  GTGGCCATGG    480
AGGTCTCTGA  CTTCCGTGGC  TCGTCTGGCT  CACCGGTCCT  ATGTGACGAA  GGGCACGCAG    540
TAGGAATGCT  CGTGTCTGTG  CTTCACTCCG  GTGGTAGGGT  CACCGCGGCA  CGGTTCACTA    600
GGCCGTGGAC  CCAAGTGCCA  ACAGATGCCA  AAACCACTAC  TGAACCCCCT  CCGGTGCCGG    660
CCAAAGGAGT  TTTCAAAGAG  GCCCCGTTGT  TTATGCCTAC  GGGAGCGGGA  AAGAGCACTC    720
GCGTCCCGTT  GGAGTACGAT  AACATGGGGC  ACAAGGTCTT  AATCTTGAAC  CCCTCAGTGG    780
CCACTGTGCG  GGCCATGGGC  CCGTACATGG  AGCGGCTGGC  GGGTAAACAT  CCAAGTATAT    840
ACTGTGGGCA  TGATACAACT  GCTTTCACAA  GGATCACTGA  CTCCCCCCTG  ACGTATTCAA    900
CCTATGGGAG  GTTTTTGGCC  AACCCTAGGC  AGATGCTACG  GGGCGTTTCG  GTGGTCATTT    960
GTGATGAGTG  CCACAGTCAT  GACTCAACCG  TGCTGTTAGG  CATTGGGAGA  GTCCGGGAGC   1020
TGGCGCGTGG  GTGCGGGGTG  CAACTAGTGC  TCTACGCCAC  CGCTACACCT  CCCGGATCCC   1080
CTATGACGCA  GCACCCTTCC  ATAATTGAGA  CAAAATTGGA  CGTGGGCGAG  ATTCCCTTTT   1140
ATGGGCATGG  AATACCCCTC  GAGCGGATGC  GAACCGGAAG  GCACCTCGTG  TTCTGCCATT   1200
CTAAGGCTGA  GTGCGAGCGC  CTTGCTGGCC  AGTTCTCCGC  TAGGGGGGTC  AATGCCATTG   1260
CCTATTATAG  GGGTAAAGAC  AGTTCTATCA  TCAAGGATGG  GGACCTGGTG  GTCTGTGCTA   1320
CAGACGCGCT  TTCCACTGGG  TACACTGGAA  ATTTCGACTC  CGTCACCGAC  TGTGGATTAG   1380
TGGTGGAGGA  GGTCGTTGAG  GTGACCCTTG  ATCCACCAT   TACCATCTCC  CTGCGGACAG   1440
TGCCTGCGTC  GGCTGAACTG  TCGATGCAAA  GACGAGGACG  CACGGGTAGG  GGCAGGTCTG   1500
GACGCTACTA  CTACGCGGGG  GTGGGCAAAG  CCCCTGCGGG  TGTGGTGCGC  TCAGGTCCTG   1560
TCTGGTCGGC  GGTGGAAGCT  GGAGTGACCT  GGTACGGAAT  GGAACCTGAC  TTGACAGCTA   1620
ACCTACTGAG  ACTTTACGAC  GACTGCCCTT  ACACCGCAGC  CGTCGCGGCT  GATATCGGAG   1680
AAGCCGCGGT  GTTCTTCTCT  GGGCTCGCCC  CATTGAGGAT  GCACCTGAT   GTCAGCTGGG   1740
CAAAAGTTCG  CGGCGTCAAC  TGGCCCCTCT  TGGTGGGTGT  TCAGCGGACC  ATGTGTCGGG   1800
AAACACTGTC  TCCCGGCCCA  TCGGATGACC  CCAATGGGC   AGGTCTGAAG  GCCCAAATC    1860
CTGTCCCACT  CCTGCTGAGG  TGGGCAATG   ATTTACCATC  TAAAGTGGCC  GGCCACCACA   1920
TAGTGGACGA  CCTGGTCCGG  AGACTCGGTG  TGGCGGAGGG  TTACGTC                  1967
```

( 2 ) INFORMATION FOR SEQ ID NO:52:

( i ) SEQUENCE CHARACTERISTICS:
        ( A ) LENGTH: 2379 base pairs
        ( B ) TYPE: nucleic acid
        ( C ) STRANDEDNESS: double (D) TOPOLOGY: linear (ii) MOLECULE TYPE: DNA (genomic)

(vi) ORIGINAL SOURCE:
(C) INDIVIDUAL ISOLATE: Heterologous HGV DNA in Vector 42

(xi) SEQUENCE DESCRIPTION: SEQ ID NO:52:

```
ATCTTGGTGT CCCGGCCCTC GTTGCGGCGT TTGGCTCGGG TGGTTGAGTG CTGTGTGATG    60
GCGGGTGAGA AGGCCACAAC CGTCCGGCTG GTCTCCAAGA TGTGTGCGAG AGGAGCTTAT   120
TTGTTCGATC ATATGGGCTC TTTTTCGCGT GCTGTCAAGG AGCGCCTGTT GGAATGGGAC   180
GCAGCTCTTG AACCTCTGTC ATTCACTAGG ACGGACTGTC GCATCATACG GGATGCCGCG   240
AGGACTTTGT CCTGCGGGCA GTGCGTCATG GGTTACCCG TGGTTGCGCG CCGTGGTGAT    300
GAGGTTCTCA TCGGCGTCTT CCAGGATGTG AATCATTTGC CTCCCGGGTT TGTTCCGACC   360
GCGCCTGTTG TCATCCGACG GTGCGGAAAG GGCTTCTTGG GGGTCACAAA GGCTGCCTTG   420
ACAGGTCGGG ATCCTGACTT ACATCCAGGG AACGTCATGG TGTTGGGGAC GGCTACGTCG   480
CGAAGCATGG GAACATGCTT GAACGGCCTG CTGTTCACGA CCTTCCATGG GGCTTCATCC   540
CGAACCATCG CCACACCCGT GGGGGCCCTT AATCCCAGAT GGTGGTCAGC CAGTGATGAT   600
GTCACGGTGT ATCCACTCCC GGATGGGGCT ACTTCGTTAA CACCTTGTAC TTGCCAGGCT   660
GAGTCCTGTT GGGTCATCAG ATCCGACGGG GCCCTATGCC ATGGCTTGAG CAAGGGGAC    720
AAGGTGGAGC TGGATGTGGC CATGGAGGTC TCTGACTTCC GTGGCTCGTC TGGCTCACCG   780
GTCCTATGTG ACGAAGGGCA CGCAGTAGGA ATGCTCGTGT CTGTGCTTCA CTCCGGTGGT   840
AGGGTCACCG CGGCACGGTT CACTAGGCCG TGGACCCAAG TGCCAACAGA TGCCAAAACC   900
ACTACTGAAC CCCCTCCGGT GCCGGCCAAA GGAGTTTTCA AAGAGGCCCC GTTGTTTATG   960
CCTACGGGAG CGGGAAAGAG CACTCGCGTC CCGTTGGAGT ACGATAACAT GGGGCACAAG  1020
GTCTTAATCT TGAACCCCTC AGTGGCCACT GTGCGGGCCA TGGGCCCGTA CATGGAGCGG  1080
CTGGCGGGTA AACATCCAAG TATATACTGT GGGCATGATA CAACTGCTTT CACAAGGATC  1140
ACTGACTCCC CCCTGACGTA TTCAACCTAT GGGAGGTTTT TGGCCAACCC TAGGCAGATG  1200
CTACGGGGCG TTTCGGTGGT CATTTGTGAT GAGTGCCACA GTCATGACTC AACCGTGCTG  1260
TTAGGCATTG GGAGAGTCCG GGAGCTGGCG CGTGGGTGCG GGGTGCAACT AGTGCTCTAC  1320
GCCACCGCTA CACCTCCCGG ATCCCCTATG ACGCAGCACC CTTCCATAAT TGAGACAAAA  1380
TTGGACGTGG GCGAGATTCC CTTTTATGGG CATGGAATAC CCCTCGAGCG GATGCGAACC  1440
GGAAGGCACC TCGTGTTCTG CCATTCTAAG GCTGAGTGCG AGCGCCTTGC TGGCCAGTTC  1500
TCCGCTAGGG GGGTCAATGC CATTGCCTAT TATAGGGGTA AAGACAGTTC TATCATCAAG  1560
GATGGGGACC TGGTGGTCTG TGCTACAGAC GCGCTTTCCA CTGGGTACAC TGGAAATTTC  1620
GACTCCGTCA CCGACTGTGG ATTAGTGGTG GAGGAGGTCG TTGAGGTGAC CCTTGATCCC  1680
ACCATTACCA TCTCCCTGCG GACAGTGCCT GCGTCGGCTG AACTGTCGAT GCAAAGACGA  1740
GGACGCACGG GTAGGGGCAG GTCTGGACGC TACTACTACG GGGGTGGG CAAAGCCCCT    1800
GCGGGTGTGG TGCGCTCAGG TCCTGTCTGG TCGGCGGTGG AAGCTGGAGT GACCTGGTAC  1860
GGAATGGAAC CTGACTTGAC AGCTAACCTA CTGAGACTTT ACGACGACTG CCCTTACACC  1920
GCAGCCGTCG CGGCTGATAT CGGAGAAGCC GCGGTGTTCT TCTCTGGGCT CGCCCCATTG  1980
AGGATGCACC CTGATGTCAG CTGGGCAAAA GTTCGCGGCG TCAACTGGCC CCTCTTGGTG  2040
GGTGTTCAGC GGACCATGTG TCGGGAAACA CTGTCTCCCG GCCCATCGGA TGACCCCCAA  2100
TGGGCAGGTC TGAAGGGCCC AAATCCTGTC CCACTCCTGC TGAGGTGGGG CAATGATTTA  2160
```

| | | | | | |
|---|---|---|---|---|---|
| CCATCTAAAG | TGGCCGGCCA | CCACATAGTG | GACGACCTGG | TCCGGAGACT | CGGTGTGGCG | 2220
| GAGGGTTACG | TCCGCTGCGA | CGCTGGGCCG | ATCTTGATGA | TCGGTCTAGC | TATCGCGGGG | 2280
| GGAATGATCT | ACGCGTCATA | CACCGGGTCG | CTAGTGGTGG | TGACAGACTG | GGATGTGAAG | 2340
| GGGGGTGGCG | CCCCCCTTTA | TCGGCATGGA | GACCAGGCC  | | | 2379

( 2 ) INFORMATION FOR SEQ ID NO:53:

( i ) SEQUENCE CHARACTERISTICS:
        ( A ) LENGTH: 2232 base pairs
        ( B ) TYPE: nucleic acid
        ( C ) STRANDEDNESS: double
        ( D ) TOPOLOGY: linear ( i i ) MOLECULE TYPE: DNA (genomic)

( v i ) ORIGINAL SOURCE:
        ( C ) INDIVIDUAL ISOLATE: Heterologous HGV DNA in Vector 23

( x i ) SEQUENCE DESCRIPTION: SEQ ID NO:53:

| | | | | | |
|---|---|---|---|---|---|
| ATCTTGGTGT | CCCGGCCCTC | GTTGCGGCGT | TTGGCTCGGG | TGGTTGAGTG | CTGTGTGATG | 60
| GCGGGTGAGA | AGGCCACAAC | CGTCCGGCTG | GTCTCCAAGA | TGTGTGCGAG | AGGAGCTTAT | 120
| TTGTTCGATC | ATATGGGCTC | TTTTCGCGT  | GCTGTCAAGG | AGCGCCTGTT | GGAATGGGAC | 180
| GCAGCTCTTG | AACCTCTGTC | ATTCACTAGG | ACGGACTGTC | GCATCATACG | GGATGCCGCG | 240
| AGGACTTTGT | CCTGCGGGCA | GTGCGTCATG | GGTTTACCCG | TGGTTGCGCG | CCGTGGTGAT | 300
| GAGGTTCTCA | TCGGCGTCTT | CCAGGATGTG | AATCATTTGC | CTCCCGGGTT | TGTTCCGACC | 360
| GCGCCTGTTG | TCATCCGACG | GTGCGGAAAG | GGCTTCTTGG | GGGTCACAAA | GGCTGCCTTG | 420
| ACAGGTCGGG | ATCCTGACTT | ACATCCAGGG | AACGTCATGG | TGTTGGGGAC | GGCTACGTCG | 480
| CGAAGCATGG | GAACATGCTT | GAACGGCCTG | CTGTTCACGA | CCTTCCATGG | GGCTTCATCC | 540
| CGAACCATCG | CCACACCCGT | GGGGGCCCTT | AATCCCAGAT | GGTGGTCAGC | CAGTGATGAT | 600
| GTCACGGTGT | ATCCACTCCC | GGATGGGGCT | ACTTCGTTAA | CACCTTGTAC | TTGCCAGGCT | 660
| GAGTCCTGTT | GGGTCATCAG | ATCCGACGGG | GCCCTATGCC | ATGGCTTGAG | CAAGGGGGAC | 720
| AAGGTGGAGC | TGGATGTGGC | CATGGAGGTC | TCTGACTTCC | GTGGCTCGTC | TGGCTCACCG | 780
| GTCCTATGTG | ACGAAGGGCA | CGCAGTAGGA | ATGCTCGTGT | CTGTGCTTCA | CTCCGGTGGT | 840
| AGGGTCACCG | CGGCACGGTT | CACTAGGCCG | TGGACCCAAG | TGCCAACAGA | TGCCAAAACC | 900
| ACTACTGAAC | CCCCTCCGGT | GCCGGCCAAA | GGAGTTTTCA | AAGAGGCCCC | GTTGTTTATG | 960
| CCTACGGGAG | CGGGAAAGAG | CACTCGCGTC | CCGTTGGAGT | ACGATAACAT | GGGGCACAAG | 1020
| GTCTTAATCT | TGAACCCCTC | AGTGGCCACT | GTGCGGGCCA | TGGGCCCGTA | CATGGAGCGG | 1080
| CTGGCGGGTA | AACATCCAAG | TATATACTGT | GGGCATGATA | CAACTGCTTT | CACAAGGATC | 1140
| ACTGACTCCC | CCCTGACGTA | TTCAACCTAT | GGGAGGTTTT | TGGCCAACCC | TAGGCAGATG | 1200
| CTACGGGGCG | TTTCGGTGGT | CATTTGTGAT | GAGTGCCACA | GTCATGACTC | AACCGTGCTG | 1260
| TTAGGCATTG | GGAGAGTCCG | GGAGCTGGCG | CGTGGGTGCG | GGGTGCAACT | AGTGCTCTAC | 1320
| GCCACCGCTA | CACCTCCCGG | ATCCCTATG  | ACGCAGCACC | CTTCCATAAT | TGAGACAAAA | 1380
| TTGGACGTGG | GCGAGATTCC | CTTTTATGGG | CATGGAATAC | CCCTCGAGCG | GATGCGAACC | 1440
| GGAAGGCACC | TCGTGTTCTG | CCATTCTAAG | GCTGAGTGCG | AGCGCCTTGC | TGGCCAGTTC | 1500
| TCCGCTAGGG | GGGTCAATGC | CATTGCCTAT | TATAGGGGTA | AAGACAGTTC | TATCATCAAG | 1560
| GATGGGGACC | TGGTGGTCTG | TGCTACAGAC | GCGCTTTCCA | CTGGGTACAC | TGGAAATTTC | 1620
| GACTCCGTCA | CCGACTGTGG | ATTAGTGGTG | GAGGAGGTCG | TTGAGGTGAC | CCTTGATCCC | 1680

| | | | | | |
|---|---|---|---|---|---|
|ACCATTACCA|TCTCCCTGCG|GACAGTGCCT|GCGTCGGCTG|AACTGTCGAT|GCAAAGACGA|1740|
|GGACGCACGG|GTAGGGGCAG|GTCTGGACGC|TACTACTACG|CGGGGGTGGG|CAAAGCCCCT|1800|
|GCGGGTGTGG|TGCGCTCAGG|TCCTGTCTGG|TCGGCGGTGG|AAGCTGGAGT|GACCTGGTAC|1860|
|GGAATGGAAC|CTGACTTGAC|AGCTAACCTA|CTGAGACTTT|ACGACGACTG|CCCTTACACC|1920|
|GCAGCCGTCG|CGGCTGATAT|CGGAGAAGCC|GCGGTGTTCT|TCTCTGGGCT|CGCCCCATTG|1980|
|AGGATGCACC|CTGATGTCAG|CTGGGCAAAA|GTTCGCGGCG|TCAACTGGCC|CCTCTTGGTG|2040|
|GGTGTTCAGC|GGACCATGTG|TCGGGAAACA|CTGTCTCCCG|GCCCATCGGA|TGACCCCAA|2100|
|TGGGCAGGTC|TGAAGGGCCC|AAATCCTGTC|CCACTCCTGC|TGAGGTGGGG|CAATGATTTA|2160|
|CCATCTAAAG|TGGCCGGCCA|CCACATAGTG|GACGACCTGG|TCCGGAGACT|CGGTGTGGCG|2220|
|GAGGGTTACG|TC| | | | |2232|

( 2 ) INFORMATION FOR SEQ ID NO:54:

( i ) SEQUENCE CHARACTERISTICS:
        ( A ) LENGTH: 573 base pairs
        ( B ) TYPE: nucleic acid
        ( C ) STRANDEDNESS: double
        ( D ) TOPOLOGY: linear ( i i ) MOLECULE TYPE: DNA (genomic)

( v i ) ORIGINAL SOURCE:
        ( C ) INDIVIDUAL ISOLATE: Heterologous HGV DNA in Vector 4

( x i ) SEQUENCE DESCRIPTION: SEQ ID NO:54:

| | | | | | |
|---|---|---|---|---|---|
|GCGCCTGTTG|TCATCCGACG|GTGCGGAAAG|GGCTTCTTGG|GGGTCACAAA|GGCTGCCTTG|60|
|ACAGGTCGGG|ATCCTGACTT|ACATCCAGGG|AACGTCATGG|TGTTGGGGAC|GGCTACGTCG|120|
|CGAAGCATGG|GAACATGCTT|GAACGGCCTG|CTGTTCACGA|CCTTCCATGG|GCTTCATCC|180|
|CGAACCATCG|CCACACCCGT|GGGGGCCCTT|AATCCCAGAT|GGTGGTCAGC|CAGTGATGAT|240|
|GTCACGGTGT|ATCCACTCCC|GGATGGGGCT|ACTTCGTTAA|CACCTTGTAC|TTGCCAGGCT|300|
|GAGTCCTGTT|GGGTCATCAG|ATCCGACGGG|GCCCTATGCC|ATGGCTTGAG|CAAGGGGGAC|360|
|AAGGTGGAGC|TGGATGTGGC|CATGGAGGTC|TCTGACTTCC|GTGGCTCGTC|TGGCTCACCG|420|
|GTCCTATGTG|ACGAAGGGCA|CGCAGTAGGA|ATGCTCGTGT|CTGTGCTTCA|CTCCGGTGGT|480|
|AGGGTCACCG|CGGCACGGTT|CACTAGGCCG|TGGACCCAAG|TGCCAACAGA|TGCCAAAACC|540|
|ACTACTGAAC|CCCCTCCGGT|GCCGGCCAAA|GGA| | |573|

( 2 ) INFORMATION FOR SEQ ID NO:55:

( i ) SEQUENCE CHARACTERISTICS:
        ( A ) LENGTH: 1290 base pairs
        ( B ) TYPE: nucleic acid
        ( C ) STRANDEDNESS: double
        ( D ) TOPOLOGY: linear ( i i ) MOLECULE TYPE: DNA (genomic)

( v i ) ORIGINAL SOURCE:
        ( C ) INDIVIDUAL ISOLATE: Heterologous HGV DNA in Vector Q ( x i ) SEQUENCE DESCRIPTION: SEQ ID NO:55:

| | | | | | |
|---|---|---|---|---|---|
|GATCTGTGGT|ATGCCATCCC|GGTACTGACC|AGCCCGGGGG|CGGGCCTTGC|GGGGATCGCT|60|
|CTCGGGTTGG|TTTTGTATTC|AGCTAACAAC|TCTGGCACTA|CCACTTGGTT|GAACCGTCTG|120|
|CTGACTACGT|TACCAAGGTC|TTCATGTATC|CCGGACAGTT|ACTTTCAGCA|AGTTGACTAT|180|
|TGCGACAAGG|TCTCAGCCGT|GCTCCGGCGC|CTGAGCCTCA|CCCGCACAGT|GGTTGCCCTG|240|

```
GTCAACAGGG  AGCCTAAGGT  GGATGAGGTA  CAGGTGGGGT  ATGTCTGGGA  CCTGTGGGAG   300

TGGATCATGC  GCCAAGTGCG  CGTGGTCATG  GCCAGACTCA  GGGCCCTCTG  CCCCGTGGTG   360

TCACTACCCT  TGTGGCATTG  CGGGGAGGGG  TGGTCCGGGG  AATGGTTGCT  TGACGGTCAT   420

GTTGAGAGTC  GCTGCCTCTG  TGGCTGCGTG  ATCACTGGTG  ACGTTCTGAA  TGGGCAACTC   480

AAAGAACCAG  TTTACTCTAC  CAAGCTGTGC  CGGCACTATT  GGATGGGGAC  TGTCCCTGTG   540

AACATGCTGG  GTTACGGTGA  AACGTCGCCT  CTCCTGGCCT  CCGACACCCC  GAAGGTTGTG   600

CCCTTCGGGA  CGTCTGGCTG  GGCTGAGGTG  GTGGTGACCA  CTACCCACGT  GGTAATCAGG   660

AGGACCTCCG  CCTATAAGCT  GCTGCGCCAG  CAAATCCTAT  CGGCTGCTGT  AGCTGAGCCC   720

TACTACGTCG  ACGGCATTCC  GGTCTCATGG  GACGCGGACG  CTCGTGCGCC  CGCCATGGTC   780

TATGGCCCTG  GGCAAAGTGT  TACCATTGAC  GGGGAGCGCT  ACACCTTGCC  TCATCAACTG   840

AGGCTCAGGA  ATGTGGCACC  CTCTGAGGTT  TCATCCGAGG  TGTCCATTGA  CATTGGGACG   900

GAGACTGAAG  ACTCAGAACT  GACTGAGGCC  GATCTGCCGC  CGGCGGCTGC  TGCTCTCCAA   960

GCGATCGAGA  ATGCTGCGAG  GATTCTTGAA  CCGCACATTG  ATGTCATCAT  GGAGGACTGC  1020

AGTACACCCT  CTCTTTGTGG  TAGTAGCCGA  GAGATGCCTG  TATGGGGAGA  AGACATCCCC  1080

CGTACTCCAT  CGCCAGCACT  TATCTCGGTT  ACTGAGAGCA  GCTCAGATGA  GAAGACCCCG  1140

TCGGTGTCCT  CCTCGCAGGA  GGATACCCCG  TCCTCTGACT  CATTCGAGGT  CATCCAAGAG  1200

TCCGAGACAG  CCGAAGGGGA  GGAAAGTGTC  TTCAACGTGG  CTCTTTCCGT  ATTAAAAGCC  1260

TTATTTCCAC  AGAGCGACGC  GACCAGGAAG                                      1290
```

( 2 ) INFORMATION FOR SEQ ID NO:56:

( i ) SEQUENCE CHARACTERISTICS:
        ( A ) LENGTH: 2388 base pairs
        ( B ) TYPE: nucleic acid
        ( C ) STRANDEDNESS: double
        ( D ) TOPOLOGY: linear ( i i ) MOLECULE TYPE: DNA (genomic)

( v i ) ORIGINAL SOURCE:
        ( C ) INDIVIDUAL ISOLATE: Heterologous HGV DNA in Vector N ( x i ) SEQUENCE DESCRIPTION: SEQ ID NO:56:

```
CGCTACACCT  TGCCTCATCA  ACTGAGGCTC  AGGAATGTGG  CACCCTCTGA  GGTTTCATCC    60

GAGGTGTCCA  TTGACATTGG  GACGGAGACT  GAAGACTCAG  AACTGACTGA  GGCCGATCTG   120

CCGCCGGCGG  CTGCTGCTCT  CCAAGCGATC  GAGAATGCTG  CGAGGATTCT  TGAACCGCAC   180

ATTGATGTCA  TCATGGAGGA  CTGCAGTACA  CCCTCTCTTT  GTGGTAGTAG  CCGAGAGATG   240

CCTGTATGGG  GAGAAGACAT  CCCCGTACT   CCATCGCCAG  CACTTATCTC  GGTTACTGAG   300

AGCAGCTCAG  ATGAGAAGAC  CCCGTCGGTG  TCCTCCTCGC  AGGAGGATAC  CCCGTCCTCT   360

GACTCATTCG  AGGTCATCCA  AGAGTCCGAG  ACAGCCGAAG  GGGAGGAAAG  TGTCTTCAAC   420

GTGGCTCTTT  CCGTATTAAA  AGCCTTATTT  CCACAGAGCG  ACGCGACCAG  GAAGCTTACC   480

GTCAAGATGT  CGTGCTGCGT  TGAAAAGAGC  GTCACGCGCT  TTTTCTCATT  GGGGTTGACG   540

GTGGCTGATG  TTGCTAGCCT  GTGTGAGATG  GAAATCCAGA  ACCATACAGC  CTATTGTGAC   600

CAGGTGCGCA  CTCCGCTTGA  ATTGCAGGTT  GGGTGCTTGG  TGGGCAATGA  ACTTACCTTT   660

GAATGTGACA  AGTGTGAGGC  TAGGCAAGAA  ACCTTGGCCT  CCTTCTCTTA  CATTTGGTCT   720

GGAGTGCCGC  TGACTAGGGC  CACGCCGGCC  AAGCCTCCCG  TGGTGAGGCC  GGTTGGCTCT   780

TTGTTAGTGG  CCGACACTAC  TAAGGTGTAT  GTTACCAATC  CAGACAATGT  GGGACGGAGG   840
```

-continued

| | | | | | | |
|---|---|---|---|---|---|---|
| GTGGACAAGG | TGACCTTCTG | GCGTGCTCCT | AGGGTTCATG | ATAAGTACCT | CGTGGACTCT | 900 |
| ATTGAGCGCG | CTAAGAGGGC | CGCTCAAGCC | TGCCTAAGCA | TGGGTTACAC | TTATGAGGAA | 960 |
| GCAATAAGGA | CTGTAAGGCC | ACATGCTGCC | ATGGGCTGGG | GATCTAAGGT | GTCGGTTAAG | 1020 |
| GACTTAGCCA | CCCCCGCGGG | GAAGATGGCC | GTCCATGACC | GGCTTCAGGA | GATACTTGAA | 1080 |
| GGGACTCCGG | TCCCCTTTAC | TCTTACTGTG | AAAAGGAGG | TGTTCTTCAA | AGACCGGAAG | 1140 |
| GAGGAGAAGG | CCCCCCGCCT | CATTGTGTTC | CCCCCCCTGG | ACTTCCGGAT | AGCTGAAAAG | 1200 |
| CTCATCTTGG | GAGACCCAGG | CCGGGTAGCC | AAGGCGGTGT | TGGGGGGGGC | CTACGCCTTC | 1260 |
| CAGTACACCC | CAAATCAGCG | AGTTAAGGAG | ATGCTCAAGC | TATGGGAGTC | TAAGAAGACC | 1320 |
| CCTTGCGCCA | TCTGTGTGGA | CGCCACCTGC | TTCGACAGTA | GCATAACTGA | AGAGGACGTG | 1380 |
| GCTTTGGAGA | CAGAGCTATA | CGCTCTGGCC | TCTGACCATC | CAGAATGGGT | GCGGGCACTT | 1440 |
| GGGAAATACT | ATGCCTCAGG | CACCATGGTC | ACCCCGGAAG | GGGTGCCCGT | CGGTGAGAGG | 1500 |
| TATTGCAGAT | CCTCGGGTGT | CCTAACAACT | AGCGCGAGCA | ACTGCTTGAC | CTGCTACATC | 1560 |
| AAGGTGAAAG | CTGCCTGTGA | GAGAGTGGGG | CTGAAAAATG | TCTCTCTTCT | CATAGCCGGC | 1620 |
| GATGACTGCT | TGATCATATG | TGAGCGGCCA | GTGTGCGACC | CAAGCGACGC | TTTGGGCAGA | 1680 |
| GCCCTAGCGA | GCTATGGGTA | CGCGTGCGAG | CCCTCATATC | ATGCATCATT | GGACACGGCC | 1740 |
| CCCTTCTGCT | CCACTTGGCT | TGCTGAGTGC | AATGCAGATG | GGAAGCGCCA | TTTCTTCCTG | 1800 |
| ACCACGGACT | TCCGGAGGCC | GCTCGCTCGC | ATGTCGAGTG | AGTATAGTGA | CCCGATGGCT | 1860 |
| TCGGCGATCG | GTTACATCCT | CCTTTATCCT | TGGCACCCCA | TCACACGGTG | GGTCATCATC | 1920 |
| CCTCATGTGC | TAACGTGCGC | ATTCAGGGGT | GGAGGCACAC | CGTCTGATCC | GGTTTGGTGC | 1980 |
| CAGGTGCATG | GTAACTACTA | CAAGTTTCCA | CTGGACAAAC | TGCCTAACAT | CATCGTGGCC | 2040 |
| CTCCACGGAC | CAGCAGCGTT | GAGGGTTACC | GCAGACACAA | CTAAAACAAA | GATGGAGGCT | 2100 |
| GGTAAGGTTC | TGAGCGACCT | CAAGCTCCCT | GGCTTAGCAG | TCCACCGAAA | GAAGGCCGGG | 2160 |
| GCGTTGCGAA | CACGCATGCT | CCGCTCGCGC | GGTTGGGCTG | AGTTGGCTAG | GGGCTTGTTG | 2220 |
| TGGCATCCAG | GCCTACGGCT | TCCTCCCCCT | GAGATTGCTG | GTATCCCGGG | GGGTTTCCCT | 2280 |
| CTCTCCCCCC | CCTATATGGG | GGTGGTACAT | CAATTGGATT | TCACAAGCCA | GAGGAGTCGC | 2340 |
| TGGCGGTGGT | TGGGGTTCTT | AGCCCTGCTC | ATCGTAGCCC | TCTTCGGG | | 2388 |

HEPATITIS G VIRUS PROTEASE

I. FIELD OF THE INVENTION

The present invention relates to the molecular biology and virology of the hepatitis G virus (HGV). More specifically, this invention relates to a novel protease produced by HGV, methods of expression, recombinant protease, protease mutants, inhibitors of HGV protease, HGV polypeptide antigens and methods for producing HGV polypeptides.

II. BACKGROUND OF THE INVENTION

Non-A, Non-B, Non-C, Non-D, Non-E hepatitis (Non-A-E hepatitis) is a transmissible disease (or family of diseases) that is believed to be virally induced, and is distinguishable from other forms of virus-associated liver disease, such as those caused by hepatitis A virus (HAV), hepatitis B virus (HBV), hepatitis C virus (HCV), delta hepatitis virus (HDV), hepatitis E virus, (HEV) cytomegalovirus (CMV), or Epstein-Barr virus (EBV). Recently a new viral species, hepatitis G virus (HGV) has been identified as associated with Non-A-E hepatitis. See, for example, PCT US95/06169, incorporated herein by reference. HGV infection has been associated with post-transfusion non-A-E hepatitis, chronic non-A-C hepatitis, hepatocellular carcinoma, transfusion associated anemia, and other diseases. Furthermore, HGV infection has been shown to exist in 1.7% of blood donors in the United States and infection with HGV has been shown to be transfusion transmissible (Linnen et al, *Science* (1996) 271:505). Thus, the need exists for an effective method for diagnosing and treating HGV infection.

Many viruses, including adenoviruses, baculoviruses, comoviruses, picornaviruses, flaviviruses, retroviruses, and togaviruses, rely on specific, virally-encoded proteases for processing polypeptides from their initial translated form into mature, active proteins. In the case of picornaviruses, all of the viral proteins are believed to arise from cleavage of a single polyprotein (B. D. Korant, *CRC Crit Rev Biotech* (1988) 8:149–57). A serine protease has been described for Hepatitis C virus, M. Houghton et al., U.S. Pat. No. 5,371,017. A co-factor to such a serine protease described by Houghton, supra, was described by Y. Tanji et al, *J Virol,* (1995) 69(3):1575. A second HCV protease was further described in M. Hijikata, *J Virol,* (1993) 67(8):4665.

Proteases have recently become a target of choice for developing antiviral therapeutics. For example, T. J. McQuade et al, *Science* (1990) 247:454–56 disclosed preparation of a peptide mimic capable of specifically inhibiting the HIV-1 protease. In HIV, the protease is believed responsible for cleavage of the initial p55 gag precursor into the core structural proteins (p17, p24, p8, and p7). Adding 1 uM inhibitor to HIV-infected peripheral blood lymphocytes in culture reduced the concentration of processed HIV p24 by about 70%. Viral maturation and levels of infectious virus were reduced by the protease inhibitor.

III. SUMMARY OF THE INVENTION

It is one object of the invention to provide an HGV protease composition comprising a purified proteolytic polypeptide complex derived from Hepatitis G virus. In one embodiment of the invention the HGV protease comprises a polypeptide having a partial internal sequence substantially as encoded by SEQ ID NO:3. In another embodiment said polypeptide complex comprises a polypeptide having a partial internal sequence substantially as encoded by SEQ ID NO:4. In a third embodiment the protease comprises a co-factor having a partial internal sequence substantially as identified by SEQ ID NO:5.

Also included in the invention is a fusion protein, comprising a fusion partner fused to a proteolytic polypeptide derived from Hepatitis G virus. In one embodiment the proteolytic polypeptide derived from Hepatitis G virus is substantially encoded by SEQ ID NO:24.

In a further aspect, the invention includes a composition comprising a polynucleotide which encodes an HGV protease complex or an active HGV protease complex analog.

Yet another aspect of the invention includes a method for producing a purified HGV protease. Such method includes the steps of: (a) transforming a host cell with a vector containing a foreign DNA encoding an HGV protease, (b) subjecting the host cell to conditions required for expression of the HGV protease, and (c) purifying the protease.

A related aspect of the invention includes a method for assaying compounds for activity against hepatitis G virus, comprising the steps of: (a) providing an active hepatitis G virus protease: (b) contacting said protease with a compound capable of inhibiting protease activity; and (c) measuring inhibition of the proteolytic activity of said hepatitis G virus protease.

IV. BRIEF DESCRIPTION OF THE FIGURES

V. DETAILED DESCRIPTION OF THE INVENTION

A. Definitions

Figure 1:
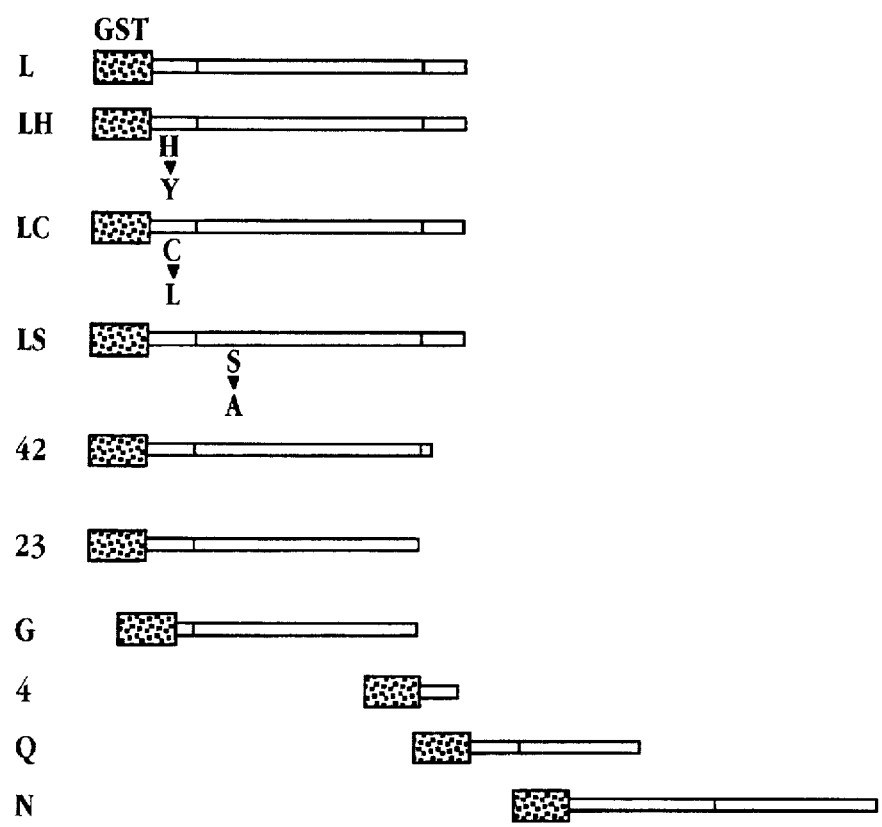
FIG. 1 shows regions of the HGV genome which were inserted into recombinant baculoviruses as they align with a schematic of the HGV polyprotein.

The terms "Hepatitis G Virus" and "HGV" refer to the viral species that is identified in PCT US95/06169, the disclosure of which are incorporated herein by reference. The HGV genome is comprised of RNA. It is known that RNA-containing viruses have relatively high rates of spontaneous mutation, reportedly on the order of $10^{-3}$ to $10^{-4}$ per incorporated nucleotide (Wieds & Knipe, "Fundamental Virology" (1986, Raven Press, N.Y.)). As heterogenicity and fluidity of genotype are inherent characteristics of RNA viruses, there will be multiple strains/isolates, which may be virulent or avirulent, within the HGV species.

Information on several different strains/isolates of HGV is disclosed herein, particularly strain or isolate PNF-2161.

Information from one strain or isolate, such as a partial genome sequence, is sufficient to allow those skilled in the art using standard techniques to isolate new strains/isolates and to identify whether such new strains/isolates are HGV. For example, several different strains/isolates are described below. These strains, which were obtained from a number of human sera (and from different geographical areas), were isolated utilizing the information from the genomic sequence of PNF-2161.

The information provided herein suggests that HGV may be distantly related to the flaviviridae, including Hepatitis C Virus. The Flaviviridae family contains a large number of viruses which are small, enveloped pathogens of man. The morphology and composition of Flavivirus particles are known, and are discussed in M. A. Brinton, in "The Viruses: The Togaviridae And Flaviviridae" (series eds. Fraenkel-Contrat and Wagner, vol. eds. Schlessinger and Schlessinger, Plenum Press, 1986), pp. 327–374. Generally, with respect to morphology, flaviviruses contain a central nucleocapsid surrounded by a lipid bilayer. Virions are spherical and have a diameter of about 40–50 nm. Their cores are about 25–30 nm in diameter. Along the outer surface of the virion envelope are projections measuring about 5–10 nm in length with terminal knobs about 2 nm in diameter. Typical examples of the family include Yellow Fever virus, West Nile virus, and Dengue Fever virus. They possess positive-stranded RNA genomes (about 11,000 nucleotides) that are slightly larger than that of HGV and encode a precursor of about 3500 amino acids. Individual proteins are cleaved from this precursor polypeptide.

The genome of HGV appears to be single-stranded RNA containing about 9400 nucleotides. The genome is positive-stranded, and possesses a continuous translational open reading frame (ORF) that encodes a polyprotein of about 2,900 amino acids. In the ORF, the structural proteins appear to be encoded in approximately the first quarter of the N-terminal region, with the majority of the polyprotein attributed to non-structural proteins. When compared with all known viral sequences, small but significant co-linear homologies are observed with the nonstructural proteins of the Flaviviridae family, and with the pestiviruses (which are now also considered to be part of the Flaviviridae family).

A schematic of a putative polyprotein encoded in the major ORF of the HGV genome is shown in FIG. 1. Probable genes of the HGV polyprotein are indicated in the figure. The Hepatitis G Virus polyprotein contains, from the amino terminus to the carboxy terminus, the nucleocapsid-like protein (C), the envelope proteins (E1 and E2), and the non-structural proteins (NS2a, NS2b, NS3, NS4a-NS4b, NS5a, NS5b). The polyprotein of HGV differs significantly from other flaviviruses in size and sequence, particularly in the structural gene regions where there is almost no homology. Furthermore, the untranslated regions of HGV appear to be quite distinct from HCV. Also, there may be considerable differences between the HGV and the flaviviruses, and HCV in particular, that have yet to be appreciated.

Due to the evolutionary relationship of the strains or isolates of HGV, putative HGV strains and isolates are identifiable by their sequence homology. "HGV variants" are defined as viral isolates that have at least about 55% global sequence homology, that is, sequence identity over a length (at least comparable to SEQ ID NO:1) of the viral genome polynucleotide sequence, to the HGV polynucleotide sequences disclosed herein. "Sequence homology" is determined essentially as follows. Two polynucleotide sequences of the same length (preferably, the entire viral genome) are considered to be homologous to one another, if, when they are aligned using the ALIGN program, over, preferably 55%, more preferable 60%, even more preferably 70%, or most preferably 80% of the nucleic acids in the highest scoring alignment are identically aligned using a ktup of 1, the default parameters and the default PAM matrix.

The ALIGN program is found in the FASTA version 1.7 suite of sequence comparison programs (Pearson, et al., 1988; Pearson, 1990; program available from William R. Pearson, Department of Biological Chemistry, Box 440, Jordan Hall, Charlottesville, Va.).

In determining whether two viruses are "highly homologous" to each other, the complete sequence of all the viral proteins (or the polyprotein) for one virus are optimally, globally aligned with the viral proteins or polyprotein of the other virus using the ALIGN program of the above suite using a ktup of 1, the default parameters and the default PAM matrix. Regions of dissimilarity or similarity are not excluded from the analysis. Differences in lengths between the two sequences are considered as mismatches. Highly homologous viruses have over, preferably 55%, more preferable 60%, even more preferably 70%, or most preferably 80% global polypeptide sequence identity.

Two nucleic acid fragments are considered to be "selectively hybridizable" to an HGV polynucleotide, if they are capable of specifically hybridizing to HGV or a variant thereof (e.g., a probe that hybridizes to HGV nucleic acid but not to polynucleotides from other members of the virus family Flaviviridae) or specifically priming a polymerase chain reaction: (i) under typical hybridization and wash conditions, as described, for example, in Maniatis, et al., pages 320–328, and 382–389, or (ii) using reduced stringency wash conditions that allow at most about 25–30% basepair mismatches, for example: 2×SSC, 0.1% SDS, room temperature twice, 30 minutes each; then 2×SSC, 0.1% SDS, 37° C. once, 30 minutes; then 2×SSC room temperature twice, 10 minutes each, or (iii) selecting primers for use in typical polymerase chain reactions (PCR) under standard conditions (for example, in Saiki, R. K, et al.), which result in specific amplification of sequences of HGV or its variants.

Preferably, highly homologous nucleic acid strands contain less than 20–30% basepair mismatches, even more preferably less than 5–20% basepair mismatches. These degrees of homology can be selected by using wash conditions of appropriate stringency for identification of clones from gene libraries (or other sources of genetic material), as is well known in the art.

An "HGV polynucleotide," as used herein, is defined as follows. For polynucleotides greater than about 100 nucleotides, HGV polynucleotides encompass polynucleotide sequences encoded by HGV variants and homologous sequences as defined in "2" above. For polynucleotides less than about 100 nucleotides in length, HGV polynucleotide encompasses sequences that selectively hybridizes to sequences of HGV or its variants. Further, HGV polynucleotides include polynucleotides encoding HGV polypeptides (see below).

An "HGV polypeptide" is defined herein as any polypeptide homologous to an HGV polypeptide. "Homology," as used herein, is defined as follows. In one embodiment, a polypeptide is homologous to an HGV polypeptide if it is encoded by nucleic acid that selectively hybridizes to sequences of HGV or its variants.

In another embodiment, a polypeptide is homologous to an HGV polypeptide if it is encoded by HGV or its variants, as defined above, polypeptides of this group are typically larger than 15, preferable 25, or more preferable 35, contiguous amino acids. Further, for polypeptides longer than about 60 amino acids, sequence comparisons for the purpose of determining "polypeptide homology" are performed using the local alignment program LALIGN. The polypeptide sequence, is compared against the HGV amino acid sequence or any of its variants, as defined above, using the LALIGN program with a ktup of 1, default parameters and the default PAM.

Any polypeptide with an optimal alignment longer than 60 amino acids and greater than 65%, preferably 70%, or more preferably 80% of identically aligned amino acids is considered to be a "homologous polypeptide." The LALIGN program is found in the FASTA version 1.7 suite of sequence comparison programs (Pearson, et al., 1988; Pearson, 1990; program available from William R. Pearson, Department of Biological Chemistry, Box 440, Jordan Hall, Charlottesville, Va.).

A polynucleotide is "derived from" HGV if it has the same or substantially the same basepair sequence as a region of an HGV genome, cDNA of HGV or complements thereof, or if it displays homology as noted under "2", "3" or "4" above.

A polypeptide is "derived from" HGV if it is (i) encoded by an open reading frame of an HGV polynucleotide, or (ii) displays homology to HGV polypeptides as noted under "2" and "5" above, or (iii) is specifically immunoreactive with HGV positive sera.

"Substantially isolated" is used in several contexts and typically refers to the at least partial purification of an HGV virus particle, component (e.g., polynucleotide or polypeptide), or related compound (e.g., anti-HGV antibodies) away from unrelated or contaminating components (e.g., serum cells, proteins, and non-anti-HGV antibodies). Methods and procedures for the isolation or purification of compounds or components of interest are described below (e.g., affinity purification of fusion proteins and recombinant production of HGV polypeptides).

In the context of the present invention, the phrase "nucleic acid sequences," when referring to sequences which encode a protein, polypeptide, or peptide, is meant to include degenerative nucleic acid sequences which encode homologous protein, polypeptide or peptide sequences as well as the disclosed sequence.

The term "HGV protease" refers to enzymes, and enzyme-cofactor complexes, derived from HGV which exhibit proteolytic activity, specifically the polypeptides encoded in the NS2B, NS3, and NS4 domains of the HGV genome. As described in Examples 5 and 6, the NS2B-NS3-NS4 region of HGV encodes multiple protease activities. The NS3 serine protease is shown, for example in Example 6, to be responsible for cleavage at the NS5A/NS5B junction, and can act in a complex with an NS4-encoded cofactor to cleave at the NS4A-B/NS5A junction. These activities both can occur in trans. Furthermore, as described, for example in Example 5, NS3 contains a cis-acting autocatalytic activity for cleavage at the NS3/NS4A-B junction. This autocatalytic activity also appears to be NS4A-B cofactor independent. As shown, for example in Example 6, NS2B encodes a second protease activity which is necessary for cleavage at the NS2B/NS3 junction.

At least one strain of HGV contains an NS2B protease believed to be substantially encoded by or within SEQ ID NO:3, an NS3 protease believed to be substantially encoded by or within SEQ ID NO:4, and an NS4 cofactor believed to be substantially encoded by or within SEQ ID NO:5. The amino and carboxy termini of the polypeptides encoded by the sequences shown in SEQ ID NOS:3, 4, and 5 are putative boundaries necessary for enzyme activity. It is understood that this sequence may vary from strain to strain, as RNA viruses like HGV are known to exhibit a great deal of variation. Further, the actual amino and carboxy termini may vary, as the protease is cleaved from a precursor polyprotein: variations in the protease amino acid sequence can result in cleavage from the polyprotein at difference points. Thus the amino- and carboxy-termini may differ from strain to strain in HGV. Furthermore, HGV protease activity may be to a greater or lesser extent, conformationally dependent. Therefore, activity may be greater when the HGV protease is expressed a part of the larger HGV polyprotein as it is naturally. However, the minimum sequence necessary for activity can be determined by routine methods. The sequence may be truncated at either end by treating an appropriate expression vector with an exonuclease (after cleavage at the 5' or 3' end of the coding sequence) to remove any desired number of base pairs. The resulting coding polynucleotide is then expressed and the sequence determined. In this manner the activity of the resulting product may be correlated with the amino acid sequence: a limited series of such experiments (removing progressively greater numbers of base pairs) determines the minimum internal sequence necessary for protease activity. It is presently believed that a portion of the protein at the carboxy terminus may exhibit helicase activity. However, helicase activity is not required of the HGV proteases of the invention.

The amino acids $His_{849}$, $Asp_{890}$, and $Ser_{1062}$ are believed to be the residues necessary for catalytic activity of NS3, based on sequence homology to the putative flavivirus proteases. Table 1 shows the alignment of the three catalytic residues for HGV protease with the same region from other flaviviruses.

TABLE 1

| Protease | Histidine | Asparagine | Serine |
|---|---|---|---|
| HGV | LETTFHGAS (SEQ ID NO: 6) | ASDDVTVYP (SEQ ID ND: 7) | FRGSSGSPV (SEQ ID NO: 8) |
| HCV | CWTVYHGAG (SEQ ID NO: 9) | DODLGWPAP (SEQ ID NO: 10) | LKGSSGGPL (SEQ ID NO: 11) |
| Yellow Fever | FHTMWHVTR (SEQ ID NO: 12) | KEDLVATGG (SEQ ID NO: 13) | PSGTSGSPI (SEQ ID NO: 14) |
| West Nile | FHTLWNTTK (SEQ ID NO: 15) | KEDRLCYGG (SEQ ID NO: 16) | PTGTSGSPI (SEQ ID NO: 17) |
| Murray Valley | FHTLWHTTR (SEQ ID NO: 18) | KEDRVTYGG (SEQ ID NO: 19) | PTGTSGSPI (SEQ ID NO: 20) |
| Kunjin Virus | FHTLWHTTK (SEQ ID NO: 21) | KEDRLCYGG (SEQ ID NO: 22) | PTGTSGSPI (SEQ ID NO: 23) |

The most direct way to verify the residues essential to the active site of a protease is to replace each residue individually with a different residue. This is easily accomplished by site-specific mutagenesis and similar techniques known in the art. If replacement of a particular residue results in a loss of activity, the essential nature of the replaced residue is confirmed. Such experiments are described in Examples 2 and 5.

An HGV protease construct "L" described in Examples 2 and 3, below, is shown as SEQ ID NO:24. This construct contains the carboxy-terminal NS2B, NS3 and amino-terminal NS4A regions from PNF-2161. This construct is shown to have complete protease activity at the NS2B/NS3, NS3/NS4A-B, NS4A-B/NS5A and NS5A/NS5B junctions. An NS2B mutant with $His_{849}$ to Tyr change is shown as SEQ ID NO:26. This construct is shown in Example 5 to lose cleavage activity at the NS2B/NS3 junction. Likewise, a second NS2B mutant with $Cys_{890}$ to Leu change is shown as SEQ ID NO:28. This construct is shown in Example 5 to lose cleavage activity at the NS2B/NS3 junction. An NS3 mutant with an $Ser_{1062}$ to Ala, described in Example 5, is shown as SEQ ID NO:30. This mutant is shown in Example 5 to lose cleavage activity at NS3/NS4A-B, NS4A-B/NS5A, NS5A/NS5B. "HGV protease analogs" refer to polypeptides which vary from the full length protease sequence by deletion, alteration and/or addition to the amino acid sequence of the native protease. HGV protease analogs include the HGV protease mutants described above, and fusion proteins comprising HGV protease, truncated protease, or protease mutants. Typically, the total number of residues changed, deleted or added to the native sequence in the mutants will be no more that about 20, preferably no more than about 10, and most preferably no more than about 5.

The term fusion protein generally refers to a polypeptide comprising an amino acid sequence drawn from two or more individual proteins. In the present invention, "fusion protein" is used to denote a polypeptide comprising the HGV protease, truncate, mutant or functional portion thereof, fused to a non-HGV protein polypeptide ("fusion partner"). Fusion proteins are most conveniently produced by expression of a fused gene, which encodes a portion of one polypeptide at the 5' end and a portion of a different polypeptide at the 3' end, where the different portions are joined in one reading frame which may be expressed in a suitable host. It is presently preferred (although not required) to position the HGV protease or analog at the carboxy terminus of the fusion protein. As the HGV protease is normally expressed within a large polyprotein, it is not expected to include cell transport signals (e.g., export or secretion signals). Suitable functional enzyme fragments are those polypeptides which exhibit quantifiable activity when expressed fused to the HGV protease. Exemplary enzymes include, without limitation, Beta-galactosidase (B-gal), Beta-lactamase, horseradish peroxidase (HRP), glucose oxidase (GO), human superoxide dismutase (hSOD), urease, and the like. These enzymes are convenient because the amount of fusion protein produced can be quantified by means of simple calorimetric assays. Alternatively, one may employ antigenic proteins or fragments, to permit simple detection and quantification of fusion proteins using antibodies or substrates specific for the fusion partner, such as glutathione-S-transferase or even another HGV fragment. The presently preferred fusion partner is glutathione-S-transferase (GST).

An "epitope" is the area of an antigenic molecule (antigen) that determines the specific antibody to which the antigen binds. An antigen or epitope is "specifically immunoreactive" with HGV positive sera when the antigen or epitope binds to antibodies present in the HGV infected sera but does not bind to antibodies present in the majority (greater than about 90%, preferably greater than 95%) of sera from individuals who are not or have not been infected with HGV. "Specifically immunoreactive" antigens or epitopes may also be immunoreactive with monoclonal or polyclonal antibodies generated against specific HGV epitopes or antigens.

An antibody or antibody composition (e.g., polyclonal antibodies) is "specifically immunoreactive" with HGV when the antibody or antibody composition is immunoreactive with an HGV antigen but not with HAV, HBV, HCV, HDV or HEV antigens. Further, "specifically immunoreactive antibodies" are not immunoreactive with antigens typically present in normal sera, not infected with or exposed to HGV.

B. General Methods

The practice of the present invention generally employs conventional techniques of molecular biology, microbiology, recombinant DNA, and immunology, which are within the skill of the art. Such techniques are explained fully in the literature. See for example J. Sambrook et al, "Molecular Cloning; A Laboratory Manual" (1989); "DNA Cloning", Vol. I and II (D. N. Glover ed. 1985); "Oligonucleotide Synthesis" (M. J. Gait ed., 1984); "Nucleic Acid Hybridization" (B. D. Hames & S. J. Higgins eds. 1984); "Transcription And Translation" (B. D. Hames & S. J. Higgins eds. 1984); "Animal Cell Culture" (R. I. Freshney ed. 1986); "Immobilized Cells And Enzymes" (IRL Press, 1986); B. Perbal, "A Practical Guide To Molecular Cloning" (1984); the series "Methods In Enzymology" (Academic Press, Inc.); "Gene Transfer Vectors For Mammalian Cells" (J. H. Miller and M. P. Calos eds. 1987, Cold Spring Harbor Laboratory); *Meth Enzymology* (1987) 154 and 155 (Wu and Grossman, and Wu, eds., respectively); Mayer & Walker, eds. (1987); "Immunochemical Methods In Cell And Molecular Biology" (Academic Press, London); Scopes, and "Handbook Of Experimental Immunology", volumes I–IV (Weir and Blackwell eds., 1986).

Both prokaryotic and eukaryotic host cells are useful for expressing desired coding sequences when appropriate control sequences compatible with the designated host are used, and are known in the art and are commercially available. Mammalian cell lines available as hosts for expression are known in the art and include many immortalized cell lines available from the American Type Culture Collection (ATCC). Suitable promoters for mammalian cells are also known. Mammalian cells may also require terminator sequences and poly-A addition sequences. Enhancer sequences which increase expression may also be included, and sequences which promote amplification of the gene may also be desirable. These genes are known in the art.

Vectors suitable for replication in mammalian cells are known in the art. For example, a vector used to express foreign DNA is Vaccinia virus. In this case the heterologous DNA is inserted into the Vaccinia genome. Techniques for the insertion of foreign DNA into the vaccinia virus genome are known in the art, and may utilize, for example, homologous recombination. The heterologous DNA is generally inserted into a gene which is non-essential to the virus, for example, the thymidine kinase gene (tk), which also provides a selectable marker. Plasmid vectors that greatly facilitate the construction of recombinant viruses have been described (see, for example, Mackett et al, *J Virol* (1984) 49:857; Chakrabarti et al, *Mol Cell Biol* (1985) 5:3403; Moss, in GENE TRANSFER VECTORS FOR MAMMALIAN CELLS (Miller and Calos, eds., Cold Spring Harbor Laboratory Press, N.Y., 1987), p. 10, and Ward et al, *Proc Nat Acad Sci* (1995) 92:6773).

Other systems for expression of eukaryotic or viral genomes include insect cells and vectors suitable for use in these cells. These systems are known in the art, and include, for example, insect expression transfer vectors derived from the baculovirus *Autographa californica* nuclear polyhedrosis virus (AcNPV), which is a helper independent, viral expression vector. Expression vectors derived from this system usually use the strong viral polyhedrin gene promoter to drive expression of heterologous genes. Currently the most commonly used transfer vector for introducing foreign genes into AcNPV is pACYM1; see Y. Matsuura, et al. *J Gen Virol*, (1987) 68:1233. Many other vectors known to those of skill in the art have also been designed for improved expression.

Methods for the introduction of heterologous DNA into the desired site in the baculovirus are known in the art. (See Summer and Smith, Texas Agricultural Experiment Station Bulletin No. 1555; Smith et al. *Mol Cell Biol* (1983) 3:2156–2165; and Luckow and Summers, *Virol* (1989) 17:31).

The signals for post-translational modifications, such as signal peptide cleavage, proteolytic cleavage, and phosphorylation, appear to be recognized by insect cells. The signals required for secretion and nuclear accumulation also appear to be conserved between the invertebrate cells and vertebrate cells.

Transformation may be by any known method for introducing polynucleotides into a host cell, including, for example, packaging the polynucleotide in a virus and transducing a host cell with the virus, and by direct uptake of the polynucleotide. The transformation procedure depends on the host to be transformed. Bacterial transformation by direct uptake generally employs treatment with calcium or rubidium chloride (Cohen, *Proc Nat Acad Sci USA* (1978) 75:1929. Mammalian transformation by direct uptake may be conducted using the calcium phosphate precipitation method of Graham and Van der Eb, *Virol* (1978) 52:546, or the various known modifications thereof. Alternatively, as is commonly used in the art, a lipofection transfection technique may be used; see P. Kitts et al., *Biotechniques*, (1993) 14(5):810.

DNA sequences, including those isolated from cDNA libraries, may be modified by known techniques, for example site-directed mutagenesis (see e.g., Zoller, *Nuc Acids Res* (1982) 10:6487). Commercially available kits for modifying DNA sequences can be obtained from many sources known to those of skill in the art, for example, Stratagene Cloning Systems, Inc., La Jolla, Calif.

The enzyme-linked immunosorbent assay (ELISA) can be used to measure either antigen or antibody concentrations. This method depends upon conjugation of an enzyme to either an antigen or an antibody, and uses the bound enzyme activity as a quantitative label. To measure antibody, the known antigen is fixed to a solid phase (e.g., a microtitre dish, plastic cup, dipstick, plastic bead, or the like), incubated with test serum dilutions, washed, incubated with anti-immunoglobulin labeled with an enzyme, and washed again. Enzymes suitable for labelling are known in the art, and include, for example, horseradish peroxidase (HRP). Enzyme activity bound to the solid phase is usually measured by adding a specific substrate, and determining product formation or substrate utilization calorimetrically. The enzyme activity bound is a direct function of the amount of antibody bound.

To measure antigen, a known specific antibody is fixed to the solid phase, the test material containing antigen is added, after an incubation the solid phase is washed, and a second enzyme-labeled antibody is added. After washing, substrate is added, and enzyme activity is measured calorimetrically, and related to antigen concentration.

Proteases of the invention may be assayed for activity by cleaving a substrate which provides detectable cleavage products. As the HGV protease is believed to cleave itself from the genomic polyprotein, one can employ this autocatalytic activity both to assay expression of the protein and determine activity. For example, if the protease is joined to its fusion partner so that an HGV protease cleavage substrate is provided, the expression product will cleave itself into fusion partner and active HGV protease. One may then assay the products, for example, by polyacrylamide gel electrophoresis or western blot, to verify that the proteins produced correspond in size to the separate fusion partner and protease proteins, as is the presently preferred method. Alternatively one may employ small peptide p-nitrophenyl esters or methylcoumarins, as cleavage may then be followed by spectrophotometric or fluorescent assays. Following the method described by E. D. Matayoshi et al. *Science* (1990) 247:231–35, one may attach a fluorescent label to one end of the substrate and a quenching molecule to the other end: cleavage is then determined by measuring the resulting increase in fluorescense. If a suitable enzyme or antigen has been employed as the fusion partner, the quantity of protein produced may easily be determined. Further, one may exclude the HGV protease n-terminal cleavage signal (preventing self-cleavage) and add a separate cleavage substrate, such as a fragment of the HGV NS3 domain including the native processing signal or a synthetic analog.

In the absence of this protease activity, the HGV polyprotein should remain in its unprocessed form, and thus render the virus noninfectious. Thus, the protease is useful for assaying pharmaceutical agents for control of HGV, as compounds which inhibit the protease activity sufficiently will also inhibit viral infectivity. Such inhibitors may take the form of organic compounds, particularly compounds which mimic the cleavage site of HGV recognized by the protease. Three of the putative cleavage sites of the HGV polyprotein are shown below:

The cleavage junctions between: NS2A/NS2B is between $Gly_{693}$-Ala; NS2B/NS3 is between $Thr_{925}$ -Ala; and NS4B-NS5A is between $Gly_{1898}$-Tyr. The other junctions may be determined by techniques known to those of skill in the art, for example by the method of Example 7.

Suitable inhibitors include peptide trifluoromethyul ketones, peptide boronic acids, peptide alpha-ketoesters, peptide difluoroketo compounds, peptide aldehydes, peptide diketones, and the like. For example, the peptide aldehyde N-acetyl-phelnylalanylglycinaldehyde is a potent inhibitor of the protease papain. One may conveniently prepare and assay large mixtures of peptides using the methods disclosed in PCT W089/10931, incorporated herein by reference. This application teaches methods for generating mixtures of peptides up to hexapeptides having all possible amino acid sequences, and further teaches assay methods for identifying those peptides capable of binding to proteases.

Other protease inhibitors may be proteins, particularly antibodies and antibody derivatives. Recombinant expression systems may be used to generate quantities of protease sufficient for production of monoclonal antibodies (MAbs) specific for the protease. Suitable antibodies for protease inhibition will bind to the protease in a manner reducing or eliminating the enzymatic activity, typically by obscuring the active site. Suitable MAbs may be used to generate derivatives such as Fab fragments, chimeric antibodies, altered antibodies, univalent antibodies, and single domain antibodies, using methods known in the art.

Protease inhibitors are screened using methods of the invention, in general, a substrate is employed which mimics the enzyme's natural substrate, but which provides a quantifiable signal when cleaved. The signal is preferably detectable by colorimetric or fluorimetric means; however, other methods such as HPLC or silica gel chromatography, GC-MS, nuclear magnetic resonance, and the like may also be useful. After optimum substrate and enzyme concentrations are determined, a candidate protease inhibitor is added to the reaction mixture at a range of concentrations The assay condition ideally should resemble the conditions under which the protease is to be inhibited in-vivo; i.e., under physiologic pH, temperature, ionic strength, etc. Suitable inhibitors will exhibit strong protease inhibition at concentrations which do not raise toxic side effects in the subject. Inhibitors which compete for binding to the protease active site may require concentrations equal to or greater than the substrate concentration, while inhibitors capable of binding irreversibly to the protease active site may be added in concentrations on the order of the enzyme concentration.

In a presently preferred embodiment, a reporter gene is placed very near (i.e., within 50 amino acids), and carboxy to, the NS3/NS4A-B cleavage site, in a vector containing NS2B, NS3 and about 50 amino acids of NS4A-B. A prospective protease inhibitor is added to the cell culture prior to infection with this vector. By structuring the reporter gene very near the cleavage site, the reporter gene will carry a small amino terminal addition of less than about 50 amino acids. In the preferred embodiment this small addition will allow natural folding of the reporter gene and will not compromise its activity. However, if the protease is inactivated the reporter gene will have more than seven hundred additional N-terminal amino acids conformationally destroying activity of the chosen reporter gene. Activity of the inhibitor can be further specifically quantified by separating insoluble fraction (containing the insoluble NS3-uncleaved reporter) from the soluble fraction containing cleaved reporter, for example, by the method of Example 4.

In another presently preferred embodiment, an inactive protease mutant is employed rather than an active enzyme. By replacing a critical residue within the active site of the protease (e.g., replacing the active site Ser of a serine protease) does not significantly alter the structure of the enzyme, and thus preserves the binding specificity. The altered enzyme still recognizes and binds to its proper substrate, but fails to effect cleavage. Thus, in one method of the invention an inactivated HGV protease is immobilized, and a mixture of candidate inhibitors added.

Inhibitors that closely mimic the enzyme's preferred recognition sequence will compete more successfully for binding than other candidate inhibitors. The poorly-binding candidates may then be separated, and the identity of the strongly-binding inhibitors determined. For example, HGV protease may be prepared substituting the native $Ser_{1062}$ with Ala, providing an enzyme capable of binding the HGV protease substrate, but incapable of cleaving it. The resulting protease mutant is the bound to a solid support, for example Sephadex beads, and packed into a column. A mixture of candidate protease inhibitors in solution is then passed through the column and fractions collected. The last fraction to elute will contain the strongest-binding compounds and provide the preferred protease inhibitor candidates.

Protease inhibitors may be administered by a variety of methods, such as intravenously, orally, intramuscularly, introperitoneally, bronchially, intranasally, and so forth. The preferred route of administration will depend upon the nature of the inhibitor. Inhibitors prepared as organic compounds may often be administered orally (which is generally preferred) if well absorbed. Protein-based inhibitors (such as most antibody derivates) must generally be administered by parenteral routes.

HGV antigens encoded by non-structural genes which emulate those created during the natural course of infection comprise another aspect of the present invention. Such antigens are structurally and conformationally superior to those made by other processes as antibodies contained in HGV-infected human serum are more likely to recognize common conformational epitopes. Such antigens may be produced by the method of the present invention as follows: Cells are co-infected with a first virus expressing an HGV protease and a second virus expressing HGV substrate including at least one entire gene of interest and its flanking sequences containing cleavage sites at either, or both ends.

The NS2A/NS2B, NS2B/NS3, and NS4A-B/NS5A cleavage sites have been determined experimentally, according to the method of Example 7. According to the present invention, the following are the determined, and predicted, sequences of the HGV genes. NS2B is shown as SEQ ID NO:32, NS3 is shown as SEQ ID NO:34, NS4A-B as SEQ ID NO:36, NS5A as SEQ ID NO:38, and NS5B as SEQ ID NO:40. Accordingly, in the method of producing HGV antigens, the above enumerated sequences should be expressed plus as much additional flanking sequences on both the amino and carboxy termini as possible without compromising expression, as is known to those of ordinary skill in the art is and vector/host dependent.

HGV polypeptides made by the present invention can be purified directly or produced recombinantly and then purified. The recombinant polypeptides of the present invention can be purified by standard protein purification procedures which may include differential precipitation, molecular sieve chromatography, ion-exchange chromatography, iso-electric focusing, gel electrophoresis and affinity chromatography. The antigens can then be screened rapidly against a large number of suspected HGV hepatitis sera using alternative immunoassays, such as, ELISAs or Protein Blot Assays (Western blots) employing the isolated antigen peptide. The antigen polypeptides fusion can be isolated as described above, usually by affinity chromatography to the fusion partner such as β-galactosidase or glutathione-S-transferase. Alternatively, the antigen itself can be purified using antibodies generated against it (see below).

The purified antigen polypeptide or fusion polypeptide containing the antigen of interest, is attached to a solid support, for example, a multi-well polystyrene plate. Sera to be tested are diluted and added to the wells. After a period of time sufficient for the binding of antibodies to the bound antigens, the sera are washed out of the wells. A labelled reporter antibody is added to each well along with an appropriate substrate: wells containing antibodies bound to the purified antigen polypeptide or fusion polypeptide containing the antigen are detected by a positive signal.

A typical format for protein blot analysis using the polypeptide antigens of the present invention is presented in Example 5. General protein blotting methods are described by Ausubel, F. M., et al., *CURRENT PROTOCOLS IN MOLECUA BIOLOGY*, John Wiley and Sons, Inc., Media Pa.

One utility for the antigens obtained by the methods of the present invention is their use as diagnostic reagents for the detection of antibodies present in the sera of test subjects infected with HGV hepatitis virus, thereby indicating infection in the subject. The antigens of the present invention can be used singly, or in combination with each other, in order to detect HGV. The antigens of the present invention may also be coupled with diagnostic assays for other hepatitis agents such as HAV, HBV, HCV, and HEV.

In one diagnostic configuration, test serum is reacted with a solid phase reagent having a surface-bound antigen obtained by the methods of the present invention, e.g., the NS5A antigen. After binding with anti-HGV antibody to the reagent and removing unbound serum components by washing, the reagent is reacted with reporter-labelled anti-human antibody to bind reporter to the reagent in proportion to the amount of bound anti-HGV antibody on the solid support. The reagent is again washed to remove unbound labelled antibody, and the amount of reporter associated with the reagent is determined. Typically, the reporter is an enzyme which is detected by incubating the solid phase in the presence of a suitable fluorometric or calorimetric substrate (Sigma, St. Louis, Mo.).

The solid surface reagent in the above assay is prepared by known techniques for attaching protein material to solid support material, such as polymeric beads, dip sticks, 96-well plate or filter material. These attachment methods generally include non-specific adsorption of the protein to the support or covalent attachment of the protein, typically through a free amine group, to a chemically reactive group on the solid support, such as an activated carboxyl, hydroxyl, or aldehyde group.

Also forming part of the invention is an assay system or kit for carrying out this diagnostic method. The kit generally includes a support with surface-bound recombinant HGV antigen (e.g., the NS5A antigen, as above), and a reporter-labelled anti-human antibody for detecting surface-bound anti-HGV antigen antibody.

In a second diagnostic configuration, known as a homogeneous assay, antibody binding to a solid support produces some change in the reaction medium which can be directly detected in the medium. Known general types of homogeneous assays proposed heretofore include (a) spin-labelled reporters, where antibody binding to the antigen is detected by a change in reported mobility (broadening of the spin splitting peaks), (b) fluorescent reporters, where binding is detected by a change in fluorescence efficiency or polarization, (c) enzyme reporters, where antibody binding causes enzyme/substrate interactions, and (d) liposome-bound reporters, where binding leads to liposome lysis and release of encapsulated reporter. The adaptation of these methods to the protein antigen of the present invention follows conventional methods for preparing homogeneous assay reagents.

In each of the assays described above, the assay method involves reacting the serum from a test individual with the protein antigen and examining the antigen for the presence of bound antibody. The examining may involve attaching a labelled anti-human antibody to the antibody being examined (for example from acute, chronic or convalescent phase) and measuring the amount of reporter bound to the solid support, as in the first method, or may involve observing the effect of antibody binding on a homogeneous assay reagent, as in the second method.

A third diagnostic configuration involves use of HGV antibodies capable of detecting HGV-specific antigens. The HGV antigens may be detected, for example, using an antigen capture assay where HGV antigens present in candidate serum samples are reacted with a HGV specific monoclonal or polyclonal antibody. The antibody is bound to a solid substrate and the antigen is then detected by a second, different labelled anti-HGV antibody. Antibodies can be prepared, utilizing the peptides of the present invention, by standard methods. Further, substantially isolated antibodies (essentially free of serum proteins which may affect reactivity) can be generated (e.g., affinity purification).

The following examples, which illustrate various methods and compositions in the invention, are intended to illustrate, but not limit the scope of the invention.

Materials

*E. coli* DNA polymerase I (Klenow fragment) can be obtained from Boehringer Mannheim Biochemicals (BMB) (Indianapolis, Ind.). T4 DNA ligase and T4 DNA polymerase may be obtained from New England Biolabs (Beverly, Mass.); Nitrocellulose and "NYTRAN" filters are obtainable from Schleicher and Schuell (Keene, N.H.).

Synthetic oligonucleotide linkers and primers may be prepared using commercially available automated oligonucleotide synthesizers. Alternatively, custom designed synthetic oligonucleotides may be purchased from commercial suppliers. cDNA synthesis kit and random priming labeling kits may be obtained from BMB (Indianapolis, Ind.) or GIBCO/BRL (Gaithersburg, Md.).

Common manipulations relevant to employing antisera and/or antibodies for screening and detection of immunoreactive protein antigens were performed essentially as described (Harlow, E., et al., *ANTIBODIES: A LABORATORY MANUAL*, Cold Spring Harbor Laboratory Press (1988), incorporated herein by reference).

EXAMPLE 1

PREPARATION OF HGV cDNA

A cDNA-insert phage library generated from serum sample PNF 2161 produced as described in PCT US95/06169, now published, was deposited with the American Type Culture Collection, 12301 Parklawn Dr., Rockville Md. 20852, and has been assigned the deposit designation ATCC 75268 (PNF 2161 cDNA source). This library was used to generate a plasmid, "p3ZHGV-6", which contains the complete ORF from the PNF-2161 genome (SEQ ID NO:1). p3ZHGV-6 is deposited at Genelabs Technologies, Inc., 505 Penobscot Drive, Redwood City, Calif., 94063.

EXAMPLE 2

Baculovirus Plasmid Transfer Vectors

Baculovirus transfer vectors pAcGl and pAcG3X are used for the expression of HGV proteins as fusions with glutathione-S-transferase (GST). Such vectors can be purchased from PharMingen (San Diego, Calif.). These vectors utilize a strong very-late baculovirus polyhedrin promoter enabling high expression levels. Further, the vectors are flexible allowing foreign genes to be placed downstream of the GST fusion in different open reading frames.

a. Recombinant Protease Construct

A baculovirus plasmid transfer vector, encoding the hydrophilic portion of NS2B, NS3 and the amino-terminal portion of NS4 (SEQ ID NO:24) is constructed as follows: 2 ug plasmid p3ZHGV-6 is incubated with 10 U BglII, 10 U StuI, in 20 ul 10 mM Tris-HCl pH 8.0, 5 mM MgCl$_2$, 100 mM NaCl for 1 hour at 37 degrees C. The BglII-StuI fragment is purified by the GeneClean kit, purchased from Bio101, according to the manufacturers instructions (Bio101, Vista, Calif.). 2 ug pAcG3×vector is digested with 10 U BamHI in 20 ul of the above described buffer for 1 hour at 37° degrees C. Plasmid DNA is also purified using the GeneClean kit. The vector is next digested with 10 U SmaI in 20 ul 33 mM Tris-acetate pH 7.9, 10 mM Mg acetate, 66 mM potassium acetate, 0.5 mM dithiothreitol (DTT), for 1 hour at 25 degrees C. The plasmid DNA is again purified with the Geneclean kit.

Plasmid and insert DNA are mixed at a ratio of 1:10 and ligated with T4 ligase for overnight at 10 degrees C in 50 mM Tris-HCl pH 7.5, 7 mM MgCl$_2$, 1 mM DTT, 1 mM ATP, 1 ug DNA, and 4 U enzyme. The ligation mixture is used to transform *E. coli* (*Epicurian Coli* XL1-Blue super competent cells, Stratagene, La Jolla, Calif.), according to the manufacturers instructions. Positive colonies are isolated and plasmids purified using Wizard™ minipreps DNA purification systems (Promega, Madison, Wis.). Purified plasmids are checked for correct inserts by BamHI/EcoRV restriction endonuclease cleavage and agarose gel analysis.

This vector will encode the Ile$_{806}$-Glu$_{1658}$ portion of the HGV polyprotein in-frame with the GST. A recombinant baculovirus vector was constructed according to the method of the this example and designated "L."

b. Recombinant Mutant Protease Constructs

Site-directed mutagenesis is utilized to generate transfer vectors which are ultimately used in studies to confirm particular active residues in NS2B and NS3. Point mutations are made by oligonucleotide-directed mutagenesis using uridylated phagemid DNA as the template and oligonucleotide primers with substitutions in codons specifying the amino acid to be changed; see T. Kunkel, *Proc Nat Acad Sci (USA)* (1985) 82:488. The particular primers shown below are used to generate the indicated changes:

1. Vector "LH" SEQ ID NO:26 "Primer H" CGAATAAA-CAAGCTAATATACCCGAG (SEQ ID NO:42).

2. Vector "LC" SEQ ID NO:28 "Primer C" CCTGAAA-CAGGAATCCCGTCACGCAG (SEQ ID NO:43).

3. Vector "LS" SEQ ID NO:30 "Primer S" GCAC-CGAGCCGACCGAGTGG (SEQ ID NO:44).

c. Other Recombinant Baculovirus Vectors

Similar methods were used to construct other transfer vectors for HGV protease characterization. These vectors are briefly described here and summarized in Table 2, below.

Vector "G", FIG. 1, containing an insert encoding 31 carboxy-terminal amino acids of NS2B and all of NS3 (SEQ ID NO:51) can be synthesized by the polymerase chain reaction (PCR) utilizing primers "GF" and "GR", according to the method of Mullis, K. B., U.S. Pat. No. 4,683,202, issued 28 Jul. 1987; and Mullis, K. B., et al., U.S. Pat. No. 4,683,195, issued 28 Jul. 1987, both of which are herein incorporated by reference. Primer GF contains a BglII site and Primer GR contains an EcoRI site which facilitate the cloning of this fragment into the pAcG1 transfer vector in-frame with the coding sequence for the GST fusion partner. Vector G encodes an HGV polyprotein corresponding to Met$_{895}$ to Arg$_{1550}$, as shown in SEQ ID NO:2.

Primer GF
5'-CGCGAGATCTCATGGGTTTACCCGTG-3' (SEQ ID NO:45).

Primer GR
5'-GCGCGAATTCTAGAGACGTAACCCTCCGCC-3' (SEQ ID NO:46).

Vectors "42" and "23," FIG. 1, are carboxy-terminal truncations of the construct L in the NS4 region. Construct 42 (SEQ ID NO:52) can be produced by PCR using the primers 42F and 42R. Primer 42F flanks an internal SpeI site and primer 42R contains an EcoRI site. The fragment amplified with 42F and 42R, and cut with SpeI/EcoRI is ligated to the L vector cut with SpeI/EcoRI. Vector 42 encodes an HGV protein corresponding to amino acids Ile$_{806}$ to Ala$_{1598}$, as shown in SEQ ID NO:2.

Primer 42F 5'-CTGCTGTTAGGCATTGG-3' (SEQ ID NO:47)

Primer 42R
5'-CGCGAATTCAGGCCTGGTCTCCATGC-3' (SEQ ID NO:48)

Vector 23 (SEQ ID NO:53) can be produced by ligating the BglII-SpeI fragment of vector L to the SpeI-EcoRI fragment from vector G. Vector 23 encodes an HGV protein corresponding to Ile$_{806}$ to Arg$_{1550}$ as shown in SEQ ID NO:2.

Vector 4 (SEQ ID NO:54) can be produced by PCR using the 4F and 4R primers shown below and the p3ZHGV-6 plasmid as a template. The fragment is cut with BglII and EcoRI and cloned into the BamHI and EcoRI digested pAcG1 transfer vector. Vector 4 encodes an HGV protein corresponding to amino acids Arg$_{1540}$ to Lys$_{1655}$ from SEQ ID NO:2.

Primer 4F 5'-GCGCAGATCTCCGCTGCGACGCTG-3' (SEQ ID NO:49).

Primer 4R 5'-GCGCGAATTCTTAGCCTGAGCCAAG-3' (SEQ ID NO:50).

Vector Q (SEQ ID NO:55), FIG. 1, encodes an HGV protein containing a carboxy-terminal portion of NS4 and amino-terminal portion of NS5A. p3ZHGV-6 was digested with HindIII and blunt ended with Klenow to make it compatible with the SmaI blunt ended cloning site of the pAcG1 vector. p3ZHGV-6 is further digested with BglII resulting in a BglII/blunt-ended HindIII fragment which is ligated into pAcG1 digested with BamHI/SmaI. Construct Q encodes a protein corresponding to amino acids Asp$_{1806}$ to Lys$_{2235}$, from SEQ ID NO:2.

Vector N (SEQ ID NO:56), FIG. 1, encodes an HGV protein containing the majority of NS5A and complete NS5B. p3ZHGV-6 was digested with Eco47.III and EcoRI, and ligated into pAcG1 digested with EcoRI and SmaI. Construct N encodes a protein corresponding to amino acids Arg$_{2078}$ to Gly$_{2873}$ (carboxy terminus of the HGV polyprotein), as shown in SEQ ID NO:2.

TABLE 2

| Vector | Base Vector | Insert | Mutations |
| --- | --- | --- | --- |
| L | pAcG3X | SEQ ID NO: 24 | None |
| LH | pAcG3X | SEQ ID NO: 26 | His$_{849}$ to Tyr |
| LC | PAcG3X | SEQ ID NO: 28 | Cys$_{890}$ to Leu |
| LS | PAcG3X | SEQ ID NO: 30 | Ser$_{1062}$ to Ala |
| 42 | pAcG3X | SEQ ID NO: 52 | None |
| 23 | pAcG3X | SEQ ID NO: 53 | None |
| 4 | pAcG1 | SEQ ID NO: 54 | None |
| Q | pAcG1 | SEQ ID NO: 55 | None |
| N | pAcG1 | SEQ ID NO: 56 | None |
| G | pAcG1 | SEQ ID NO: 51 | None |

EXAMPLE 3

Production of Recombinant Baculovirus

*Spodoptera frugiperda* insect cell culture Sf21 and a derivative of *Autografa californica* nuclear polyhedrosis virus "BACULOGOLD" (PharMingen, San Diego, Calif.) are used for expression of HGV polypeptides. Established protocols are used for insect cell cultivation and for generation of recombinant baculoviruses by co-transfection of baculovirus plasmid transfer vectors with linearized baculovirus DNA (L. King et al, The baculovirus expression system. *A laboratory guide*, Chapman & Hall, London, New York, Tokyo, Melbourne, Madras, 1992). For convenience herein, the names of the transfer vectors produced above will be utilized to designate the corresponding recombinant baculovirus and expression products.

Briefly, the recombinant baculovirus plasmid transfer vector L can be co-trasnsfected with linearized baculovirus DNA ("BACULOGOLD") and the recombinant viruses selected as white foci in the presence of X-gal (King. supra). Monolayers of Sf21 cells are infected with the progeny of individual selected plaques and incubated at 27 degrees C. and harvested at 60 hours post infection. Cells are washed with phosphate buffered saline (PBS) and lysed in TNN buffer (50 mM Tris-HCl pH 8.0, 150 mM NaCl, 0.5% "NONIDET-P40").

The cell lysates are subject to centrifugation in a microfuge at 14,000 rpm for 10 minutes. Pellets (containing insoluble HGV proteins) and supernatant (containing soluble HGV proteins), together with a wild-type baculovirus-infected cell lysate (as control) are separated by sodium dodecyl sulfate polyacrylamide gel electrophoresis (SDS-PAGE). The expressed recombinant HGV proteins are identified as additional bands on the gel stained with Coomassie blue as compared with the wild-type lane.

EXAMPLE 4

Purification of HGV-GST Fusion Proteins

It is beneficial to utilize purified HGV polypeptides produced according to the method of the present inventions. Several purification techniques are known in the art. Briefly, two such methods are describe below.

1. Affinity Chromatography

GST-HGV fusion proteins may be purified by glutathione-affinity chromatography according to the method described by A. H. Davies, *Bio/technology*, 11:993, incorporated herein by reference.

2. Partial Purification of Inclusion Bodies

The insoluble pellet obtained in the method of Example 6, is washed with 0.2M sodium phosphate pH 8.0–150 mM NaCl. The pellet is then sonicated for 5 min. in a Branson Sonier 450 sonicater set at output 6 at a 20 sec. cycle for 5 min. (so as not to causing excessive foaming or heating of the sample). The sonicated mixture is again subject to centrifugation in a microfuge at 14,000 rpm for 10 minutes. Both the soluble and insoluble fractions are taken and analyzed by SDS-PAGE for the presence of HGV proteins. Further extraction may be necessary as shown below if the HGV proteins are present in the insoluble fraction.

The pellet from above is solubilized in 100 mM Tris-HCl pH 8.0, 150 mM NaCl, 10 mM CHAPS (3-[3-Cholamidopropyl)-dimethylammonio]-1-propane-sulfonate) (Sigma). The pellet is then sonicated for 5 min. in a Branson Sonier 450 sonicater set at output 6 at a 20 sec. cycle for 5 min. (so as not to causing excessive foaming or heating of the sample). The sonicated mixture is again subject to centrifugation in a microfuge at 14,000 rpm for 10 minutes. Both the soluble and insoluble fractions are taken and analyzed by SDS-PAGE for the presence of HGV proteins. Further extraction may be necessary and can be performed by methods known to those of skill in the art, essentially repeating the steps above with more aggressive buffers.

EXAMPLE 5

Western Blot of HGV Proteins

The recombinant HGV proteins produced according to the expression methodologies described herein can be further characterized by western blot analysis. The antigen from an SDS-PAGE gel run as above is transferred to a nitrocellulose filter. The membrane is then blocked for 2 hours using a solution of 1% bovine serum albumin, 3% normal goat serum, 0.25% gelatin, 100 mM NaPO$_4$, 100 mM NaCl, and 1% nonfat dry milk. Following incubation the membrane is washed with Tris HCl, pH 7.5 and incubated with polyclonal rabbit anti-PEP4 (1:1,000) (see PCT US95/06169, Example 9, herein incorporated by reference for this HGV protein specific serum and others utilized herein) for 2 hrs. with rocking at room temperature.

The membrane is washed twice for three minutes each time in TBS plus "TWEEN 20" (0.05%), and then washed twice for five minutes each time in TBS. The membrane is then incubated with secondary antibody (Promega anti-rabbit IgG-Alkaline Phosphatase conjugate, 1:7,500), for 1 hour with rocking at room temperature. The membrane is then washed twice×5 minutes in TBS+"TWEEN 20", then twice×5 minutes in TBS.

Bound antibody is detected by incubating the membrane in a substrate solution containing 5-bromo-4-chloro-3-indolyl-phosphate (BCIP), and nitro blue tetrazolium salt (NBT) (Sigma) in pH 9.5 buffer (100 mM Tris, 100 mM NaCl, 5 mM MgCl$_2$). Color development is allowed to proceed for approximately 15 minutes at which point color development is halted by 3 washes in distilled H$_2$O.

Figure 2A:
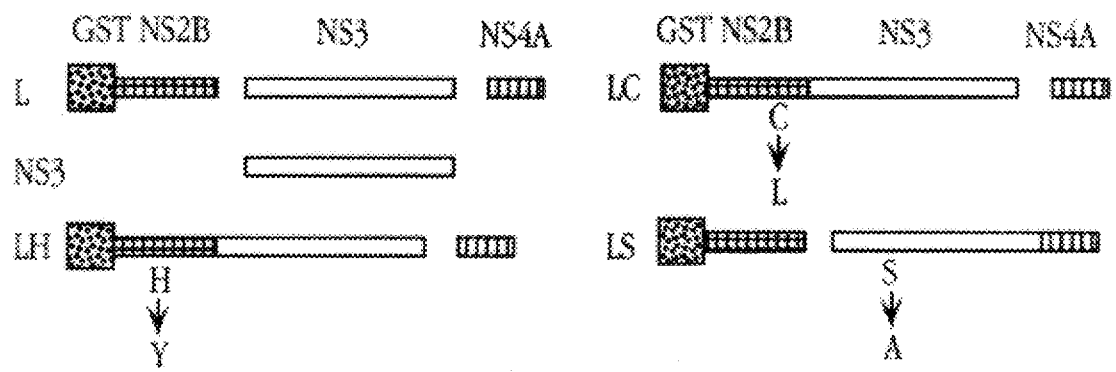
FIG. 2 shows a schematic of recombinant baculovirus vectors containing HGV protease inserts and an SDS-PAGE of extracts of Sf21 insect cells which had been infected with the recombinant viruses shown.
Figure 2B:
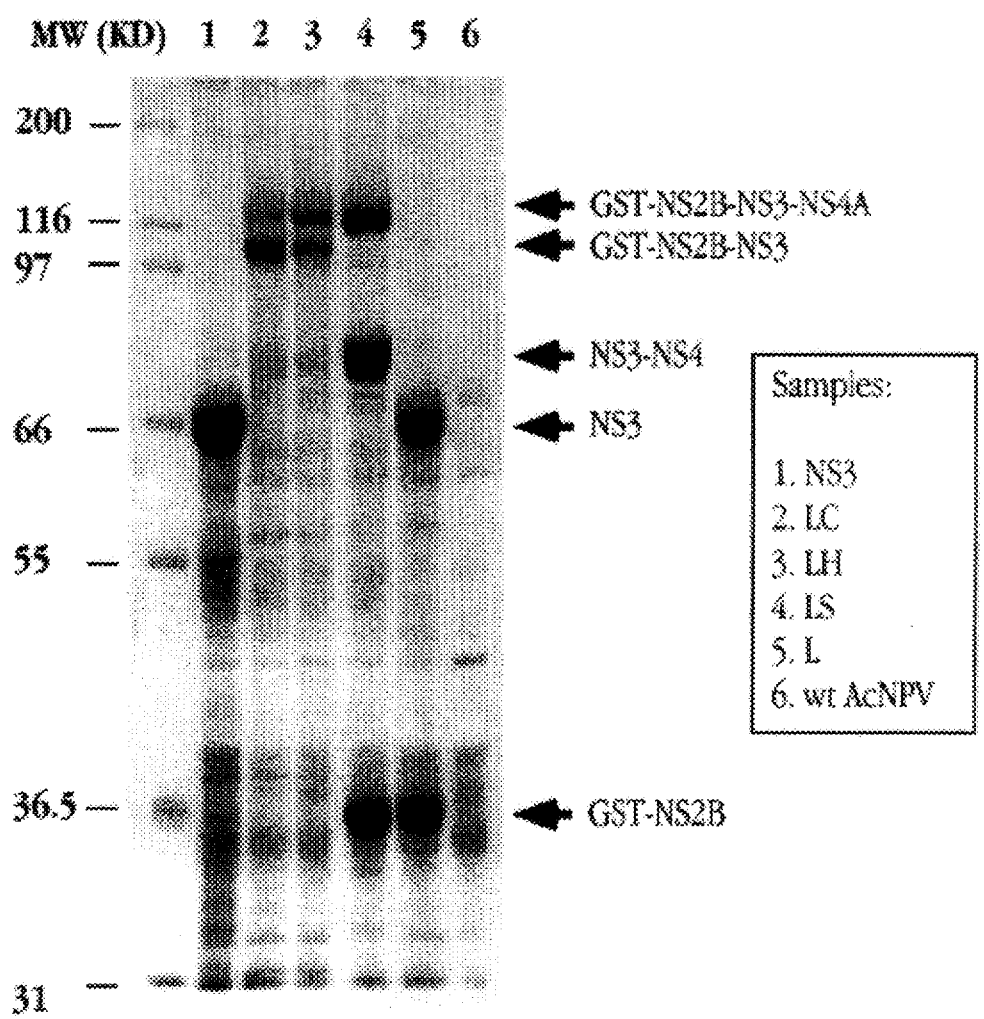

Construct L was expressed as a GST fusion in baculovirus. Insect cell extracts were run on an SDS-PAGE. It can be seen from FIG. 2, lane 5, that proteins migrate to sizes expected for NS3 and NS2B-GST indicating that the expressed protein is self-cleaved. Further, constructs LH, LC, and LS containing point mutations in the NS2B and NS3, as described in Example 2, are shown in FIG. 2, lanes 3, 2, and 4, respectively. It is apparent that the His to Tyr and Cys to Leu mutations in NS2B result in the loss of cleavage at the NS2B/NS3 junction, as demonstrated by the presence of the high molecular weight band migrating at the size expected for GST-NS2B-NS3. Furthermore, the loss of activity appears to be complete as there is virtually no GST-NS2B or NS3 products present in these lanes. The Ser to Ala mutation in construct LS, also described in Example 2, has no effect on cleavage at the NS2B/NS3 junction, demonstrated by the large amount of GST-NS2B present in lane 4. LS was unable to cleave at the NS3/NS4A-B junction, however, demonstrated by the large amount of protein migrating to the expected size for NS3-NS4-truncate. Identity of these proteins was further confirmed using anti-NS2B, NS3 and GST polyclonal rabbit antisera (rabbit sera described in PCT application US95/06169, Example 9, now published, GST monoclonal antibodies commercially available, for example, from Sierra Biosource, Gilroy, CA) results not shown.

EXAMPLE 6

CO-INFECTIONS DEMONSTRATING PROTEASE ACTIVITY

The HGV protease activity was further characterized by co-infection of insect cells by two (or more) of the baculovirus recombinant vectors described in Example 2. The results of these experiments are summarized in Table 3, below. Co-infections can easily be performed by those of skill in the art. Such co-infections contain at least one HGV protease construct, which may or may not, include a point mutation. By way of example, co-infection experiments may be performed as is described below for the co-infection of Vector L and Vector N.

Semi-confluent monolayers of Sf21 cells are grown in 150 cm$^2$ tissue culture flasks in TC-100 medium, prepared according to the manufacturers instructions (GIBCO-BRL, Bethesda, Md.) and supplemented with 10% fetal calf serum (FCS) (Gemini, Calabasas, Calif.). The medium is discarded and monolayers are either: (a) co-infected with recombinant baculovirus L and N at a multiplicity of infection (m.o.i.) of 2 and 10, respectively; (b) infected with recombinant baculovirus L, at an m.o.i. of 2; (c) infected with recombinant baculovirus N, at an m.o.i. of 10; or (d) wild-type baculovirus, at an m.o.i. of 10. Adsorbsion of viruses was allowed to proceed at room temperature for 1 hour on a slow rocker. 30 ml of fresh TC-100/10% FCS is added to the tissue culture flask and incubation continues at 27 degrees C. At 60 hours post-infection, monolayers were washed with PBS and lysed with TNN buffer according to the procedure describe in Example 3.

Soluble and insoluble fractions can be separated and compared for the presence of HGV proteins according to the method of Example 4. The soluble fraction is further purified using the Glutathione-Sepharose 4B (Pharmacia, Uppsala, Sweden), according to the method of Example 5.

Figure 3:
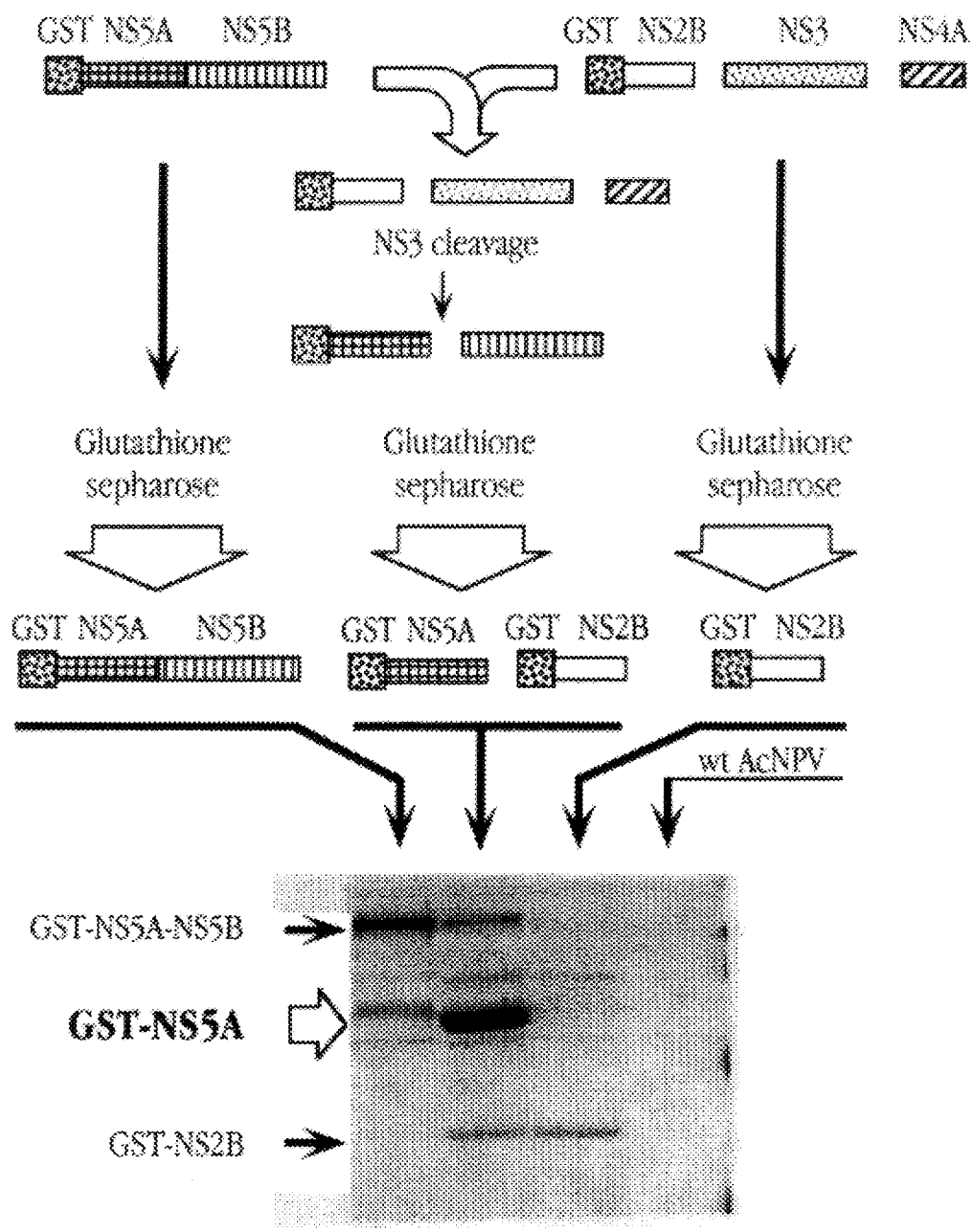
FIG. 3 shows a schematic diagram representing the co-infection of recombinant baculoviruses, one containing an HGV protease and a second containing an HGV polyprotein cleavage substrate. The purified GST fusion proteins are shown as analyzed by SDS-PAGE.

The purified HGV proteins from each experiment (a)–(d), above, were analyzed by 12% SDS-PAGE. The results are shown in FIG. 3, and summarized in Table 3.

TABLE 3

| Insert | Site 1 | Site 2 | Site 3* | Site 4* |
|--------|--------|--------|---------|---------|
| L      | +      | +      | +       | +       |
| LH     | −      | +      | +       | +       |
| LC     | −      | +      | +       | +       |
| LS     | +      | −      | −       | −       |
| 42     | +      | +      | +       | +       |
| 23     | +      | ND     | −       | +       |
| 23 + 4 | +      | ND     | +       | +       |
| G      | −      | ND     | ND      | ND      |

Site 1 is the cleavage site between NS2B and NS3.
Site 2 is the cleavage site between NS3 and NS4A-B.
Site 3 is the cleavage site between NS4A-B and NS5A.
Site 4 is the cleavage site between NS5A and NS5B.
*Studies conducted for Site 3 all included insect cells co-infected with a first vector having the insert shown in the first column and with a second vector having the insert Q described in Example 2. Likewise, studies conducted for Site 4 all included insect cells co-infected with a first vector having the insert shown in the first column and a second vector having the insert N described in Example 2.

The results summarized in Table 4 indicate that cleavage at the NS2B/NS3 junction (Site 1) occurs in cis. For example, Vector L is autocatalytic (FIG. 3, lane 5). Furthermore, the results indicate that such cleavage requires the presence of the carboxy terminal portion of NS2B. For example, the failure of constructs LH and LC to cleave at Site 1 (FIG. 3, Lanes 2 and 3) indicate the vital importance of $His_{849}$ and $Cys_{890}$ for function of NS2B. Further evidence of the importance of $His_{849}$ and $Cys_{890}$ as part of the NS2B catalytic domain is shown by the inability of Vector G (which does not include $His_{849}$ and $Cys_{890}$) to cleave at the NS2B/NS3 junction.

In contrast NS2B does not appear to be critical to cleavage at the NS3/NS4A-B junction (Site 2) as the point mutations in constructs LH and LC do not affect cleavage in cis. Construct LS, however, which is unable to cleave at the NS3/NS4A-B junction (FIG. 3, Lane 4) indicates the vital importance of the $Ser_{1062}$ residue of NS3.

Figure 4A:
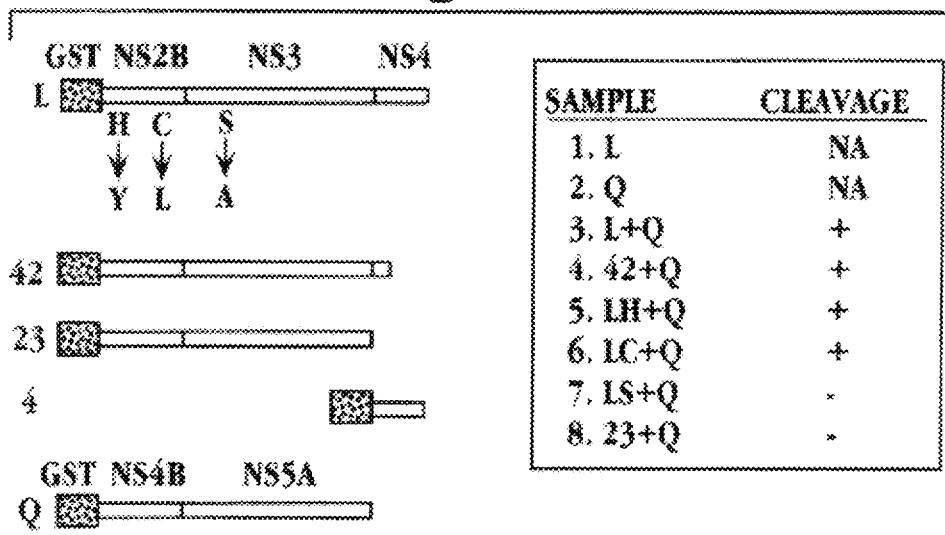
FIG. 4 shows various recombinant baculovirus constructs used to determine the proteolytic regions of HGV necessary for cleavage at the NS4/NS5 junction. Also, contained in FIG. 4 are two western blots of the same SDS-PAGE, using either anti-GST (top) or anti-NS4B as the reporter (bottom).
Figure 4B:
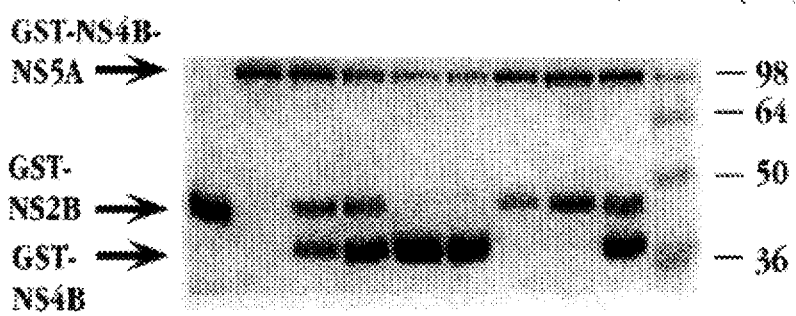
Figure 4C:
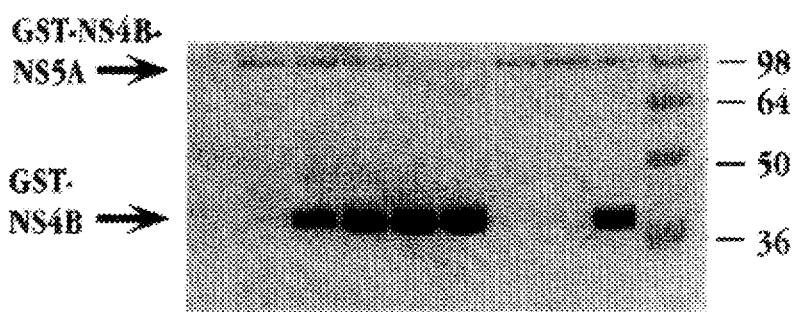

Cleavage at the NS4/NS5A junction (Site 3) is shown to occur in trans and require the presence of NS3 and the amino terminal portion of NS4A–B. From FIG. 4 it can be seen that the Q construct is cleaved when co-infected with L, 42, LH, and LC, lanes 3, 4, 5, and 6, respectively. However, where the critical Serine residue is absent, in the LS construct, no cleavage is observed with the Q substrate.

Co-infections of vector Q with vector 23 (FIG. 4, lane 8) failed to effect cleavage at the NS4/NS5A junction, however, when Q, 23 and 4 were co-infected cleavage at Site 3 is observed. This indicates the requirement of an NS4 co-factor supplied in trans by vector 4.

Figure 5A:
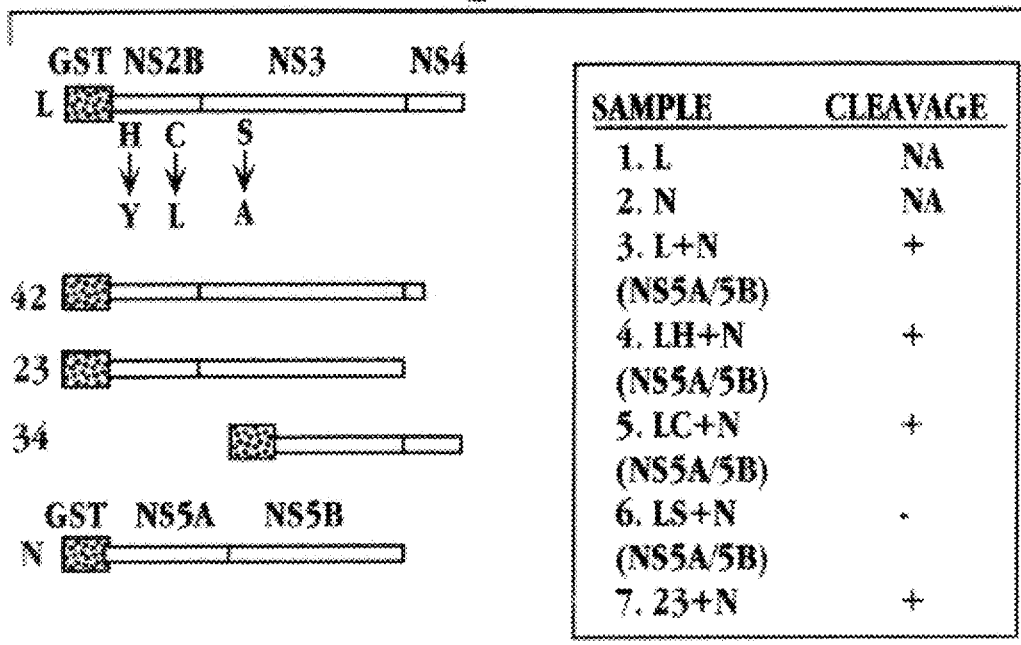
FIG. 5 shows an SDS-PAGE of insect cell lysates infected with one or more HGV constructs indicated schematically and designed to demonstrate cleavage at the NS5A/NS5B junction.
Figure 5B:
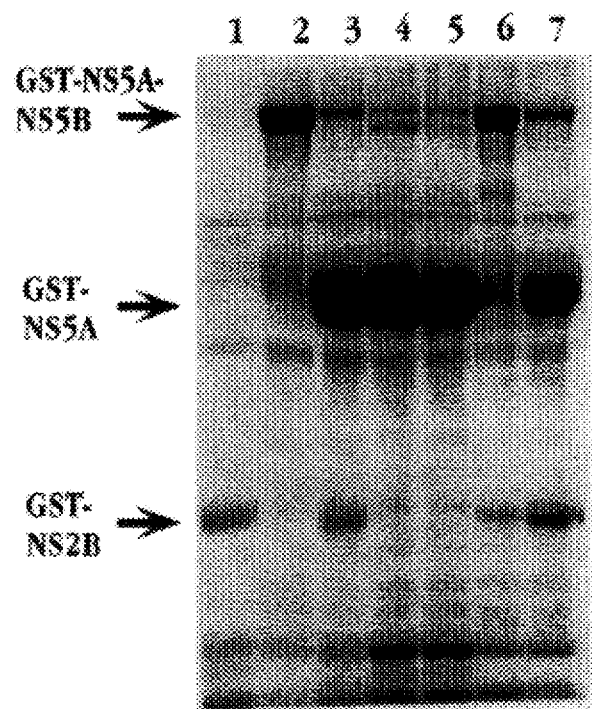

Similar results as with vector Q are seen with vector N demonstrating that cleavage at Site 4 (NS5A/NS5B) occurs in trans and is NS3 dependent (see FIG. 5). However, vector 23 co-infected with vector N was able to produce a cleavage event at Site 4 indicating that the NS4 co-factor is not obligatory for cleavage at this site.

EXAMPLE 7

Expression of Larger Antigens in Vaccinia

Various regions of the HGV genome were integrated in to vaccinia virus genome for expression (see Example 16, PCT patent application US95/06169, now published), herein incorporated by reference. Vector 14 described therein can be utilized below for determination of the HGV polyprotein cleavage sites as this full-length polypeptide, which encodes the HGV protease functions, should be processed naturally as it is during the normal course of infection. The amino acid sequence of the N-terminus of each protein is deduced as described in J. Virol (1993), 67:2832–2843, briefly as follows.

BS-C-1 cells (1×10 ), available from the ATCC, infected with a recombinant vaccinia virus expressing full length HGV polyprotein at an m.o.i. of 10 pfu/cell are incubated with 5 ml Valine, Methionine, and Cysteine-free medium supplemented with $^3$H-Valine (200 uci/ml), $^{35}$S-Methionine, and/or $^{35}$S-Cysteine (50 uci/ml) for 2 hr. The cells are harvested and lysed according to known techniques.

The cell lysates are incubated with protein-A Sepharose beads preincubated (1 hr.) with rabbit polyclonal anti-HGV antiserum, described above. The samples are incubated for 4 hr. at 4 degrees C. The samples are then washed with buffers containing mild detergent known to those of skill in the art. The beads are collected by centrifugation and denatured in protein denaturation buffer containing 2% SDS, and heated at 100 degrees C for 10 min. The supernatant is loaded on an SDS-polyacrylamide gel. After electrophoresis, the proteins on the gel are transferred to PVDF membrane by a standard western blot technique.

The PVDF membrane is exposed to X-ray film and the region(s) containing radioactive bands are cut out and subject to N-terminal protein sequence analysis by Edman Degradation. Typically 20 cycles are carried out.

The radioactivity profiles for labelled amino acid (or combination thereof) is determined by scintillation counting from each cycle of sequence reactions and the $^3$H-Valine, $^{35}$S-Methionine and $^{35}$S-Cysteine profiles from sequencing reactions are compared to the predicted HGV sequence deduced from the isolated nucleic acid to map the amino termini for each HGV protein.

Experiments conducted according to the above method were performed and resulted in the identification of the following cleavage junctions: NS2A/NS2B, NS2B/NS3, and NS4/NS5A. These sites are incorporated with predicted site based on sequence homology with other flaviviruses to form three HGV proteins NS2B (SEQ ID NO:33), NS3 (SEQ ID NO:35), and NS4A-B (SEQ ID NO:37).

It is to be emphasized that the terms and descriptions used herein are preferred embodiments set forth by way of illustration only, and are not intended as limitations on the many variations which those of skill in the art will recognize to be possible in practicing the invention. Modifications and other uses will occur to those skilled in the art which are encompassed within the spirit of the invention or defined by the scope of the following claims.

---

It is claimed:

1. A composition, comprising
an isolated Hepatitis G virus protease.

2. The composition of claim 1, wherein said protease is an NS2B protease encoded by a polynucleotide whose sequence is contained within SEQ ID NO:3.

3. The composition of claim 1, wherein said protease is an NS3 protease encoded by a polynucleotide whose sequence is contained within SEQ ID NO:4.

4. The composition of claim 1, wherein said Hepatitis G virus protease comprises a co-factor encoded by a polynucleotide whose sequence is contained within SEQ ID NO:5.

5. A fusion protein comprising a fusion partner fused to a Hepatitis G virus protease.

6. The fusion protein of claim 5, wherein said fusion partner comprises glutathione-S-transferase.

7. The fusion protein of claim 5, wherein said protease is encoded by a polynucleotide whose sequence is contained within SEQ ID NO:24.

8. The composition of claim 1, wherein said HGV protease comprises a polypeptide encoded by a polynucleotide whose sequence is contained within SEQ ID NO:32.

9. The composition of claim 1, wherein said HGV protease comprises a polypeptide encoded by a polynucleotide whose sequence is contained within SEQ ID NO:34.

10. The composition of claim 1, wherein said HGV protease comprises a polypeptide encoded by a polynucleotide whose sequence is contained within SEQ ID NO:36.

* * * * *